US012247978B2

(12) United States Patent
Altin et al.

(10) Patent No.: US 12,247,978 B2
(45) Date of Patent: Mar. 11, 2025

(54) COMPOSITIONS AND METHODS FOR DETECTION AND TREATMENT OF CORONAVIRUS INFECTION

(71) Applicants: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

(72) Inventors: John Altin, Flagstaff, AZ (US); Jason Ladner, Flagstaff, AZ (US)

(73) Assignee: Arizona Board of Regents on behalf of Northern Arizona University, Flagstaff, AZ (US)

( * ) Notice: Subject to any disclaimer, the term of this patent is extended or adjusted under 35 U.S.C. 154(b) by 688 days.

(21) Appl. No.: 17/395,330

(22) Filed: Aug. 5, 2021

(65) Prior Publication Data

US 2022/0042992 A1 Feb. 10, 2022

Related U.S. Application Data

(60) Provisional application No. 63/061,344, filed on Aug. 5, 2020.

(51) Int. Cl.

*G01N 33/569* (2006.01)
*A61K 31/18* (2006.01)

(Continued)

(52) U.S. Cl.

CPC ....... *G01N 33/56983* (2013.01); *A61K 31/18* (2013.01); *A61K 31/22* (2013.01);

(Continued)

(58) Field of Classification Search

CPC ......... G01N 33/56983; G01N 33/6884; G01N 2333/165; G01N 2800/12;

(Continued)

(56) References Cited

U.S. PATENT DOCUMENTS

| | | | |
|---|---|---|---|
| 4,816,567 | A | 3/1989 | Cabilly et al. |
| 4,935,493 | A | 6/1990 | Kudo et al. |

(Continued)

FOREIGN PATENT DOCUMENTS

| | | | |
|---|---|---|---|
| EP | 0173494 | A2 | 3/1986 |
| EP | 0125023 | B1 | 6/1991 |

(Continued)

OTHER PUBLICATIONS

Fafi-Kremer S, et al. Serologic responses to SARS-CoV-2 infection among hospital staff with mild disease in eastern France. EBioMedicine. Sep. 2020. Epub Jul. 31, 2020 (Year: 2020).*

(Continued)

*Primary Examiner* — Christopher L Chin
*Assistant Examiner* — Christina Lusi
(74) *Attorney, Agent, or Firm* — Booth Udall Fuller, PLC; Rodney J. Fuller

(57) ABSTRACT

The present disclosure includes a multiplexed peptide assay to generate an epitope-resolved view of antibody reactivity across all human coronaviruses (CoVs). PepSeq accurately classifies SARS-CoV-2 exposure status and reveals epitopes across the Spike and Nucleocapsid proteins. Two of these represent recurrent reactivities to conserved, functionally-important sites in the S2 subunit of Spike, regions that we show are also targeted for the endemic CoVs in pre-pandemic controls. At one of these sites, we demonstrate that the SARS-CoV-2 response strongly and recurrently cross-reacts with the endemic virus hCoV-OC43. The disclosed epitope-resolved analysis reveals new CoV targets for the develop- (Continued)

ment of diagnostics, vaccines and therapeutics, including a site that may have broad neutralizing potential.

5 Claims, 26 Drawing Sheets

Specification includes a Sequence Listing.

(51) Int. Cl.

| | |
|---|---|
| ***A61K 31/22*** | (2006.01) |
| ***A61K 31/40*** | (2006.01) |
| ***A61K 31/7052*** | (2006.01) |
| ***A61K 39/215*** | (2006.01) |
| ***A61P 11/00*** | (2006.01) |
| ***C12N 7/00*** | (2006.01) |
| ***G01N 33/68*** | (2006.01) |

(52) U.S. Cl.

CPC .......... *A61K 31/40* (2013.01); *A61K 31/7052* (2013.01); *A61K 39/215* (2013.01); *A61P 11/00* (2018.01); *C12N 7/00* (2013.01); *G01N 33/6884* (2013.01); *C12N 2770/20034* (2013.01); *G01N 2333/165* (2013.01); *G01N 2800/12* (2013.01); *G01N 2800/245* (2013.01); *G01N 2800/50* (2013.01)

(58) Field of Classification Search

CPC ......... G01N 2800/245; G01N 2800/50; G01N 2469/20; A61K 31/18; A61K 31/22; A61K 31/40; A61K 31/7052; A61K 39/215; A61K 39/12; A61P 11/00; A61P 31/14; C12N 7/00; C12N 2770/20034; C12N 2770/20022

USPC ............................... 435/7.1, 4; 436/501, 536

See application file for complete search history.

(56) References Cited

U.S. PATENT DOCUMENTS

| | | | |
|---|---|---|---|
| 5,225,539 | A | 7/1993 | Winter |
| 5,545,806 | A | 8/1996 | Lonberg et al. |
| 5,545,807 | A | 8/1996 | Surani et al. |
| 5,569,825 | A | 10/1996 | Lonberg et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,661,016 | A | 8/1997 | Longerg et al. |
| 5,693,761 | A | 12/1997 | Queen et al. |
| 5,693,762 | A | 12/1997 | Queen et al. |

FOREIGN PATENT DOCUMENTS

| | | | | |
|---|---|---|---|---|
| EP | 0171496 B1 | 5/1993 | | |
| WO | 1986/001533 A1 | 3/1986 | | |
| WO | 1987/002671 A1 | 5/1987 | | |
| WO | 2018/102659 A1 | 6/2018 | | |
| WO | 2019/162454 A1 | 8/2019 | | |
| WO | 2020/036811 A1 | 2/2020 | | |
| WO | 2020/095324 A1 | 5/2020 | | |
| WO | WO-2021188969 A2 * | 9/2021 | ............. | A61K 39/12 |

OTHER PUBLICATIONS

Lederman et al. "A single amino acid substitution in a common African allele of the CD4 molecule ablates binding of the monoclonal antibody OKT4" Mol Immunol. Nov. 1991; 28(11):1171-81 (Year: 1991).*

Abedini et al. A single-point mutation converts the highly amyloidogenic human islet amyloid polypeptide into a potent fibrillization inhibitor. J Am Chem Soc. Sep. 19, 2007;129(37):11300-1. (Year: 2007).*

Tsitrin et al. Conversion of a transmembrane to a water-soluble protein complex by a single point mutation. Nat Struct Biol. Oct. 2002;9(10):729-33. (Year: 2002).*

Yuan, M., et al. A highly conserved cryptic epitope in the receptor-binding domains of SARS-CoV-2 and SARSCoV. Science 2020; 368(6491):630-633.

Gostic, K. M., et al. Potent protection against H5N1 and H7N9 influenza via childhood hemagglutinin imprinting. Science 2016; 354(6313):722-726.

Monto, A. S., et al. The Doctrine of Original Antigenic Sin: Separating Good From Evil. J Infect Dis 2017; 215(12):1782-1788.

Gorse, G. J., et al. Prevalence of antibodies to four human coronaviruses is lower in nasal secretions than in serum. Clin Vaccine Immunol 2010; 17(12):1875-1880.

Khan, S., et al. Analysis of Serologic Cross-Reactivity Between Common Human Coronaviruses and SARS-CoV-2 Using Coronavirus Antigen Microarray. bioRxiv 2020; 2020.03.24.006544.

Ladner, J. T., et al. Epitope-resolved profiling of the SARS-CoV-2 antibody response identifies cross-reactivity with endemic human coronaviruses. Cell Rep Med 2021; 2(1):100189.

Shiryaev, S. A., et al. New details of HCV NS3/4A proteinase functionality revealed by a high-throughput cleavage assay. PLoS One 2012; 7(4):e35759.

Centers for Disease Control and Prevention (CDC). Revised U.S. surveillance case definition for severe acute respiratory syndrome (SARS) and update on SARS cases—United States and worldwide, Dec. 2003. Morb Mortal Wkly Rep 2003; 52(49):1202-1206.

Jia, N., et al. Emergence of human infection with Jingmen tick virus in China: A retrospective study. EBioMedicine 2019; 43:317-324.

Woolhouse, M. E. J., et al. Epidemiological characteristics of human-infective RNA viruses. Sci Data 2018; 5:180017.

Roberts, R. W., et al. RNA-peptide fusions for the in vitro selection of peptides and proteins. Proc Natl Acad Sci 1997; 94(23):12297-12302.

Walls, A. C., et al. Structure, Function, and Antigenicity of the SARS-CoV-2 Spike Glycoprotein. Cell 2020; 181(2):281-292.e6.

World Health Organization (WHO). Draft landscape of COVID-19 candidate vaccines. 2020.

Pinana, J. L., et al. Seasonal human coronaviruses respiratory tract infection in recipients of allogenic hematopoietic stem cell transplantation. J Infect Dis 2021:223(9):1564-1575.

Elshabrawy, H. A., et al. Human Monoclonal Antibodies against Highly Conserved HR1 and HR2 Domains of the SARS-CoV Spike Protein Are More Broadly Neutralizing. PLoS ONE 2012; 7(11):e50366.

Kozbor, D., et al. A human hybrid mveloma for production of human monoclonal antibodies. J Immunol 1984; 133(6):3001-3005.

Munson, P. J., et al. Ligand: a versatile computerized approach for characterization of ligand-binding systems. Anal Biochem 1980; 107(1):220-239.

Jones, P. T., et al. Replacing the complementarity-determining regions in a human antibody with those from a mouse Nature 1986; 321(6069):522-525.

Riechmann, L., et al. Reshaping human antibodies for therapy. Nature 1988; 332(6162):323-327.

Presta, L. G. Antibody Engineering. Curr Opin Biotechnol 1992; 3(4):394-398.

Liu, A. Y., et al. Chimeric mouse-human IgG1 antibody that can mediate lysis of cancer cells. Proc Natl Acad Sci USA 1987; 84(10):3439-3443.

Sun, L. K., et al. Chimeric antibody with human constant regions and mouse variable regions directed against carcinoma-associated antigen 17-1A. Proc Natl Acad Sci USA 1987; 84:214-218.

Better, M., et al. *Escherichia coli* secretion of an active chimeric antibody fragment. Science 1988; 240 (4855):1041-1043.

Morrison, S. L. Transfectomas provide novel chimeric antibodies. Science 1985; 229(4719):1202-1207.

OI, V. T., et al. Chimeric Antibodies. BioTechniques 1986; 4:214-221.

Verhoeyen, M., et al. Reshaping human antibodies: grafting an antilysozyme activity. Science 1988; 239(4847):1534-1536.

Beidler, C. B., et al. Cloning and High Level Expression of a Chimeric Antibody With Specificity for Human Carcinoembryonic Antigen. J Immunol 1988; 141(11):4053-4060.

(56) References Cited

OTHER PUBLICATIONS

Hoogenboom, H. R., et al. By-passing immunisation. Human antibodies from synthetic repertoires of germline VH gene segments rearranged in vitro. J Mol Biol 1992; 227(2):381-388.
Marks, J. D., et al. By-passing immunization. Human antibodies from V-gene libraries displayed on phage. J Mol Biol 1991; 222(3):581-597.
Boerner, P., et al. Production of antigen-specific human monoclonal antibodies from in vitro-primed human splenocytes. J Immunol 1991; 147(1):86-95.
Marks, J. D., et al. By-passing immunization: building high affinity human antibodies by chain shuffling. Biotechnology 1992; 10(7):779-783.
Lonberg, N., et al. Antigen-specific human antibodies from mice comprising four distinct genetic modifications. Nature 1994; 368(6474): 856-859.
Morrison, S. L. Success in specification. Nature 1994; 368:812-813.
Fishwild, D. M., et al. High-avidity human IgG kappa monoclonal antibodies from a novel strain of minilocus transgenic mice. Nature Biotechnology 1996; 14(7):845-851.
Neuberger, M. Generating high-avidity human Mabs in mice. Nature Biotechnology 1996; 14:826.
Lonberg, N., et al. Human antibodies from transgenic mice. Intern Rev Immunol 1995; 13(1):65-93.
Zhu, N., et al. A Novel Coronavirus from Patients with Pneumonia in China, 2019. N Eng J Med 2020; 382(8):727-733.
Callow, K. A., et al. The time course of the immune response to experimental coronavirus infection of man. Epidemiol Infect 1990; 105(2):435-446.
Dijkman, R., et al. Human coronavirus NL63 and 229E seroconversion in children. J. Clin Microbiol 2008; 46(7):2368-2373.
Liu, A., et al. Antibody responses against SARS-CoV-2 in COVID-19 patients. J. Med. Virol 2021; 93(1):144-148.
Ni, L., et al. Detection of SARS-CoV-2-Specific Humoral and Cellular Immunity in COVID-19 Convalescent Individuals. Immunity 2020; 52(6):971-977.e3.
Casadevall, A., et al. The convalescent sera option for containing COVID-19. J Clin Invest 2020; 130(4):1545-1548.
Thanh Le, T., et al. The COVID-19 vaccine development landscape. Nat Rev Drug Discov 2020; 19(5):305-306.
Krammer, F., et al. Serology assays to manage COVID-19. Science 2020; 368(6495):1060-1061.
Deeks, J. J., et al. Antibody tests for identification of current and past infection with SARS-CoV-2. Cochrane Database Syst Rev 2020; 6(6):CD013652.
Whitman, J. D., et al. Test performance evaluation of SARS-CoV-2 serological assays. medRxiv 2020; 2020.04.25.20074856.
Nie, J., et al. Establishment and validation of a pseudovirus neutralization assay for SARS-CoV-2. Emerg Microbes Infect 2020; 9(1):680-686.
Lu, R., et al. Genomic characterisation and epidemiology of 2019 novel coronavirus: implications for virus origins and receptor binding. Lancet 2020; 395(10224):565-574.
Grifoni, A., et al. Targets of T Cell Responses to SARS-CoV-2 Coronavirus in Humans with COVID-19 Disease and Unexposed Individuals. Cell 2020; 181(7):1489-1501.e15.
LV, H., et al. Cross-reactive Antibody Response between SARSCoV-2 and SARS-CoV Infections. Cell Rep 2020; 31:107725.
Pinto, D., et al. Cross-neutralization of SARS-CoV-2 by a human monoclonal SARS-CoV antibody. Nature 2020; 583(7815):290-295.
Friesen, R. H. E., et al. A common solution to group 2 influenza virus neutralization. Proc Natl Acad Sci USA 2014; 111(1):445-450.
Du, L., et al. The spike protein of SARSCoV—a target for vaccine and therapeutic development. Nat Rev Microbiol 2009; 7(3):226-236.
Pillay, T. A. Gene of the month: the 2019-nCoV/SARS-CoV-2 novel coronavirus spike protein. J Clin Pathol 2020; 73(7):366-369.
Robbiani, D. F., et al. Convergent Antibody Responses to SARSCoV-2 Infection in Convalescent Individuals. bioRxiv 2020; 2020.05.13.092619.
Chi, X., et al. A neutralizing human antibody binds to the N-terminal domain of the Spike protein of SARS-CoV-2. Science 2020; 369(6504):650-655.
Hansen, J., et al. Studies in humanized mice and convalescent humans yield a SARS-CoV-2 antibody cocktail. Science 2020; 369(6506):1010-1014.
Zost, S. J., et al. Potently neutralizing human antibodies that block SARS-CoV-2 receptor binding and protect animals. bioRxiv 2020; 2020.05.22.111005.
Poh, C. M., et al. Two linear epitopes on the SARS-CoV-2 spike protein that elicit neutralising antibodies in COVID-19 patients. Nat Commun 2020; 11(1):2806.
Hoofnagle, J. H., et al. Antibody to hepatitis B core antigen. A sensitive indicator of hepatitis B virus replication. N Engl J Med 1974; 290(24):1336-1340.
Lubroth, J., et al. Absence of protein 2C from clarified foot-and-mouth disease virus vaccines provides the basis for distinguishing convalescent from vaccinated animals. Vaccine 1996; 14(5):419-427.
Halstead, S. B., et al. Antibody-enhanced dengue virus infection in primate leukocytes. Nature 1977; 265(5596):739-741.
Katzelnick, L. C., et al. Antibody-dependent enhancement of severe dengue disease in humans. Science 2017; 358 (6365):929-932.
Khurana, S., et al. Vaccine-induced anti-HA2 antibodies promote virus fusion and enhance influenza virus respiratory disease. Sci Transl Med 2013; 5(200):200ra114.
Eroshenko, N., et al. Implications of antibody-dependent enhancement of infection for SARS-CoV-2 countermeasures. Nat Biotechnol 2020; 38(7):789-791.
Fleri, W., et al. The Immune Epitope Database and Analysis Resource in Epitope Discovery and Synthetic Vaccine Design. Front Immunol 2017; 8:278.
Lucchese, G., et al. Peptidology: short amino acid modules in cell biology and immunology. Amino Acids 2007; 33(4):703-707.
Price, J. V., et al. On silico peptide microarrays for high-resolution mapping of antibody epitopes and diverse protein-protein interactions. Nat Med 2012; 18(9):1434-1440.
Larman, H. B., et al. Autoantigen discovery with a synthetic human peptidome. Nat Biotechnol 2011; 29(6):535-541.
Xu, G. J., et al. Viral immunology. Comprehensive serological profiling of human populations using a synthetic human virome. Science 2015; 348(6239):aaa0698.
Kozlov, I. A., et al. A highly scalable peptide-based assay system for proteomics. PLoS One 2012; 7(6):e37441.
Kohler, G., et al. Continuous cultures of fused cells secreting antibody of predefined specificity. Nature 1975; 256(5517):495-497.
Kozbor, D., et al. The production of monoclonal antibodies from human lymphocytes. Immunology Today 1983; 4(3):72-79.
Cote, R. J., et al. Generation of human monoclonal antibodies reactive with cellular antigens. Proc Natl Acad Sci USA 1983; 80(7):2026-2030.
Fink, Z. W., et al. PepSIRF: a flexible and comprehensive tool for the analysis of data from highly-multiplexed DNA-barcoded peptide assays. arXiv 2020; 2007.05050.
Mina, M. J., et al. Measles virus infection diminishes preexisting antibodies that offer protection from other pathogens. Science 2019; 366(6465):599-606.
Waterhouse, A., et al. SWISS-MODEL: homology modelling of protein structures and complexes. Nucleic Acids Res 2018; 46(W1):W296-W303.
Walls, A. C., et al. Tectonic conformational changes of a coronavirus spike glycoprotein promote membrane fusion. Proc Natl Acad Sci USA 2017; 114(42):11157-11162.
Keng, C. T., et al. Amino acids 1055 to 1192 in the S2 region of severe acute respiratory syndrome coronavirus S protein induce neutralizing antibodies: implications for the development of vaccines and antiviral agents. J Virol 2005; 79(6):3289-3296.
Lai, S. C., et al. Characterization of neutralizing monoclonal antibodies recognizing a 15-residues epitope on the spike protein HR2

(56) References Cited

OTHER PUBLICATIONS region of severe acute respiratory syndrome coronavirus (SARS-CoV). J Biomed Sci 2005; 12(5):711-727.
Tan, C. W., et al. A SARS-CoV-2 surrogate virus neutralization test (sVNT) based on antibody-mediated blockage of ACE2-spike (RBD) protein-protein interaction. Nat Biotechnol 2020; 38(9):1073-1078.
Xia, S., et al. A pan-coronavirus fusion inhibitor targeting the HR1 domain of human coronavirus spike. Sci Adv 2019; 5(4):eaav4580.
Liu, S., et al. Interaction between heptad repeat 1 and 2 regions in spike protein of SARS associated coronavirus: Implications for virus fusogenic mechanism and identification of fusion inhibitors. Lancet 2004; 363(9413):938-947.
Routledge, E., et al. Analysis of murine coronavirus surface glycoprotein functions by using monoclonal antibodies. J Virol 1991; 65(1):254-262.
Chang, C. K., et al. Multiple nucleic acid binding sites and intrinsic disorder of severe acute respiratory syndrome coronavirus nucleocapsid protein: implications for ribonucleocapsid protein packaging. J Virol 2009; 83(5):2255-2264.
Amanat, F., et al. A serological assay to detect SARS-CoV-2 seroconversion in humans. Nat Med 2020; 26(7):1033-1036.

* cited by examiner

```
Beta1-HR2 Peptide  APDVMLNISTPKLPDFKEELDQWFKNQTSV  SEQ ID NO: 14
             OC43  APYVMLNTSIPNLPDFKEELDQWFKNQTSV  SEQ ID NO: 463
            SARS2  VNNTVYDPLQPELDSFKEELDKYFKNHTSP  SEQ ID NO: 354

Beta1-S12 Peptide  TTGYRFTNF---EPFTVNSVNDSLEPVGGLYEI  SEQ ID NO: 13
             OC43  TTGYRFTNF---EPFTVNSVNDSLEPVGGLYEI  SEQ ID NO: 13
            SARS2  SQSIIAYTMSLGAENSVAYSNNS---------I  SEQ ID NO: 464
```

FIG. 5B

SEQUENCE LISTING

```
<160> NUMBER OF SEQ ID NOS: 464

<210> SEQ ID NO 1
<211> LENGTH: 30
<212> TYPE: PRT
<213> ORGANISM: SARS-CoV-2

<400> SEQUENCE: 1

Ser Phe Lys Glu Glu Leu Asp Lys Tyr Phe Lys Asn His Thr Ser Pro
1               5                   10                  15

Asp Val Asp Leu Gly Asp Ile Ser Gly Ile Asn Ala Ser Val
            20                  25                  30


<210> SEQ ID NO 2
<211> LENGTH: 30
<212> TYPE: PRT
<213> ORGANISM: SARS-CoV-2

<400> SEQUENCE: 2

Ser Lys Pro Ser Lys Arg Ser Phe Ile Glu Asp Leu Leu Phe Asn Lys
1               5                   10                  15

Val Thr Leu Ala Asp Ala Gly Phe Ile Lys Gln Tyr Gly Asp
            20                  25                  30


<210> SEQ ID NO 3
```

-continued

<211> LENGTH: 30
<212> TYPE: PRT
<213> ORGANISM: SARS-CoV-2

<400> SEQUENCE: 3

```
Asn Ala Ala Ile Val Leu Gln Leu Pro Gln Gly Thr Thr Leu Pro Lys
1               5                   10                  15

Gly Phe Tyr Ala Glu Gly Ser Arg Gly Gly Ser Gln Ala Ser
            20                  25                  30
```

<210> SEQ ID NO 4
<211> LENGTH: 30
<212> TYPE: PRT
<213> ORGANISM: SARS-CoV-2

<400> SEQUENCE: 4

```
Gly Asp Ala Ala Leu Ala Leu Leu Leu Leu Asp Arg Leu Asn Gln Leu
1               5                   10                  15

Glu Ser Lys Met Ser Gly Lys Gly Gln Gln Gln Gln Gly Gln
            20                  25                  30
```

<210> SEQ ID NO 5
<211> LENGTH: 30
<212> TYPE: PRT
<213> ORGANISM: Aichivirus A

<400> SEQUENCE: 5

```
Ser Leu Ile Lys Arg Gln Gly Asn Arg Val Ile Asp Ala Glu Pro Arg
1               5                   10                  15

Glu Ile Pro Leu Glu Tyr Ala Asp Asp Leu Leu Glu Ala Met
            20                  25                  30
```

<210> SEQ ID NO 6
<211> LENGTH: 30
<212> TYPE: PRT
<213> ORGANISM: Aichivirus A

<400> SEQUENCE: 6

```
Glu Ala Cys Trp Lys Cys Ser Gln Asp Lys Pro Arg Arg Lys Tyr Asn
1               5                   10                  15

Thr Val Pro Pro Glu Glu Trp Leu Tyr Asp Ser Asp Val Gln
            20                  25                  30
```

<210> SEQ ID NO 7
<211> LENGTH: 30
<212> TYPE: PRT
<213> ORGANISM: Aichivirus A

<400> SEQUENCE: 7

```
Ala Leu Pro Gly Ile Arg Arg Gln Gly Leu Leu Thr Leu Ser Ala Asp
1               5                   10                  15

Thr Glu Thr Asn Gln Thr Leu Asn Lys Ile Thr Glu Ser Val
            20                  25                  30
```

<210> SEQ ID NO 8
<211> LENGTH: 30
<212> TYPE: PRT
<213> ORGANISM: Aichivirus A

<400> SEQUENCE: 8

```
Lys Phe Phe Asp Lys Leu Ala Leu Leu Ser Leu Pro Gly Ala Tyr Gln
1               5                   10                  15
```

Ala Lys Thr Pro Glu Glu Arg Ala Leu Ala Gly Ala Leu Thr
20 25 30

<210> SEQ ID NO 9
<211> LENGTH: 30
<212> TYPE: PRT
<213> ORGANISM: Aichivirus A

<400> SEQUENCE: 9

Thr Gln Ser Gly Asn Ala Ala Ile Leu Thr Gly Ser Thr Ala Pro Ser
1 5 10 15

Phe Leu Ala Tyr Pro Thr Ala Thr Pro Val Pro Leu Pro Asn
20 25 30

<210> SEQ ID NO 10
<211> LENGTH: 30
<212> TYPE: PRT
<213> ORGANISM: Aichivirus A

<400> SEQUENCE: 10

Gly Ser Ser Asn Lys Val Gly Ser Arg Phe Ser Lys Trp Trp Glu Pro
1 5 10 15

Ala Ala Ala Arg Ala Leu Glu Arg Ala Thr Asp Ser Ala Ile
20 25 30

<210> SEQ ID NO 11
<211> LENGTH: 30
<212> TYPE: PRT
<213> ORGANISM: Alphacoronavirus 1

<400> SEQUENCE: 11

Met Ala Thr Gln Gly Pro Arg Val Asn Trp Gly Asp Glu Pro Ser Lys
1 5 10 15

Arg Arg Gly Arg Ser Asn Ser Arg Gly Arg Lys Ser Ser Asp
20 25 30

<210> SEQ ID NO 12
<211> LENGTH: 30
<212> TYPE: PRT
<213> ORGANISM: Alphapapillomavirus 9

<400> SEQUENCE: 12

Met Ser Leu Trp Arg Pro Ser Glu Ala Thr Val Tyr Leu Pro Pro Ala
1 5 10 15

Pro Val Ser Lys Val Val Ser Thr Asp Glu Tyr Val Thr Arg
20 25 30

<210> SEQ ID NO 13
<211> LENGTH: 30
<212> TYPE: PRT
<213> ORGANISM: Betacoronavirus 1

<400> SEQUENCE: 13

Thr Thr Gly Tyr Arg Phe Thr Asn Phe Glu Pro Phe Thr Val Asn Ser
1 5 10 15

Val Asn Asp Ser Leu Glu Pro Val Gly Gly Leu Tyr Glu Ile
20 25 30

<210> SEQ ID NO 14
<211> LENGTH: 30
<212> TYPE: PRT
<213> ORGANISM: Betacoronavirus 1

<400> SEQUENCE: 14

Ala Pro Asp Val Met Leu Asn Ile Ser Thr Pro Lys Leu Pro Asp Phe
1               5                   10                  15

Lys Glu Glu Leu Asp Gln Trp Phe Lys Asn Gln Thr Ser Val
            20                  25                  30

<210> SEQ ID NO 15
<211> LENGTH: 30
<212> TYPE: PRT
<213> ORGANISM: Betacoronavirus 1

<400> SEQUENCE: 15

Lys Trp Ala Asp Gln Ser Asp Gln Phe Arg Asn Val Gln Thr Arg Gly
1               5                   10                  15

Arg Arg Ala Gln Pro Lys Gln Thr Val Thr Ser Gln Gln Pro
            20                  25                  30

<210> SEQ ID NO 16
<211> LENGTH: 30
<212> TYPE: PRT
<213> ORGANISM: Enterovirus A

<400> SEQUENCE: 16

Ala Ala Asn Thr Ala Ala Ser Ala His Ser Leu Gly Thr Gly Arg Val
1               5                   10                  15

Pro Ala Leu Gln Ala Ala Glu Thr Gly Ala Ser Ser Asn Ser
            20                  25                  30

<210> SEQ ID NO 17
<211> LENGTH: 30
<212> TYPE: PRT
<213> ORGANISM: Enterovirus A

<400> SEQUENCE: 17

Val Ser Asp Tyr Ile Lys Gly Leu Gly Asp Ala Phe Gly Val Gly Phe
1               5                   10                  15

Thr Asp Ala Val Ser Arg Glu Val Glu Ala Leu Lys Asn His
            20                  25                  30

<210> SEQ ID NO 18
<211> LENGTH: 30
<212> TYPE: PRT
<213> ORGANISM: Enterovirus A

<400> SEQUENCE: 18

Asp Ser Ile Ala Asp Met Ile Asp Gln Ala Val Asn Asn Gln Val Asn
1               5                   10                  15

Arg Ser Leu Thr Ala Met Gln Val Leu Pro Thr Ala Ala Asn
            20                  25                  30

<210> SEQ ID NO 19
<211> LENGTH: 30
<212> TYPE: PRT
<213> ORGANISM: Enterovirus A

<400> SEQUENCE: 19

Asp Met Ala Asn Ala Ala Lys Gly Phe Glu Trp Ile Ser Asn Lys Ile
1               5                   10                  15

Ser Lys Phe Ile Asp Trp Ile Lys Glu Lys Ile Ile Pro Ala
            20                  25                  30

-continued

<210> SEQ ID NO 20
<211> LENGTH: 30
<212> TYPE: PRT
<213> ORGANISM: Enterovirus A

<400> SEQUENCE: 20

Pro Pro Lys Phe Arg Pro Val Arg Ile Ser Leu Asp Glu Lys Pro Ala
1               5                   10                  15

Pro Asp Ala Ile Ser Asp Leu Leu Ala Ser Val Asp Ser Glu
            20                  25                  30

<210> SEQ ID NO 21
<211> LENGTH: 30
<212> TYPE: PRT
<213> ORGANISM: Enterovirus A

<400> SEQUENCE: 21

Asn Leu Glu Ala Ile Asp Leu His Thr Ser Ala Gly Tyr Pro Tyr Ser
1               5                   10                  15

Ala Leu Gly Ile Lys Lys Arg Asp Ile Leu Asp Pro Thr Thr
            20                  25                  30

<210> SEQ ID NO 22
<211> LENGTH: 30
<212> TYPE: PRT
<213> ORGANISM: Enterovirus A

<400> SEQUENCE: 22

Asp Lys Arg Leu Glu Val Asp Phe Glu Thr Ala Leu Phe Ser Lys Tyr
1               5                   10                  15

Ile Gly Asn Lys Ile Tyr Glu Pro Asp Glu Tyr Met Ile Gln
            20                  25                  30

<210> SEQ ID NO 23
<211> LENGTH: 30
<212> TYPE: PRT
<213> ORGANISM: Enterovirus A

<400> SEQUENCE: 23

Asp Lys Arg Leu Glu Val Asp Phe Glu Thr Ala Leu Phe Ser Lys Tyr
1               5                   10                  15

Ile Gly Asn Lys Ile Tyr Glu Pro Asp Glu Tyr Met Ile Gln
            20                  25                  30

<210> SEQ ID NO 24
<211> LENGTH: 30
<212> TYPE: PRT
<213> ORGANISM: Enterovirus A

<400> SEQUENCE: 24

Val Ser Lys Met Lys Phe Tyr Met Asp Lys Tyr Gly Leu Asp Leu Pro
1               5                   10                  15

Tyr Ser Thr Tyr Val Lys Asp Glu Leu Arg Ser Met Asp Lys
            20                  25                  30

<210> SEQ ID NO 25
<211> LENGTH: 30
<212> TYPE: PRT
<213> ORGANISM: Enterovirus A

<400> SEQUENCE: 25

Phe Thr Asn Ile Asn Tyr Tyr Lys Asp Ser Tyr Ala Ala Ser Ala Ala
1               5                   10                  15

Lys His Asp Phe Thr Gln Asp Pro Gly Lys Phe Thr Gln Pro
20 25 30

<210> SEQ ID NO 26
<211> LENGTH: 30
<212> TYPE: PRT
<213> ORGANISM: Enterovirus A

<400> SEQUENCE: 26

Ser Asn Lys Glu Thr Gly Arg Leu Ser Ile Asn Gly Pro Thr Arg Thr
1 5 10 15

Lys Leu Glu Pro Ser Ala Phe Tyr Asp Val Phe Glu Gly Ser
20 25 30

<210> SEQ ID NO 27
<211> LENGTH: 30
<212> TYPE: PRT
<213> ORGANISM: Enterovirus B

<400> SEQUENCE: 27

Gln Gln Val Pro Ala Leu Thr Ala Val Glu Thr Gly His Thr Ser Gln
1 5 10 15

Val Ala Pro Ser Asp Thr Ile Gln Thr Arg His Val His Asn
20 25 30

<210> SEQ ID NO 28
<211> LENGTH: 30
<212> TYPE: PRT
<213> ORGANISM: Enterovirus B

<400> SEQUENCE: 28

Val Glu Gly Ala Ile Gly Arg Val Ala Asp Thr Ile Arg Ser Gly Pro
1 5 10 15

Ser Asn Ser Glu Ala Val Pro Ala Leu Thr Ala Ala Glu Thr
20 25 30

<210> SEQ ID NO 29
<211> LENGTH: 30
<212> TYPE: PRT
<213> ORGANISM: Enterovirus B

<400> SEQUENCE: 29

Lys Asp Ala Gly Tyr Pro Val Ile Asn Ala Pro Ser Lys Thr Lys Leu
1 5 10 15

Glu Pro Ser Val Phe His Gln Val Phe Glu Gly Asn Lys Glu
20 25 30

<210> SEQ ID NO 30
<211> LENGTH: 30
<212> TYPE: PRT
<213> ORGANISM: Enterovirus B

<400> SEQUENCE: 30

Asn Arg Gln Asp Phe Thr Gln Asp Pro Ser Arg Phe Thr Glu Pro Val
1 5 10 15

Gln Asp Val Leu Ile Lys Thr Leu Pro Ala Leu Asn Ser Pro
20 25 30

<210> SEQ ID NO 31
<211> LENGTH: 30
<212> TYPE: PRT
<213> ORGANISM: Enterovirus B -continued

<400> SEQUENCE: 31

Ala Leu Tyr Gln Asn Asp Pro Glu Ser Ala Leu Asn Arg Ala Val Gly
1 5 10 15

Arg Val Ala Asp Thr Val Ala Ser Gly Pro Val Asn Thr Glu
20 25 30

<210> SEQ ID NO 32
<211> LENGTH: 30
<212> TYPE: PRT
<213> ORGANISM: Enterovirus B

<400> SEQUENCE: 32

Ala Ser Glu Val Thr Val Ser Asp Thr Gln Pro Ser Gly Pro Ser Asn
1 5 10 15

Ser Val Ser Val Pro Met Leu Thr Ala Ala Glu Thr Gly His
20 25 30

<210> SEQ ID NO 33
<211> LENGTH: 30
<212> TYPE: PRT
<213> ORGANISM: Enterovirus B

<400> SEQUENCE: 33

Asp Val Val Glu Ala Ile Glu Ser Ala Val Ala Arg Val Ala Asp Thr
1 5 10 15

Ile Ser Ser Gly Pro Thr Asn Ser Gln Ala Val Pro Ala Leu
20 25 30

<210> SEQ ID NO 34
<211> LENGTH: 30
<212> TYPE: PRT
<213> ORGANISM: Enterovirus B

<400> SEQUENCE: 34

Ser Pro Phe Val Arg Gln Thr Val Phe Tyr Gln Asn Asp Val Gln Asn
1 5 10 15

Ala Ile Asp Arg Ala Met Thr Arg Val Ala Asp Thr Met Pro
20 25 30

<210> SEQ ID NO 35
<211> LENGTH: 30
<212> TYPE: PRT
<213> ORGANISM: Enterovirus B

<400> SEQUENCE: 35

Asn Glu Pro Ser Asn Ala Ile Glu Arg Ala Met Val Arg Val Ala Asp
1 5 10 15

Thr Met Ala Ser Gly Pro Ala Asn Ser Glu Gln Ile Pro Ala
20 25 30

<210> SEQ ID NO 36
<211> LENGTH: 30
<212> TYPE: PRT
<213> ORGANISM: Enterovirus B

<400> SEQUENCE: 36

Ser Gln Asp Asn Lys Leu Gln Gly Asp Val Glu Glu Ala Ile Glu Arg
1 5 10 15

Ala Val Val His Val Ala Asp Thr Met Arg Ser Gly Pro Ser
20 25 30

<210> SEQ ID NO 37
<211> LENGTH: 30
<212> TYPE: PRT
<213> ORGANISM: Enterovirus D

<400> SEQUENCE: 37

Ile Thr Asp Tyr Ile Gln Ser Leu Gly Asn Ala Phe Gly Ala Gly Phe
1 5 10 15

Thr Glu Thr Ile Ser Ser Lys Ala Lys Glu Val Gln Asp Met
20 25 30

<210> SEQ ID NO 38
<211> LENGTH: 30
<212> TYPE: PRT
<213> ORGANISM: Enterovirus D

<400> SEQUENCE: 38

Ile Ile Lys Thr Ala Thr Asp Thr Val Lys Ser Glu Ile Asn Ala Glu
1 5 10 15

Leu Gly Val Val Pro Ser Leu Asn Ala Val Glu Thr Gly Ala
20 25 30

<210> SEQ ID NO 39
<211> LENGTH: 30
<212> TYPE: PRT
<213> ORGANISM: Enterovirus D

<400> SEQUENCE: 39

Lys Asp Lys Arg Leu Lys Val Asp Phe Glu Glu Ala Ile Phe Ser Lys
1 5 10 15

Tyr Val Gly Asn Lys Thr Met Leu Met Asp Glu Tyr Met Glu
20 25 30

<210> SEQ ID NO 40
<211> LENGTH: 30
<212> TYPE: PRT
<213> ORGANISM: Enterovirus D

<400> SEQUENCE: 40

Gly Val Ile Pro Ser Leu Asn Ala Ala Glu Thr Gly Ala Thr Ser Asn
1 5 10 15

Thr Thr Pro Glu Glu Ala Ile Gln Thr Arg Ala Val Ile Asn
20 25 30

<210> SEQ ID NO 41
<211> LENGTH: 30
<212> TYPE: PRT
<213> ORGANISM: Enterovirus D

<400> SEQUENCE: 41

Arg Asp Ile Phe Asn Arg Gln Thr Arg Asp Thr Thr Glu Met Thr Lys
1 5 10 15

Met Leu Asp Lys Tyr Gly Val Asp Leu Pro Phe Val Thr Phe
20 25 30

<210> SEQ ID NO 42
<211> LENGTH: 30
<212> TYPE: PRT
<213> ORGANISM: Enterovirus D

<400> SEQUENCE: 42

Arg Gly Lys Glu Arg Ala Pro Asn Ala Leu Asn Ala Ile Ile Gly Asn

```
1               5                   10                  15

Arg Asp Ser Val Lys Ala Met Pro His Asn Ile Val Thr Thr
            20                  25                  30


<210> SEQ ID NO 43
<211> LENGTH: 30
<212> TYPE: PRT
<213> ORGANISM: Enterovirus D

<400> SEQUENCE: 43

Leu Phe Gln Gly Pro Pro Gln Phe Arg Glu Ile Lys Ile Ser Val Ser
1               5                   10                  15

Pro Glu Thr Pro Ala Pro Asp Ala Ile Asn Asp Leu Leu Arg
            20                  25                  30


<210> SEQ ID NO 44
<211> LENGTH: 30
<212> TYPE: PRT
<213> ORGANISM: Enterovirus D

<400> SEQUENCE: 44

Ala Asn Tyr Lys Gly Lys Glu Lys Thr Pro Asn Ala Leu Asn Ala Leu
1               5                   10                  15

Ile Gly Asn Arg Asp Asn Val Lys Thr Met Thr His Asn Ile
            20                  25                  30


<210> SEQ ID NO 45
<211> LENGTH: 30
<212> TYPE: PRT
<213> ORGANISM: Enterovirus E

<400> SEQUENCE: 45

Arg Arg Tyr Phe Thr Ala Glu Gln Gly Lys Ile Glu Tyr Ile Glu Lys
1               5                   10                  15

Ser Lys Glu Ala Gly Tyr Pro Ile Ile Asn Ala Pro Thr Gln
            20                  25                  30


<210> SEQ ID NO 46
<211> LENGTH: 30
<212> TYPE: PRT
<213> ORGANISM: Enterovirus E

<400> SEQUENCE: 46

Lys Phe Thr Glu Ala Val Asn Ala Phe Lys Gly Leu Asp Trp Ile Ala
1               5                   10                  15

Ala Lys Phe Ser Lys Phe Leu Asp Trp Ile Lys Ser Lys Ile
            20                  25                  30


<210> SEQ ID NO 47
<211> LENGTH: 30
<212> TYPE: PRT
<213> ORGANISM: Enterovirus E

<400> SEQUENCE: 47

Ser Val Asp Ser Glu Asp Val Arg Glu Tyr Cys Arg Gln Lys Gly Trp
1               5                   10                  15

Ile Val Gln Glu Lys Ile Thr Lys Glu Ser Leu Glu Arg Asn
            20                  25                  30


<210> SEQ ID NO 48
<211> LENGTH: 30
<212> TYPE: PRT
```

<213> ORGANISM: Human alphaherpesvirus 1

<400> SEQUENCE: 48

Trp Met Arg Arg Arg Thr Gln Lys Ala Pro Lys Arg Ile Arg Leu Pro
1 5 10 15

His Ile Arg Glu Asp Asp Gln Pro Ser Ala His Gln Pro Leu
20 25 30

<210> SEQ ID NO 49
<211> LENGTH: 30
<212> TYPE: PRT
<213> ORGANISM: Human alphaherpesvirus 1

<400> SEQUENCE: 49

Gly Asp Phe Asp Glu Ala Lys Leu Ala Glu Ala Arg Glu Met Ile Arg
1 5 10 15

Tyr Met Ala Leu Val Ser Ala Met Glu His Thr Glu His Lys
20 25 30

<210> SEQ ID NO 50
<211> LENGTH: 30
<212> TYPE: PRT
<213> ORGANISM: Human alphaherpesvirus 1

<400> SEQUENCE: 50

Pro Leu Asp Gly Cys Gly Pro Leu His Pro Ser Trp Val Ser Leu Met
1 5 10 15

Pro Pro Lys Gln Val Pro Glu Thr Val Val Asp Ala Ala Cys
20 25 30

<210> SEQ ID NO 51
<211> LENGTH: 30
<212> TYPE: PRT
<213> ORGANISM: Human alphaherpesvirus 1

<400> SEQUENCE: 51

Ala Trp Gly Gln Val His Asp Trp Thr Glu Gln Thr Asp Pro Trp Phe
1 5 10 15

Leu Asp Gly Leu Gly Met Asp Arg Met Tyr Trp Arg Asp Thr
20 25 30

<210> SEQ ID NO 52
<211> LENGTH: 30
<212> TYPE: PRT
<213> ORGANISM: Human alphaherpesvirus 1

<400> SEQUENCE: 52

Ala Trp Gly Gln Val His Asp Trp Thr Glu Gln Thr Asp Pro Trp Phe
1 5 10 15

Leu Asp Gly Leu Gly Met Asp Arg Met Tyr Trp Arg Asp Thr
20 25 30

<210> SEQ ID NO 53
<211> LENGTH: 30
<212> TYPE: PRT
<213> ORGANISM: Human alphaherpesvirus 1

<400> SEQUENCE: 53

Pro Ser Thr Gln Thr Arg Ala Pro Leu Pro Thr Glu Pro Ala Phe Pro
1 5 10 15

Pro Ala Ala Thr Gly Ser Gln Pro Glu Ala Ser Asn Ala Glu
20 25 30

<210> SEQ ID NO 54
<211> LENGTH: 30
<212> TYPE: PRT
<213> ORGANISM: Human alphaherpesvirus 1

<400> SEQUENCE: 54

His Arg Pro Ala Pro Gly Ser Pro Pro Gly Ile Pro Glu Tyr Ala Glu
1 5 10 15

Asp Pro Tyr Ala Ile Ser Tyr Gly Gly Gln Leu Asp Arg Tyr
20 25 30

<210> SEQ ID NO 55
<211> LENGTH: 30
<212> TYPE: PRT
<213> ORGANISM: Human alphaherpesvirus 1

<400> SEQUENCE: 55

Ala Ala Pro Ala Ser Pro Tyr Ile Glu Ala Glu Asn Pro Leu Tyr Asp
1 5 10 15

Trp Gly Gly Ser Ala Leu Phe Ser Pro Pro Gly Arg Thr Gly
20 25 30

<210> SEQ ID NO 56
<211> LENGTH: 30
<212> TYPE: PRT
<213> ORGANISM: Human alphaherpesvirus 1

<400> SEQUENCE: 56

Trp His Ile Pro Ser Ile Gln Asp Ala Ala Thr Pro Tyr His Pro Pro
1 5 10 15

Ala Thr Pro Asn Asn Met Gly Leu Ile Ala Gly Ala Val Gly
20 25 30

<210> SEQ ID NO 57
<211> LENGTH: 30
<212> TYPE: PRT
<213> ORGANISM: Human alphaherpesvirus 1

<400> SEQUENCE: 57

Arg Ser Met Ala Glu Ser Asp Val Val Met Glu Asp Val Ala Ile Ala
1 5 10 15

Glu Arg Ala Leu Gly Leu Ser Ala Phe Gly Val Ala Gly Gly
20 25 30

<210> SEQ ID NO 58
<211> LENGTH: 30
<212> TYPE: PRT
<213> ORGANISM: Human alphaherpesvirus 1

<400> SEQUENCE: 58

Ala Ser Gly Lys Gly Pro Thr Tyr Ile Arg Val Ala Asp Ser Glu Leu
1 5 10 15

Tyr Ala Asp Trp Ser Ser Asp Ser Glu Gly Glu Arg Asp Gln
20 25 30

<210> SEQ ID NO 59
<211> LENGTH: 30
<212> TYPE: PRT
<213> ORGANISM: Human alphaherpesvirus 2

<400> SEQUENCE: 59

-continued

Phe Trp Val Arg Arg Arg Ala Gln Met Ala Pro Lys Arg Leu Arg Leu
1               5                   10                  15

Pro His Ile Arg Asp Asp Asp Ala Pro Pro Ser His Gln Pro
            20                  25                  30

<210> SEQ ID NO 60
<211> LENGTH: 30
<212> TYPE: PRT
<213> ORGANISM: Human alphaherpesvirus 2

<400> SEQUENCE: 60

Glu Ala Tyr Tyr Ser Glu Ser Glu Asp Glu Ala Ala Asn Asp Phe Leu
1               5                   10                  15

Val Arg Met Gly Arg Gln Gln Ser Val Leu Arg Arg Arg Arg
            20                  25                  30

<210> SEQ ID NO 61
<211> LENGTH: 30
<212> TYPE: PRT
<213> ORGANISM: Human alphaherpesvirus 2

<400> SEQUENCE: 61

Asp Gln Thr Leu Gln Leu His Arg Glu Gly Val Ser Thr Gln Asp Pro
1               5                   10                  15

Arg Phe Val Gly Ala Phe Met Ala Ala Lys Ala Ala His Leu
            20                  25                  30

<210> SEQ ID NO 62
<211> LENGTH: 30
<212> TYPE: PRT
<213> ORGANISM: Human alphaherpesvirus 2

<400> SEQUENCE: 62

Pro Ser Glu Ala Val Arg Pro Ser Arg Ile Pro Arg Ala Pro Arg Val
1               5                   10                  15

Pro Arg Glu Pro Arg Val Pro Arg Glu Pro Arg Glu Pro Arg
            20                  25                  30

<210> SEQ ID NO 63
<211> LENGTH: 30
<212> TYPE: PRT
<213> ORGANISM: Human alphaherpesvirus 2

<400> SEQUENCE: 63

Ala Ser Gly Pro His Glu Thr Ile Thr Ala Leu Val Gly Ala Val Thr
1               5                   10                  15

Ser Leu Gln Gln Glu Leu Ala His Met Arg Ala Arg Thr Asn
            20                  25                  30

<210> SEQ ID NO 64
<211> LENGTH: 30
<212> TYPE: PRT
<213> ORGANISM: Human alphaherpesvirus 2

<400> SEQUENCE: 64

Arg Arg Arg His Glu Val Glu Gln Pro Glu Tyr Asp Cys Gly Arg Asp
1               5                   10                  15

Glu Pro Asp Arg Asp Phe Pro Tyr Tyr Pro Gly Glu Ala Arg
            20                  25                  30

<210> SEQ ID NO 65
<211> LENGTH: 30

-continued

<212> TYPE: PRT
<213> ORGANISM: Human alphaherpesvirus 2

<400> SEQUENCE: 65

Lys Lys Gly Thr Ser Ala Leu Leu Ser Ser Lys Val Thr Asn Met Val
1               5                   10                  15

Leu Arg Lys Arg Asn Lys Ala Arg Tyr Ser Pro Leu His Asn
            20                  25                  30

<210> SEQ ID NO 66
<211> LENGTH: 30
<212> TYPE: PRT
<213> ORGANISM: Human alphaherpesvirus 2

<400> SEQUENCE: 66

Ala Gly Val Tyr Asp Ala Val Arg Thr Trp Gly Pro Asp Ala Glu Ala
1               5                   10                  15

Glu Pro Asp Gln Met Glu Asn Thr Tyr Leu Leu Pro Asp Asp
            20                  25                  30

<210> SEQ ID NO 67
<211> LENGTH: 30
<212> TYPE: PRT
<213> ORGANISM: Human alphaherpesvirus 2

<400> SEQUENCE: 67

Ala Pro His Ala Trp Gly Met Leu Asn Asp Met Gln Trp Leu Ala Ser
1               5                   10                  15

Ser Asp Ser Glu Glu Glu Thr Glu Val Gly Ile Ser Asp Asp
            20                  25                  30

<210> SEQ ID NO 68
<211> LENGTH: 30
<212> TYPE: PRT
<213> ORGANISM: Human alphaherpesvirus 2

<400> SEQUENCE: 68

Asp Arg Asp Ser Ser Met Ser Leu Ala Asp Phe His Gly Glu Glu Phe
1               5                   10                  15

Glu Lys Leu Tyr Glu His Leu Glu Ala Met Gly Phe Gly Glu
            20                  25                  30

<210> SEQ ID NO 69
<211> LENGTH: 30
<212> TYPE: PRT
<213> ORGANISM: Human alphaherpesvirus 2

<400> SEQUENCE: 69

Asp Pro Ile Tyr Asp Glu Val Ala Pro Asp His Glu Ala Glu Leu Tyr
1               5                   10                  15

Ala Arg Val Gln Arg Pro Gly Pro Val Pro Asp Ala Glu Pro
            20                  25                  30

<210> SEQ ID NO 70
<211> LENGTH: 30
<212> TYPE: PRT
<213> ORGANISM: Human alphaherpesvirus 3

<400> SEQUENCE: 70

Leu Glu Asn Ala His Glu His His Gly Val Tyr Asn Gln Gly Arg Gly
1               5                   10                  15

Ile Asp Ser Gly Glu Arg Leu Met Gln Pro Thr Gln Met Ser

-continued 20 25 30

<210> SEQ ID NO 71
<211> LENGTH: 30
<212> TYPE: PRT
<213> ORGANISM: Human alphaherpesvirus 3

<400> SEQUENCE: 71

Ala Val Ala Pro Thr Ser Ala Ala Thr Arg Lys Pro Asp Pro Ala Val
1 5 10 15

Ala Pro Thr Ser Ala Ala Ser Arg Lys Pro Asp Pro Ala Val
20 25 30

<210> SEQ ID NO 72
<211> LENGTH: 30
<212> TYPE: PRT
<213> ORGANISM: Human alphaherpesvirus 3

<400> SEQUENCE: 72

Lys Gly Leu Lys Gln Leu Pro Glu Gly Met Asp Pro Phe Ala Glu Lys
1 5 10 15

Pro Asn Ala Thr Asp Thr Pro Ile Glu Glu Ile Gly Asp Ser
20 25 30

<210> SEQ ID NO 73
<211> LENGTH: 30
<212> TYPE: PRT
<213> ORGANISM: Human alphaherpesvirus 3

<400> SEQUENCE: 73

Asp Lys Phe Arg Glu Ala Gln Glu Met Ile Lys Tyr Met Thr Leu Val
1 5 10 15

Ser Ala Ala Glu Arg Gln Glu Ser Lys Ala Arg Lys Lys Asn
20 25 30

<210> SEQ ID NO 74
<211> LENGTH: 30
<212> TYPE: PRT
<213> ORGANISM: Human alphaherpesvirus 3

<400> SEQUENCE: 74

His Ala Glu Ser Ser Trp Val Asn Arg Gly Glu Ser Ser Arg Lys Ala
1 5 10 15

Tyr Asp His Asn Ser Pro Tyr Ile Trp Pro Arg Asn Asp Tyr
20 25 30

<210> SEQ ID NO 75
<211> LENGTH: 30
<212> TYPE: PRT
<213> ORGANISM: Human alphaherpesvirus 3

<400> SEQUENCE: 75

Val Val Thr Thr Glu Thr Lys Ser Val Val Lys Glu Gly Ile Glu Asn
1 5 10 15

His Val Tyr Pro Thr Asp Met Ser Thr Leu Pro Glu Lys Ser
20 25 30

<210> SEQ ID NO 76
<211> LENGTH: 30
<212> TYPE: PRT
<213> ORGANISM: Human alphaherpesvirus 3

<400> SEQUENCE: 76

His Gln Pro Asn Asp Ser Ser Gly Ser Glu Asp Asp Phe Glu Asp Ile
1 5 10 15

Asp Glu Val Val Ala Ala Phe Arg Glu Ala Arg Leu Arg His
20 25 30

<210> SEQ ID NO 77
<211> LENGTH: 30
<212> TYPE: PRT
<213> ORGANISM: Human alphaherpesvirus 3

<400> SEQUENCE: 77

Glu Pro Met Tyr Ala Gln Val Arg Lys Pro Lys Ser Arg Thr Asp Thr
1 5 10 15

Gln Thr Thr Gly Arg Ile Thr Asn Arg Ser Arg Ala Arg Ser
20 25 30

<210> SEQ ID NO 78
<211> LENGTH: 30
<212> TYPE: PRT
<213> ORGANISM: Human alphaherpesvirus 3

<400> SEQUENCE: 78

Ile Pro Ala Asp Glu Glu Ala Pro Thr Thr Pro Glu Asp Pro Arg His
1 5 10 15

Pro Leu His Ala His Gln Leu Val Pro Asn Ser Leu Asn Val
20 25 30

<210> SEQ ID NO 79
<211> LENGTH: 30
<212> TYPE: PRT
<213> ORGANISM: Human betaherpesvirus 5

<400> SEQUENCE: 79

Ala Pro Thr Pro Thr Phe Ala Gly Thr Gln Thr Pro Val Asn Gly Asn
1 5 10 15

Ser Pro Trp Ala Pro Thr Ala Pro Leu Pro Gly Asp Met Asn
20 25 30

<210> SEQ ID NO 80
<211> LENGTH: 30
<212> TYPE: PRT
<213> ORGANISM: Human betaherpesvirus 5

<400> SEQUENCE: 80

Pro Ala Asn Trp Pro Arg Glu Arg Ala Trp Ala Leu Lys Asn Pro His
1 5 10 15

Leu Ala Tyr Asn Pro Phe Arg Met Pro Thr Thr Ser Thr Ala
20 25 30

<210> SEQ ID NO 81
<211> LENGTH: 30
<212> TYPE: PRT
<213> ORGANISM: Human betaherpesvirus 5

<400> SEQUENCE: 81

Ser Thr Pro Arg Ala Ala Val Thr Gln Thr Ala Ser Gln Asn Ala Ala
1 5 10 15

Asp Glu Val Trp Ala Leu Arg Asp Gln Thr Ala Glu Ser Pro
20 25 30

<210> SEQ ID NO 82

<211> LENGTH: 30
<212> TYPE: PRT
<213> ORGANISM: Human betaherpesvirus 5

<400> SEQUENCE: 82

Val Lys Tyr Gln Ala Leu Ala Thr Ala Ser Gly Glu Glu Val Ala Ala
1 5 10 15

Leu Ser His His Asp Ser Leu Glu Ser Arg Arg Leu Arg Glu
20 25 30

<210> SEQ ID NO 83
<211> LENGTH: 30
<212> TYPE: PRT
<213> ORGANISM: Human betaherpesvirus 5

<400> SEQUENCE: 83

Ala Ser Glu Ala Leu Asp Pro His Ala Phe His Leu Leu Leu Asn Thr
1 5 10 15

Tyr Gly Arg Pro Ile Arg Leu Leu Arg Glu Asn Thr Thr Gln
20 25 30

<210> SEQ ID NO 84
<211> LENGTH: 30
<212> TYPE: PRT
<213> ORGANISM: Human betaherpesvirus 5

<400> SEQUENCE: 84

Pro Ser Leu Lys Pro Thr Leu Gly Gly Lys Ala Val Val Gly Arg Pro
1 5 10 15

Pro Ser Val Pro Val Ser Gly Ser Ala Pro Gly Arg Leu Ser
20 25 30

<210> SEQ ID NO 85
<211> LENGTH: 30
<212> TYPE: PRT
<213> ORGANISM: Human betaherpesvirus 5

<400> SEQUENCE: 85

Gln Gln Asn Gly Thr Asp Ser Leu Asp Gly Arg Thr Gly Thr Gln Asp
1 5 10 15

Lys Gly Gln Lys Pro Asn Leu Leu Asp Arg Leu Arg His Arg
20 25 30

<210> SEQ ID NO 86
<211> LENGTH: 30
<212> TYPE: PRT
<213> ORGANISM: Human betaherpesvirus 5

<400> SEQUENCE: 86

Glu Gln Pro Thr Glu Thr Pro Pro Glu Asp Leu Asp Thr Leu Ser Leu
1 5 10 15

Ala Ile Glu Ala Ala Ile Gln Asp Leu Arg Asn Lys Ser Gln
20 25 30

<210> SEQ ID NO 87
<211> LENGTH: 30
<212> TYPE: PRT
<213> ORGANISM: Human betaherpesvirus 5

<400> SEQUENCE: 87

Ala Ser Thr Thr Pro Thr Tyr Pro Ala Val Thr Thr Val Tyr Pro Pro
1 5 10 15

Ser Ser Thr Ala Lys Ser Ser Val Ser Asn Ala Pro Pro Val
            20                  25                  30

<210> SEQ ID NO 88
<211> LENGTH: 30
<212> TYPE: PRT
<213> ORGANISM: Human betaherpesvirus 5

<400> SEQUENCE: 88

Ala Leu Tyr Met Gly Ser Arg Arg Ile Pro Arg Lys Pro Arg Tyr Thr
1               5                   10                  15

Arg Leu Pro Lys His Asp Pro Asp Glu Phe Trp Thr Lys Thr
            20                  25                  30

<210> SEQ ID NO 89
<211> LENGTH: 30
<212> TYPE: PRT
<213> ORGANISM: Human betaherpesvirus 5

<400> SEQUENCE: 89

Gly Arg Gly Ser Pro Leu Thr Ile Glu Ser His Leu Ser Asp Asn Glu
1               5                   10                  15

Glu Asp Pro Ile Arg Tyr Tyr Val Ser Val Tyr Asp Glu Leu
            20                  25                  30

<210> SEQ ID NO 90
<211> LENGTH: 30
<212> TYPE: PRT
<213> ORGANISM: Human betaherpesvirus 6

<400> SEQUENCE: 90

Ser Asp Pro Leu Glu Ala Phe Lys Thr Val Asn Arg His Asn Trp Ser
1               5                   10                  15

Asp Glu Gln Arg Glu His Phe Tyr Asp Leu Arg Asn Leu Tyr
            20                  25                  30

<210> SEQ ID NO 91
<211> LENGTH: 30
<212> TYPE: PRT
<213> ORGANISM: Human betaherpesvirus 6

<400> SEQUENCE: 91

Arg Lys Gln Lys Lys Leu Asp Leu Leu Gly Ser Trp Thr Lys Glu Lys
1               5                   10                  15

Asn Asp Lys Ala Ile Val His Ser Arg Glu Val Thr Gly Asp
            20                  25                  30

<210> SEQ ID NO 92
<211> LENGTH: 30
<212> TYPE: PRT
<213> ORGANISM: Human betaherpesvirus 6

<400> SEQUENCE: 92

Asn Thr Ala Ala Asn Ala Asp Val Phe Asp Pro Val His Arg Leu Val
1               5                   10                  15

Ser Glu Gln Thr Gly Thr Pro Phe Val Leu Asn Asn Ser Asp
            20                  25                  30

<210> SEQ ID NO 93
<211> LENGTH: 30
<212> TYPE: PRT
<213> ORGANISM: Human betaherpesvirus 6

<400> SEQUENCE: 93

Pro Glu Ser Asp Ser Val Asp Asn Ala Gly Gly Lys Ile Leu Ile Lys
1 5 10 15

Lys Glu Thr Leu Gly Gly Arg Asp Val Arg Ala Thr Thr Pro
20 25 30

<210> SEQ ID NO 94
<211> LENGTH: 30
<212> TYPE: PRT
<213> ORGANISM: Human betaherpesvirus 6

<400> SEQUENCE: 94

Lys Leu Pro Gly Asn Gly Glu Arg Glu Ile Asp Leu Ala Leu Gln Lys
1 5 10 15

Val Lys Ala Gly Glu Arg Glu Thr Ser Asp Phe Lys Val Gly
20 25 30

<210> SEQ ID NO 95
<211> LENGTH: 30
<212> TYPE: PRT
<213> ORGANISM: Human betaherpesvirus 6

<400> SEQUENCE: 95

Gly Asp Glu Tyr Ser Gln Glu Asp Ala Leu Lys Met Leu Lys Ala Ile
1 5 10 15

Lys Ser Leu Asp Glu Ser Tyr Arg Arg Lys Pro Ser Ser Ser
20 25 30

<210> SEQ ID NO 96
<211> LENGTH: 30
<212> TYPE: PRT
<213> ORGANISM: Human betaherpesvirus 6

<400> SEQUENCE: 96

Glu Ile Ser Asp Asn Ile Tyr Ser Ser Pro Lys Asn Ser Ile Tyr Leu
1 5 10 15

Lys Ser Lys Ser Gln Gln Ser Thr Thr Lys Phe Thr Asp Thr
20 25 30

<210> SEQ ID NO 97
<211> LENGTH: 30
<212> TYPE: PRT
<213> ORGANISM: Human betaherpesvirus 6

<400> SEQUENCE: 97

Thr Thr His Ser Thr Glu Thr Gly Val Ser Pro His Asn Val Ser Leu
1 5 10 15

Ile Lys Asp Leu Arg Asp Lys Asp Gly Phe Arg Lys Gln Lys
20 25 30

<210> SEQ ID NO 98
<211> LENGTH: 30
<212> TYPE: PRT
<213> ORGANISM: Human betaherpesvirus 6

<400> SEQUENCE: 98

Val Gln Ser Pro Phe Arg Leu Pro Asn Ala Asp Leu Ser Arg Asp Leu
1 5 10 15

Asp Ser Ala Ser Phe Lys Asp Ala Leu Asp Leu Lys Leu Pro
20 25 30

<210> SEQ ID NO 99
<211> LENGTH: 30
<212> TYPE: PRT
<213> ORGANISM: Human betaherpesvirus 6

<400> SEQUENCE: 99

Lys Glu Lys Arg Lys Val Glu Asp Ile Asp Lys Lys Lys Glu Asp Glu
1 5 10 15

Lys Arg Lys Gln Glu Glu Lys Lys Arg Asn Asp Glu Asp Lys
20 25 30

<210> SEQ ID NO 100
<211> LENGTH: 30
<212> TYPE: PRT
<213> ORGANISM: Human betaherpesvirus 7

<400> SEQUENCE: 100

Leu Lys Asn Leu Leu Asn Ser Arg Lys Arg Asp Pro Leu Phe Gln Asn
1 5 10 15

Phe Ser Phe Thr Glu Lys Met Gln Pro Val Arg Ser Pro Phe
20 25 30

<210> SEQ ID NO 101
<211> LENGTH: 30
<212> TYPE: PRT
<213> ORGANISM: Human betaherpesvirus 7

<400> SEQUENCE: 101

Gln Leu Val Lys Asp Val Lys Trp Thr Pro Ser Ser Ser Leu Leu Asp
1 5 10 15

Leu Ser Arg Arg Asn Asp Leu Leu Gln Lys Glu Leu Phe Glu
20 25 30

<210> SEQ ID NO 102
<211> LENGTH: 30
<212> TYPE: PRT
<213> ORGANISM: Human betaherpesvirus 7

<400> SEQUENCE: 102

Asn Lys Ile Asp Tyr His Ser Thr Phe Phe Leu Pro Glu Asn Glu Val
1 5 10 15

Asn Arg Gln Asn Gly Val Gln Ser Arg Asp Gln Leu Ser Lys
20 25 30

<210> SEQ ID NO 103
<211> LENGTH: 30
<212> TYPE: PRT
<213> ORGANISM: Human betaherpesvirus 7

<400> SEQUENCE: 103

Asp Leu Ile Asp Leu Glu Asn Ser Val Gln Lys Asp Asp Asp Ile Val
1 5 10 15

Asn Lys Leu Val Ser His Leu Thr His Ser Glu Glu Asp Val
20 25 30

<210> SEQ ID NO 104
<211> LENGTH: 30
<212> TYPE: PRT
<213> ORGANISM: Human betaherpesvirus 7

<400> SEQUENCE: 104

Gln Asp Phe Asp Ser Gly Ser Leu Leu Thr Gly Lys Glu Thr Gln Asn
1 5 10 15

Thr Ile Phe Gly Ala Ser Lys Ala Gln Glu Asn Gly Asp Lys
20 25 30

<210> SEQ ID NO 105
<211> LENGTH: 30
<212> TYPE: PRT
<213> ORGANISM: Human betaherpesvirus 7

<400> SEQUENCE: 105

Ala Thr Pro Ile Glu Arg Ser Ser Arg Ser Ala Ser Ile Ile Ser Gly
1 5 10 15

Glu Ser Val Pro Gly Phe Phe Asn Asp Gln Glu Arg Leu Ser
20 25 30

<210> SEQ ID NO 106
<211> LENGTH: 30
<212> TYPE: PRT
<213> ORGANISM: Human betaherpesvirus 7

<400> SEQUENCE: 106

Arg Arg Lys Arg Glu Leu Glu Thr Asn Lys Asp Ile Val Tyr Val Gln
1 5 10 15

Leu Gln Tyr Leu Tyr Asp Thr Leu Lys Asp Tyr Ile Asn Thr
20 25 30

<210> SEQ ID NO 107
<211> LENGTH: 30
<212> TYPE: PRT
<213> ORGANISM: Human betaherpesvirus 7

<400> SEQUENCE: 107

Pro Val Leu Asn Ile Ser Arg Pro Gly Ser Thr Thr Pro Ser Gly Asn
1 5 10 15

Ser Ala Arg Tyr Gly Asn Asn Thr Pro Arg Ser Ile Thr Pro
20 25 30

<210> SEQ ID NO 108
<211> LENGTH: 30
<212> TYPE: PRT
<213> ORGANISM: Human betaherpesvirus 7

<400> SEQUENCE: 108

Asn Ser Val Leu Gln Ala Thr Gln Ser Val Gln Ala Gln Val Lys Glu
1 5 10 15

Pro Leu Asp Ser Ser Pro Pro Tyr Leu Lys Thr Asn Lys Asp
20 25 30

<210> SEQ ID NO 109
<211> LENGTH: 30
<212> TYPE: PRT
<213> ORGANISM: Human betaherpesvirus 7

<400> SEQUENCE: 109

Lys Arg Arg Lys Glu Ile Val His Glu Asn Leu Gln Ser Phe Asp Asp
1 5 10 15

Glu His Asn Glu Met Ser Leu Pro Pro Gln Asp Gln Lys Ser
20 25 30

<210> SEQ ID NO 110
<211> LENGTH: 30
<212> TYPE: PRT
<213> ORGANISM: Human coronavirus 229E

<400> SEQUENCE: 110

Tyr Thr Val Pro Asp Leu Val Val Glu Gln Tyr Asn Gln Thr Ile Leu
1 5 10 15

Asn Leu Thr Ser Glu Ile Ser Thr Arg Glu Asn Lys Ser Ala
20 25 30

<210> SEQ ID NO 111
<211> LENGTH: 30
<212> TYPE: PRT
<213> ORGANISM: Human coronavirus 229E

<400> SEQUENCE: 111

Ser Asp Arg Asn His Asn Ser Gln Asp Asp Ile Met Lys Ala Val Ala
1 5 10 15

Ala Ala Leu Lys Ser Leu Gly Phe Asp Lys Pro Gln Glu Lys
20 25 30

<210> SEQ ID NO 112
<211> LENGTH: 30
<212> TYPE: PRT
<213> ORGANISM: Human coronavirus 229E

<400> SEQUENCE: 112

Glu Phe Asn Pro Ser Gln Thr Ser Pro Ala Thr Val Glu Pro Val Arg
1 5 10 15

Asp Glu Val Ser Ile Glu Thr Asp Ile Ile Asp Glu Val Asn
20 25 30

<210> SEQ ID NO 113
<211> LENGTH: 30
<212> TYPE: PRT
<213> ORGANISM: Human coronavirus 229E

<400> SEQUENCE: 113

Gly Ala Met Leu Ser Glu Asn Phe Thr Ser Tyr Gly Phe Ser Asn Val
1 5 10 15

Val Glu Met Pro Lys Phe Phe Tyr Ala Ser Asn Gly Thr Tyr
20 25 30

<210> SEQ ID NO 114
<211> LENGTH: 30
<212> TYPE: PRT
<213> ORGANISM: Human coronavirus 229E

<400> SEQUENCE: 114

Ser Asn Gln Asp Asp Ile Met Ala Ala Val Ala Ala Ala Leu Glu Lys
1 5 10 15

Leu Gly Phe Glu Arg Pro Asn Asp Ala Ser Gln Pro Gln Lys
20 25 30

<210> SEQ ID NO 115
<211> LENGTH: 30
<212> TYPE: PRT
<213> ORGANISM: Human coronavirus HKU1

<400> SEQUENCE: 115

Asp Tyr Ala Leu Pro Ser Ser Arg Arg Lys Arg Arg Gly Ile Ser Ser
1 5 10 15

Pro Tyr Arg Phe Val Thr Phe Glu Pro Phe Asn Val Ser Phe
20 25 30

<210> SEQ ID NO 116
<211> LENGTH: 30
<212> TYPE: PRT
<213> ORGANISM: Human coronavirus HKU1

<400> SEQUENCE: 116

```
Lys Pro Asp Met Ala Asp Glu Ile Ala Ser Leu Val Leu Ala Lys Leu
1               5                   10                  15

Gly Lys Asp Ser Lys Pro Gln Gln Val Thr Lys Gln Asn Ala
            20                  25                  30
```

<210> SEQ ID NO 117
<211> LENGTH: 30
<212> TYPE: PRT
<213> ORGANISM: Human coronavirus NL63

<400> SEQUENCE: 117

```
Phe Gly Leu Gln Asp Gly Phe Tyr Ser Ala Asn Phe Leu Asp Asp Asn
1               5                   10                  15

Val Leu Pro Glu Thr Tyr Val Ala Leu Pro Ile Tyr Tyr Gln
            20                  25                  30
```

<210> SEQ ID NO 118
<211> LENGTH: 30
<212> TYPE: PRT
<213> ORGANISM: Human coronavirus NL63

<400> SEQUENCE: 118

```
Asn Thr Val Leu Asn Ala Ser Ile Pro Glu Ser Lys Pro Leu Ala Asp
1               5                   10                  15

Asp Asp Ser Ala Ile Ile Glu Ile Val Asn Glu Val Leu His
            20                  25                  30
```

<210> SEQ ID NO 119
<211> LENGTH: 30
<212> TYPE: PRT
<213> ORGANISM: Human coronavirus NL63

<400> SEQUENCE: 119

```
Glu Arg Trp Arg Met Arg Arg Gly Gln Arg Val Asp Leu Pro Pro Lys
1               5                   10                  15

Val His Phe Tyr Tyr Leu Gly Thr Gly Pro His Lys Asp Leu
            20                  25                  30
```

<210> SEQ ID NO 120
<211> LENGTH: 30
<212> TYPE: PRT
<213> ORGANISM: Human coronavirus NL63

<400> SEQUENCE: 120

```
Val Ser Asn Gly Gly Asn Asn Cys Thr Thr Ala Val Met Thr Tyr Ser
1               5                   10                  15

Asn Phe Gly Ile Cys Ala Asp Gly Ser Leu Ile Pro Val Arg
            20                  25                  30
```

<210> SEQ ID NO 121
<211> LENGTH: 30
<212> TYPE: PRT
<213> ORGANISM: Human gammaherpesvirus 4

<400> SEQUENCE: 121

```
Pro Gly Arg Arg Pro Phe Phe His Pro Val Gly Gln Ala Asp Tyr Phe
```

```
1               5                   10                  15

Glu Tyr His Gln Glu Gly Gly Pro Asp Gly Glu Pro Asp Met
            20                  25                  30


<210> SEQ ID NO 122
<211> LENGTH: 30
<212> TYPE: PRT
<213> ORGANISM: Human gammaherpesvirus 4

<400> SEQUENCE: 122

Ser Pro Ser Leu Pro Ser Ser Lys Lys Gly Ala Asp Glu Phe Glu Ala
1               5                   10                  15

Trp Leu Glu Ala Gln Asp Ala Asn Phe Glu Asp Val Gln Arg
            20                  25                  30


<210> SEQ ID NO 123
<211> LENGTH: 30
<212> TYPE: PRT
<213> ORGANISM: Human gammaherpesvirus 4

<400> SEQUENCE: 123

Met Met Asp Pro Asn Ser Thr Ser Glu Asp Val Lys Phe Thr Pro Asp
1               5                   10                  15

Pro Tyr Gln Val Pro Phe Val Gln Ala Phe Asp Gln Ala Thr
            20                  25                  30


<210> SEQ ID NO 124
<211> LENGTH: 30
<212> TYPE: PRT
<213> ORGANISM: Human gammaherpesvirus 4

<400> SEQUENCE: 124

Gln His Ala Ser Gly Glu Gly Pro Gly Ile Asn Pro Ile Ser Lys Thr
1               5                   10                  15

Glu Leu Gln Ala Ile Met Leu Ala Leu His Glu Gln Asn Gln
            20                  25                  30


<210> SEQ ID NO 125
<211> LENGTH: 30
<212> TYPE: PRT
<213> ORGANISM: Human gammaherpesvirus 4

<400> SEQUENCE: 125

Glu Gln Glu Tyr Gly Asp Lys Glu Val Lys Leu Pro His Trp Thr Pro
1               5                   10                  15

Thr Leu His Thr Phe Gln Val Pro Lys Asn Tyr Thr Lys Ala
            20                  25                  30


<210> SEQ ID NO 126
<211> LENGTH: 30
<212> TYPE: PRT
<213> ORGANISM: Human gammaherpesvirus 4

<400> SEQUENCE: 126

Gly Pro Arg His Arg Asp Gly Val Arg Arg Pro Gln Lys Arg Pro Ser
1               5                   10                  15

Cys Ile Gly Cys Lys Gly Ala His Gly Gly Thr Gly Thr Gly
            20                  25                  30


<210> SEQ ID NO 127
<211> LENGTH: 30
<212> TYPE: PRT
```

<213> ORGANISM: Human gammaherpesvirus 4

<400> SEQUENCE: 127

Gln Pro Met Glu Gly Pro Leu Val Pro Glu Gln Trp Met Phe Pro Gly
1               5                   10                  15

Ala Ala Leu Ser Gln Arg Val Arg Pro Gly Val Ala Gln Ser
            20                  25                  30

<210> SEQ ID NO 128
<211> LENGTH: 30
<212> TYPE: PRT
<213> ORGANISM: Human gammaherpesvirus 4

<400> SEQUENCE: 128

Met His Pro Leu Thr His Gln Ser Ile Pro Asn Asp Pro Asp Ser Pro
1               5                   10                  15

Glu Pro Arg Ser Pro Thr Val Phe Tyr Asn Ile Pro Pro Met
            20                  25                  30

<210> SEQ ID NO 129
<211> LENGTH: 30
<212> TYPE: PRT
<213> ORGANISM: Human gammaherpesvirus 4

<400> SEQUENCE: 129

Leu Pro Pro Arg Val Arg Gly Gly Gly Arg Val Ser Ala Ala Ala Ile
1               5                   10                  15

Thr Trp Val Pro Lys Pro Asn Val Glu Val Trp Pro Val Asp
            20                  25                  30

<210> SEQ ID NO 130
<211> LENGTH: 30
<212> TYPE: PRT
<213> ORGANISM: Human gammaherpesvirus 4

<400> SEQUENCE: 130

Arg Lys Pro Gly Gly Pro Trp Arg Pro Glu Pro Asn Thr Ser Ser Pro
1               5                   10                  15

Ser Met Pro Glu Leu Ser Pro Val Leu Gly Leu His Gln Gly
            20                  25                  30

<210> SEQ ID NO 131
<211> LENGTH: 30
<212> TYPE: PRT
<213> ORGANISM: Human gammaherpesvirus 4

<400> SEQUENCE: 131

Ser Pro Ile His Glu Pro Glu Ser His Asn Ser Pro Glu Ala Pro Ile
1               5                   10                  15

Leu Phe Pro Asp Asp Trp Tyr Pro Pro Ser Ile Asp Pro Ala
            20                  25                  30

<210> SEQ ID NO 132
<211> LENGTH: 30
<212> TYPE: PRT
<213> ORGANISM: Human mastadenovirus A

<400> SEQUENCE: 132

Leu Ala Ala Pro Arg Arg Gly Asn Val Tyr Trp Val Arg Asp Ala Val
1               5                   10                  15

Thr Gly Thr Arg Val Pro Val Arg Thr Arg Pro Pro His Pro
            20                  25                  30

<210> SEQ ID NO 133
<211> LENGTH: 30
<212> TYPE: PRT
<213> ORGANISM: Human mastadenovirus A

<400> SEQUENCE: 133

```
Ile Glu Ser Leu Val Asp Lys Met Ser Arg Trp Lys Thr Tyr Ala Gln
1               5                   10                  15

Glu Arg His Glu Trp Glu Glu Arg Gln Pro Lys Pro Val Pro
            20                  25                  30
```

<210> SEQ ID NO 134
<211> LENGTH: 30
<212> TYPE: PRT
<213> ORGANISM: Human mastadenovirus A

<400> SEQUENCE: 134

```
Glu Glu Asn Asp Asp Phe Asn Pro Val Tyr Pro Phe Asp Pro Tyr Asp
1               5                   10                  15

Thr Ala His Val Pro Phe Val Thr Pro Pro Phe Thr Ser Ser
            20                  25                  30
```

<210> SEQ ID NO 135
<211> LENGTH: 30
<212> TYPE: PRT
<213> ORGANISM: Human mastadenovirus A

<400> SEQUENCE: 135

```
Met Ser Lys Asp Ile Pro Thr Pro Tyr Met Trp Ser Phe Gln Pro Gln
1               5                   10                  15

Met Gly Leu Ala Ala Gly Ala Ala Gln Asp Tyr Ser Ser Lys
            20                  25                  30
```

<210> SEQ ID NO 136
<211> LENGTH: 30
<212> TYPE: PRT
<213> ORGANISM: Human mastadenovirus A

<400> SEQUENCE: 136

```
Pro Pro Gly Phe Tyr Thr Gly Glu Phe Asp Leu Pro Glu Gly Asn Asp
1               5                   10                  15

Gly Phe Leu Trp Asp Asp Val Thr Asp Ser Leu Phe Ser Pro
            20                  25                  30
```

<210> SEQ ID NO 137
<211> LENGTH: 30
<212> TYPE: PRT
<213> ORGANISM: Human mastadenovirus A

<400> SEQUENCE: 137

```
Val Leu Glu Tyr Met Lys Val Asp Pro Asn Ile Gln Pro Asp Val Lys
1               5                   10                  15

Ile Arg Pro Ile Lys Lys Val Ala Pro Gly Leu Gly Val Gln
            20                  25                  30
```

<210> SEQ ID NO 138
<211> LENGTH: 30
<212> TYPE: PRT
<213> ORGANISM: Human mastadenovirus A

<400> SEQUENCE: 138

-continued

```
Glu Ala Pro Pro Pro Ser Tyr Glu Thr Val Met Ala Ala Ala Gln Thr
1               5                   10                  15

Ser Ala Leu Glu Ala Pro Tyr Val Pro Pro Arg Tyr Leu Ala
            20                  25                  30


<210> SEQ ID NO 139
<211> LENGTH: 30
<212> TYPE: PRT
<213> ORGANISM: Human mastadenovirus A

<400> SEQUENCE: 139

Gly His Tyr Arg Ala Pro Trp Gly Ala His Thr Arg Gly Arg Thr Gly
1               5                   10                  15

Arg Thr Thr Val Asp Asp Val Ile Asp Ser Val Val Ala Asp
            20                  25                  30


<210> SEQ ID NO 140
<211> LENGTH: 30
<212> TYPE: PRT
<213> ORGANISM: Human mastadenovirus A

<400> SEQUENCE: 140

Leu Lys Asp Gln Asn Phe Gln Gln Lys Val Val Asp Gly Leu Ala Ser
1               5                   10                  15

Gly Ile Asn Gly Val Val Asp Ile Ala Asn Gln Ala Val Gln
            20                  25                  30


<210> SEQ ID NO 141
<211> LENGTH: 30
<212> TYPE: PRT
<213> ORGANISM: Human mastadenovirus A

<400> SEQUENCE: 141

Asn Asn Pro Gln Val Val Phe Tyr Thr Glu Asp Val Asn Leu Glu Met
1               5                   10                  15

Pro Asp Thr His Leu Val Phe Lys Pro Thr Val Thr Asp Gly
            20                  25                  30


<210> SEQ ID NO 142
<211> LENGTH: 30
<212> TYPE: PRT
<213> ORGANISM: Human mastadenovirus B

<400> SEQUENCE: 142

Arg Ala Ser Arg Arg Arg Gln Arg His Asp Arg Gln Arg Gly Leu Val
1               5                   10                  15

Trp Glu Asp Glu Asp Ser Ala Asp Asp Ser Ser Val Leu Asp
            20                  25                  30


<210> SEQ ID NO 143
<211> LENGTH: 30
<212> TYPE: PRT
<213> ORGANISM: Human mastadenovirus B

<400> SEQUENCE: 143

Trp Pro Ala Ala Leu Val Tyr Gln Glu Ser Pro Ala Pro Thr Thr Val
1               5                   10                  15

Leu Leu Pro Arg Asp Ala Gln Ala Glu Val Gln Met Thr Asn
            20                  25                  30


<210> SEQ ID NO 144
<211> LENGTH: 30
```

<212> TYPE: PRT
<213> ORGANISM: Human mastadenovirus B

<400> SEQUENCE: 144

Thr Leu Val Thr Arg Ala Asp Glu Pro Pro Ser Tyr Glu Glu Ala Val
1 5 10 15

Lys Leu Gly Met Pro Thr Thr Arg Pro Val Ala His Met Ala
20 25 30

<210> SEQ ID NO 145
<211> LENGTH: 30
<212> TYPE: PRT
<213> ORGANISM: Human mastadenovirus B

<400> SEQUENCE: 145

Ser Phe Asn Pro Val Tyr Pro Tyr Glu Asp Glu Ser Thr Ser Gln His
1 5 10 15

Pro Phe Ile Asn Pro Gly Phe Ile Ser Pro Asn Gly Phe Thr
20 25 30

<210> SEQ ID NO 146
<211> LENGTH: 30
<212> TYPE: PRT
<213> ORGANISM: Human mastadenovirus B

<400> SEQUENCE: 146

Thr Val Asp Asp Thr Asp Gly Thr Leu Gln Glu Asn Ile Gly Thr Thr
1 5 10 15

Thr Pro Leu Val Lys Thr Gly His Ser Ile Gly Leu Ser Leu
20 25 30

<210> SEQ ID NO 147
<211> LENGTH: 30
<212> TYPE: PRT
<213> ORGANISM: Human mastadenovirus B

<400> SEQUENCE: 147

Pro Pro Leu Gln Pro Phe Asp Pro Pro Thr Leu His Asp Leu Tyr Asp
1 5 10 15

Leu Glu Val Asp Gly Pro Asp Asp Pro Asn Glu Glu Ala Val
20 25 30

<210> SEQ ID NO 148
<211> LENGTH: 30
<212> TYPE: PRT
<213> ORGANISM: Human mastadenovirus B

<400> SEQUENCE: 148

Glu Glu Ile Glu Ala Asp Val Glu Gln Asp Pro Gly Tyr Val Thr Pro
1 5 10 15

Ala Glu His Glu Glu Glu Leu Lys Arg Phe Leu Asp Arg Glu
20 25 30

<210> SEQ ID NO 149
<211> LENGTH: 30
<212> TYPE: PRT
<213> ORGANISM: Human mastadenovirus C

<400> SEQUENCE: 149

Asp Met Asn Asp His Ala Ile Arg Gly Asp Thr Phe Ala Thr Arg Ala
1 5 10 15

Glu Glu Lys Arg Ala Glu Ala Glu Ala Ala Ala Glu Ala Ala 20 25 30

<210> SEQ ID NO 150
<211> LENGTH: 30
<212> TYPE: PRT
<213> ORGANISM: Human mastadenovirus C

<400> SEQUENCE: 150

Ala Ala Thr Gln Lys Gln Arg Arg Pro Asp Ser Lys Thr Leu Thr Lys
1 5 10 15

Pro Lys Lys Ser Thr Ala Ala Ala Ala Ala Gly Gly Gly Ala
20 25 30

<210> SEQ ID NO 151
<211> LENGTH: 30
<212> TYPE: PRT
<213> ORGANISM: Human mastadenovirus C

<400> SEQUENCE: 151

Thr Thr Asp Tyr Arg Asn Thr Thr Ala Thr Gly Leu Thr Ser Ala Leu
1 5 10 15

Asn Leu Pro Gln Val His Ala Phe Val Asn Asp Trp Ala Ser
20 25 30

<210> SEQ ID NO 152
<211> LENGTH: 30
<212> TYPE: PRT
<213> ORGANISM: Human mastadenovirus C

<400> SEQUENCE: 152

Pro Ser Ala Pro Ala Val Ser Thr Val Asp Glu Ala Ile Glu Ser Val
1 5 10 15

Val Gln Gly Ala Arg His Tyr Ala Asn Leu Lys Asn Arg Arg
20 25 30

<210> SEQ ID NO 153
<211> LENGTH: 30
<212> TYPE: PRT
<213> ORGANISM: Human mastadenovirus C

<400> SEQUENCE: 153

Ala Arg Asn Tyr Thr Pro Thr Pro Pro Pro Val Ser Thr Val Asp Ala
1 5 10 15

Ala Ile Gln Thr Val Val Arg Gly Ala Arg Arg Tyr Ala Lys
20 25 30

<210> SEQ ID NO 154
<211> LENGTH: 30
<212> TYPE: PRT
<213> ORGANISM: Human mastadenovirus C

<400> SEQUENCE: 154

Glu Val Leu Asp Glu Glu Glu Glu Met Met Glu Asp Trp Asp Ser Leu
1 5 10 15

Asp Glu Glu Ala Ser Glu Ala Glu Glu Val Ser Asp Glu Thr
20 25 30

<210> SEQ ID NO 155
<211> LENGTH: 30
<212> TYPE: PRT
<213> ORGANISM: Human mastadenovirus C

<400> SEQUENCE: 155

```
Ala Arg Arg Thr Gly Arg Arg Ala Ala Met Arg Ala Ala Arg Arg Leu
1               5                   10                  15

Ala Ala Gly Ile Val Thr Val Pro Pro Arg Ser Arg Arg Arg
            20                  25                  30


<210> SEQ ID NO 156
<211> LENGTH: 30
<212> TYPE: PRT
<213> ORGANISM: Human mastadenovirus C

<400> SEQUENCE: 156

Ile Ala Pro Met Ala Thr Gly Val Leu Gly His His Thr Pro Val Thr
1               5                   10                  15

Leu Asp Leu Pro Pro Pro Ala Asp Thr Gln Gln Lys Pro Val
            20                  25                  30


<210> SEQ ID NO 157
<211> LENGTH: 30
<212> TYPE: PRT
<213> ORGANISM: Human mastadenovirus C

<400> SEQUENCE: 157

Ser Tyr Glu Ser Val Val Ser Ala Ala Ser Val Ala Ala Ala Leu Gly
1               5                   10                  15

Ser Pro Phe Asp Ala Pro Leu Asp Pro Pro Phe Val Pro Pro
            20                  25                  30


<210> SEQ ID NO 158
<211> LENGTH: 30
<212> TYPE: PRT
<213> ORGANISM: Human mastadenovirus C

<400> SEQUENCE: 158

Thr Thr Arg Pro Arg Leu Leu Gly Glu Glu Glu Tyr Leu Asn Asn Ser
1               5                   10                  15

Leu Leu Gln Pro Gln Arg Glu Lys Asn Leu Pro Pro Ala Phe
            20                  25                  30


<210> SEQ ID NO 159
<211> LENGTH: 30
<212> TYPE: PRT
<213> ORGANISM: Human mastadenovirus D

<400> SEQUENCE: 159

Pro Glu Asp Ala Arg Pro Val Val Ser Asp Glu Met Leu Ala Arg Trp
1               5                   10                  15

Leu Gly Thr Arg Asp Pro Gln Ala Leu Glu Gln Arg Arg Lys
            20                  25                  30


<210> SEQ ID NO 160
<211> LENGTH: 30
<212> TYPE: PRT
<213> ORGANISM: Human mastadenovirus D

<400> SEQUENCE: 160

Met Thr Lys Arg Leu Arg Val Glu Asp Asp Phe Asn Pro Ile Tyr Pro
1               5                   10                  15

Tyr Gly Tyr Ala Arg Asn Gln Asn Ile Pro Phe Leu Thr Pro
            20                  25                  30


<210> SEQ ID NO 161
```

-continued

<211> LENGTH: 30
<212> TYPE: PRT
<213> ORGANISM: Human mastadenovirus D

<400> SEQUENCE: 161

Glu Ser Tyr Lys Asn Glu Ile Lys Lys Leu Thr Tyr Lys Asn Asn Lys
1 5 10 15

Thr Thr Phe Glu Asp Ser Gly Asn Tyr Glu His Gln Lys Leu
20 25 30

<210> SEQ ID NO 162
<211> LENGTH: 30
<212> TYPE: PRT
<213> ORGANISM: Human orthopneumovirus

<400> SEQUENCE: 162

Glu Lys Ile Asn Gln Ser Leu Thr Phe Ile Arg Lys Ser Asp Glu Leu
1 5 10 15

Leu His Asn Val Asn Val Gly Lys Ser Thr Thr Asn Ile Met
20 25 30

<210> SEQ ID NO 163
<211> LENGTH: 30
<212> TYPE: PRT
<213> ORGANISM: Human orthopneumovirus

<400> SEQUENCE: 163

Phe Glu Ala Phe Asn Phe Val Pro Cys Ser Ile Cys Ser Gly Asn Pro
1 5 10 15

Thr Cys Trp Ala Ile Cys Lys Arg Ile Pro Asn Lys Lys Pro
20 25 30

<210> SEQ ID NO 164
<211> LENGTH: 30
<212> TYPE: PRT
<213> ORGANISM: Human orthopneumovirus

<400> SEQUENCE: 164

Asn Tyr Gln Arg Lys Pro Leu Val Ser Phe Lys Glu Asp Pro Thr Pro
1 5 10 15

Ser Asp Asn Pro Phe Ser Lys Leu Tyr Lys Glu Thr Ile Glu
20 25 30

<210> SEQ ID NO 165
<211> LENGTH: 30
<212> TYPE: PRT
<213> ORGANISM: Human orthopneumovirus

<400> SEQUENCE: 165

Asn Lys Leu Gly Leu Lys Glu Lys Glu Lys Asp Lys Ile Lys Ser Asn
1 5 10 15

Asn Glu Gln Asp Glu Asn Asn Ser Val Ile Thr Thr Ile Ile
20 25 30

<210> SEQ ID NO 166
<211> LENGTH: 30
<212> TYPE: PRT
<213> ORGANISM: Human orthopneumovirus

<400> SEQUENCE: 166

Ser Thr Tyr Met Leu Thr Asn Ser Glu Leu Leu Ser Leu Ile Asn Asp
1 5 10 15

-continued

Met Pro Ile Thr Asn Asp Gln Lys Lys Leu Met Ser Ser Asn
20 25 30

<210> SEQ ID NO 167
<211> LENGTH: 30
<212> TYPE: PRT
<213> ORGANISM: Human orthopneumovirus

<400> SEQUENCE: 167

Thr Asn Lys Pro Ser Thr Lys Pro His Pro Lys Ile Pro Pro Lys Lys
1 5 10 15

Pro Lys Asp Asp Tyr His Phe Glu Val Phe Asn Phe Val Pro
20 25 30

<210> SEQ ID NO 168
<211> LENGTH: 30
<212> TYPE: PRT
<213> ORGANISM: Human orthopneumovirus

<400> SEQUENCE: 168

Cys Ser Ile Cys Gly Asn Asn Gln Leu Cys Lys Ser Ile Cys Lys Thr
1 5 10 15

Ile Pro Gly Asn Lys Pro Lys Lys Lys Pro Thr Ile Lys Pro
20 25 30

<210> SEQ ID NO 169
<211> LENGTH: 30
<212> TYPE: PRT
<213> ORGANISM: Human papillomavirus

<400> SEQUENCE: 169

Gln Ala Ile Thr Cys Gln Lys Pro Thr Pro Glu Lys Glu Lys Pro Asp
1 5 10 15

Pro Tyr Lys Asn Leu Ser Phe Trp Glu Val Asn Leu Lys Glu
20 25 30

<210> SEQ ID NO 170
<211> LENGTH: 30
<212> TYPE: PRT
<213> ORGANISM: Human papillomavirus

<400> SEQUENCE: 170

Pro Pro Ala Glu Lys Lys Asp Pro Tyr Ala Asp Leu Thr Phe Trp Glu
1 5 10 15

Val Asp Leu Lys Glu Arg Phe Ser Leu Glu Leu Asp Gln Phe
20 25 30

<210> SEQ ID NO 171
<211> LENGTH: 30
<212> TYPE: PRT
<213> ORGANISM: Human papillomavirus

<400> SEQUENCE: 171

Ala Gly Lys Glu Gly Asp Ser Ile Pro Met Glu Gly Thr Asp Tyr Tyr
1 5 10 15

Ile Ala Arg Gln Asp Ser Lys Leu Ala Ser His Ile Tyr Tyr
20 25 30

<210> SEQ ID NO 172
<211> LENGTH: 30
<212> TYPE: PRT
<213> ORGANISM: Human polyomavirus 1

<400> SEQUENCE: 172

Ala His Gln Pro Asp Phe Gly Thr Trp Asn Ser Ser Glu Val Pro Thr
1 5 10 15

Tyr Gly Thr Glu Glu Trp Glu Ser Trp Trp Ser Ser Phe Asn
20 25 30

<210> SEQ ID NO 173
<211> LENGTH: 30
<212> TYPE: PRT
<213> ORGANISM: Human polyomavirus 1

<400> SEQUENCE: 173

Arg Val Phe Asp Gly Thr Glu Arg Leu Pro Gly Asp Pro Asp Met Ile
1 5 10 15

Arg Tyr Ile Asp Lys Gln Gly Gln Leu Gln Thr Lys Met Leu
20 25 30

<210> SEQ ID NO 174
<211> LENGTH: 30
<212> TYPE: PRT
<213> ORGANISM: Human polyomavirus 3

<400> SEQUENCE: 174

Leu Ser Asp Glu Ile Gln Arg Leu Leu Arg Asp Leu Glu Tyr Gly Phe
1 5 10 15

Arg Ala Thr Leu Ala Ser Ile Gly Glu Ser Asp Pro Val Asn
20 25 30

<210> SEQ ID NO 175
<211> LENGTH: 30
<212> TYPE: PRT
<213> ORGANISM: Human polyomavirus 3

<400> SEQUENCE: 175

Asn Ile Trp Gln Ser Ser Gln Ile Pro Thr Tyr Gly Thr Pro Asp Trp
1 5 10 15

Asp Glu Trp Trp Ser Gln Phe Asn Thr Tyr Trp Glu Glu Glu
20 25 30

<210> SEQ ID NO 176
<211> LENGTH: 30
<212> TYPE: PRT
<213> ORGANISM: Human polyomavirus 3

<400> SEQUENCE: 176

Leu Gln Ser Val His Lys Pro Ile His Ala Pro Tyr Ser Gly Met Ala
1 5 10 15

Leu Val Pro Ile Pro Glu Tyr Gln Leu Glu Thr Gly Ile Pro
20 25 30

<210> SEQ ID NO 177
<211> LENGTH: 30
<212> TYPE: PRT
<213> ORGANISM: Human respirovirus 1

<400> SEQUENCE: 177

Asp Glu Asp Ile Thr Asp Ile Glu Asn Lys Ile Ala Arg Arg Leu Ala
1 5 10 15

Asp Arg Lys Gln Arg Leu Ser Gln Ala Asn Asn Lys Arg Asp
20 25 30

<210> SEQ ID NO 178
<211> LENGTH: 30
<212> TYPE: PRT
<213> ORGANISM: Human respirovirus 1

<400> SEQUENCE: 178

Asn Glu Thr Thr Asp Tyr Ser Ser Glu Gly Ile Glu Asp Leu Val Phe
1 5 10 15

Asp Ile Leu Asp Leu Lys Gly Lys Thr Lys Ser His Arg Tyr
20 25 30

<210> SEQ ID NO 179
<211> LENGTH: 30
<212> TYPE: PRT
<213> ORGANISM: Human respirovirus 1

<400> SEQUENCE: 179

Gly Ala Ile Glu Val Ala Ile Asp His Thr Asp Ile Thr Phe Gly Ala
1 5 10 15

Glu Asp Thr Ala Asp Arg Asp Asn Lys Asn Trp Ala Asn Asp
20 25 30

<210> SEQ ID NO 180
<211> LENGTH: 30
<212> TYPE: PRT
<213> ORGANISM: Human respirovirus 3

<400> SEQUENCE: 180

Lys Lys Gln Gly Ser Gln Pro Pro Thr Asn Pro Thr Asn Arg Thr Asn
1 5 10 15

Gln Asp Glu Ile Asp Asp Leu Phe Asn Ala Phe Gly Ser Asn
20 25 30

<210> SEQ ID NO 181
<211> LENGTH: 30
<212> TYPE: PRT
<213> ORGANISM: Human respirovirus 3

<400> SEQUENCE: 181

Glu Gln Ala Thr Glu Ser Asp Asn Ile Lys Thr Glu Gln Gln Asn Ile
1 5 10 15

Arg Asp Arg Leu Asn Lys Arg Leu Asn Asp Lys Lys Lys Gln
20 25 30

<210> SEQ ID NO 182
<211> LENGTH: 30
<212> TYPE: PRT
<213> ORGANISM: Human respirovirus 3

<400> SEQUENCE: 182

Ile Val Leu Ile Asn Ser Ile Lys Ser Glu Arg Ala His Glu Ser Leu
1 5 10 15

Leu Gln Asp Ile Asn Asn Glu Phe Met Glu Val Thr Glu Lys
20 25 30

<210> SEQ ID NO 183
<211> LENGTH: 30
<212> TYPE: PRT
<213> ORGANISM: Human respirovirus 3

<400> SEQUENCE: 183

Glu Asn Arg Ala Asp Gln Glu Gln Gly Gly Glu Pro Gln Ser Ser Ile
1 5 10 15

```
Ile Gln Tyr Ala Trp Ala Glu Gly Asn Arg Asn Asp Asp Arg
            20                  25                  30


<210> SEQ ID NO 184
<211> LENGTH: 30
<212> TYPE: PRT
<213> ORGANISM: Human respirovirus 3

<400> SEQUENCE: 184

Ser Ile Lys Ser Glu Lys Ala His Glu Ser Leu Leu Arg Asp Ile Asn
1               5                   10                  15

Asn Glu Phe Ile Gly Ile Thr Glu Lys Ile Gln Met Ala Ser
            20                  25                  30


<210> SEQ ID NO 185
<211> LENGTH: 30
<212> TYPE: PRT
<213> ORGANISM: Human respirovirus 3

<400> SEQUENCE: 185

Ser Thr His Gln Glu Asp Asp Lys Arg Ile Lys Lys Gly Gly Lys Gly
1               5                   10                  15

Lys Asp Trp Phe Lys Lys Ser Lys Asp Thr Asp Asn Gln Thr
            20                  25                  30


<210> SEQ ID NO 186
<211> LENGTH: 30
<212> TYPE: PRT
<213> ORGANISM: Human respirovirus 3

<400> SEQUENCE: 186

Met Glu Ser Asp Ala Lys Asn Tyr Gln Val Met Asp Ser Trp Glu Glu
1               5                   10                  15

Glu Ser Arg Asp Lys Ser Thr Asn Ile Ser Ser Ala Leu Asn
            20                  25                  30


<210> SEQ ID NO 187
<211> LENGTH: 30
<212> TYPE: PRT
<213> ORGANISM: Human respirovirus 3

<400> SEQUENCE: 187

Ser Leu Glu Ser Ile Gly Thr Pro Asp Thr Arg Ser Ile Ser Val Val
1               5                   10                  15

Thr Ala Ala Thr Pro Asp Asp Glu Glu Glu Ile Leu Met Lys
            20                  25                  30


<210> SEQ ID NO 188
<211> LENGTH: 30
<212> TYPE: PRT
<213> ORGANISM: Human rubulavirus 2

<400> SEQUENCE: 188

Pro Gln Arg Thr Ser Gly Met Ser Ser Glu Glu Phe Gln His Ser Met
1               5                   10                  15

Asn Gln Tyr Ile Arg Ala Met His Glu Gln Tyr Arg Gly Ser
            20                  25                  30


<210> SEQ ID NO 189
<211> LENGTH: 30
<212> TYPE: PRT
<213> ORGANISM: Human rubulavirus 2
```

<400> SEQUENCE: 189

Met Ala Glu Glu Pro Thr Tyr Thr Thr Glu Gln Val Asp Glu Leu Ile
1 5 10 15

His Ala Gly Leu Gly Thr Val Asp Phe Phe Leu Ser Arg Pro
20 25 30

<210> SEQ ID NO 190
<211> LENGTH: 30
<212> TYPE: PRT
<213> ORGANISM: Human rubulavirus 2

<400> SEQUENCE: 190

Gln Leu Pro Arg Gly Arg Gln Pro Ile Ser Asp Pro Phe Ala Gly Ala
1 5 10 15

Asn Asp Arg Glu Ile Gly Gly Gln Ala Asn Asp Thr Pro Val
20 25 30

<210> SEQ ID NO 191
<211> LENGTH: 30
<212> TYPE: PRT
<213> ORGANISM: Influenza A virus

<400> SEQUENCE: 191

Pro Ser Ser Ser Ala Gly Leu Lys Asp Asp Leu Leu Glu Asn Leu Gln
1 5 10 15

Ala Tyr Gln Lys Arg Met Gly Val Gln Met Gln Arg Phe Lys
20 25 30

<210> SEQ ID NO 192
<211> LENGTH: 30
<212> TYPE: PRT
<213> ORGANISM: Influenza A virus

<400> SEQUENCE: 192

Leu Ala Thr Gly Met Arg Asn Val Pro Glu Lys Gln Thr Arg Gly Ile
1 5 10 15

Phe Gly Ala Ile Ala Gly Phe Ile Glu Asn Gly Trp Glu Gly
20 25 30

<210> SEQ ID NO 193
<211> LENGTH: 30
<212> TYPE: PRT
<213> ORGANISM: Influenza A virus

<400> SEQUENCE: 193

Ser Glu Gln Ala Ala Glu Ala Met Glu Ile Ala Ser Gln Ala Arg Gln
1 5 10 15

Met Val Gln Ala Met Arg Thr Val Gly Thr His Pro Ser Ser
20 25 30

<210> SEQ ID NO 194
<211> LENGTH: 30
<212> TYPE: PRT
<213> ORGANISM: Influenza A virus

<400> SEQUENCE: 194

Asn Pro Leu Ile Arg His Glu Asn Arg Met Val Leu Ala Ser Thr Thr
1 5 10 15

Ala Lys Ala Met Glu Gln Met Ala Gly Ser Ser Glu Gln Ala
20 25 30

<210> SEQ ID NO 195
<211> LENGTH: 30
<212> TYPE: PRT
<213> ORGANISM: Influenza A virus

<400> SEQUENCE: 195

Arg Thr Leu Asp Tyr His Asp Ser Asn Val Lys Asn Leu Tyr Glu Lys
1 5 10 15

Val Arg Ser Gln Leu Lys Asn Asn Ala Lys Glu Ile Gly Asn
20 25 30

<210> SEQ ID NO 196
<211> LENGTH: 30
<212> TYPE: PRT
<213> ORGANISM: Influenza A virus

<400> SEQUENCE: 196

Ile Trp Asp Pro Asn Gly Trp Thr Gly Thr Asp Asn Asn Phe Ser Ile
1 5 10 15

Lys Gln Asp Ile Val Gly Ile Asn Glu Trp Ser Gly Tyr Ser
20 25 30

<210> SEQ ID NO 197
<211> LENGTH: 30
<212> TYPE: PRT
<213> ORGANISM: Influenza A virus

<400> SEQUENCE: 197

Ala Thr Cys Glu Gln Ile Ala Asp Ala Gln His Arg Ser His Arg Gln
1 5 10 15

Met Ala Thr Thr Thr Asn Pro Leu Ile Lys His Glu Asn Arg
20 25 30

<210> SEQ ID NO 198
<211> LENGTH: 30
<212> TYPE: PRT
<213> ORGANISM: Influenza A virus

<400> SEQUENCE: 198

Val Glu Thr Tyr Val Leu Ser Ile Ile Pro Ser Gly Pro Leu Lys Ala
1 5 10 15

Glu Ile Ala Gln Lys Leu Glu Asp Val Phe Ala Gly Lys Asn
20 25 30

<210> SEQ ID NO 199
<211> LENGTH: 30
<212> TYPE: PRT
<213> ORGANISM: Influenza A virus

<400> SEQUENCE: 199

Asn Pro His Arg Ile Leu Asp Gly Ile Asp Cys Thr Leu Ile Asp Ala
1 5 10 15

Leu Leu Gly Asp Pro His Cys Asp Gly Phe Gln Asn Glu Thr
20 25 30

<210> SEQ ID NO 200
<211> LENGTH: 30
<212> TYPE: PRT
<213> ORGANISM: Influenza B virus

<400> SEQUENCE: 200

Phe Ala Val Glu Arg Pro Ile Ala Leu Ser Lys Gln Ala Val Arg Lys

-continued

```
1               5                   10                  15

Met Leu Ser Met Asn Ile Glu Gly Arg Asp Ala Asp Val Lys
            20                  25                  30


<210> SEQ ID NO 201
<211> LENGTH: 30
<212> TYPE: PRT
<213> ORGANISM: Influenza B virus

<400> SEQUENCE: 201

Thr Thr Arg Pro Ile Ile Arg Pro Ala Thr Leu Ala Pro Pro Ser Asn
1               5                   10                  15

Lys Arg Thr Arg Asn Pro Ser Pro Glu Arg Ala Thr Thr Ser
            20                  25                  30


<210> SEQ ID NO 202
<211> LENGTH: 30
<212> TYPE: PRT
<213> ORGANISM: Influenza B virus

<400> SEQUENCE: 202

Gly Thr Phe Asn Ala Gly Glu Phe Ser Leu Pro Thr Phe Asp Ser Leu
1               5                   10                  15

Asn Ile Thr Ala Ala Ser Leu Asn Asn Asp Gly Leu Asp Asn
            20                  25                  30


<210> SEQ ID NO 203
<211> LENGTH: 30
<212> TYPE: PRT
<213> ORGANISM: Influenza B virus

<400> SEQUENCE: 203

Arg Thr Arg Gly Lys Leu Cys Pro Glu Cys Leu Asn Cys Thr Asp Leu
1               5                   10                  15

Asp Val Ala Leu Gly Arg Pro Met Cys Val Gly Thr Thr Pro
            20                  25                  30


<210> SEQ ID NO 204
<211> LENGTH: 30
<212> TYPE: PRT
<213> ORGANISM: Influenza B virus

<400> SEQUENCE: 204

Thr Asn Pro Ile Glu Ile Pro Ile Lys Gln Thr Ile Pro Asn Phe Phe
1               5                   10                  15

Phe Gly Arg Asp Thr Ala Glu Asp Tyr Asp Asp Leu Asp Tyr
            20                  25                  30


<210> SEQ ID NO 205
<211> LENGTH: 30
<212> TYPE: PRT
<213> ORGANISM: Influenza B virus

<400> SEQUENCE: 205

Ser Leu Ser Glu Leu Glu Val Lys Asn Leu Gln Arg Leu Ser Gly Ala
1               5                   10                  15

Met Asp Glu Leu His Ser Glu Ile Leu Glu Leu Asp Glu Lys
            20                  25                  30


<210> SEQ ID NO 206
<211> LENGTH: 30
<212> TYPE: PRT
```

<213> ORGANISM: Influenza B virus

<400> SEQUENCE: 206

Ser Asn Ser Pro His Val Val Lys Thr Ala Thr Gln Gly Glu Val Asn
1               5                   10                  15

Val Thr Gly Val Ile Pro Leu Thr Thr Thr Pro Thr Lys Ser
            20                  25                  30

<210> SEQ ID NO 207
<211> LENGTH: 30
<212> TYPE: PRT
<213> ORGANISM: Influenza B virus

<400> SEQUENCE: 207

Met Ser Asn Met Asp Ile Asp Gly Ile Asn Thr Gly Thr Ile Asp Lys
1               5                   10                  15

Ala Pro Glu Glu Ile Thr Ser Gly Thr Ser Gly Thr Thr Arg
            20                  25                  30

<210> SEQ ID NO 208
<211> LENGTH: 30
<212> TYPE: PRT
<213> ORGANISM: Influenza B virus

<400> SEQUENCE: 208

Asn Thr Ala Lys Thr Met Asn Gly Met Gly Lys Gly Glu Asp Val Gln
1               5                   10                  15

Lys Leu Ala Glu Glu Leu Gln Ser Asn Ile Gly Val Leu Arg
            20                  25                  30

<210> SEQ ID NO 209
<211> LENGTH: 30
<212> TYPE: PRT
<213> ORGANISM: Influenza C virus

<400> SEQUENCE: 209

Gly Glu Ala Asp Asp His His Gly Asp Gln Glu Met Arg Glu Leu Leu
1               5                   10                  15

Ser Gly Leu Asp Tyr Glu Ala Arg Cys Ile Ser Gln Ser Gly
            20                  25                  30

<210> SEQ ID NO 210
<211> LENGTH: 30
<212> TYPE: PRT
<213> ORGANISM: Influenza C virus

<400> SEQUENCE: 210

Tyr Leu Leu Pro Pro Lys Phe Gly Arg Cys Pro Leu Ala Ala Lys Glu
1               5                   10                  15

Glu Ser Ile Pro Lys Ile Pro Asp Gly Leu Leu Ile Pro Thr
            20                  25                  30

<210> SEQ ID NO 211
<211> LENGTH: 30
<212> TYPE: PRT
<213> ORGANISM: Macaca mulatta polyomavirus 1

<400> SEQUENCE: 211

Pro Thr Tyr Gly Thr Asp Glu Trp Glu Gln Trp Trp Asn Ala Phe Asn
1               5                   10                  15

Glu Glu Asn Leu Phe Cys Ser Glu Glu Met Pro Ser Ser Asp
            20                  25                  30

<210> SEQ ID NO 212
<211> LENGTH: 30
<212> TYPE: PRT
<213> ORGANISM: Macaca mulatta polyomavirus 1

<400> SEQUENCE: 212

Val Gly Val Leu Asp Trp Leu Arg Asn Ser Asp Asp Asp Asp Asp Asp
1 5 10 15

Glu Asp Gly Gly Glu Lys Asn Met Glu Asp Ser Gly His Glu
20 25 30

<210> SEQ ID NO 213
<211> LENGTH: 30
<212> TYPE: PRT
<213> ORGANISM: Mamastrovirus 1

<400> SEQUENCE: 213

Arg Glu Leu Val Ile Asn Thr Leu Val Asn Gln Gly Ile Ser Arg Asp
1 5 10 15

Arg Ala Thr Tyr Ile Gly Met Ser Ala Tyr Pro Asn Val Glu
20 25 30

<210> SEQ ID NO 214
<211> LENGTH: 30
<212> TYPE: PRT
<213> ORGANISM: Mamastrovirus 1

<400> SEQUENCE: 214

Asp Ile Ile Asp Thr Ser Asp Glu Glu Tyr Glu Asn Glu Thr Asp Arg
1 5 10 15

Val Thr Leu Leu Ser Thr Leu Val Asn Gln Gly Met Thr Met
20 25 30

<210> SEQ ID NO 215
<211> LENGTH: 30
<212> TYPE: PRT
<213> ORGANISM: Mamastrovirus 1

<400> SEQUENCE: 215

Phe Asp Glu Asp Pro Ile Ala Thr Leu His Ala Val Asp Ala Glu Arg
1 5 10 15

Lys Ile Arg Arg Ala Ile Phe Asn Ala Leu Met Glu Glu Gly
20 25 30

<210> SEQ ID NO 216
<211> LENGTH: 30
<212> TYPE: PRT
<213> ORGANISM: Mamastrovirus 1

<400> SEQUENCE: 216

Asp Gln Arg Glu Lys Tyr Arg His Val His Glu Trp Tyr Val Asp Asn
1 5 10 15

Leu Leu Asn Arg His Val Leu Leu Pro Ser Gly Glu Val Thr
20 25 30

<210> SEQ ID NO 217
<211> LENGTH: 30
<212> TYPE: PRT
<213> ORGANISM: Mamastrovirus 1

<400> SEQUENCE: 217

-continued

```
Thr Ser Ile Pro Arg Ser Arg Ala Ser Gly His Gly Tyr Glu Ser Asp
1               5                   10                  15

Asn Thr Glu Tyr Leu Asp Ala Pro Asp Ser Ala Asp Gln Phe
            20                  25                  30


<210> SEQ ID NO 218
<211> LENGTH: 30
<212> TYPE: PRT
<213> ORGANISM: Mamastrovirus 1

<400> SEQUENCE: 218

Glu Glu Tyr Gly Pro Thr Pro Trp Gly Pro Gln Ala Phe Ile Lys Ser
1               5                   10                  15

Phe Asp Lys Phe Phe Tyr Ala Glu Pro Ile Asp Phe Phe Ser
            20                  25                  30


<210> SEQ ID NO 219
<211> LENGTH: 30
<212> TYPE: PRT
<213> ORGANISM: Mamastrovirus 1

<400> SEQUENCE: 219

Asp Arg Ala Thr Leu Leu Ser Thr Leu Leu Asn Gln Gly Ile Ser Val
1               5                   10                  15

Glu Arg Ala Thr Arg Ile Thr Asn Gly Ala Phe Pro Ala Arg
            20                  25                  30


<210> SEQ ID NO 220
<211> LENGTH: 30
<212> TYPE: PRT
<213> ORGANISM: Mamastrovirus 1

<400> SEQUENCE: 220

Asp Asp Glu Ala Asp Arg Phe Asp Leu His Ser Ser Tyr Gly Ser Glu
1               5                   10                  15

Pro Glu Asp Asp Asp Glu Asn Asn Arg Val Thr Leu Leu Ser
            20                  25                  30


<210> SEQ ID NO 221
<211> LENGTH: 30
<212> TYPE: PRT
<213> ORGANISM: Mamastrovirus 6

<400> SEQUENCE: 221

Val Thr Ser Asp Asp Thr Asp Tyr Asp Thr Asp Thr Glu Asp Glu Asp
1               5                   10                  15

Glu Phe Phe Gly Glu Asp Pro Ile Ala Ala Leu His Ala Val
            20                  25                  30


<210> SEQ ID NO 222
<211> LENGTH: 30
<212> TYPE: PRT
<213> ORGANISM: Mamastrovirus 6

<400> SEQUENCE: 222

Ser Ala Asp Gly Ala Asn Glu Pro Val Glu Met Leu Ile Pro Val Asn
1               5                   10                  15

Glu Trp Asn Met Lys Ala Gln Tyr Gly Gly Asn Gly Thr Leu
            20                  25                  30


<210> SEQ ID NO 223
<211> LENGTH: 30
```

<212> TYPE: PRT
<213> ORGANISM: Norwalk virus

<400> SEQUENCE: 223

Lys Gly Leu Ser Asp Glu Glu Tyr Glu Glu Tyr Lys Arg Val Arg Glu
1 5 10 15

Glu Arg Asn Gly Lys Tyr Ser Ile Glu Glu Tyr Leu Gln Asp
20 25 30

<210> SEQ ID NO 224
<211> LENGTH: 30
<212> TYPE: PRT
<213> ORGANISM: Norwalk virus

<400> SEQUENCE: 224

Asp Asp Phe Lys Leu Lys Gly Lys Leu Trp Ala Asp Asp Asp Arg Ser
1 5 10 15

Val Asp Tyr Asn Glu Arg Leu Asn Phe Glu Ala Pro Pro Ser
20 25 30

<210> SEQ ID NO 225
<211> LENGTH: 30
<212> TYPE: PRT
<213> ORGANISM: Norwalk virus

<400> SEQUENCE: 225

Ile Ser Gly Leu Pro Asp Leu Thr Thr Val Pro Gln Pro Asp Ala Thr
1 5 10 15

Asn Thr Ala Phe Ser Val Pro Pro Leu Ser Leu Arg Glu Asn
20 25 30

<210> SEQ ID NO 226
<211> LENGTH: 30
<212> TYPE: PRT
<213> ORGANISM: Norwalk virus

<400> SEQUENCE: 226

Ala Pro Asp Ile Glu Lys Ala Lys Arg Asp Phe Pro Gly Gln Pro Asp
1 5 10 15

Met Trp Lys Asp His Phe Arg Pro Asp Phe Ser His Ile Lys
20 25 30

<210> SEQ ID NO 227
<211> LENGTH: 30
<212> TYPE: PRT
<213> ORGANISM: Norwalk virus

<400> SEQUENCE: 227

Thr Thr Gly Phe Phe Arg Pro Tyr Gln Asp Trp Asn Lys Lys Pro Leu
1 5 10 15

Pro Thr Val Asp Asp Ser Lys Leu Lys Lys Val Ala Asn Ile
20 25 30

<210> SEQ ID NO 228
<211> LENGTH: 30
<212> TYPE: PRT
<213> ORGANISM: Norwalk virus

<400> SEQUENCE: 228

Asn Asn Tyr Asp Pro Thr Glu Glu Ile Pro Ala Pro Leu Gly Thr Pro
1 5 10 15

Asp Phe Val Gly Lys Ile Gln Gly Val Leu Thr Gln Thr Thr 20 25 30

<210> SEQ ID NO 229
<211> LENGTH: 30
<212> TYPE: PRT
<213> ORGANISM: Norwalk virus

<400> SEQUENCE: 229

Ala Tyr Ser Val Pro Pro Leu Ser Gln Arg Glu Val Gly Glu Ala Lys
1 5 10 15

Glu Pro Leu Pro Gly Ser Ile Leu Glu Met Trp Asp Gly Glu
20 25 30

<210> SEQ ID NO 230
<211> LENGTH: 30
<212> TYPE: PRT
<213> ORGANISM: Norwalk virus

<400> SEQUENCE: 230

Asp Glu Glu Tyr Asp Glu Tyr Lys Lys Ile Arg Glu Glu Arg Gly Gly
1 5 10 15

Lys Tyr Ser Ile Gln Glu Tyr Leu Glu Asp Arg Glu Arg Phe
20 25 30

<210> SEQ ID NO 231
<211> LENGTH: 30
<212> TYPE: PRT
<213> ORGANISM: Norwalk virus

<400> SEQUENCE: 231

Met Met Met Ala Ser Lys Asp Ala Pro Thr Asn Met Asp Gly Thr Ser
1 5 10 15

Gly Ala Gly Gln Leu Val Pro Glu Ala Asn Thr Ala Glu Pro
20 25 30

<210> SEQ ID NO 232
<211> LENGTH: 30
<212> TYPE: PRT
<213> ORGANISM: Norwalk virus

<400> SEQUENCE: 232

Val Val Ser Tyr Ser Val Lys Asp Gly Val Ser Gly Leu Pro Asp Leu
1 5 10 15

Ser Thr Val Arg Gln Pro Glu Glu Ser Asn Thr Ala Phe Ser
20 25 30

<210> SEQ ID NO 233
<211> LENGTH: 30
<212> TYPE: PRT
<213> ORGANISM: Parechovirus A

<400> SEQUENCE: 233

Gln Asp Ile His Leu Ile Asp Asp Leu Gly Gln Thr Arg Lys Glu Lys
1 5 10 15

Asp Ile Glu Met Leu Cys Asn Cys Ile Ser Ser Val Pro Phe
20 25 30

<210> SEQ ID NO 234
<211> LENGTH: 30
<212> TYPE: PRT
<213> ORGANISM: Parechovirus A

<400> SEQUENCE: 234

Thr Thr Asn Leu Thr Gln His Pro Ser Ala Pro Thr Ile Pro Phe Thr
1 5 10 15

Pro Asp Phe Arg Asn Val Asp Asn Phe His Ser Met Ala Tyr
20 25 30

<210> SEQ ID NO 235
<211> LENGTH: 30
<212> TYPE: PRT
<213> ORGANISM: Parechovirus A

<400> SEQUENCE: 235

Ser Ala Pro Thr Met Pro Phe Thr Pro Asp Phe Ser Asn Val Asp Thr
1 5 10 15

Phe His Ser Met Ala Tyr Asp Val Thr Thr Gly Glu Lys Asn
20 25 30

<210> SEQ ID NO 236
<211> LENGTH: 30
<212> TYPE: PRT
<213> ORGANISM: Parechovirus A

<400> SEQUENCE: 236

Gln Ile His Lys Ser Pro Val Tyr Gly Ala Val Glu Val Lys Met Gly
1 5 10 15

Pro Ala Val Leu Ser Lys Ser Asp Pro Arg Leu Glu Glu Pro
20 25 30

<210> SEQ ID NO 237
<211> LENGTH: 30
<212> TYPE: PRT
<213> ORGANISM: Rhinovirus A

<400> SEQUENCE: 237

Val Pro Ile Thr Gln Asn Pro Val Glu Asn Tyr Ile Asp Glu Val Leu
1 5 10 15

Asn Glu Val Leu Val Val Pro Asn Ile Lys Glu Ser His Pro
20 25 30

<210> SEQ ID NO 238
<211> LENGTH: 30
<212> TYPE: PRT
<213> ORGANISM: Rhinovirus A

<400> SEQUENCE: 238

Glu Gln Tyr Ile Asp Gly Val Leu Asn Glu Val Leu Ile Val Pro Asn
1 5 10 15

Ile Asn Glu Ser His Pro Ser Thr Ser Asn Ala Ala Pro Ala
20 25 30

<210> SEQ ID NO 239
<211> LENGTH: 30
<212> TYPE: PRT
<213> ORGANISM: Rhinovirus A

<400> SEQUENCE: 239

Ser Ala Ile Phe Gln Gly Pro Ile Ser Leu Gly Ala Pro Pro Pro Pro
1 5 10 15

Ala Ile Ala Asp Leu Leu Gln Ser Val Arg Thr Pro Glu Val
20 25 30

<210> SEQ ID NO 240

-continued

<211> LENGTH: 30
<212> TYPE: PRT
<213> ORGANISM: Rhinovirus A

<400> SEQUENCE: 240

Ile Phe Gln Gly Pro Ile Asp Met Arg Asn Pro Pro Pro Pro Ala Ile
1 5 10 15

Thr Asp Leu Leu Gln Ala Val Arg Thr Pro Glu Val Ile Lys
20 25 30

<210> SEQ ID NO 241
<211> LENGTH: 30
<212> TYPE: PRT
<213> ORGANISM: Rhinovirus A

<400> SEQUENCE: 241

Ala Asp Glu Gln Gly Ile Thr Asp Tyr Ile His Thr Leu Gly Glu Ala
1 5 10 15

Phe Gly Ala Gly Phe Val Asp Asn Ile Lys Asp Gln Ile Gln
20 25 30

<210> SEQ ID NO 242
<211> LENGTH: 30
<212> TYPE: PRT
<213> ORGANISM: Rhinovirus A

<400> SEQUENCE: 242

Val Met Glu Gln Asn Pro Val Glu Lys Tyr Thr Glu Ala Val Leu Asn
1 5 10 15

Glu Val Leu Ala Val Pro Asn Ile Thr Pro Ser Asn Ser Gln
20 25 30

<210> SEQ ID NO 243
<211> LENGTH: 30
<212> TYPE: PRT
<213> ORGANISM: Rhinovirus A

<400> SEQUENCE: 243

Asn Pro Ser Gly Glu Asp Met Thr Leu Phe Cys Gln Met Val Ser Ser
1 5 10 15

Val Pro Phe Ile Pro Pro Met Ala Asp Leu Pro Asp Lys Gly
20 25 30

<210> SEQ ID NO 244
<211> LENGTH: 30
<212> TYPE: PRT
<213> ORGANISM: Rhinovirus A

<400> SEQUENCE: 244

Lys Leu Gln Pro Ser Val Phe Tyr Asp Val Phe Pro Gly Ser Lys Glu
1 5 10 15

Pro Ala Val Leu Thr Ser Asn Asp Pro Arg Leu Glu Val Asp
20 25 30

<210> SEQ ID NO 245
<211> LENGTH: 30
<212> TYPE: PRT
<213> ORGANISM: Rhinovirus A

<400> SEQUENCE: 245

Asp Phe Ile Ala Asp Glu Gln Gly Leu Gly Asp Tyr Ile Thr Ser Leu
1 5 10 15

Gly Arg Ala Phe Gly Thr Gly Phe Thr Asp Gln Ile Ser Ala
20 25 30

<210> SEQ ID NO 246
<211> LENGTH: 30
<212> TYPE: PRT
<213> ORGANISM: Rhinovirus A

<400> SEQUENCE: 246

Pro Pro Pro Pro Ala Ile Met Asp Leu Leu Lys Ser Val Lys Asn Pro
1 5 10 15

Glu Val Ile Lys Tyr Cys Glu Asp Asn Lys Trp Ile Ile Pro
20 25 30

<210> SEQ ID NO 247
<211> LENGTH: 30
<212> TYPE: PRT
<213> ORGANISM: Rhinovirus A

<400> SEQUENCE: 247

Thr Ile Ser Gln Thr Asp Ala Leu Thr Glu Gly Leu Gly Asp Glu Leu
1 5 10 15

Glu Glu Val Ile Val Glu Lys Thr Lys Gln Thr Leu Ala Ser
20 25 30

<210> SEQ ID NO 248
<211> LENGTH: 30
<212> TYPE: PRT
<213> ORGANISM: Rhinovirus B

<400> SEQUENCE: 248

Glu Cys Ile Asn Asp Leu Leu Arg Ser Val Asp Ser Glu Glu Val Arg
1 5 10 15

Glu Tyr Cys Lys Arg Lys Asn Trp Ile Ile Pro Gln Ile Pro
20 25 30

<210> SEQ ID NO 249
<211> LENGTH: 30
<212> TYPE: PRT
<213> ORGANISM: Rhinovirus B

<400> SEQUENCE: 249

Gln Ser Leu His Gln Glu Thr Ala Leu Thr Glu Gly Leu Glu Asp Glu
1 5 10 15

Leu Met Glu Val Ile Val Asp Lys Thr Gln Gln Thr Leu Ala
20 25 30

<210> SEQ ID NO 250
<211> LENGTH: 30
<212> TYPE: PRT
<213> ORGANISM: Rhinovirus B

<400> SEQUENCE: 250

Val Val Pro Glu His Gln Leu Ala Ser His Thr Gln Gly Asn Val Ser
1 5 10 15

Val Lys Tyr Lys Tyr Thr His Pro Gly Glu Gln Gly Ile Asp
20 25 30

<210> SEQ ID NO 251
<211> LENGTH: 30
<212> TYPE: PRT
<213> ORGANISM: Rhinovirus B

<400> SEQUENCE: 251

Gln Leu Ala Ser His Asp Gly Gly Thr Val Ser Val Lys Tyr Lys Phe
1 5 10 15

Thr His Pro Gly Asp Gln Gly Ile Asp Leu Ser Thr Ala Glu
20 25 30

<210> SEQ ID NO 252
<211> LENGTH: 30
<212> TYPE: PRT
<213> ORGANISM: Rhinovirus B

<400> SEQUENCE: 252

Ile Ser Asp Leu Leu Lys Ser Val Asp Ser Glu Glu Ile Arg Glu Tyr
1 5 10 15

Cys Lys Gln Lys Asn Trp Leu Ile Pro Glu Ile Pro Thr Asn
20 25 30

<210> SEQ ID NO 253
<211> LENGTH: 30
<212> TYPE: PRT
<213> ORGANISM: Rhinovirus B

<400> SEQUENCE: 253

His Thr Gln Ser Val Pro Ala Leu Thr Ala Asn Glu Thr Gly Ala Thr
1 5 10 15

Leu Pro Thr Arg Pro Ser Asp Asn Val Glu Thr Arg Thr Thr
20 25 30

<210> SEQ ID NO 254
<211> LENGTH: 30
<212> TYPE: PRT
<213> ORGANISM: Rhinovirus B

<400> SEQUENCE: 254

Ala Ala Thr Lys Met Asp Phe Ser Gln Asp Pro Ser Lys Phe Thr Glu
1 5 10 15

Pro Val Lys Asp Val Met Ile Lys Thr Ala Pro Ala Leu Asn
20 25 30

<210> SEQ ID NO 255
<211> LENGTH: 30
<212> TYPE: PRT
<213> ORGANISM: Rhinovirus B

<400> SEQUENCE: 255

Glu Asp Glu Leu Glu Glu Val Val Ile Asp Lys Met Lys Gln Val Thr
1 5 10 15

Ala Ser Ser Gln Ser Gly Pro Lys His Thr Gln Lys Val Pro
20 25 30

<210> SEQ ID NO 256
<211> LENGTH: 30
<212> TYPE: PRT
<213> ORGANISM: Rhinovirus B

<400> SEQUENCE: 256

Glu Leu Asn Met Asn Pro Ile Asn Thr Pro Thr Lys Ser Lys Leu His
1 5 10 15

Pro Ser Val Phe Tyr Asn Val Phe Pro Gly Asp Lys Glu Pro
20 25 30

<210> SEQ ID NO 257
<211> LENGTH: 30
<212> TYPE: PRT
<213> ORGANISM: Rhinovirus B

<400> SEQUENCE: 257

Leu Met Lys Asp Thr Gln Thr Ile Ser Gln Thr Glu Ala Leu Thr Glu
1 5 10 15

Gly Phe Glu Glu Glu Leu Glu Glu Val Val Val Asp Lys Met
20 25 30

<210> SEQ ID NO 258
<211> LENGTH: 30
<212> TYPE: PRT
<213> ORGANISM: Rhinovirus B

<400> SEQUENCE: 258

Asp Val Leu Glu Glu Val Ile Val Asp Lys Ala Lys Gln Thr Ile Ala
1 5 10 15

Ser Ile Asn Ser Asn Ser Lys Tyr Thr Gln Gln Val Pro Thr
20 25 30

<210> SEQ ID NO 259
<211> LENGTH: 30
<212> TYPE: PRT
<213> ORGANISM: Rhinovirus C

<400> SEQUENCE: 259

Val Glu His Asn Leu Thr Ala Ile Phe Gln Gly Leu Gly Asp Asp Thr
1 5 10 15

Thr Pro Gly Phe Ile Ile Asp Leu Leu Ser Ala Ser Lys Asp
20 25 30

<210> SEQ ID NO 260
<211> LENGTH: 30
<212> TYPE: PRT
<213> ORGANISM: Rhinovirus C

<400> SEQUENCE: 260

Asn Pro Val Glu Asp Phe Ile Asp Thr Thr Leu Lys Glu Val Leu Val
1 5 10 15

Val Pro Asp Thr His Pro Ser Gly Pro Val His Thr Thr Arg
20 25 30

<210> SEQ ID NO 261
<211> LENGTH: 30
<212> TYPE: PRT
<213> ORGANISM: Rhinovirus C

<400> SEQUENCE: 261

Ala His Gln Gly Leu Val Ser Asp Tyr Val Asn Gln Leu Gly Ala Ala
1 5 10 15

Phe Gly Asp Gly Phe Ser Ser Asn Ile Lys Asp His Leu Thr
20 25 30

<210> SEQ ID NO 262
<211> LENGTH: 30
<212> TYPE: PRT
<213> ORGANISM: Rhinovirus C

<400> SEQUENCE: 262

Ala Tyr Ile Gly Gly Thr Asn Ala Asn Val Gly Tyr Asn His Thr His
1 5 10 15

Pro Gly Glu Ile Gly His Glu Ile Gly Arg Asn Thr Gly Arg
20 25 30

<210> SEQ ID NO 263
<211> LENGTH: 30
<212> TYPE: PRT
<213> ORGANISM: Rhinovirus C

<400> SEQUENCE: 263

Thr Asn Asp Leu Gln Asn Asn Asp Pro Ile Asp Thr Tyr Val His Asp
1 5 10 15

Val Leu Asn Glu Val Val Val Val Pro Asp Thr Lys Pro Ser
20 25 30

<210> SEQ ID NO 264
<211> LENGTH: 30
<212> TYPE: PRT
<213> ORGANISM: Rhinovirus C

<400> SEQUENCE: 264

Asp Thr Pro Met Ile Thr Gln Asp Lys Asn Thr Leu Gln Asn Pro Val
1 5 10 15

Glu Gln Phe Val Asp Asp Val Leu Glu Glu Val Leu Val Val
20 25 30

<210> SEQ ID NO 265
<211> LENGTH: 30
<212> TYPE: PRT
<213> ORGANISM: Rhinovirus C

<400> SEQUENCE: 265

Ile Pro Glu His Gln Leu Ala Tyr Ala Gly Gly Ala Asn Ala Ser Val
1 5 10 15

Gly Tyr Lys His Thr His Pro Gly Glu Asn Gly His Lys Ile
20 25 30

<210> SEQ ID NO 266
<211> LENGTH: 30
<212> TYPE: PRT
<213> ORGANISM: Rhinovirus C

<400> SEQUENCE: 266

Ser Ser Leu Ser Glu His Gln Gly Val Thr Asp Tyr Ile Thr Gln Leu
1 5 10 15

Gly Ser Ala Phe Gly Asp Gly Phe Thr Ser Ser Ile Lys Gln
20 25 30

<210> SEQ ID NO 267
<211> LENGTH: 30
<212> TYPE: PRT
<213> ORGANISM: Rhinovirus C

<400> SEQUENCE: 267

Leu Arg Pro Tyr Asn Asn Leu Ala Gln Thr Gln Gly Pro Ile Ser Asp
1 5 10 15

Tyr Val Thr Gln Leu Gly Asn Ala Phe Gly Asn Gly Phe Thr
20 25 30

<210> SEQ ID NO 268
<211> LENGTH: 30
<212> TYPE: PRT
<213> ORGANISM: Rhinovirus C

<400> SEQUENCE: 268

Asp Pro Val Ser Asp Phe Ile Asp Ala Thr Leu Gln Glu Val Leu Val
1 5 10 15

Val Pro Glu Thr Lys Pro Ser Gly Pro Gln His Thr Thr Lys
20 25 30

<210> SEQ ID NO 269
<211> LENGTH: 30
<212> TYPE: PRT
<213> ORGANISM: Rhinovirus C

<400> SEQUENCE: 269

Pro Ile Asn Thr Pro Ser Thr Thr Lys Leu Tyr Pro Ser Val Phe Tyr
1 5 10 15

Glu Ile Phe Pro Gly Glu Lys Glu Pro Ala Val Leu Ser Asp
20 25 30

<210> SEQ ID NO 270
<211> LENGTH: 30
<212> TYPE: PRT
<213> ORGANISM: Rotavirus A

<400> SEQUENCE: 270

Ile Asp Met Ser Lys Glu Phe Asn Gln Lys Asn Ile Lys Thr Leu Asp
1 5 10 15

Glu Trp Glu Ser Gly Lys Asn Pro Tyr Glu Pro Ser Glu Val
20 25 30

<210> SEQ ID NO 271
<211> LENGTH: 30
<212> TYPE: PRT
<213> ORGANISM: Rotavirus A

<400> SEQUENCE: 271

Asn Glu Arg Leu Gln Glu Lys Glu Ile Glu Lys Asn Ala Asp Ala Ile
1 5 10 15

Met Glu Asn Lys Asn Gly Asn Lys Lys Gln Gln Leu Ser Asp
20 25 30

<210> SEQ ID NO 272
<211> LENGTH: 30
<212> TYPE: PRT
<213> ORGANISM: Rotavirus A

<400> SEQUENCE: 272

Lys Glu Ile Glu Asn Asn Thr Asp Val Thr Met Glu Asn Lys Asn Lys
1 5 10 15

Asn Lys Asn Lys Asn Asn Asn Arg Lys Gln Gln Leu Ser Asp
20 25 30

<210> SEQ ID NO 273
<211> LENGTH: 30
<212> TYPE: PRT
<213> ORGANISM: Rotavirus C

<400> SEQUENCE: 273

Lys Arg Arg Asn Val Gln Gln Lys Asp Val Glu Lys Glu Lys Gln Ile
1 5 10 15

Glu Lys Met Glu Glu Lys Glu Ile Lys Glu Val Lys Glu Gln
20 25 30

<210> SEQ ID NO 274
<211> LENGTH: 30
<212> TYPE: PRT
<213> ORGANISM: Rotavirus H

<400> SEQUENCE: 274

Ile Lys Thr Val Pro Leu Glu Asn Glu Leu Lys Gln Lys Glu Lys Gln
1               5                   10                  15

Arg Asp Asn Lys Glu Lys Asn Glu Lys Glu Asn Lys Asp Glu
            20                  25                  30

<210> SEQ ID NO 275
<211> LENGTH: 30
<212> TYPE: PRT
<213> ORGANISM: SARS-CoV-2

<400> SEQUENCE: 275

Phe Asn Gly Leu Thr Gly Thr Gly Val Leu Thr Glu Ser Asn Lys Lys
1               5                   10                  15

Phe Leu Pro Phe Gln Gln Phe Gly Arg Asp Ile Ala Asp Thr
            20                  25                  30

<210> SEQ ID NO 276
<211> LENGTH: 30
<212> TYPE: PRT
<213> ORGANISM: SARS-CoV-2

<400> SEQUENCE: 276

Gly Val Leu Thr Glu Ser Asn Lys Lys Phe Leu Pro Phe Gln Gln Phe
1               5                   10                  15

Gly Arg Asp Ile Ala Asp Thr Thr Asp Ala Val Arg Asp Pro
            20                  25                  30

<210> SEQ ID NO 277
<211> LENGTH: 30
<212> TYPE: PRT
<213> ORGANISM: SARS-CoV-2

<400> SEQUENCE: 277

Lys Lys Phe Leu Pro Phe Gln Gln Phe Gly Arg Asp Ile Ala Asp Thr
1               5                   10                  15

Thr Asp Ala Val Arg Asp Pro Gln Thr Leu Glu Ile Leu Asp
            20                  25                  30

<210> SEQ ID NO 278
<211> LENGTH: 30
<212> TYPE: PRT
<213> ORGANISM: SARS-CoV-2

<400> SEQUENCE: 278

Lys Phe Leu Pro Phe Gln Gln Phe Gly Arg Asp Ile Ala Asp Thr Thr
1               5                   10                  15

Asp Ala Val Arg Asp Pro Gln Thr Leu Glu Ile Leu Asp Ile
            20                  25                  30

<210> SEQ ID NO 279
<211> LENGTH: 30
<212> TYPE: PRT
<213> ORGANISM: SARS-CoV-2

<400> SEQUENCE: 279

Phe Leu Pro Phe Gln Gln Phe Gly Arg Asp Ile Ala Asp Thr Thr Asp 1 5 10 15

Ala Val Arg Asp Pro Gln Thr Leu Glu Ile Leu Asp Ile Thr
20 25 30

<210> SEQ ID NO 280
<211> LENGTH: 30
<212> TYPE: PRT
<213> ORGANISM: SARS-CoV-2

<400> SEQUENCE: 280

Leu Pro Phe Gln Gln Phe Gly Arg Asp Ile Ala Asp Thr Thr Asp Ala
1 5 10 15

Val Arg Asp Pro Gln Thr Leu Glu Ile Leu Asp Ile Thr Pro
20 25 30

<210> SEQ ID NO 281
<211> LENGTH: 30
<212> TYPE: PRT
<213> ORGANISM: SARS-CoV-2

<400> SEQUENCE: 281

Gln Ile Leu Pro Asp Pro Ser Lys Pro Ser Lys Arg Ser Phe Ile Glu
1 5 10 15

Asp Leu Leu Phe Asn Lys Val Thr Leu Ala Asp Ala Gly Phe
20 25 30

<210> SEQ ID NO 282
<211> LENGTH: 30
<212> TYPE: PRT
<213> ORGANISM: SARS-CoV-2

<400> SEQUENCE: 282

Asp Pro Ser Lys Pro Ser Lys Arg Ser Phe Ile Glu Asp Leu Leu Phe
1 5 10 15

Asn Lys Val Thr Leu Ala Asp Ala Gly Phe Ile Lys Gln Tyr
20 25 30

<210> SEQ ID NO 283
<211> LENGTH: 30
<212> TYPE: PRT
<213> ORGANISM: SARS-CoV-2

<400> SEQUENCE: 283

Pro Ser Lys Pro Ser Lys Arg Ser Phe Ile Glu Asp Leu Leu Phe Asn
1 5 10 15

Lys Val Thr Leu Ala Asp Ala Gly Phe Ile Lys Gln Tyr Gly
20 25 30

<210> SEQ ID NO 284
<211> LENGTH: 30
<212> TYPE: PRT
<213> ORGANISM: SARS-CoV-2

<400> SEQUENCE: 284

Ser Ser Val Leu Asn Asp Ile Leu Ser Arg Leu Asp Lys Val Glu Ala
1 5 10 15

Glu Val Gln Ile Asp Arg Leu Ile Thr Gly Arg Leu Gln Ser
20 25 30

<210> SEQ ID NO 285
<211> LENGTH: 30
<212> TYPE: PRT

<213> ORGANISM: SARS-CoV-2

<400> SEQUENCE: 285

Asn Thr Val Tyr Asp Pro Leu Gln Pro Glu Leu Asp Ser Phe Lys Glu
1 5 10 15

Glu Leu Asp Lys Tyr Phe Lys Asn His Thr Ser Pro Asp Val
20 25 30

<210> SEQ ID NO 286
<211> LENGTH: 30
<212> TYPE: PRT
<213> ORGANISM: SARS-CoV-2

<400> SEQUENCE: 286

Thr Val Tyr Asp Pro Leu Gln Pro Glu Leu Asp Ser Phe Lys Glu Glu
1 5 10 15

Leu Asp Lys Tyr Phe Lys Asn His Thr Ser Pro Asp Val Asp
20 25 30

<210> SEQ ID NO 287
<211> LENGTH: 30
<212> TYPE: PRT
<213> ORGANISM: SARS-CoV-2

<400> SEQUENCE: 287

Tyr Asp Pro Leu Gln Pro Glu Leu Asp Ser Phe Lys Glu Glu Leu Asp
1 5 10 15

Lys Tyr Phe Lys Asn His Thr Ser Pro Asp Val Asp Leu Gly
20 25 30

<210> SEQ ID NO 288
<211> LENGTH: 30
<212> TYPE: PRT
<213> ORGANISM: SARS-CoV-2

<400> SEQUENCE: 288

Asp Pro Leu Gln Pro Glu Leu Asp Ser Phe Lys Glu Glu Leu Asp Lys
1 5 10 15

Tyr Phe Lys Asn His Thr Ser Pro Asp Val Asp Leu Gly Asp
20 25 30

<210> SEQ ID NO 289
<211> LENGTH: 30
<212> TYPE: PRT
<213> ORGANISM: SARS-CoV-2

<400> SEQUENCE: 289

Leu Gln Pro Glu Leu Asp Ser Phe Lys Glu Glu Leu Asp Lys Tyr Phe
1 5 10 15

Lys Asn His Thr Ser Pro Asp Val Asp Leu Gly Asp Ile Ser
20 25 30

<210> SEQ ID NO 290
<211> LENGTH: 30
<212> TYPE: PRT
<213> ORGANISM: SARS-CoV-2

<400> SEQUENCE: 290

Gln Pro Glu Leu Asp Ser Phe Lys Glu Glu Leu Asp Lys Tyr Phe Lys
1 5 10 15

Asn His Thr Ser Pro Asp Val Asp Leu Gly Asp Ile Ser Gly
20 25 30

<210> SEQ ID NO 291
<211> LENGTH: 30
<212> TYPE: PRT
<213> ORGANISM: SARS-CoV-2

<400> SEQUENCE: 291

Pro Glu Leu Asp Ser Phe Lys Glu Glu Leu Asp Lys Tyr Phe Lys Asn
1 5 10 15

His Thr Ser Pro Asp Val Asp Leu Gly Asp Ile Ser Gly Ile
20 25 30

<210> SEQ ID NO 292
<211> LENGTH: 30
<212> TYPE: PRT
<213> ORGANISM: SARS-CoV-2

<400> SEQUENCE: 292

Glu Leu Asp Ser Phe Lys Glu Glu Leu Asp Lys Tyr Phe Lys Asn His
1 5 10 15

Thr Ser Pro Asp Val Asp Leu Gly Asp Ile Ser Gly Ile Asn
20 25 30

<210> SEQ ID NO 293
<211> LENGTH: 30
<212> TYPE: PRT
<213> ORGANISM: SARS-CoV-2

<400> SEQUENCE: 293

Leu Asp Ser Phe Lys Glu Glu Leu Asp Lys Tyr Phe Lys Asn His Thr
1 5 10 15

Ser Pro Asp Val Asp Leu Gly Asp Ile Ser Gly Ile Asn Ala
20 25 30

<210> SEQ ID NO 294
<211> LENGTH: 30
<212> TYPE: PRT
<213> ORGANISM: SARS-CoV-2

<400> SEQUENCE: 294

Asp Ser Phe Lys Glu Glu Leu Asp Lys Tyr Phe Lys Asn His Thr Ser
1 5 10 15

Pro Asp Val Asp Leu Gly Asp Ile Ser Gly Ile Asn Ala Ser
20 25 30

<210> SEQ ID NO 295
<211> LENGTH: 30
<212> TYPE: PRT
<213> ORGANISM: SARS-CoV-2

<400> SEQUENCE: 295

Asn Thr Pro Lys Asp His Ile Gly Thr Arg Asn Pro Ala Asn Asn Ala
1 5 10 15

Ala Ile Val Leu Gln Leu Pro Gln Gly Thr Thr Leu Pro Lys
20 25 30

<210> SEQ ID NO 296
<211> LENGTH: 30
<212> TYPE: PRT
<213> ORGANISM: SARS-CoV-2

<400> SEQUENCE: 296

Thr Pro Lys Asp His Ile Gly Thr Arg Asn Pro Ala Asn Asn Ala Ala
1 5 10 15

Ile Val Leu Gln Leu Pro Gln Gly Thr Thr Leu Pro Lys Gly
20 25 30

<210> SEQ ID NO 297
<211> LENGTH: 30
<212> TYPE: PRT
<213> ORGANISM: SARS-CoV-2

<400> SEQUENCE: 297

Pro Lys Asp His Ile Gly Thr Arg Asn Pro Ala Asn Asn Ala Ala Ile
1 5 10 15

Val Leu Gln Leu Pro Gln Gly Thr Thr Leu Pro Lys Gly Phe
20 25 30

<210> SEQ ID NO 298
<211> LENGTH: 30
<212> TYPE: PRT
<213> ORGANISM: SARS-CoV-2

<400> SEQUENCE: 298

Lys Asp His Ile Gly Thr Arg Asn Pro Ala Asn Asn Ala Ala Ile Val
1 5 10 15

Leu Gln Leu Pro Gln Gly Thr Thr Leu Pro Lys Gly Phe Tyr
20 25 30

<210> SEQ ID NO 299
<211> LENGTH: 30
<212> TYPE: PRT
<213> ORGANISM: SARS-CoV-2

<400> SEQUENCE: 299

Asp His Ile Gly Thr Arg Asn Pro Ala Asn Asn Ala Ala Ile Val Leu
1 5 10 15

Gln Leu Pro Gln Gly Thr Thr Leu Pro Lys Gly Phe Tyr Ala
20 25 30

<210> SEQ ID NO 300
<211> LENGTH: 30
<212> TYPE: PRT
<213> ORGANISM: SARS-CoV-2

<400> SEQUENCE: 300

His Ile Gly Thr Arg Asn Pro Ala Asn Asn Ala Ala Ile Val Leu Gln
1 5 10 15

Leu Pro Gln Gly Thr Thr Leu Pro Lys Gly Phe Tyr Ala Glu
20 25 30

<210> SEQ ID NO 301
<211> LENGTH: 30
<212> TYPE: PRT
<213> ORGANISM: SARS-CoV-2

<400> SEQUENCE: 301

Ile Gly Thr Arg Asn Pro Ala Asn Asn Ala Ala Ile Val Leu Gln Leu
1 5 10 15

Pro Gln Gly Thr Thr Leu Pro Lys Gly Phe Tyr Ala Glu Gly
20 25 30

<210> SEQ ID NO 302
<211> LENGTH: 30

-continued

<212> TYPE: PRT
<213> ORGANISM: SARS-CoV-2

<400> SEQUENCE: 302

Gly Thr Arg Asn Pro Ala Asn Asn Ala Ala Ile Val Leu Gln Leu Pro
1 5 10 15

Gln Gly Thr Thr Leu Pro Lys Gly Phe Tyr Ala Glu Gly Ser
20 25 30

<210> SEQ ID NO 303
<211> LENGTH: 30
<212> TYPE: PRT
<213> ORGANISM: SARS-CoV-2

<400> SEQUENCE: 303

Thr Arg Asn Pro Ala Asn Asn Ala Ala Ile Val Leu Gln Leu Pro Gln
1 5 10 15

Gly Thr Thr Leu Pro Lys Gly Phe Tyr Ala Glu Gly Ser Arg
20 25 30

<210> SEQ ID NO 304
<211> LENGTH: 30
<212> TYPE: PRT
<213> ORGANISM: SARS-CoV-2

<400> SEQUENCE: 304

Arg Asn Pro Ala Asn Asn Ala Ala Ile Val Leu Gln Leu Pro Gln Gly
1 5 10 15

Thr Thr Leu Pro Lys Gly Phe Tyr Ala Glu Gly Ser Arg Gly
20 25 30

<210> SEQ ID NO 305
<211> LENGTH: 30
<212> TYPE: PRT
<213> ORGANISM: SARS-CoV-2

<400> SEQUENCE: 305

Asn Pro Ala Asn Asn Ala Ala Ile Val Leu Gln Leu Pro Gln Gly Thr
1 5 10 15

Thr Leu Pro Lys Gly Phe Tyr Ala Glu Gly Ser Arg Gly Gly
20 25 30

<210> SEQ ID NO 306
<211> LENGTH: 30
<212> TYPE: PRT
<213> ORGANISM: SARS-CoV-2

<400> SEQUENCE: 306

Pro Ala Asn Asn Ala Ala Ile Val Leu Gln Leu Pro Gln Gly Thr Thr
1 5 10 15

Leu Pro Lys Gly Phe Tyr Ala Glu Gly Ser Arg Gly Gly Ser
20 25 30

<210> SEQ ID NO 307
<211> LENGTH: 30
<212> TYPE: PRT
<213> ORGANISM: SARS-CoV-2

<400> SEQUENCE: 307

Ala Asn Asn Ala Ala Ile Val Leu Gln Leu Pro Gln Gly Thr Thr Leu
1 5 10 15

Pro Lys Gly Phe Tyr Ala Glu Gly Ser Arg Gly Gly Ser Gln 20 25 30

<210> SEQ ID NO 308
<211> LENGTH: 30
<212> TYPE: PRT
<213> ORGANISM: SARS-CoV-2

<400> SEQUENCE: 308

Asn Asn Ala Ala Ile Val Leu Gln Leu Pro Gln Gly Thr Thr Leu Pro
1 5 10 15

Lys Gly Phe Tyr Ala Glu Gly Ser Arg Gly Gly Ser Gln Ala
20 25 30

<210> SEQ ID NO 309
<211> LENGTH: 30
<212> TYPE: PRT
<213> ORGANISM: SARS-CoV-2

<400> SEQUENCE: 309

Ala Ala Ile Val Leu Gln Leu Pro Gln Gly Thr Thr Leu Pro Lys Gly
1 5 10 15

Phe Tyr Ala Glu Gly Ser Arg Gly Gly Ser Gln Ala Ser Ser
20 25 30

<210> SEQ ID NO 310
<211> LENGTH: 30
<212> TYPE: PRT
<213> ORGANISM: SARS-CoV-2

<400> SEQUENCE: 310

Ala Ile Val Leu Gln Leu Pro Gln Gly Thr Thr Leu Pro Lys Gly Phe
1 5 10 15

Tyr Ala Glu Gly Ser Arg Gly Gly Ser Gln Ala Ser Ser Arg
20 25 30

<210> SEQ ID NO 311
<211> LENGTH: 30
<212> TYPE: PRT
<213> ORGANISM: SARS-CoV-2

<400> SEQUENCE: 311

Ile Val Leu Gln Leu Pro Gln Gly Thr Thr Leu Pro Lys Gly Phe Tyr
1 5 10 15

Ala Glu Gly Ser Arg Gly Gly Ser Gln Ala Ser Ser Arg Ser
20 25 30

<210> SEQ ID NO 312
<211> LENGTH: 30
<212> TYPE: PRT
<213> ORGANISM: SARS-CoV-2

<400> SEQUENCE: 312

Val Leu Gln Leu Pro Gln Gly Thr Thr Leu Pro Lys Gly Phe Tyr Ala
1 5 10 15

Glu Gly Ser Arg Gly Gly Ser Gln Ala Ser Ser Arg Ser Ser
20 25 30

<210> SEQ ID NO 313
<211> LENGTH: 30
<212> TYPE: PRT
<213> ORGANISM: SARS-CoV-2

<400> SEQUENCE: 313

-continued

```
Leu Gln Leu Pro Gln Gly Thr Thr Leu Pro Lys Gly Phe Tyr Ala Glu
1               5                   10                  15

Gly Ser Arg Gly Gly Ser Gln Ala Ser Ser Arg Ser Ser Ser
            20                  25                  30


<210> SEQ ID NO 314
<211> LENGTH: 30
<212> TYPE: PRT
<213> ORGANISM: SARS-CoV-2

<400> SEQUENCE: 314

Gln Leu Pro Gln Gly Thr Thr Leu Pro Lys Gly Phe Tyr Ala Glu Gly
1               5                   10                  15

Ser Arg Gly Gly Ser Gln Ala Ser Ser Arg Ser Ser Ser Arg
            20                  25                  30


<210> SEQ ID NO 315
<211> LENGTH: 30
<212> TYPE: PRT
<213> ORGANISM: SARS-CoV-2

<400> SEQUENCE: 315

Leu Pro Gln Gly Thr Thr Leu Pro Lys Gly Phe Tyr Ala Glu Gly Ser
1               5                   10                  15

Arg Gly Gly Ser Gln Ala Ser Ser Arg Ser Ser Ser Arg Ser
            20                  25                  30


<210> SEQ ID NO 316
<211> LENGTH: 30
<212> TYPE: PRT
<213> ORGANISM: SARS-CoV-2

<400> SEQUENCE: 316

Pro Gln Gly Thr Thr Leu Pro Lys Gly Phe Tyr Ala Glu Gly Ser Arg
1               5                   10                  15

Gly Gly Ser Gln Ala Ser Ser Arg Ser Ser Ser Arg Ser Arg
            20                  25                  30


<210> SEQ ID NO 317
<211> LENGTH: 30
<212> TYPE: PRT
<213> ORGANISM: SARS-CoV-2

<400> SEQUENCE: 317

Gln Gly Thr Thr Leu Pro Lys Gly Phe Tyr Ala Glu Gly Ser Arg Gly
1               5                   10                  15

Gly Ser Gln Ala Ser Ser Arg Ser Ser Ser Arg Ser Arg Asn
            20                  25                  30


<210> SEQ ID NO 318
<211> LENGTH: 30
<212> TYPE: PRT
<213> ORGANISM: SARS-CoV-2

<400> SEQUENCE: 318

Ala Gly Asn Gly Gly Asp Ala Ala Leu Ala Leu Leu Leu Leu Asp Arg
1               5                   10                  15

Leu Asn Gln Leu Glu Ser Lys Met Ser Gly Lys Gly Gln Gln
            20                  25                  30


<210> SEQ ID NO 319
```

-continued

```
<211> LENGTH: 30
<212> TYPE: PRT
<213> ORGANISM: SARS-CoV-2

<400> SEQUENCE: 319

Ile Gly Thr Arg Asn Pro Ala Asn Asn Ala Ser Ile Val Leu Gln Leu
1               5                   10                  15

Pro Gln Gly Thr Thr Leu Pro Lys Gly Phe Tyr Ala Glu Gly
            20                  25                  30


<210> SEQ ID NO 320
<211> LENGTH: 30
<212> TYPE: PRT
<213> ORGANISM: SARS-CoV-2

<400> SEQUENCE: 320

Gly Thr Arg Asn Pro Ser Asn Asn Ala Ala Ile Val Leu Gln Leu Pro
1               5                   10                  15

Gln Gly Thr Thr Leu Pro Lys Gly Phe Tyr Ala Glu Gly Ser
            20                  25                  30


<210> SEQ ID NO 321
<211> LENGTH: 30
<212> TYPE: PRT
<213> ORGANISM: SARS-CoV-2

<400> SEQUENCE: 321

Gln Leu Pro Gln Gly Thr Thr Leu Pro Lys Gly Phe Tyr Ala Glu Gly
1               5                   10                  15

Ser Arg Gly Gly Ser Gln Ala Ser Ser Arg Ser Ser Leu Arg
            20                  25                  30


<210> SEQ ID NO 322
<211> LENGTH: 30
<212> TYPE: PRT
<213> ORGANISM: SARS-CoV-2

<400> SEQUENCE: 322

Ala Ile Val Leu Gln Leu Pro Gln Gly Thr Thr Leu Pro Lys Gly Phe
1               5                   10                  15

Tyr Ala Glu Gly Ser Arg Gly Gly Ser Gln Ala Tyr Ser Arg
            20                  25                  30


<210> SEQ ID NO 323
<211> LENGTH: 30
<212> TYPE: PRT
<213> ORGANISM: SARS-CoV-2

<400> SEQUENCE: 323

Ile Gly Thr Arg Asn Pro Ala Asn Asn Ala Ala Ile Val Leu Gln Leu
1               5                   10                  15

Pro Gln Gly Thr Thr Leu Pro Lys Gly Phe Tyr Ala Lys Gly
            20                  25                  30


<210> SEQ ID NO 324
<211> LENGTH: 30
<212> TYPE: PRT
<213> ORGANISM: SARS-CoV-2

<400> SEQUENCE: 324

Gly Ile Val Asn Asn Thr Val Tyr Asp Pro Leu Gln Pro Glu Leu Glu
1               5                   10                  15
```

Ser Phe Lys Glu Glu Leu Asp Lys Tyr Phe Lys Asn His Thr
20 25 30

<210> SEQ ID NO 325
<211> LENGTH: 30
<212> TYPE: PRT
<213> ORGANISM: SARS-CoV-2

<400> SEQUENCE: 325

Val Asn Asn Thr Val Tyr Asp Pro Leu Gln Pro Glu Leu Glu Ser Phe
1 5 10 15

Lys Glu Glu Leu Asp Lys Tyr Phe Lys Asn His Thr Ser Pro
20 25 30

<210> SEQ ID NO 326
<211> LENGTH: 30
<212> TYPE: PRT
<213> ORGANISM: SARS-CoV-2

<400> SEQUENCE: 326

Tyr Asp Pro Leu Gln Pro Glu Leu Asp Ser Phe Lys Glu Glu Leu Asp
1 5 10 15

Lys Tyr Phe Lys Asn His Thr Ser Leu Asp Val Asp Leu Gly
20 25 30

<210> SEQ ID NO 327
<211> LENGTH: 30
<212> TYPE: PRT
<213> ORGANISM: SARS-CoV-2

<400> SEQUENCE: 327

Thr Gly Val Leu Thr Glu Ser Asn Lys Lys Phe Leu Pro Phe Gln Gln
1 5 10 15

Phe Gly Arg Asp Ile Ala Asp Thr Thr Asp Ala Val Arg Asp
20 25 30

<210> SEQ ID NO 328
<211> LENGTH: 30
<212> TYPE: PRT
<213> ORGANISM: SARS-CoV-2

<400> SEQUENCE: 328

Asp Phe Gly Gly Phe Asn Phe Ser Gln Ile Leu Pro Asp Pro Ser Lys
1 5 10 15

Pro Ser Lys Arg Ser Phe Ile Glu Asp Leu Leu Phe Asn Lys
20 25 30

<210> SEQ ID NO 329
<211> LENGTH: 30
<212> TYPE: PRT
<213> ORGANISM: SARS-CoV-2

<400> SEQUENCE: 329

Gly Gly Phe Asn Phe Ser Gln Ile Leu Pro Asp Pro Ser Lys Pro Ser
1 5 10 15

Lys Arg Ser Phe Ile Glu Asp Leu Leu Phe Asn Lys Val Thr
20 25 30

<210> SEQ ID NO 330
<211> LENGTH: 30
<212> TYPE: PRT
<213> ORGANISM: SARS-CoV-2

<400> SEQUENCE: 330

Asn Phe Ser Gln Ile Leu Pro Asp Pro Ser Lys Pro Ser Lys Arg Ser
1               5                   10                  15

Phe Ile Glu Asp Leu Leu Phe Asn Lys Val Thr Leu Ala Asp
            20                  25                  30

<210> SEQ ID NO 331
<211> LENGTH: 30
<212> TYPE: PRT
<213> ORGANISM: SARS-CoV-2

<400> SEQUENCE: 331

Ser Gln Ile Leu Pro Asp Pro Ser Lys Pro Ser Lys Arg Ser Phe Ile
1               5                   10                  15

Glu Asp Leu Leu Phe Asn Lys Val Thr Leu Ala Asp Ala Gly
            20                  25                  30

<210> SEQ ID NO 332
<211> LENGTH: 30
<212> TYPE: PRT
<213> ORGANISM: SARS-CoV-2

<400> SEQUENCE: 332

Ile Leu Pro Asp Pro Ser Lys Pro Ser Lys Arg Ser Phe Ile Glu Asp
1               5                   10                  15

Leu Leu Phe Asn Lys Val Thr Leu Ala Asp Ala Gly Phe Ile
            20                  25                  30

<210> SEQ ID NO 333
<211> LENGTH: 30
<212> TYPE: PRT
<213> ORGANISM: SARS-CoV-2

<400> SEQUENCE: 333

Leu Pro Asp Pro Ser Lys Pro Ser Lys Arg Ser Phe Ile Glu Asp Leu
1               5                   10                  15

Leu Phe Asn Lys Val Thr Leu Ala Asp Ala Gly Phe Ile Lys
            20                  25                  30

<210> SEQ ID NO 334
<211> LENGTH: 30
<212> TYPE: PRT
<213> ORGANISM: SARS-CoV-2

<400> SEQUENCE: 334

Pro Asp Pro Ser Lys Pro Ser Lys Arg Ser Phe Ile Glu Asp Leu Leu
1               5                   10                  15

Phe Asn Lys Val Thr Leu Ala Asp Ala Gly Phe Ile Lys Gln
            20                  25                  30

<210> SEQ ID NO 335
<211> LENGTH: 30
<212> TYPE: PRT
<213> ORGANISM: SARS-CoV-2

<400> SEQUENCE: 335

Lys Pro Ser Lys Arg Ser Phe Ile Glu Asp Leu Leu Phe Asn Lys Val
1               5                   10                  15

Thr Leu Ala Asp Ala Gly Phe Ile Lys Gln Tyr Gly Asp Cys
            20                  25                  30

<210> SEQ ID NO 336
<211> LENGTH: 30
<212> TYPE: PRT
<213> ORGANISM: SARS-CoV-2

<400> SEQUENCE: 336

Pro Ser Lys Arg Ser Phe Ile Glu Asp Leu Leu Phe Asn Lys Val Thr
1               5                   10                  15

Leu Ala Asp Ala Gly Phe Ile Lys Gln Tyr Gly Asp Cys Leu
            20                  25                  30

<210> SEQ ID NO 337
<211> LENGTH: 30
<212> TYPE: PRT
<213> ORGANISM: SARS-CoV-2

<400> SEQUENCE: 337

Ser Lys Arg Ser Phe Ile Glu Asp Leu Leu Phe Asn Lys Val Thr Leu
1               5                   10                  15

Ala Asp Ala Gly Phe Ile Lys Gln Tyr Gly Asp Cys Leu Gly
            20                  25                  30

<210> SEQ ID NO 338
<211> LENGTH: 30
<212> TYPE: PRT
<213> ORGANISM: SARS-CoV-2

<400> SEQUENCE: 338

Lys Arg Ser Phe Ile Glu Asp Leu Leu Phe Asn Lys Val Thr Leu Ala
1               5                   10                  15

Asp Ala Gly Phe Ile Lys Gln Tyr Gly Asp Cys Leu Gly Asp
            20                  25                  30

<210> SEQ ID NO 339
<211> LENGTH: 30
<212> TYPE: PRT
<213> ORGANISM: SARS-CoV-2

<400> SEQUENCE: 339

Phe Ile Glu Asp Leu Leu Phe Asn Lys Val Thr Leu Ala Asp Ala Gly
1               5                   10                  15

Phe Ile Lys Gln Tyr Gly Asp Cys Leu Gly Asp Ile Ala Ala
            20                  25                  30

<210> SEQ ID NO 340
<211> LENGTH: 30
<212> TYPE: PRT
<213> ORGANISM: SARS-CoV-2

<400> SEQUENCE: 340

Ile Glu Asp Leu Leu Phe Asn Lys Val Thr Leu Ala Asp Ala Gly Phe
1               5                   10                  15

Ile Lys Gln Tyr Gly Asp Cys Leu Gly Asp Ile Ala Ala Arg
            20                  25                  30

<210> SEQ ID NO 341
<211> LENGTH: 30
<212> TYPE: PRT
<213> ORGANISM: SARS-CoV-2

<400> SEQUENCE: 341

Glu Asp Leu Leu Phe Asn Lys Val Thr Leu Ala Asp Ala Gly Phe Ile
1               5                   10                  15

Lys Gln Tyr Gly Asp Cys Leu Gly Asp Ile Ala Ala Arg Asp
20 25 30

<210> SEQ ID NO 342
<211> LENGTH: 30
<212> TYPE: PRT
<213> ORGANISM: SARS-CoV-2

<400> SEQUENCE: 342

Tyr Phe Lys Asn His Thr Ser Pro Asp Val Asp Leu Gly Asp Ile Pro
1 5 10 15

Gly Ile Asn Ala Ser Val Val Asn Ile Gln Lys Glu Ile Asp
20 25 30

<210> SEQ ID NO 343
<211> LENGTH: 30
<212> TYPE: PRT
<213> ORGANISM: SARS-CoV-2

<400> SEQUENCE: 343

Leu Pro Asp Pro Ser Lys Pro Ser Lys Arg Ser Phe Ile Glu Asp Ile
1 5 10 15

Leu Phe Asn Lys Val Thr Leu Ala Asp Ala Gly Phe Ile Lys
20 25 30

<210> SEQ ID NO 344
<211> LENGTH: 30
<212> TYPE: PRT
<213> ORGANISM: SARS-CoV-2

<400> SEQUENCE: 344

Phe Ser Gln Ile Leu Pro Asp Ser Ser Lys Pro Ser Lys Arg Ser Phe
1 5 10 15

Ile Glu Asp Leu Leu Phe Asn Lys Val Thr Leu Ala Asp Ala
20 25 30

<210> SEQ ID NO 345
<211> LENGTH: 30
<212> TYPE: PRT
<213> ORGANISM: SARS-CoV-2

<400> SEQUENCE: 345

Phe Lys Asn Leu Arg Glu Phe Val Phe Lys Asn Ile Asp Gly Tyr Phe
1 5 10 15

Asn Ile Tyr Ser Lys His Thr Pro Ile Asn Leu Val Arg Asp
20 25 30

<210> SEQ ID NO 346
<211> LENGTH: 30
<212> TYPE: PRT
<213> ORGANISM: SARS-CoV-2

<400> SEQUENCE: 346

Lys Asp Phe Gly Gly Phe Asn Phe Ser Gln Ile Leu Pro Asp Pro Ser
1 5 10 15

Lys Pro Ser Lys Arg Ser Phe Ile Glu Asp Leu Leu Phe Asn
20 25 30

<210> SEQ ID NO 347
<211> LENGTH: 30
<212> TYPE: PRT
<213> ORGANISM: SARS-CoV-2

<400> SEQUENCE: 347

Gly Phe Asn Phe Ser Gln Ile Leu Pro Asp Pro Ser Lys Pro Ser Lys
1 5 10 15

Arg Ser Phe Ile Glu Asp Leu Leu Phe Asn Lys Val Thr Leu
20 25 30

<210> SEQ ID NO 348
<211> LENGTH: 30
<212> TYPE: PRT
<213> ORGANISM: SARS-CoV-2

<400> SEQUENCE: 348

Asp Val Val Ile Gly Ile Val Asn Asn Thr Val Tyr Asp Pro Leu Gln
1 5 10 15

Pro Glu Leu Asp Ser Phe Lys Glu Glu Leu Asp Lys Tyr Phe
20 25 30

<210> SEQ ID NO 349
<211> LENGTH: 30
<212> TYPE: PRT
<213> ORGANISM: SARS-CoV-2

<400> SEQUENCE: 349

Val Val Ile Gly Ile Val Asn Asn Thr Val Tyr Asp Pro Leu Gln Pro
1 5 10 15

Glu Leu Asp Ser Phe Lys Glu Glu Leu Asp Lys Tyr Phe Lys
20 25 30

<210> SEQ ID NO 350
<211> LENGTH: 30
<212> TYPE: PRT
<213> ORGANISM: SARS-CoV-2

<400> SEQUENCE: 350

Val Ile Gly Ile Val Asn Asn Thr Val Tyr Asp Pro Leu Gln Pro Glu
1 5 10 15

Leu Asp Ser Phe Lys Glu Glu Leu Asp Lys Tyr Phe Lys Asn
20 25 30

<210> SEQ ID NO 351
<211> LENGTH: 30
<212> TYPE: PRT
<213> ORGANISM: SARS-CoV-2

<400> SEQUENCE: 351

Ile Gly Ile Val Asn Asn Thr Val Tyr Asp Pro Leu Gln Pro Glu Leu
1 5 10 15

Asp Ser Phe Lys Glu Glu Leu Asp Lys Tyr Phe Lys Asn His
20 25 30

<210> SEQ ID NO 352
<211> LENGTH: 30
<212> TYPE: PRT
<213> ORGANISM: SARS-CoV-2

<400> SEQUENCE: 352

Gly Ile Val Asn Asn Thr Val Tyr Asp Pro Leu Gln Pro Glu Leu Asp
1 5 10 15

Ser Phe Lys Glu Glu Leu Asp Lys Tyr Phe Lys Asn His Thr
20 25 30

<210> SEQ ID NO 353
<211> LENGTH: 30
<212> TYPE: PRT
<213> ORGANISM: SARS-CoV-2

<400> SEQUENCE: 353

Ile Val Asn Asn Thr Val Tyr Asp Pro Leu Gln Pro Glu Leu Asp Ser
1 5 10 15

Phe Lys Glu Glu Leu Asp Lys Tyr Phe Lys Asn His Thr Ser
20 25 30

<210> SEQ ID NO 354
<211> LENGTH: 30
<212> TYPE: PRT
<213> ORGANISM: SARS-CoV-2

<400> SEQUENCE: 354

Val Asn Asn Thr Val Tyr Asp Pro Leu Gln Pro Glu Leu Asp Ser Phe
1 5 10 15

Lys Glu Glu Leu Asp Lys Tyr Phe Lys Asn His Thr Ser Pro
20 25 30

<210> SEQ ID NO 355
<211> LENGTH: 30
<212> TYPE: PRT
<213> ORGANISM: SARS-CoV-2

<400> SEQUENCE: 355

Asn Asn Thr Val Tyr Asp Pro Leu Gln Pro Glu Leu Asp Ser Phe Lys
1 5 10 15

Glu Glu Leu Asp Lys Tyr Phe Lys Asn His Thr Ser Pro Asp
20 25 30

<210> SEQ ID NO 356
<211> LENGTH: 30
<212> TYPE: PRT
<213> ORGANISM: SARS-CoV-2

<400> SEQUENCE: 356

Val Tyr Asp Pro Leu Gln Pro Glu Leu Asp Ser Phe Lys Glu Glu Leu
1 5 10 15

Asp Lys Tyr Phe Lys Asn His Thr Ser Pro Asp Val Asp Leu
20 25 30

<210> SEQ ID NO 357
<211> LENGTH: 30
<212> TYPE: PRT
<213> ORGANISM: SARS-CoV-2

<400> SEQUENCE: 357

Pro Leu Gln Pro Glu Leu Asp Ser Phe Lys Glu Glu Leu Asp Lys Tyr
1 5 10 15

Phe Lys Asn His Thr Ser Pro Asp Val Asp Leu Gly Asp Ile
20 25 30

<210> SEQ ID NO 358
<211> LENGTH: 30
<212> TYPE: PRT
<213> ORGANISM: SARS-CoV-2

<400> SEQUENCE: 358

Phe Lys Glu Glu Leu Asp Lys Tyr Phe Lys Asn His Thr Ser Pro Asp 1 5 10 15

Val Asp Leu Gly Asp Ile Ser Gly Ile Asn Ala Ser Val Val
20 25 30

<210> SEQ ID NO 359
<211> LENGTH: 30
<212> TYPE: PRT
<213> ORGANISM: SARS-CoV-2

<400> SEQUENCE: 359

Leu Gln Leu Glu Leu Asp Ser Phe Lys Glu Glu Leu Asp Lys Tyr Phe
1 5 10 15

Lys Asn His Thr Ser Pro Asp Val Asp Leu Gly Asp Ile Ser
20 25 30

<210> SEQ ID NO 360
<211> LENGTH: 30
<212> TYPE: PRT
<213> ORGANISM: SARS-CoV-2

<400> SEQUENCE: 360

Phe Lys Glu Glu Leu Asp Lys Tyr Phe Lys Asn His Thr Ser Leu Asp
1 5 10 15

Val Asp Leu Gly Asp Ile Ser Gly Ile Asn Ala Ser Val Val
20 25 30

<210> SEQ ID NO 361
<211> LENGTH: 30
<212> TYPE: PRT
<213> ORGANISM: SARS-CoV-2

<400> SEQUENCE: 361

Asn Asn Ala Ala Ile Val Leu Gln Leu Pro Gln Gly Thr Thr Leu Ser
1 5 10 15

Lys Gly Phe Tyr Ala Glu Gly Ser Arg Gly Gly Ser Gln Ala
20 25 30

<210> SEQ ID NO 362
<211> LENGTH: 30
<212> TYPE: PRT
<213> ORGANISM: SARS-CoV-2

<400> SEQUENCE: 362

Asp Arg Leu Asn Glu Val Ala Lys Asn Leu Asn Glu Ser Leu Ile Asp
1 5 10 15

Leu Gln Glu Leu Gly Lys Tyr Glu Gln Tyr Ile Lys Trp Pro
20 25 30

<210> SEQ ID NO 363
<211> LENGTH: 30
<212> TYPE: PRT
<213> ORGANISM: SARS-CoV-2

<400> SEQUENCE: 363

Leu Asn Glu Val Ala Lys Asn Leu Asn Glu Ser Leu Ile Asp Leu Gln
1 5 10 15

Glu Leu Gly Lys Tyr Glu Gln Tyr Ile Lys Trp Pro Trp Tyr
20 25 30

<210> SEQ ID NO 364
<211> LENGTH: 30
<212> TYPE: PRT

<213> ORGANISM: SARS-CoV-2

<400> SEQUENCE: 364

Lys Leu Asp Asp Lys Asp Pro Asn Phe Lys Asp Gln Val Ile Leu Leu
1 5 10 15

Asn Lys His Ile Asp Ala Tyr Lys Thr Phe Pro Pro Thr Glu
20 25 30

<210> SEQ ID NO 365
<211> LENGTH: 30
<212> TYPE: PRT
<213> ORGANISM: SARS-CoV-2

<400> SEQUENCE: 365

Gly Ala Ile Ser Ser Val Leu Asn Asp Ile Leu Ser Arg Leu Asp Lys
1 5 10 15

Val Glu Ala Glu Val Gln Ile Asp Arg Leu Ile Thr Gly Arg
20 25 30

<210> SEQ ID NO 366
<211> LENGTH: 30
<212> TYPE: PRT
<213> ORGANISM: SARS-CoV-2

<400> SEQUENCE: 366

Ile Ser Ser Val Leu Asn Asp Ile Leu Ser Arg Leu Asp Lys Val Glu
1 5 10 15

Ala Glu Val Gln Ile Asp Arg Leu Ile Thr Gly Arg Leu Gln
20 25 30

<210> SEQ ID NO 367
<211> LENGTH: 30
<212> TYPE: PRT
<213> ORGANISM: SARS-CoV-2

<400> SEQUENCE: 367

Val Leu Asn Asp Ile Leu Ser Arg Leu Asp Lys Val Glu Ala Glu Val
1 5 10 15

Gln Ile Asp Arg Leu Ile Thr Gly Arg Leu Gln Ser Leu Gln
20 25 30

<210> SEQ ID NO 368
<211> LENGTH: 30
<212> TYPE: PRT
<213> ORGANISM: SARS-CoV-2

<400> SEQUENCE: 368

Leu Asn Asp Ile Leu Ser Arg Leu Asp Lys Val Glu Ala Glu Val Gln
1 5 10 15

Ile Asp Arg Leu Ile Thr Gly Arg Leu Gln Ser Leu Gln Thr
20 25 30

<210> SEQ ID NO 369
<211> LENGTH: 30
<212> TYPE: PRT
<213> ORGANISM: SARS-CoV-2

<400> SEQUENCE: 369

Asp Glu Thr Gln Ala Leu Pro Gln Arg Gln Lys Lys Gln Gln Ile Val
1 5 10 15

Thr Leu Leu Pro Ala Ala Asp Leu Asp Asp Phe Ser Lys Gln
20 25 30

<210> SEQ ID NO 370
<211> LENGTH: 30
<212> TYPE: PRT
<213> ORGANISM: SARS-CoV-2

<400> SEQUENCE: 370

Ala Val Arg Asp Pro Gln Thr Leu Glu Ile Leu Asp Ile Thr Pro Cys
1 5 10 15

Ser Phe Gly Gly Val Ser Val Ile Thr Pro Gly Thr Asn Thr
20 25 30

<210> SEQ ID NO 371
<211> LENGTH: 30
<212> TYPE: PRT
<213> ORGANISM: SARS-CoV-2

<400> SEQUENCE: 371

Arg Ala Thr Arg Arg Ile Arg Gly Gly Asp Gly Lys Met Lys Asp Leu
1 5 10 15

Ser Pro Arg Trp Tyr Phe Tyr Tyr Leu Gly Thr Gly Pro Glu
20 25 30

<210> SEQ ID NO 372
<211> LENGTH: 30
<212> TYPE: PRT
<213> ORGANISM: SARS-CoV-2

<400> SEQUENCE: 372

Ala Thr Arg Arg Ile Arg Gly Gly Asp Gly Lys Met Lys Asp Leu Ser
1 5 10 15

Pro Arg Trp Tyr Phe Tyr Tyr Leu Gly Thr Gly Pro Glu Ala
20 25 30

<210> SEQ ID NO 373
<211> LENGTH: 30
<212> TYPE: PRT
<213> ORGANISM: SARS-CoV-2

<400> SEQUENCE: 373

Arg Ile Arg Gly Gly Asp Gly Lys Met Lys Asp Leu Ser Pro Arg Trp
1 5 10 15

Tyr Phe Tyr Tyr Leu Gly Thr Gly Pro Glu Ala Gly Leu Pro
20 25 30

<210> SEQ ID NO 374
<211> LENGTH: 30
<212> TYPE: PRT
<213> ORGANISM: SARS-CoV-2

<400> SEQUENCE: 374

Ile Arg Gly Gly Asp Gly Lys Met Lys Asp Leu Ser Pro Arg Trp Tyr
1 5 10 15

Phe Tyr Tyr Leu Gly Thr Gly Pro Glu Ala Gly Leu Pro Tyr
20 25 30

<210> SEQ ID NO 375
<211> LENGTH: 30
<212> TYPE: PRT
<213> ORGANISM: SARS-CoV-2

<400> SEQUENCE: 375

Arg Gly Gly Asp Gly Lys Met Lys Asp Leu Ser Pro Arg Trp Tyr Phe
1 5 10 15

Tyr Tyr Leu Gly Thr Gly Pro Glu Ala Gly Leu Pro Tyr Gly
20 25 30

<210> SEQ ID NO 376
<211> LENGTH: 30
<212> TYPE: PRT
<213> ORGANISM: SARS-CoV-2

<400> SEQUENCE: 376

Gly Gly Asp Gly Lys Met Lys Asp Leu Ser Pro Arg Trp Tyr Phe Tyr
1 5 10 15

Tyr Leu Gly Thr Gly Pro Glu Ala Gly Leu Pro Tyr Gly Ala
20 25 30

<210> SEQ ID NO 377
<211> LENGTH: 30
<212> TYPE: PRT
<213> ORGANISM: SARS-CoV-2

<400> SEQUENCE: 377

Gly Asp Gly Lys Met Lys Asp Leu Ser Pro Arg Trp Tyr Phe Tyr Tyr
1 5 10 15

Leu Gly Thr Gly Pro Glu Ala Gly Leu Pro Tyr Gly Ala Asn
20 25 30

<210> SEQ ID NO 378
<211> LENGTH: 30
<212> TYPE: PRT
<213> ORGANISM: SARS-CoV-2

<400> SEQUENCE: 378

Asp Gly Lys Met Lys Asp Leu Ser Pro Arg Trp Tyr Phe Tyr Tyr Leu
1 5 10 15

Gly Thr Gly Pro Glu Ala Gly Leu Pro Tyr Gly Ala Asn Lys
20 25 30

<210> SEQ ID NO 379
<211> LENGTH: 30
<212> TYPE: PRT
<213> ORGANISM: SARS-CoV-2

<400> SEQUENCE: 379

Gly Lys Met Lys Asp Leu Ser Pro Arg Trp Tyr Phe Tyr Tyr Leu Gly
1 5 10 15

Thr Gly Pro Glu Ala Gly Leu Pro Tyr Gly Ala Asn Lys Asp
20 25 30

<210> SEQ ID NO 380
<211> LENGTH: 30
<212> TYPE: PRT
<213> ORGANISM: SARS-CoV-2

<400> SEQUENCE: 380

Lys Met Lys Asp Leu Ser Pro Arg Trp Tyr Phe Tyr Tyr Leu Gly Thr
1 5 10 15

Gly Pro Glu Ala Gly Leu Pro Tyr Gly Ala Asn Lys Asp Gly
20 25 30

<210> SEQ ID NO 381
<211> LENGTH: 30

<212> TYPE: PRT
<213> ORGANISM: SARS-CoV-2

<400> SEQUENCE: 381

Met Lys Asp Leu Ser Pro Arg Trp Tyr Phe Tyr Tyr Leu Gly Thr Gly
1               5                   10                  15

Pro Glu Ala Gly Leu Pro Tyr Gly Ala Asn Lys Asp Gly Ile
            20                  25                  30

<210> SEQ ID NO 382
<211> LENGTH: 30
<212> TYPE: PRT
<213> ORGANISM: SARS-CoV-2

<400> SEQUENCE: 382

Gly Thr Thr Leu Pro Lys Gly Phe Tyr Ala Glu Gly Ser Arg Gly Gly
1               5                   10                  15

Ser Gln Ala Ser Ser Arg Ser Ser Ser Arg Ser Arg Asn Ser
            20                  25                  30

<210> SEQ ID NO 383
<211> LENGTH: 30
<212> TYPE: PRT
<213> ORGANISM: SARS-CoV-2

<400> SEQUENCE: 383

Ser Pro Ala Arg Met Ala Gly Asn Gly Gly Asp Ala Ala Leu Ala Leu
1               5                   10                  15

Leu Leu Leu Asp Arg Leu Asn Gln Leu Glu Ser Lys Met Ser
            20                  25                  30

<210> SEQ ID NO 384
<211> LENGTH: 30
<212> TYPE: PRT
<213> ORGANISM: SARS-CoV-2

<400> SEQUENCE: 384

Ala Arg Met Ala Gly Asn Gly Gly Asp Ala Ala Leu Ala Leu Leu Leu
1               5                   10                  15

Leu Asp Arg Leu Asn Gln Leu Glu Ser Lys Met Ser Gly Lys
            20                  25                  30

<210> SEQ ID NO 385
<211> LENGTH: 30
<212> TYPE: PRT
<213> ORGANISM: SARS-CoV-2

<400> SEQUENCE: 385

Arg Met Ala Gly Asn Gly Gly Asp Ala Ala Leu Ala Leu Leu Leu Leu
1               5                   10                  15

Asp Arg Leu Asn Gln Leu Glu Ser Lys Met Ser Gly Lys Gly
            20                  25                  30

<210> SEQ ID NO 386
<211> LENGTH: 30
<212> TYPE: PRT
<213> ORGANISM: SARS-CoV-2

<400> SEQUENCE: 386

Met Ala Gly Asn Gly Gly Asp Ala Ala Leu Ala Leu Leu Leu Leu Asp
1               5                   10                  15

Arg Leu Asn Gln Leu Glu Ser Lys Met Ser Gly Lys Gly Gln

-continued 20 25 30

<210> SEQ ID NO 387
<211> LENGTH: 30
<212> TYPE: PRT
<213> ORGANISM: SARS-CoV-2

<400> SEQUENCE: 387

Gly Asn Gly Gly Asp Ala Ala Leu Ala Leu Leu Leu Leu Asp Arg Leu
1 5 10 15

Asn Gln Leu Glu Ser Lys Met Ser Gly Lys Gly Gln Gln Gln
20 25 30

<210> SEQ ID NO 388
<211> LENGTH: 30
<212> TYPE: PRT
<213> ORGANISM: SARS-CoV-2

<400> SEQUENCE: 388

Asn Gly Gly Asp Ala Ala Leu Ala Leu Leu Leu Leu Asp Arg Leu Asn
1 5 10 15

Gln Leu Glu Ser Lys Met Ser Gly Lys Gly Gln Gln Gln Gln
20 25 30

<210> SEQ ID NO 389
<211> LENGTH: 30
<212> TYPE: PRT
<213> ORGANISM: SARS-CoV-2

<400> SEQUENCE: 389

Gly Gly Asp Ala Ala Leu Ala Leu Leu Leu Leu Asp Arg Leu Asn Gln
1 5 10 15

Leu Glu Ser Lys Met Ser Gly Lys Gly Gln Gln Gln Gln Gly
20 25 30

<210> SEQ ID NO 390
<211> LENGTH: 30
<212> TYPE: PRT
<213> ORGANISM: SARS-CoV-2

<400> SEQUENCE: 390

Asp Ala Ala Leu Ala Leu Leu Leu Leu Asp Arg Leu Asn Gln Leu Glu
1 5 10 15

Ser Lys Met Ser Gly Lys Gly Gln Gln Gln Gln Gly Gln Thr
20 25 30

<210> SEQ ID NO 391
<211> LENGTH: 30
<212> TYPE: PRT
<213> ORGANISM: SARS-CoV-2

<400> SEQUENCE: 391

Leu Ala Leu Leu Leu Leu Asp Arg Leu Asn Gln Leu Glu Ser Lys Met
1 5 10 15

Ser Gly Lys Gly Gln Gln Gln Gln Gly Gln Thr Val Thr Lys
20 25 30

<210> SEQ ID NO 392
<211> LENGTH: 30
<212> TYPE: PRT
<213> ORGANISM: SARS-CoV-2

<400> SEQUENCE: 392

-continued

```
Leu Leu Asp Arg Leu Asn Gln Leu Glu Ser Lys Met Ser Gly Lys Gly
1               5                   10                  15

Gln Gln Gln Gln Gly Gln Thr Val Thr Lys Lys Ser Ala Ala
            20                  25                  30


<210> SEQ ID NO 393
<211> LENGTH: 30
<212> TYPE: PRT
<213> ORGANISM: SARS-CoV-2

<400> SEQUENCE: 393

Arg Ala Thr Arg Arg Ile Arg Gly Gly Asp Gly Lys Met Lys Tyr Leu
1               5                   10                  15

Ser Pro Arg Trp Tyr Phe Tyr Tyr Leu Gly Thr Gly Pro Glu
            20                  25                  30


<210> SEQ ID NO 394
<211> LENGTH: 30
<212> TYPE: PRT
<213> ORGANISM: SARS-CoV-2

<400> SEQUENCE: 394

Asn Ala Ala Ile Val Leu Gln Leu Pro Gln Gly Thr Thr Leu Ser Lys
1               5                   10                  15

Gly Phe Tyr Ala Glu Gly Ser Arg Gly Gly Ser Gln Ala Ser
            20                  25                  30


<210> SEQ ID NO 395
<211> LENGTH: 30
<212> TYPE: PRT
<213> ORGANISM: SARS-CoV-2

<400> SEQUENCE: 395

Ser Asp Ala Ala Leu Ala Leu Leu Leu Leu Asp Arg Leu Asn Gln Leu
1               5                   10                  15

Glu Ser Lys Met Ser Gly Lys Gly Gln Gln Gln Gln Ser Gln
            20                  25                  30


<210> SEQ ID NO 396
<211> LENGTH: 30
<212> TYPE: PRT
<213> ORGANISM: SARS-CoV-2

<400> SEQUENCE: 396

Gly Lys Met Lys Asp Leu Ser Pro Arg Trp Tyr Phe Tyr Tyr Leu Gly
1               5                   10                  15

Thr Gly Pro Glu Ala Gly Leu Leu Tyr Gly Ala Asn Lys Asp
            20                  25                  30


<210> SEQ ID NO 397
<211> LENGTH: 30
<212> TYPE: PRT
<213> ORGANISM: SARS-CoV-2

<400> SEQUENCE: 397

Gly Thr Thr Leu Pro Lys Gly Phe Tyr Ala Glu Gly Ser Arg Gly Gly
1               5                   10                  15

Ser Gln Ala Ser Ser Arg Tyr Ser Ser Arg Ser Arg Asn Ser
            20                  25                  30


<210> SEQ ID NO 398
```

<211> LENGTH: 30
<212> TYPE: PRT
<213> ORGANISM: SARS-CoV-2

<400> SEQUENCE: 398

Asp Gly Lys Met Lys Asp Leu Ser Pro Arg Trp Tyr Phe Tyr Tyr Leu
1               5                   10                  15

Gly Thr Gly Ser Glu Ala Gly Leu Pro Tyr Gly Ala Asn Lys
            20                  25                  30

<210> SEQ ID NO 399
<211> LENGTH: 30
<212> TYPE: PRT
<213> ORGANISM: SARS-CoV-2

<400> SEQUENCE: 399

Asn Gly Gly Asp Ala Ala Leu Ala Leu Leu Leu Leu Asp Arg Leu Asn
1               5                   10                  15

Gln Leu Glu Thr Lys Met Ser Gly Lys Gly Gln Gln Gln Gln
            20                  25                  30

<210> SEQ ID NO 400
<211> LENGTH: 30
<212> TYPE: PRT
<213> ORGANISM: SARS-CoV-2

<400> SEQUENCE: 400

Val Lys Gln Ile Tyr Lys Thr Pro Pro Ile Lys Asp Phe Gly Gly Phe
1               5                   10                  15

Asn Phe Ser Gln Ile Leu Pro Asp Pro Ser Lys Pro Ser Lys
            20                  25                  30

<210> SEQ ID NO 401
<211> LENGTH: 30
<212> TYPE: PRT
<213> ORGANISM: SARS-CoV-2

<400> SEQUENCE: 401

Gln Met Ala Tyr Arg Phe Asn Gly Ile Gly Val Thr Gln Asn Val Leu
1               5                   10                  15

Tyr Glu Asn Gln Lys Leu Ile Ala Asn Gln Phe Asn Ser Ala
            20                  25                  30

<210> SEQ ID NO 402
<211> LENGTH: 30
<212> TYPE: PRT
<213> ORGANISM: SARS-CoV-2

<400> SEQUENCE: 402

Leu Tyr Gln Asp Val Asn Cys Thr Glu Val Pro Val Ala Ile His Ala
1               5                   10                  15

Asp Gln Leu Thr Pro Thr Trp Arg Val Tyr Ser Thr Gly Ser
            20                  25                  30

<210> SEQ ID NO 403
<211> LENGTH: 30
<212> TYPE: PRT
<213> ORGANISM: SARS-CoV-2

<400> SEQUENCE: 403

Tyr Gln Asp Val Asn Cys Thr Glu Val Pro Val Ala Ile His Ala Asp
1               5                   10                  15

-continued

Gln Leu Thr Pro Thr Trp Arg Val Tyr Ser Thr Gly Ser Asn
20 25 30

<210> SEQ ID NO 404
<211> LENGTH: 30
<212> TYPE: PRT
<213> ORGANISM: SARS-CoV-2

<400> SEQUENCE: 404

Thr Glu Val Pro Val Ala Ile His Ala Asp Gln Leu Thr Pro Thr Trp
1 5 10 15

Arg Val Tyr Ser Thr Gly Ser Asn Val Phe Gln Thr Arg Ala
20 25 30

<210> SEQ ID NO 405
<211> LENGTH: 30
<212> TYPE: PRT
<213> ORGANISM: SARS-CoV-2

<400> SEQUENCE: 405

Glu Val Pro Val Ala Ile His Ala Asp Gln Leu Thr Pro Thr Trp Arg
1 5 10 15

Val Tyr Ser Thr Gly Ser Asn Val Phe Gln Thr Arg Ala Gly
20 25 30

<210> SEQ ID NO 406
<211> LENGTH: 30
<212> TYPE: PRT
<213> ORGANISM: SARS-CoV-2

<400> SEQUENCE: 406

Phe Asn Phe Ser Gln Ile Leu Pro Asp Pro Ser Lys Pro Ser Lys Arg
1 5 10 15

Ser Phe Ile Glu Asp Leu Leu Phe Asn Lys Val Thr Leu Ala
20 25 30

<210> SEQ ID NO 407
<211> LENGTH: 30
<212> TYPE: PRT
<213> ORGANISM: SARS-CoV-2

<400> SEQUENCE: 407

Arg Ser Phe Ile Glu Asp Leu Leu Phe Asn Lys Val Thr Leu Ala Asp
1 5 10 15

Ala Gly Phe Ile Lys Gln Tyr Gly Asp Cys Leu Gly Asp Ile
20 25 30

<210> SEQ ID NO 408
<211> LENGTH: 30
<212> TYPE: PRT
<213> ORGANISM: SARS-CoV-2

<400> SEQUENCE: 408

Ser Phe Ile Glu Asp Leu Leu Phe Asn Lys Val Thr Leu Ala Asp Ala
1 5 10 15

Gly Phe Ile Lys Gln Tyr Gly Asp Cys Leu Gly Asp Ile Ala
20 25 30

<210> SEQ ID NO 409
<211> LENGTH: 30
<212> TYPE: PRT
<213> ORGANISM: SARS-CoV-2

<400> SEQUENCE: 409

Gly Arg Arg Gly Pro Glu Gln Thr Gln Gly Asn Phe Gly Asp Gln Glu
1 5 10 15

Leu Ile Arg Gln Gly Thr Asp Tyr Lys His Trp Pro Gln Ile
20 25 30

<210> SEQ ID NO 410
<211> LENGTH: 30
<212> TYPE: PRT
<213> ORGANISM: SARS-CoV-2

<400> SEQUENCE: 410

Ser Phe Ile Glu Asp Leu Leu Phe Asn Lys Val Thr Leu Ala Asp Val
1 5 10 15

Gly Phe Ile Lys Gln Tyr Gly Asp Cys Leu Gly Asp Ile Ala
20 25 30

<210> SEQ ID NO 411
<211> LENGTH: 30
<212> TYPE: PRT
<213> ORGANISM: SARS-CoV-2

<400> SEQUENCE: 411

Pro Asn Ile Thr Asn Leu Cys Pro Phe Gly Glu Val Phe Asn Ala Thr
1 5 10 15

Arg Phe Thr Ser Val Tyr Ala Trp Asn Arg Lys Arg Ile Ser
20 25 30

<210> SEQ ID NO 412
<211> LENGTH: 30
<212> TYPE: PRT
<213> ORGANISM: SARS-CoV-2

<400> SEQUENCE: 412

Ser Phe Ile Glu Asp Leu Leu Phe Asn Lys Val Thr Leu Ala Asp Ala
1 5 10 15

Gly Phe Ile Lys Gln Tyr Gly Asp Cys Leu Gly Asp Ile Val
20 25 30

<210> SEQ ID NO 413
<211> LENGTH: 30
<212> TYPE: PRT
<213> ORGANISM: Torque teno midi virus

<400> SEQUENCE: 413

Leu Gln Lys Thr Val Gln Ile Lys Asn Pro Lys Lys Gln Ala Pro Glu
1 5 10 15

Ser Phe Leu His Thr Trp Asp Phe Arg Arg Gly Phe Val Thr
20 25 30

<210> SEQ ID NO 414
<211> LENGTH: 30
<212> TYPE: PRT
<213> ORGANISM: Torque teno midi virus 11

<400> SEQUENCE: 414

Gln Gln His Thr Lys Leu Gln Leu Leu Gln Leu Ile Asn Asn Leu Lys
1 5 10 15

Lys Lys Gln Lys Leu Ile Gln Leu Gln Thr Gly Ile Leu Asp
20 25 30

-continued

<210> SEQ ID NO 415
<211> LENGTH: 30
<212> TYPE: PRT
<213> ORGANISM: Torque teno midi virus 12

<400> SEQUENCE: 415

Gln Ile Glu Asn Pro Glu Arg Gln Asp Pro Arg Ser Ile Leu His Gln
1 5 10 15

Trp Asp Tyr Arg Arg Gly Phe Ile Lys Glu Arg Ala Leu Lys
20 25 30

<210> SEQ ID NO 416
<211> LENGTH: 30
<212> TYPE: PRT
<213> ORGANISM: Torque teno midi virus 7

<400> SEQUENCE: 416

Ile Gln Ile Val Asn Pro Glu Lys Gln Ser Pro Glu Thr Ile Ile His
1 5 10 15

Pro Trp Asp Tyr Arg Arg Gly Leu Ile Lys Glu Lys Ala Leu
20 25 30

<210> SEQ ID NO 417
<211> LENGTH: 30
<212> TYPE: PRT
<213> ORGANISM: Torque teno midi virus 8

<400> SEQUENCE: 417

Lys Ala Met Leu Arg Asp Trp Asp Tyr Arg Arg Gly Ile Ile Thr Thr
1 5 10 15

Thr Ala Leu Lys Arg Met Ser Glu His Leu Gln Thr Asp Ser
20 25 30

<210> SEQ ID NO 418
<211> LENGTH: 30
<212> TYPE: PRT
<213> ORGANISM: Torque teno midi virus 8

<400> SEQUENCE: 418

Glu Asn Leu Gln Gln Leu Ile Leu His Gln Gln Gln Gln Gln Gln Lys
1 5 10 15

Leu Lys Ser Asn Ile Leu Lys Leu Leu Met Asp Leu Lys His
20 25 30

<210> SEQ ID NO 419
<211> LENGTH: 30
<212> TYPE: PRT
<213> ORGANISM: Torque teno midi virus 9

<400> SEQUENCE: 419

Ser Gln Glu Ile Pro Gln Thr Gln Asn Leu Gln Glu Leu Ile Gln Gln
1 5 10 15

Gln Gln Gln Gln Gln Gln Gln Leu Lys Tyr Asn Ile Leu Lys
20 25 30

<210> SEQ ID NO 420
<211> LENGTH: 30
<212> TYPE: PRT
<213> ORGANISM: Torque teno virus

<400> SEQUENCE: 420

Gln Leu Gln Gln Gln Leu Gln Phe Leu Thr Arg Glu Met Phe Lys Thr
1 5 10 15

-continued

Gln Ala Gly Leu His Ile Asn Pro Met Leu Leu Asn Gln Arg
20 25 30

<210> SEQ ID NO 421
<211> LENGTH: 9
<212> TYPE: PRT
<213> ORGANISM: SARS-CoV-2

<400> SEQUENCE: 421

Phe Lys Glu Glu Leu Asp Lys Tyr Phe
1 5

<210> SEQ ID NO 422
<211> LENGTH: 6
<212> TYPE: PRT
<213> ORGANISM: SARS-CoV-2

<400> SEQUENCE: 422

Glu Asp Leu Leu Phe Asn
1 5

<210> SEQ ID NO 423
<211> LENGTH: 13
<212> TYPE: PRT
<213> ORGANISM: SARS-CoV-2

<400> SEQUENCE: 423

Leu Pro Phe Gln Gln Phe Gly Arg Asp Ile Ala Asp Thr
1 5 10

<210> SEQ ID NO 424
<211> LENGTH: 30
<212> TYPE: PRT
<213> ORGANISM: SARS-CoV-2

<400> SEQUENCE: 424

Phe Lys Asn Leu Arg Glu Phe Val Phe Lys Asn Ile Asp Gly Tyr Phe
1 5 10 15

Lys Ile Tyr Ser Lys His Thr Pro Ile Asn Leu Val Arg Asp
20 25 30

<210> SEQ ID NO 425
<211> LENGTH: 30
<212> TYPE: PRT
<213> ORGANISM: SARS-CoV-2

<400> SEQUENCE: 425

Arg Thr Phe Leu Leu Lys Tyr Asn Glu Asn Gly Thr Ile Thr Asp Ala
1 5 10 15

Val Asp Cys Ala Leu Asp Pro Leu Ser Glu Thr Lys Cys Thr
20 25 30

<210> SEQ ID NO 426
<211> LENGTH: 30
<212> TYPE: PRT
<213> ORGANISM: SARS-CoV-2

<400> SEQUENCE: 426

Pro Asn Ile Thr Asn Leu Cys Pro Phe Gly Glu Val Phe Asn Ala Thr
1 5 10 15

Arg Phe Ala Ser Val Tyr Ala Trp Asn Arg Lys Arg Ile Ser
20 25 30

<210> SEQ ID NO 427
<211> LENGTH: 30
<212> TYPE: PRT
<213> ORGANISM: SARS-CoV-2

<400> SEQUENCE: 427

Ile Arg Gly Asp Glu Val Arg Gln Ile Ala Pro Gly Gln Thr Gly Lys
1 5 10 15

Ile Ala Asp Tyr Asn Tyr Lys Leu Pro Asp Asp Phe Thr Gly
20 25 30

<210> SEQ ID NO 428
<211> LENGTH: 24
<212> TYPE: PRT
<213> ORGANISM: SARS-CoV-2

<400> SEQUENCE: 428

Leu Asp Ser Lys Val Gly Gly Asn Tyr Asn Tyr Leu Tyr Arg Leu Phe
1 5 10 15

Arg Lys Ser Asn Leu Lys Pro Phe
20

<210> SEQ ID NO 429
<211> LENGTH: 30
<212> TYPE: PRT
<213> ORGANISM: SARS-CoV-2

<400> SEQUENCE: 429

Asn Gly Val Glu Gly Phe Asn Cys Tyr Phe Pro Leu Gln Ser Tyr Gly
1 5 10 15

Phe Gln Pro Thr Asn Gly Val Gly Tyr Gln Pro Tyr Arg Val
20 25 30

<210> SEQ ID NO 430
<211> LENGTH: 28
<212> TYPE: PRT
<213> ORGANISM: SARS-CoV-2

<400> SEQUENCE: 430

Asn Leu Val Lys Asn Lys Cys Val Asn Phe Asn Phe Asn Gly Leu Thr
1 5 10 15

Gly Thr Gly Val Leu Thr Glu Ser Asn Lys Lys Phe
20 25

<210> SEQ ID NO 431
<211> LENGTH: 29
<212> TYPE: PRT
<213> ORGANISM: SARS-CoV-2

<400> SEQUENCE: 431

Glu Val Pro Val Ala Ile His Ala Asp Gln Leu Thr Pro Thr Trp Arg
1 5 10 15

Val Tyr Ser Thr Gly Ser Asn Val Phe Gln Thr Arg Ala
20 25

<210> SEQ ID NO 432
<211> LENGTH: 22
<212> TYPE: PRT
<213> ORGANISM: SARS-CoV-2

<400> SEQUENCE: 432

Ala Gly Cys Leu Ile Gly Ala Glu His Val Asn Asn Ser Tyr Glu Cys

-continued

```
1               5                   10                  15

Asp Ile Pro Ile Gly Ala
            20


<210> SEQ ID NO 433
<211> LENGTH: 7
<212> TYPE: PRT
<213> ORGANISM: SARS-CoV-2

<400> SEQUENCE: 433

Val Lys Gln Ile Tyr Lys Thr
1               5


<210> SEQ ID NO 434
<211> LENGTH: 30
<212> TYPE: PRT
<213> ORGANISM: SARS-CoV-2

<400> SEQUENCE: 434

Ser Ser Thr Ala Ser Ala Leu Gly Lys Leu Gln Asp Val Val Asn Gln
1               5                   10                  15

Asn Ala Gln Ala Leu Asn Thr Leu Val Lys Gln Leu Ser Ser
            20                  25                  30


<210> SEQ ID NO 435
<211> LENGTH: 7
<212> TYPE: PRT
<213> ORGANISM: SARS-CoV-2

<400> SEQUENCE: 435

Glu Glu Leu Asp Lys Tyr Phe
1               5


<210> SEQ ID NO 436
<211> LENGTH: 30
<212> TYPE: PRT
<213> ORGANISM: SARS-CoV-2

<400> SEQUENCE: 436

Tyr Phe Lys Asn His Thr Ser Pro Asp Val Asp Leu Gly Asp Ile Ser
1               5                   10                  15

Gly Ile Asn Ala Ser Val Val Asn Ile Gln Lys Glu Ile Asp
            20                  25                  30


<210> SEQ ID NO 437
<211> LENGTH: 12
<212> TYPE: PRT
<213> ORGANISM: SARS-CoV-2

<400> SEQUENCE: 437

Asp Arg Leu Asn Glu Val Ala Lys Asn Leu Asn Glu
1               5                   10


<210> SEQ ID NO 438
<211> LENGTH: 6
<212> TYPE: PRT
<213> ORGANISM: SARS-CoV-2

<400> SEQUENCE: 438

Gly Ser Asn Gln Asn Gly
1               5


<210> SEQ ID NO 439
```

<211> LENGTH: 29
<212> TYPE: PRT
<213> ORGANISM: SARS-CoV-2

<400> SEQUENCE: 439

Gly Lys Met Lys Asp Leu Ser Pro Arg Trp Tyr Phe Tyr Tyr Leu Gly
1 5 10 15

Thr Gly Pro Glu Ala Gly Leu Pro Tyr Gly Ala Asn Lys
20 25

<210> SEQ ID NO 440
<211> LENGTH: 20
<212> TYPE: PRT
<213> ORGANISM: SARS-CoV-2

<400> SEQUENCE: 440

Val Ala Thr Glu Gly Ala Leu Asn Thr Pro Lys Asp His Ile Gly Thr
1 5 10 15

Arg Asn Pro Ala
20

<210> SEQ ID NO 441
<211> LENGTH: 4
<212> TYPE: PRT
<213> ORGANISM: SARS-CoV-2

<400> SEQUENCE: 441

Thr Leu Pro Lys
1

<210> SEQ ID NO 442
<211> LENGTH: 7
<212> TYPE: PRT
<213> ORGANISM: SARS-CoV-2

<400> SEQUENCE: 442

Leu Leu Asp Arg Leu Asn Gln
1 5

<210> SEQ ID NO 443
<211> LENGTH: 30
<212> TYPE: PRT
<213> ORGANISM: SARS-CoV-2

<400> SEQUENCE: 443

Thr Val Thr Lys Lys Ser Ala Ala Glu Ala Ser Lys Lys Pro Arg Gln
1 5 10 15

Lys Arg Thr Ala Thr Lys Ala Tyr Asn Val Thr Gln Ala Phe
20 25 30

<210> SEQ ID NO 444
<211> LENGTH: 21
<212> TYPE: PRT
<213> ORGANISM: SARS-CoV-2

<400> SEQUENCE: 444

Gln Thr Gln Gly Asn Phe Gly Asp Gln Glu Leu Ile Arg Gln Gly Thr
1 5 10 15

Asp Tyr Lys His Trp
20

<210> SEQ ID NO 445
<211> LENGTH: 16

-continued

```
<212> TYPE: PRT
<213> ORGANISM: SARS-CoV-2

<400> SEQUENCE: 445

Phe Lys Asp Gln Val Ile Leu Leu Asn Lys His Ile Asp Ala Tyr Lys
1               5                   10                  15


<210> SEQ ID NO 446
<211> LENGTH: 8
<212> TYPE: PRT
<213> ORGANISM: SARS-CoV-2

<400> SEQUENCE: 446

Pro Lys Lys Asp Lys Lys Lys Lys
1               5


<210> SEQ ID NO 447
<211> LENGTH: 13
<212> TYPE: PRT
<213> ORGANISM: SARS-CoV-2

<400> SEQUENCE: 447

Gln Thr Val Thr Leu Leu Pro Ala Ala Asp Leu Asp Asp
1               5                   10


<210> SEQ ID NO 448
<211> LENGTH: 10
<212> TYPE: PRT
<213> ORGANISM: SARS-CoV-2

<400> SEQUENCE: 448

Glu Glu Leu Asp Lys Tyr Phe Lys Asn His
1               5                   10


<210> SEQ ID NO 449
<211> LENGTH: 63
<212> TYPE: PRT
<213> ORGANISM: SARS-CoV-2

<400> SEQUENCE: 449

Val Lys Gln Ile Tyr Lys Thr Pro Pro Ile Lys Asp Phe Gly Gly Phe
1               5                   10                  15

Asn Phe Ser Gln Ile Leu Pro Asp Pro Ser Lys Pro Ser Lys Arg Phe
            20                  25                  30

Ile Glu Asp Leu Leu Phe Asn Lys Val Thr Leu Ala Asp Ala Gly Phe
        35                  40                  45

Ile Lys Gln Tyr Gly Asp Cys Leu Gly Asp Ile Ala Ala Arg Asp
    50                  55                  60


<210> SEQ ID NO 450
<211> LENGTH: 63
<212> TYPE: PRT
<213> ORGANISM: SARS-CoV-2

<400> SEQUENCE: 450

Val Lys Gln Met Tyr Lys Thr Pro Thr Leu Lys Tyr Phe Gly Gly Phe
1               5                   10                  15

Asn Phe Ser Gln Ile Leu Pro Asp Pro Leu Lys Pro Thr Lys Arg Phe
            20                  25                  30

Ile Glu Asp Leu Leu Phe Asn Lys Val Thr Leu Ala Asp Ala Gly Phe
        35                  40                  45

Met Lys Gln Tyr Gly Glu Cys Leu Gly Asp Ile Asn Ala Arg Asp
```

50 55 60

<210> SEQ ID NO 451
<211> LENGTH: 70
<212> TYPE: PRT
<213> ORGANISM: SARS-CoV-2

<400> SEQUENCE: 451

Val Lys Ser Ser Gln Ser Ser Pro Ile Ile Pro Gly Phe Gly Gly Asp
1 5 10 15

Phe Asn Leu Thr Leu Leu Glu Pro Val Ser Ile Ser Thr Gly Ser Ala
20 25 30

Arg Ser Ile Glu Ser Asp Ala Leu Leu Phe Asp Lys Val Thr Ile Ala
35 40 45

Ile Asp Pro Gly Tyr Met Gln Gly Tyr Asp Asp Cys Met Gln Gln Gly
50 55 60

Pro Ala Ser Ala Arg Asp
65 70

<210> SEQ ID NO 452
<211> LENGTH: 67
<212> TYPE: PRT
<213> ORGANISM: SARS-CoV-2

<400> SEQUENCE: 452

Leu Met Asn Gly Val Thr Leu Ser Thr Lys Gly Leu Lys Val Asn Phe
1 5 10 15

Asn Val Asp Asp Ile Asn Phe Ser Pro Val Leu Gly Cys Leu Gly Ser
20 25 30

Glu Cys Ala Ser Ile Lys Glu Ala Asp Ser Leu Ser Leu Phe Asp Lys
35 40 45

Val Lys Leu Ser Asp Val Gly Asn Phe Asn Cys Thr Gly Gly Ala Glu
50 55 60

Ile Arg Asp
65

<210> SEQ ID NO 453
<211> LENGTH: 69
<212> TYPE: PRT
<213> ORGANISM: SARS-CoV-2

<400> SEQUENCE: 453

Leu Met Gln Gly Val Thr Leu Ser Ser Asn Leu Asn Thr Asn Leu His
1 5 10 15

Ser Asp Val Asp Asn Ile Asp Phe Lys Ser Leu Leu Gly Cys Leu Gly
20 25 30

Ser Gln Leu Cys Leu Gly Glu Asp Ser Leu Ser Ser Leu Phe Asn Val
35 40 45

Lys Leu Ser Asp Val Gly Phe Val Glu Ala Tyr Asn Asn Thr Gly Gly
50 55 60

Ser Glu Ile Arg Asp
65

<210> SEQ ID NO 454
<211> LENGTH: 66
<212> TYPE: PRT
<213> ORGANISM: SARS-CoV-2

<400> SEQUENCE: 454

-continued

Asp Lys Lys Ala Phe Thr Leu Ala Asn Val Ser Ser Gly Asp Tyr Asn
1               5                   10                  15

Leu Ser Ser Val Ile Pro Ser Leu Pro Thr Ser Gly Ser Arg Val Ala
            20                  25                  30

Gly Ala Ile Glu Asp Ile Leu Phe Ser Lys Leu Val Thr Ser Gly Leu
        35                  40                  45

Gly Thr Val Asp Ala Asp Tyr Lys Ser Cys Thr Lys Gly Leu Ser Ile
    50                  55                  60

Ala Asp
65

<210> SEQ ID NO 455
<211> LENGTH: 68
<212> TYPE: PRT
<213> ORGANISM: SARS-CoV-2

<400> SEQUENCE: 455

Asp Ser Asn Ala Phe Ser Leu Ala Asn Val Thr Ser Phe Gly Asp Tyr
1               5                   10                  15

Asn Leu Ser Ser Val Leu Pro Gln Arg Ile Asn Arg Ile Ser Ser Arg
            20                  25                  30

Ile Ala Gly Ala Leu Glu Asp Leu Leu Phe Ser Lys Val Val Thr Ser
        35                  40                  45

Gly Leu Gly Thr Val Asp Val Asp Tyr Lys Ser Cys Thr Lys Gly Leu
    50                  55                  60

Ser Ile Ala Asp
65

<210> SEQ ID NO 456
<211> LENGTH: 57
<212> TYPE: PRT
<213> ORGANISM: SARS-CoV-2

<400> SEQUENCE: 456

Asp Val Val Ile Gly Ile Val Asn Asn Thr Val Tyr Asp Pro Leu Gln
1               5                   10                  15

Pro Glu Asp Ser Phe Lys Glu Glu Leu Asp Lys Tyr Phe Lys Asn His
            20                  25                  30

Thr Ser Pro Asp Val Asp Leu Gly Asp Ile Ser Gly Ile Asn Ala Ser
        35                  40                  45

Val Val Asn Ile Gln Lys Glu Ile Asp
    50                  55

<210> SEQ ID NO 457
<211> LENGTH: 55
<212> TYPE: PRT
<213> ORGANISM: SARS-CoV-2

<400> SEQUENCE: 457

Asp Val Val Ile Gly Ile Asn Asn Thr Val Tyr Asp Pro Pro Glu Leu
1               5                   10                  15

Asp Ser Phe Lys Glu Glu Leu Asp Lys Tyr Phe Lys Asn His Thr Ser
            20                  25                  30

Pro Asp Val Asp Leu Gly Asp Ile Ser Gly Ile Asn Ala Ser Val Val
        35                  40                  45

Asn Ile Gln Lys Glu Ile Asp
    50                  55

<210> SEQ ID NO 458
<211> LENGTH: 60
<212> TYPE: PRT
<213> ORGANISM: SARS-CoV-2

<400> SEQUENCE: 458

```
Gln Val Thr Tyr Gln Asn Ile Ser Thr Asn Leu Pro Pro Pro Leu Leu
1               5                   10                  15

Gly Asn Ser Thr Gly Ile Asp Phe Gln Asp Glu Leu Asp Glu Phe Phe
            20                  25                  30

Lys Asn Val Ser Thr Ser Ile Pro Asn Phe Gly Ser Leu Thr Gln Ile
        35                  40                  45

Asn Thr Thr Leu Leu Asp Leu Thr Tyr Glu Met Leu
    50                  55                  60
```

<210> SEQ ID NO 459
<211> LENGTH: 56
<212> TYPE: PRT
<213> ORGANISM: SARS-CoV-2

<400> SEQUENCE: 459

```
Ala Val Asn Tyr Thr Lys Ala Pro Tyr Val Met Leu Asn Thr Ser Ile
1               5                   10                  15

Pro Asn Leu Pro Asp Phe Lys Glu Glu Leu Asp Gln Trp Phe Lys Asn
            20                  25                  30

Gln Thr Ser Val Ala Pro Asp Ser Leu Asp Tyr Ile Asn Val Thr Phe
        35                  40                  45

Leu Asp Leu Gln Val Glu Met Asn
    50                  55
```

<210> SEQ ID NO 460
<211> LENGTH: 56
<212> TYPE: PRT
<213> ORGANISM: SARS-CoV-2

<400> SEQUENCE: 460

```
Ser Val Asn Thr Lys Ala Pro Phe Ile Tyr Leu Asn Asn Ser Ile Pro
1               5                   10                  15

Asn Leu Ser Asp Phe Ala Glu Leu Ser Leu Trp Phe Lys Asn His Thr
            20                  25                  30

Ser Ile Ala Pro Asn Leu Thr Phe Asn Ser His Ile Asn Ala Thr Phe
        35                  40                  45

Leu Asp Leu Tyr Tyr Glu Met Asn
    50                  55
```

<210> SEQ ID NO 461
<211> LENGTH: 63
<212> TYPE: PRT
<213> ORGANISM: SARS-CoV-2

<400> SEQUENCE: 461

```
Asn Val Thr Phe Val Asn Ile Ser Arg Glu Leu Gln Thr Ile Val Pro
1               5                   10                  15

Glu Tyr Ile Asp Val Asn Lys Thr Leu Gln Glu Leu Ser Tyr Lys Leu
            20                  25                  30

Pro Asn Tyr Thr Val Pro Asp Leu Val Val Glu Gln Tyr Asn Gln Ile
        35                  40                  45

Leu Asn Leu Thr Ser Glu Ile Ser Thr Leu Glu Asn Lys Ser Ala
    50                  55                  60
```

```
<210> SEQ ID NO 462
<211> LENGTH: 66
<212> TYPE: PRT
<213> ORGANISM: SARS-CoV-2

<400> SEQUENCE: 462

Asn Val Thr Phe Val Asn Ile Ser Arg Val Glu Leu His Thr Val Ile
1               5                   10                  15

Pro Asp Tyr Val Asp Val Asn Lys Thr Leu Gln Glu Phe Ala Gln Asn
            20                  25                  30

Leu Pro Lys Tyr Val Lys Pro Asn Phe Asp Leu Thr Pro Phe Asn Leu
        35                  40                  45

Thr Tyr Leu Asn Leu Ser Glu Glu Lys Leu Lys Gln Leu Glu Ala Lys
    50                  55                  60

Thr Ala
65


<210> SEQ ID NO 463
<211> LENGTH: 30
<212> TYPE: PRT
<213> ORGANISM: SARS-CoV-2

<400> SEQUENCE: 463

Ala Pro Tyr Val Met Leu Asn Thr Ser Ile Pro Asn Leu Pro Asp Phe
1               5                   10                  15

Lys Glu Glu Leu Asp Gln Trp Phe Lys Asn Gln Thr Ser Val
            20                  25                  30


<210> SEQ ID NO 464
<211> LENGTH: 23
<212> TYPE: PRT
<213> ORGANISM: SARS-CoV-2

<400> SEQUENCE: 464

Ser Gln Ser Ile Ile Ala Tyr Thr Met Ser Leu Gly Ala Glu Asn Ser
1               5                   10                  15

Val Ala Tyr Ser Asn Asn Ser
            20
```

COMPOSITIONS AND METHODS FOR DETECTION AND TREATMENT OF CORONAVIRUS INFECTION

CROSS REFERENCE TO RELATED APPLICATIONS

This application claims the benefit of U.S. Provisional Application No. 63/061,344, filed on Aug. 5, 2020, the content of which is incorporated herein by reference in its entirety.

STATEMENT REGARDING FEDERALLY SPONSORED RESEARCH

This invention was made with government support under U24AI152172 and U54MD012388 awarded by the National Institute of Health. The government has certain rights in this invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 155,047 byte ASCII (text) file named "91482.251PAT_Seq Listing_ST25" created on Aug. 5, 2021.

TECHNICAL FIELD

The present invention is related to compositions and methods for diagnosing, treating, and preventing disease and predicting immune response to disease, and more particularly, is related to compositions and methods for diagnosing, treatment, prevention, and prognosis of coronavirus infections.

BACKGROUND

Severe acute respiratory syndrome coronavirus 2 (SARS-CoV-2) is a single-stranded RNA virus in the Coronaviridae family that emerged in late 2019 and has caused morbidity, mortality and economic disruption on a global scale with few precedents (Zhu et al., 2020). The Coronaviridae family includes four species/strains that are endemic in the human population and usually associated with mild, self-limiting upper respiratory tract infections: HCoV-229E, HCoV-NL63, HCoV-HKU1 and HCoV-OC43 (Betacoronavirus 1 species). Two other species, MERS-CoV and SARS-CoV, have recently emerged to cause severe disease in humans. Like the other human-infecting coronavirus (CoV) species (Callow et al., 1990; Dijkman et al., 2008), SARS-CoV-2 infection can elicit a robust antibody response in humans (Liu et al., 2020; Ni et al., 2020) and this response represents the major focus of widespread efforts to develop accurate diagnostics, as well as strategies for passive and active immunization against infection (Casadevall and Pirofski, 2020; Thanh Le et al., 2020; Krammer and Simon, 2020). Existing serological assays for SARS-CoV-2 antibody reactivity generally use full-length viral proteins or domains—Spike (S), Nucleocapsid (N), or the receptor-binding domain (RBD) of S—as antigenic baits, followed by enzyme-linked or fluorescent detection (Krammer and Simon, 2020). These assays provide a single measure of antibody reactivity, which represents a composite signal across many epitopes, and are able to detect viral exposure with a range of accuracies (Deeks et al., 2020; Whitman et al., 2020). Neutralization assays using either native or pseudotyped viruses have also been developed (Nie et al., 2020). It remains to be seen how these different assays will perform as diagnostics or correlates of the protection conferred by infection or vaccination.

Relative to protein-based analyses of the humoral response, epitope-level assays have the potential to add several layers of information. First, although SARS-CoV-2 proteins are generally distinct from other human-infecting Coronaviruses, some regions of strong homology exist (Lu et al., 2020; Zhu et al., 2020), meaning that there is the potential for immune cross-reactivity that can only be resolved at the epitope level. Indeed, it was recently demonstrated that a large fraction of non-exposed individuals have T cell reactivity to SARS-CoV-2 peptides, indicating cross-reactivity with existing responses, possibly those generated against homologous peptides from endemic CoV strains (Grifoni et al., 2020). In the case of antibody responses, cross-reactivity has been described between the more closely related SARS-CoV and SARS-CoV-2 (Lv et al., 2020; Pinto et al., 2020). Epitope-resolved analyses therefore have the potential to identify antigens that may discriminate related CoVs, leading to more specific diagnostic assays. High levels of sequence conservation may also indicate functional essentiality; therefore, by highlighting potentially cross-reactive epitopes in conserved regions of the proteome, epitope-level assays can identify antibodies and targets with therapeutic potential, against which viral escape may be more difficult (Friesen et al., 2014).

A second rationale for generating epitope-resolved views is that antibody recognition of different protein regions can have divergent functional consequences, including neutralization potential. For coronaviruses, antibodies binding the surface-exposed, receptor-binding S protein exhibit the greatest neutralizing potential (Du et al., 2009; Pillay, 2020), but these antibodies can recognize a wide variety of epitopes within the protein, each with the potential for different functional consequences. This likely accounts for the imperfect correlation between the titers of S-binding antibodies and viral neutralization activity across individuals (Robbiani et al., 2020). Due to its interaction with the host entry receptor (the angiotensin converting enzyme 2—ACE2), the RBD of S represents the predominant target of vaccination and monoclonal antibody development strategies, and a growing number of antibodies against this domain have been described (Chi et al., 2020; Hansen et al., 2020; Robbiani et al., 2020: Zost et al., 2020). However, antibodies against epitopes outside of the RBD have also been shown to have neutralizing activity (Chi et al., 2020; Poh et al., 2020): these may act in various ways, including by preventing important protease cleavage events and/or conformational changes required for successful entry into cells. On the other hand, antibodies that recognize epitopes within the N protein, which coats the viral genome and is contained within mature viral particles, likely provide little or no neutralization potential, but may be useful signatures for differentiating vaccine responses from those resulting from natural virus infection, a strategy already used for other viruses (Hoofnagle et al., 1974; Lubroth et al., 1996). In addition to different neutralization potential, it is possible that unfavorable distributions of epitope reactivity can contribute to immunopathology, for example through antibody dependent enhancement (Halstead and O'rourke, 1977; Katzelnick et al., 2017; Khurana et al., 2013), although this phenomenon remains to be demonstrated for SARS-CoV-2 (Eroshenko et al., 2020).

Peptide sub-sequences have been used for decades as probes to detect antibodies recognizing linear epitopes within the full-length proteins from which they are derived (Fleri et al., 2017; Lucchese et al., 2007). Although unable to detect antibodies whose binding depends on elements that are distal in the primary sequence, this strategy has the advantage that it enables the highly-efficient design and synthesis of antigen baits. In its simplest format, peptides can be used individually, for example in separate wells in an ELISA. A recent study used this approach to identify two linear epitopes in S protein that were targeted by neutralizing antibodies in SARS-CoV-2 convalescent donors (Poh et al., 2020). More powerful assays involve sets of peptides that are assayed in multiplex—using either spatial addressing, in the case of peptide arrays (Price et al., 2012), or DNA indexing, in the case of phage display libraries (Larman et al., 2011). Using the latter approach, the highly-multiplexed and epitope-resolved detection of antibodies to viruses has been demonstrated with high sensitivity and specificity (Xu et al., 2015).

SUMMARY

A need exists for methods of diagnosing, treating, preventing, and determining an immune response to coronavirus infections, including COVID-19 caused by SARS-CoV-2 infection. A high-resolution understanding of the antibody response to SARS-CoV-2 is important for the design of effective diagnostics, vaccines and therapeutics. However, SARS-CoV-2 antibody epitopes remain largely uncharacterized, and it is unknown whether and how the response may cross-react with related viruses.

The present disclosure presents a synthetic biology approach to highly-multiplexed peptide-based serological assays in which libraries of peptide baits—each covalently coupled to a DNA barcode—are synthesized from high-complexity DNA pools using a simple and fully in vitro approach. Library synthesis takes advantage of in vitro transcription and translation, including an intramolecular coupling mediated by puromycin (Kozlov et al., 2012) and the DNA-barcoded peptides can then be used to probe serum antibodies using a high-throughput sequencing read-out. We use this platform to synthesize libraries of overlapping 30mers covering all human coronavirus (CoV) proteomes and assay these against sera from pre-pandemic and SARS-CoV-2 convalescent donors. Our results demonstrate accurate detection of SARS-CoV-2 exposure and reveal multiple immunodominant antibody epitopes, including at least one in which antibody responses cross-react between SARS-CoV-2 and an endemic human CoV.

In some aspects, the present disclosure relates to a method of detecting in a sample the presence of an antibody that binds to a spike protein or a nucleocapsid protein of a severe acute respiratory syndrome-associated coronavirus (SARS-CoV), the method comprising: providing a biological sample from a subject suspected to be infected with a SARS-CoV; contacting the biological sample with a peptide comprising an amino acid sequence having at least 85% sequence identity to an amino acid sequence selected from the group consisting of SEQ ID NOs: 1-4, 275-412, and 421-423; and detecting antigen-antibody complexes formed. In one aspect, the method comprises contacting the biological sample with a peptide comprising an amino acid sequence having at least 85%, at least 90%, at least 91%, at least 92%, at least 93%, at least 94%, at least 95%, at least 96%, at least 97%, at least 98%, or at least 99/6 sequence identity to an amino acid sequence selected from the group consisting of SEQ ID NOs: 1-4, 275-412, and 421-423.

In other aspects, the present disclosure includes methods for diagnosing, prognosing or monitoring the treatment of a coronavirus infection in a subject by detecting in a sample from the subject the presence or absence of an antibody to a peptide comprising an amino acid sequence selected from the group consisting of SEQ ID NOS: 1-4 and SEQ ID NOS: 421-423. In various embodiments, methods for diagnosing, prognosing or monitoring the treatment of a coronavirus infection in a subject may comprise the step of detecting in a sample from the subject the presence or absence of an antibody to at least one of a first peptide, a second peptide, a third peptide, and a fourth peptide. The first peptide may comprise a first amino acid sequence comprising SEQ ID NO: 421: the second peptide may comprise a second amino acid sequence comprising SEQ ID NO: 422; the third peptide may comprise a third amino acid sequence comprising SEQ ID NO: 3; and the fourth peptide may comprise a fourth amino acid sequence comprising SEQ ID NO: 4. Further, methods of serologically detecting an antibody to coronavirus in a sample may comprise the steps of contacting the sample with a peptide under conditions sufficient to allow the binding of the antibody to the peptide, wherein the peptide comprises an amino acid sequence selected from the group consisting of SEQ ID NOS: 1-4 and SEQ ID NOS: 421-423, and detecting formation of an antibody-peptide complex comprising the antibody and the peptide. The formation of the antibody-peptide complex is indicative of an antibody to an epitope of a coronavirus antigen being present in the sample. In some embodiments, the coronavirus is severe acute respiratory syndrome coronavirus 2 (SARS-CoV-2).

The present disclosure further includes a peptide reactive with an antibody specific to coronavirus. The peptide may comprise an amino acid sequence selected from the group consisting of SEQ ID NOS: 1-4, 11, 13-15, 110-120, 275-412, and 421-423. In one aspect, the peptide comprises an amino acid sequence having at least 85%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOS: 1-4, 11, 13-15, 110-120, 275-412, and 421-423. In some embodiments, a synthesized peptide is provided comprising an amino acid sequence selected from the group consisting of SEQ ID NOS: 1-4 and 421-423 or an amino acid sequence having at least 85%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOS: 1-4 and 421-423. According to further embodiments, an immunogenic composition is provided. The immunogenic composition may comprise a peptide comprising an amino acid sequence selected from the group consisting of SEQ ID NOS: 1-4, 11, 13-15, 110-120, 275-412, and 421-423. The immunogenic composition may comprise a peptide comprising an amino acid sequence selected from the group consisting of SEQ ID NOS: 1-423. A method of eliciting an immune response in a subject may comprise the step of administering to the subject an immunogenic composition including a peptide comprising an amino acid sequence selected from the group consisting of SEQ ID NOS: 1-423, or from the group consisting of SEQ ID NOS: 1-4, 11, 13-15, 110-120, 275-412, and 421-423, or from the group consisting of SEQ ID NOS: 1-4 and 421-423. The immunogenic composition may further comprise a pharmaceutically acceptable carrier or adjuvant. Thus, a method of recruiting an antiviral antibody in a subject to prevent or limit a coronavirus infection in the subject is provided herein, wherein the antiviral antibody is specific to coronavirus.

In certain aspects, the present disclosure provides a method of detecting in a sample the presence of an antibody that binds to a spike protein or a nucleocapsid protein of a severe acute respiratory syndrome-associated coronavirus (SARS-CoV), the method comprising: providing a biological sample from a subject suspected to be infected with a SARS-CoV; contacting the biological sample with a peptide comprising an amino acid sequence selected from the group consisting of SEQ ID NOs: 1-4, 275-412, and 421-423; and detecting antigen-antibody complexes formed.

In one aspect, the method comprises the step of: detecting in the biological sample from the subject the presence or absence of an antibody to at least one of a first peptide, a second peptide, a third peptide, and a fourth peptide; wherein the first peptide comprises a first amino acid sequence comprising SEQ ID NO: 1: the second peptide comprises a second amino acid sequence comprising SEQ ID NO: 2; the third peptide comprises a third amino acid sequence comprising SEQ ID NO: 3; and the fourth peptide comprises a fourth amino acid sequence comprising SEQ ID NO: 4. In another aspect, the method comprises detecting in the biological sample from the subject the presence or absence of an antibody to the first peptide, second peptide, third peptide, and fourth peptide.

In some aspects, the method comprises the step of detecting in the biological sample from the subject the presence or absence of: a first antibody to a peptide comprising an amino sequence comprising SEQ ID NO: 421; a second antibody to a peptide comprising an amino sequence comprising SEQ ID NO: 422; and/or a third antibody to a peptide comprising an amino sequence comprising SEQ ID NO: 423. In one aspect, the method comprises detecting in the biological sample from the subject the presence or absence of the first antibody, the second antibody, and the third antibody.

In some aspects, the SARS-CoV is severe acute respiratory syndrome coronavirus 2 (SARS-CoV-2). In other aspects, the biological sample is whole blood, serum, or plasma. In yet other aspects, the method of detecting antigen-antibody complexes comprises a technique selected from the group consisting of flow cytometry, immunohistochemistry, enzyme-linked immunosorbent assay (ELISA), Western Blot, and immunoaffinity chromatography.

In certain aspects, the present disclosure relates to an immunogenic composition, comprising: a peptide comprising an amino acid sequence selected from the group consisting of SEQ ID NOs: 1-4, 275-412, and 421-423; and a pharmaceutically acceptable carrier or adjuvant. In other aspects, the present disclosure relates to an immunogenic composition, comprising: a peptide comprising an amino acid sequence selected from the group consisting of SEQ ID NOs: 424-447; and a pharmaceutically acceptable carrier or adjuvant. In yet other aspects, the present disclosure relates to an immunogenic composition, comprising: a peptide comprising an amino acid sequence selected from the group consisting of SEQ ID NOs: 1-4, 275-412, and 421-447 or an amino acid sequence having at least 85%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs: 1-4, 275-412, and 421-447; and a pharmaceutically acceptable carrier or adjuvant.

In one aspect, the immunogenic composition comprises: a first peptide comprising an amino sequence comprising SEQ ID NO: 421; a second peptide comprising an amino sequence comprising SEQ ID NO: 422; and/or a third peptide comprising an amino sequence comprising SEQ ID NO: 423.

In another aspect, the immunogenic composition comprises: a first peptide comprising an amino sequence comprising SEQ ID NO: 435; a second peptide comprising an amino sequence comprising SEQ ID NO: 441; a third peptide comprising an amino sequence comprising SEQ ID NO: 442; and/or a fourth peptide comprising an amino sequence comprising SEQ ID NO: 447.

In one aspect, the immunogenic composition comprises: a first peptide comprising an amino sequence comprising SEQ ID NO: 1; a second peptide comprising an amino sequence comprising SEQ ID NO: 2, a third peptide comprising an amino sequence comprising SEQ ID NO: 3; and/or a fourth peptide comprising an amino sequence comprising SEQ ID NO: 4.

In another aspect, the immunogenic composition comprises: a first peptide comprising an amino sequence comprising SEQ ID NO: 422; a second peptide comprising an amino sequence comprising SEQ ID NO: 423; a third peptide comprising an amino sequence comprising SEQ ID NO: 435; a fourth peptide comprising an amino sequence comprising SEQ ID NO: 441; a fifth peptide comprising an amino sequence comprising SEQ ID NO: 442; and/or a sixth peptide comprising an amino sequence comprising SEQ ID NO: 447.

In other aspects, the present disclosure relates to a method of eliciting an immune response in a subject, the method comprising administering to the subject an immunogenic composition disclosed herein.

In certain aspects, the present disclosure provides a method of detecting in a sample the presence of an antibody that binds to a spike protein or a nucleocapsid protein of a severe acute respiratory syndrome-associated coronavirus (SARS-CoV), the method comprising: providing a biological sample from a subject suspected to be infected with a SARS-CoV; contacting the biological sample with a peptide comprising an amino acid sequence selected from the group consisting of SEQ ID NOs: 424-447; and detecting antigen-antibody complexes formed.

In one aspect, the method comprises the step of detecting in the biological sample from the subject the presence or absence of: a first antibody to a peptide comprising an amino sequence comprising SEQ ID NO: 435; a second antibody to a peptide comprising an amino sequence comprising SEQ ID NO: 441; a third antibody to a peptide comprising an amino sequence comprising SEQ ID NO: 442; and/or a fourth antibody to a peptide comprising an amino sequence comprising SEQ ID NO: 447.

In yet another aspect, the disclosure provides a method of detecting in a sample the presence of an antibody that binds to a spike protein or a nucleocapsid protein of a severe acute respiratory syndrome-associated coronavirus (SARS-CoV), the method comprising: providing a biological sample from a subject suspected to be infected with a SARS-CoV; contacting the biological sample with a peptide comprising an amino acid sequence selected from the group consisting of SEQ ID NOs: 1-4, 275-412, and 421-447 or an amino acid sequence having at least 85%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs: 1-4, 275-412, and 421-447; and detecting antigen-antibody complexes formed.

In one aspect, the method comprises the step of detecting in the biological sample from the subject the presence or absence of: a first antibody to a peptide comprising an amino sequence comprising SEQ ID NO: 422; a second antibody to a peptide comprising an amino sequence comprising SEQ ID NO: 423; a third antibody to a peptide comprising an amino sequence comprising SEQ ID NO: 435; a fourth antibody to a peptide comprising an amino sequence comprising SEQ ID NO: 441; a fifth antibody to a peptide comprising an amino sequence comprising SEQ ID NO: 442; and/or a sixth antibody to a peptide comprising an amino sequence comprising SEQ ID NO: 447. In another aspect, the method comprises the step of detecting in the biological sample from the subject the presence or absence of the first antibody, second antibody, third antibody, fourth antibody, fifth antibody, and sixth antibody.

In some aspects, the present disclosure provides a method for diagnosing, prognosing or monitoring the treatment of a coronavirus infection in a subject, the method comprising the step of: detecting in a sample from the subject the presence or absence of an antibody to at least one of a first peptide, a second peptide, a third peptide, and a fourth peptide; wherein the first peptide comprises a first amino acid sequence selected from the group consisting of SEQ ID NOs: 1-4, 11, 13-15, 110-120, 275-412, and 421-423; wherein the second peptide comprises a second amino acid sequence selected from the group consisting of SEQ ID NOs: 1-4, 11, 13-15, 110-120, 275-412, and 421-423; wherein the third peptide comprises a third amino acid sequence selected from the group consisting of SEQ ID NOs: 1-4, 11, 13-15, 110-120, 275-412, and 421-423; wherein the fourth peptide comprises a fourth amino acid sequence selected from the group consisting of SEQ ID NOs: 1-4, 11, 13-15, 110-120, 275-412, and 421-423; and wherein the first peptide, second peptide, third peptide, and fourth peptide comprise different amino acid sequences.

In other aspects, the present disclosure provides a method of serologically detecting an antibody to coronavirus in a sample, the method comprising the steps of: contacting the sample with a peptide, under conditions sufficient to allow the binding of the antibody to the peptide, wherein the peptide comprises an amino acid sequence selected from the group consisting of SEQ ID NOs: 1-4, 11, 13-15, 110-120, 275-412, and 421-423; and detecting formation of an antibody-peptide complex comprising the antibody and the peptide, wherein formation of the antibody-peptide complex is indicative of an antibody to an epitope of a coronavirus antigen being present in the sample.

In some aspects, the amino acid sequence is selected from the group consisting of SEQ ID NOs: 1-4 and 421-423. In other aspects, the subject is human.

In other aspects, the present invention provides a peptide reactive with an antibody specific to coronavirus, where in the peptide comprises an amino acid sequence selected from the group consisting of SEQ ID NOs: 1-4, 11, 13-15, 110-120, 275-412, and 421-423. In one aspect, the present invention provides a peptide reactive with an antibody specific to coronavirus, where in the peptide comprises an amino acid sequence selected from the group consisting of 1-4, 275-412, and 421-447.

In other aspects, the present invention provides an immunogenic composition, comprising: a peptide comprising an amino acid sequence selected from the group consisting of SEQ ID NOs: 1-447.

In yet other aspects, the present disclosure relates to a method of eliciting an immune response in a subject, the method comprising: administering to the subject an immunogenic composition including a peptide comprising an amino acid sequence selected from the group consisting of SEQ ID NOs: 1-423. In one aspect, the present disclosure relates to a method of eliciting an immune response in a subject, the method comprising: administering to the subject an immunogenic composition including a peptide comprising an amino acid sequence selected from the group consisting of SEQ ID NOs: 1-447.

In some aspects, the present invention provides a method of recruiting an antiviral antibody in a subject to limit a coronavirus infection in the subject, the method comprising: administering a peptide to the subject, wherein the peptide comprises an amino acid sequence selected from the group consisting of SEQ ID NOs: 1-4, wherein the antiviral antibody is specific to coronavirus. In one aspect, the present invention provides a method of recruiting an antiviral antibody in a subject to limit a coronavirus infection in the subject, the method comprising: administering a peptide to the subject, wherein the peptide comprises an amino acid sequence selected from the group consisting of SEQ ID NOs: 1-4, 275-412, and 421-447; wherein the antiviral antibody is specific to coronavirus.

The foregoing features and elements may be combined in various combinations without exclusivity, unless expressly indicated otherwise. These features and elements as well as the operation thereof will become more apparent in light of the following description. It should be understood, however, the following description is intended to be exemplary in nature and non-limiting.

BRIEF DESCRIPTION OF THE FIGURES

Illustrative and exemplary embodiments of the invention are shown in the drawings in which:

FIGS. 5A-5D illustrate Spike HR2 antibodies elicited by SARS-CoV-2 strongly cross-react with the homologous region of Betacoronavirus 1.

DETAILED DESCRIPTION

Figure 1A:
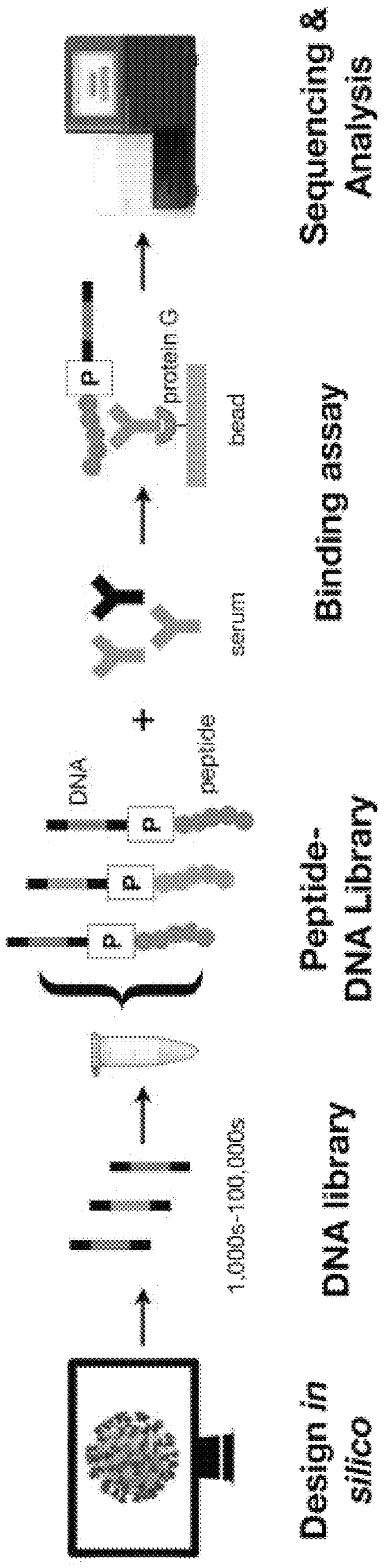
FIGS. 1A-1D illustrate epitope-resolved CoV serology using a highly-multiplexed peptide-based assay.

It is to be understood that unless specifically stated otherwise, references to “a,” “an,” and/or “the” may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

Generally, some embodiments of the present invention can be used to develop diagnostics, therapies, and vaccines for coronavirus infection based on the peptides and epitopes identified in the present disclosure. Among the various aspects of the present invention is the provision of one or more targets for diagnosing, treating, and preventing coronavirus infection in a subject. The disclosed epitope regions of coronaviruses, including SARS-CoV-2, indicate uses including serological assays, vaccines for eliciting antibodies, and predicting an individual's antibody response to a coronavirus infection.

The invention may comprise methods for detecting the presence of, exposure to, or infection by a particular virus in a sample. The invention may further comprise methods of population screening, predicting immune response or disease outcome in an individual, serological assays, and neutralization assays. The invention may further comprise a method of eliciting neutralization antibodies to coronavirus.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject or organism. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues.

The terms "peptide," "polypeptide," and "protein" are used interchangeably herein to refer to polymers of amino acids of any length, chemically or biochemically modified or derivatized amino acids, and polypeptides having modified peptide backbones. These terms also include proteins that are post-translationally modified through reactions that include glycosylation, acetylation and phosphorylation. The term "at least a portion" of a polypeptide means a portion having the minimal size characteristics of such sequences, or any larger fragment of the full length molecule, up to and including the full length molecule. For example, a portion of a polypeptide may be 4 to 15 amino acids, or may be 4 amino acids, 5 amino acids, 6 amino acids, 7 amino acids, and so on, up to a full length polypeptide. A portion of a polypeptide useful as an epitope may be as short as 4 amino acids. A portion of a polypeptide that performs the function of the full-length polypeptide would generally be longer than 4 amino acids.

The term "amino acid" refers to naturally occurring and synthetic amino acids, as well as amino acid analogs and amino acid mimetics that function in a manner similar to naturally occurring amino acids. Naturally occurring amino acids are those encoded by the genetic code, as well as those amino acids that are later modified. Unnatural amino acids are not encoded by the genetic code and can, but do not necessarily have the same basic structure as a naturally occurring amino acid. "Amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to by either the three letter symbols or by the one-letter symbols recommended by the IUPAC, the IUAPC letter code are as follows: G=Glycine; A=Alanine; L=Leucine; M=Methionine; F=Phenylalanine; W=Tryptophan; K=Lysine; Q=Glutamine; E=Glutamic Acid; S=Serine; P=Proline; V=Valine; I=Isoleucine; C=Cysteine; Y=Tyrosine; H=Histidine; R=Arginine; N=Asparagine; D=Aspartic Acid; T=Threonine.

The terms "homologous" and "similar" refer to the relationship between proteins that possess a "common evolutionary origin," including proteins from superfamilies (e.g., the immunoglobulin superfamily) and homologous proteins from different species. Such proteins (and their encoding genes) have sequence homology, as reflected by their sequence similarity, whether in terms of percent similarity or the presence of specific residues or motifs as conserved positions. In a specific embodiment, two peptide sequences are "substantially homologous or similar" when at least about 80%, or at least about 90%, or at least about 95) of the amino acids match over the defined lengths of the amino acid sequences.

The term "variant" applies to both amino acid and nucleic acid sequences. Because of the degeneracy of the genetic code, a large number of functionally identical nucleic acids encode any given protein. For instance, the codons GCA, GCC, GCG and GCU all encode the amino acid alanine. Variants may include individual substitutions, deletions or additions to a nucleic acid, peptide, polypeptide, or protein sequence which alters, adds or deletes a single amino acid or a small percentage of amino acids in the encoded sequence.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide.

Amino acids other than those indicated as conserved may differ in a protein so that the percent protein or amino acid sequence similarity between any two proteins of similar function may vary and may be, for example, from 70% to 99% as determined according to an alignment scheme. A "variant" also includes a polypeptide which has at least 60% amino acid identity as determined by BLAST or FASTA algorithms, preferably at least 75% most preferably at least 85%, and even more preferably at least 90%, and still more preferably at least 95%, and which has the same or substantially similar properties or functions as the native or parent protein to which it is compared. A particular variant is a "gain-of-function" variant, meaning a polypeptide variant in which the change of at least one given amino acid residue in a protein or enzyme improves a specific function of the polypeptide, including, but not limited to protein activity. The change in amino acid residue can be replacement of an amino acid with one having similar properties.

The term "antibody" is used herein in the broadest sense and refers generally to a molecule that contains at least one antigen binding site that immunospecifically binds to a particular antigen target of interest. The term "antibody" thus includes but is not limited to native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term "antibody," thus, includes full length antibodies and/or their variants, as well as fragments thereof. Binding of an antibody to a target can cause a variety of effects, such as but not limited to where such binding modulates, decreases, increases, antagonizes, agonizes, mitigates, alleviates, blocks, inhibits, abrogates and/or interferes with at least one target activity or binding, or with receptor activity or binding, in vitro, in situ, and/or in vivo.

Antibodies (Abs) can be assigned to different classes, which differ in their biological properties, functional locations, and ability to deal with different antigens. There are five major classes of immunoglobulins (Ig): IgA, IgD, IgE, IgG, and IgM, and several of these may be further divided into subclasses (isotypes), e.g., IgG1, IgG2, IgG3, IgG4, IgA, and IgA2. The classes of immunoglobulins differ in their biological properties, functional locations, and interactions with different antigens. Immunoglobulin G (IgG), the major antibody in serum, is a heterotetrameric protein with two heavy chains and two light chains. IgG can be cleaved into three 50-kd fragments: two Fab fragments that bind antigen (F=fragment, ab=antigen binding), and an Fc fragment that crystallizes readily and does not bind antigen. The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The term "antigen" refers to any substance that triggers the immune system to produce antibodies against it. An antigen acts by stimulating the proliferation of the small number of cells that were already forming an antibody capable of recognizing the antigen.

Antibodies have specific and high affinity for the antigens that elicited their synthesis. Synthetic peptides can serve as antigens to stimulate the formation of specific antibodies. An antibody recognizes, on a large molecule, a specific group or cluster of amino acids called an epitope.

As used herein, the term "epitope" refers to a portion of an antigenic molecule to which an antibody is produced and to which the antibody will bind. For example, a "Coronavirus epitope" comprises the part of a coronavirus protein to which an anti-coronavirus antibody specifically binds. Epitopes can comprise linear amino acid residues (i.e., residues within the epitope are arranged sequentially one after another in a linear fashion), nonlinear amino acid residues, or both linear and nonlinear amino acid residues.

The terms "immunogen" and "immunogenic" refer to any compound or substance that is capable of eliciting an immune response in a human or non-human individual to the compound or substance, such as an antigen.

As used herein, the term "binding" refers to an attractive interaction between two molecules which results in a stable association in which the molecules are in close proximity to each other. Molecular binding can be classified into the following types: non-covalent, reversible covalent and irreversible covalent. Molecules that can participate in molecular binding include proteins, nucleic acids, carbohydrates, lipids, and small organic molecules such as pharmaceutical compounds. For example, proteins that form stable complexes with other molecules are often referred to as receptors while their binding partners are called ligands. Nucleic acids can also form stable complex with themselves or others, for example, DNA-protein complex, DNA-DNA complex, DNA-RNA complex.

As used herein, the term "specific binding" refers to the specificity of a binder, e.g., a protein or an antibody, such that it preferentially binds to a target, such as a polypeptide antigen, a receptor, or an antibody. When referring to a binding partner, e.g., protein, nucleic acid, antibody or other affinity capture agent, etc., "specific binding" can include a binding reaction of two or more binding partners with high affinity and/or complementarity to ensure selective hybridization under designated assay conditions. Typically, specific binding will be at least three times the standard deviation of the background signal. Thus, under designated conditions the binding partner binds to its particular target molecule and does not bind in a significant amount to other molecules present in the sample. Recognition by a binder or an antibody of a particular target in the presence of other potential interfering substances is one characteristic of such binding. Preferably, binders, antibodies or antibody fragments, peptides, or fusion peptides that are specific for or bind specifically to a target bind to the target with higher affinity than binding to other non-target substances. Also preferably, binders, antibodies or antibody fragments, peptides, or fusion peptides that are specific for or bind specifically to a target avoid binding to a significant percentage of non-target substances, e.g., non-target substances present in a testing sample. The binding affinity of an antibody to a target antigen, antigenic fragment, peptide, or fusion peptide, comprising the cognate epitope can be readily determined using any of a number of methods available in the art including, but not limited to, enzyme linked immunosorbent assay (ELISA). In some embodiments, binders, antibodies or antibody fragments, peptides, or fusion peptides of the present disclosure avoid binding greater than about 90% of non-target substances, although higher percentages are clearly contemplated and preferred. For example, binders, antibodies or antibody fragments, peptides, or fusion peptides of the present disclosure avoid binding about 91%, about 92%, about 93%, about 94%, about 95%, about 96%, about 97%, about 98%, about 99%, and about 99% or more of non-target substances. In other embodiments, binders, antibodies or antibody fragments, peptides, or fusion peptides of the present disclosure avoid binding greater than about 10%, 20%, 30%, 40%, 50%, 60%, or 70%, or greater than about 75%, or greater than about 80%, or greater than about 85% of non-target substances.

A target or a marker may be any molecular structure produced by a cell, expressed inside the cell, accessible on the cell surface, or secreted by the cell. A marker may be any protein, carbohydrate, fat, nucleic acid, catalytic site, or any target of these such as an enzyme, glycoprotein, cell membrane, virus, cell, organ, organelle, or any uni- or multimolecular structure or any other such structure now known or yet to be disclosed whether alone or in combination. A target may also be called a marker and the terms are used interchangeably.

A target may be represented by the sequence of amino acids, or sequence of one or more strands of a nucleic acid from which it may be derived. For example, a target may be represented by a protein sequence. Alternatively, a target may be represented by a nucleic acid sequence, the protein or peptide or the fragments thereof encoded by the nucleic acid sequence. Examples of such nucleic acids include both single stranded and double stranded nucleic acid sequences including miRNA, tRNA, siRNA, mRNA, cDNA, or genomic DNA sequences including complimentary sequences. The concept of a marker is not limited to the products of the exact nucleic acid sequence or protein sequence by which it may be represented. Rather, a marker encompasses all molecules that may be detected by a method of assessing the expression of the marker. Examples of molecules encompassed by a marker include point mutations, silent mutations, deletions, frameshift mutations, translocations, alternative splicing derivatives, differentially methylated sequences, differentially modified protein sequences, truncations, soluble forms of cell membrane associated markers, and any other variation that results in a product that may be identified as the marker. The term "target" further encompasses the products (i.e., proteins) of the gene or a gene allele thereof, whose expression or activity is directly or indirectly associated with a particular phenotype or cellular condition, or physiological characteristic.

Indirect methods of detecting a marker generally involve assessing the expression of material created from a genomic DNA template such as an RNA or protein molecule. Such expression may be assessed by any of a number of methods used currently in the art and yet to be developed. Examples include any nucleic acid detection method including the following nonlimiting examples, microarray RNA analysis, RNA in situ hybridization, RNAse protection assay, Northern blot, reverse transcription PCR, and quantitative reverse transcription PCR. Other examples include any process of detecting expression that uses an antibody including the following nonlimiting examples, flow cytometry, immunohistochemistry, ELISA, Western blot, Northwestern blot, and immunoaffinity chromatography. Antibodies may be monoclonal, polyclonal, or any antibody fragment including a Fab, $F(ab)_2$, Fv, scFv, phage display antibody, peptibody, multispecific ligand, or any other reagent with specific binding to a target. Other methods of assessing protein expression include the following nonlimiting examples: HPLC, mass spectrometry, protein microarray analysis, PAGE analysis, isoelectric focusing, 2-D gel electrophoresis, and enzymatic assays.

One aspect of the disclosure encompasses methods of eliciting an immune response in a subject by administering to the subject an immunogenic composition. The methods may include recruiting an antiviral antibody in the subject, to protect the subject against a coronavirus infection. The methods, vaccines, and therapeutics may include including a peptide comprising an amino acid sequence selected from the group consisting of SEQ ID NOS: 1-4 and 421-423. The methods, vaccines, and therapeutics may include, for example, a monoclonal antibody produced using the peptides disclosed herein.

Agents that interact with a therapeutic target to result in a desirable therapeutic effect may include a pharmaceutically active ingredient or pharmaceutically acceptable salt thereof, a drug, a toxin, a chemical, a small organic molecule, a large molecule or peptide or an antibody. Large-molecule pharmaceuticals refer to pharmaceutical agents having a molecular weight greater than about 1000 Daltons, e.g., peptidic drugs, vaccines and hormones. The term "antibody" is used herein in the broadest sense and refers generally to a molecule that contains at least one antigen binding site that immunospecifically binds to a particular antigen target of interest. Antibody thus includes but is not limited to native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term, thus, includes full length antibodies and/or their variants as well as immunologically active fragments thereof, thus encompassing, antibody fragments capable of binding to a biological molecule (such as an antigen or receptor) or portions thereof, including, but not being limited to, Fab, Fab', F(ab')2, facb, pFc', Fd, Fv or scFv (See, e.g., CURRENT PROTOCOLS IN IMMUNOLOGY, (Colligan et al., eds., John Wiley & Sons, Inc., NY, 1994-2001).

The screening or creation, identification and selection of appropriate therapeutic agent through the target identified herein can be accomplished by a variety of methods. One approach is to use structural knowledge about the target protein to design a candidate molecule with which it will precisely interact. An example would be computer assisted molecular design. A second approach is to use combinatorial or other libraries of molecules, whereby a large library of molecules is screened for inhibitory effect with regard to the target gene or protein expression, or ability to inhibit the transcriptional factor activity of the target protein. In a further example, a panel of antibodies may be screened for their ability to inhibit the target protein.

The term "monoclonal antibody" as used herein refers to an antibody obtained from a population of substantially homogeneous antibodies, i.e., the individual antibodies comprising the population are identical except for possible naturally occurring mutations that may be present in minor amounts. Various procedures known in the art may be used for the production of polyclonal or monoclonal antibodies to Coronavirus polypeptides or derivatives or analogs thereof. For the production of antibodies, various host animals can be immunized by injection with the antigenic polypeptide, including but not limited to rabbits, mice, rats, sheep, goats, etc. For preparation of monoclonal antibodies directed toward the Coronavirus polypeptides, any technique that provides for the production of antibody molecules by continuous cell lines in culture may be used. These include but are not limited to the hybridoma technique originally developed by Kohler and Milstein (Nature 256:495-497, 1975), as well as the trioma technique, the human B-cell hybridoma technique (Kozbor et al., Immunology Today 4:72, 1983; Cote et al., Proc. Natl. Acad. Sci. U.S.A. 80:2026-2030, 1983), and the EBV-hybridoma technique to produce human monoclonal antibodies (Cole et al., in Monoclonal Antibodies and Cancer Therapy, Alan R. Liss, Inc., pp. 77-96, 1985).

In the preparation of the pharmaceutical compositions comprising the antibodies described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

In other embodiments there is provided a pharmaceutical composition including an antibody or fragment as described above together with a pharmaceutically acceptable carrier, diluent or excipient. As used herein, "carrier(s)" can be used interchangeably with "excipient(s)" Carriers include any substance that may be administered with the one or more disclosed compounds with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, and oils (including petroleum, animal, vegetable or synthetic oils). Thus, the pharmaceutical compositions may generally comprise a pharmaceutically acceptable carrier and a pharmacologically effective amount of the antibodies, or mixture of antibodies. The pharmaceutical composition may be formulated as powders, granules, solutions, suspensions, aerosols, solids, pills, tablets, capsules, gels, topical creams, suppositories, transdermal patches, and other formulations known in the art.

The pharmaceutical compositions described herein may be administered by any means that enables the active agent to reach the agent's site of action in the body of the subject. The dosage administered varies depending upon factors, such as: pharmacodynamic characteristics; mode and route of administration; age, health, and weight of the recipient subject; nature and extent of symptoms; concurrent treatments; and frequency of treatment.

As used herein, the terms "administration" and "administering" of an agent to a subject include any route of introducing or delivering the agent to a subject to perform its intended function. Administration can be carried out by any suitable route, including intravenously, intramuscularly, intraperitoneally, inhalationally, intranasally, or subcutaneously. Administration includes self-administration and the administration by another.

The term "effective amount" or "therapeutically effective amount" refers to that amount of an agent or combination of agents as described herein that is sufficient to effect the intended application including, but not limited to, disease treatment and/or disease prevention. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells. The specific dose will vary depending on the particular agents chosen, the dosing regimen to be followed, whether the agent is administered in combination with other agents, timing of administration, the tissue to which it is administered, and the physical delivery system in which the compound is carried.

The terms "treatment," "treating," "treat," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

As used herein, the term "patient" or "subject" refers to any organism to which a provided composition is or may be administered, e.g., for experimental, diagnostic, prophylactic, cosmetic, and/or therapeutic purposes. For example, subject may refer to a human or a non-human animal. In some aspects, subject refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In further embodiments, the subject is a human.

The following examples are given for illustrative and non-limiting purposes of the present invention.

EXAMPLES

In this example, a multiplexed peptide assay ('PepSeq') was used to generate an epitope-resolved view of antibody reactivity across all human coronaviruses (CoVs). PepSeq accurately classified SARS-CoV-2 exposure status and revealed epitopes across the Spike and Nucleocapsid proteins. Two of these epitopes represent recurrent reactivities to conserved, functionally-important sites in the S2 subunit of Spike, regions that we show are also targeted for the endemic CoVs in pre-pandemic controls. At one of these sites, we demonstrate that the SARS-CoV-2 response strongly and recurrently cross-reacts with the endemic virus hCoV-OC43. Our epitope-resolved analysis reveals new targets for the development of diagnostics, vaccines and therapeutics, including a site that may have broad neutralizing potential.

Methods

Samples

COVID-19 convalescent serum and plasma samples were collected at four clinical sites from patients who had tested positive for SARS-CoV-2 by RT-PCR a median of 28.5 days prior. Pre-pandemic negative control samples were collected from two sites. Pre-pandemic negative control serum samples were characterized using our SCV2 library (n=17). These samples were collected during January 2015 from multiple locations in California. Pre-pandemic negative control serum samples characterized using our HV library (n=33) were collected during 2019 (latest collections were during the first week of December). Serum was obtained from whole blood using lithium heparin gel plasma separator tubes followed by centrifugation.

PepSeq Library Design

We designed two different libraries of peptides in order to assess antibody reactivity to SARS-CoV-2 peptides and to peptides from other human-infecting coronaviruses. The first set of peptides, referred to herein as the "human virome" (HV) peptides, was designed to broadly cover potential epitope diversity for all viruses known to infect humans. To generate this design, we downloaded all protein sequences available in UniProt, on Nov. 19, 2018, that were linked to 474 viral species-level taxonomy IDs. Following a series of quality filters to remove identical sequences, those that were too short (<30 aa), those that contained recombinant non-viral sequences and those that were taxonomically misclassified, we were left with 1,300,994 target protein sequences. In order to control for sampling bias within the database, we randomly subsampled overrepresented virus species, including no more than 2000 and 4000 sequences for viruses with RNA and DNA genomes, respectively. Additional protein sequences were allowed for DNA viruses because they often contain larger genomes and proteomes (i.e., more distinct genes). When down-sampling, priority was given to proteins from the Swiss-Prot database, which have been manually reviewed. The final down-sampled target set included 148,215 protein sequences and 88.78 M amino acids.

Our HV peptides were designed using an epitope-centric set cover design algorithm, with a focus on optimizing 9mer (i.e., 9 amino acid long) epitope coverage using 30mer peptides. To reduce the runtime and memory requirements of the algorithm, we partitioned our target protein sequences according to taxonomy. Given the high levels of genetic divergence between viral families and genera, we do not expect that this partitioning substantially impacted our final design. Including a small set of negative control peptides selected from eukaryotic proteins, this design included 244,000 unique 30mer peptides, and represents approximately 70% of all potential 9mer epitopes contained within the target protein sequences. Each of these peptides was represented by a single nucleotide encoding. This design does not contain any peptides derived from SARS-CoV-2, but does contain full proteome coverage of the other six coronaviruses known to infect humans: Human coronavirus 229E (NCBI taxID: 11137), Human coronavirus NL63 (NCBI taxID: 277944), Human coronavirus HKU1 (NCBI taxID: 290028), Betacoronavirus 1 (NCBI taxID: 694003, includes Human coronavirus OC43), Severe acute respiratory syndrome-related coronavirus (NCBI taxID: 694009, "SARS"), and Middle East respiratory syndrome-related coronavirus (NCBI taxID: 1335626, "MERS").

Our second design (SCV2) focused almost entirely on SARS-CoV-2, including high density tiling of peptides across the two most immunogenic SARS-CoV-2 proteins: the spike glycoprotein (S) and the nucleocapsid protein (N). As targets for this design, we utilized 2303 SARS-CoV-2 genome sequences downloaded from GISAID on Apr. 3, 2020, along with six locally generated sequences. Using these genomes, we first generated consensus amino acid sequences for the S and N proteins. In our design, we included all of the unique 30mer peptides contained in these consensus sequences, equivalent to a 1-step sliding window approach (Shiryaev et al., 2012). Additionally, we used the same epitope-centric set cover design algorithm used for HV in order to capture amino acid-level polymorphisms present within our full set of target genomes. This aspect of the design ensured that 100% of the unique 16mer peptides present in the S and N proteins from the 2309 SARS-CoV-2 genomes were represented in our design. In total, this design included 1550 30mer peptides from the S protein and 557 30mer peptides from the N protein. Each of these peptides was represented by three different nucleotide encodings. This design also included a set of 373 control peptides. These controls represent a subset of the HV peptides, which we have determined are commonly recognized by IgG antibodies in human sera (unpublished results). Therefore, we expect that some fraction of these controls will be recognized by antibodies in each blood sample tested. Collectively, these peptides were designed from 55 different virus species, including the four endemic human coronaviruses.

PepSeq Library Synthesis and Assay

Libraries of covalently-coupled peptide:DNA conjugates were prepared from pools of DNA oligonucleotide templates in bulk enzymatic reactions using the method described previously (Kozlov et al., 2012), with minor modifications as noted hereafter. Briefly, pools of ssDNA templates (Agilent) were PCR-amplified and the dsDNA products were used as templates for in vitro transcription (Ampliscribe). The resulting mRNA was ligated to a hairpin oligonucleotide adapter bearing a puromycin molecule tethered by a PEG spacer and, following buffer exchange, the reaction mix was used as a template in an in vitro translation reaction (PURExpress, NEB). Constructs bearing mRNA—comprising of (i) mRNA, (ii) mRNA+adapter, (iii) mRNA+adapter+peptide—were isolated using magnetic beads coated with a DNA oligo complementary to a 30-mer sequence in the mRNA constant region. A reverse transcription reaction, primed by the adapter hairpin, was used to generate cDNA, after which RNase was applied to remove mRNA. Product was buffer-exchanged, quantified by running on a gel against standard DNA oligos of known concentrations, and used without further modifications or purification.

To perform serological assays, 5 uL of a 1:10 dilution of serum in Superblock T20 (Thermo) was added to 0.1 pmol of PepSeq library for a total volume of 10 uL and was incubated at 20° C. overnight. The binding reaction was applied to pre-washed protein G-bearing beads (Thermo) for 15 minutes, after which beads were washed 10 times with 1×PBST (washing steps were performed on an EpMotion robot, Eppendorf). After the final wash, beads were resuspended in 30 uL of water and heated to 95° C. for 5 minutes to elute bound product. Elutions were amplified and indexed using barcoded DNA oligos. Following PCR cleanup, products were pooled, quantified and sequenced on a NextSeq instrument (Illumina).

PepSeq Data Analysis

We used PepSIRF v1.3.0 (Fink et al., 2020), along with custom scripts, to analyze the PepSeq HTS data. The data analysis included three primary steps: 1) demultiplexing and assignment of reads to peptides, 2) calculation of enrichment Z-scores individually for each assay and peptide and 3) identification of enriched peptides for each sample based on the consistency of Z-scores across replicates.

Demultiplexing and assignment of reads to peptides was done using the demux module of PepSIRF (Fink et al., 2020), allowing up to 1 mismatch within each of the index sequences and up to 2 mismatches with the expected DNA tag (90 nt in length). Z-scores were calculated using a method adapted from (Mina et al., 2019). This process involved the generation of peptide bins, each of which contained ≥300 peptides with similar starting abundance in our PepSeq assay. Starting abundance for each peptide was estimated using buffer-only controls. In total, 4-8 independent buffer-only controls were used to generate the bins for this study. The raw read counts from each of these controls were first normalized to reads per million (RPM) using the column sum normalization method in the norm module of PepSIRF. This was to ensure that independent assays were weighted evenly, regardless of differences in the depth of sequencing. Bins were then generated using the bin PepSIRF module.

Z-scores were calculated using the zscore module of PepSIRF, and each Z-score corresponds to the number of standard deviations away from the mean, with the mean and standard deviation calculated independently for the peptides from each bin. It is important that the mean and standard deviation reflect the distribution of unenriched peptides within a bin. Therefore, these calculations were based on the 75% highest density interval of read counts within each bin. Prior to Z-score calculation, RPM counts for each peptide were further normalized by subtracting the average RPM count observed within our superblock-only controls. This second normalization step controlled for variability in peptide starting abundance within a bin. Finally, the "p_enrich" module of PepSIRF was used to determine which peptides had been enriched through our assay. This module identifies peptides that meet or exceed minimum thresholds, in both replicates, for Z-score and normalized read count. Decision tree analysis was conducted using the DecisionTreeClassifier method in the Scikit-learn Python module, v0.20.1.

Visualization of Protein Structure

To visualize our identified SARS-CoV-2 epitopes within the 3D conformational structure of the S protein, we utilized the cryo-electron microscopy (Cryo-EM) structure available in the RCSB Protein Data Bank (PDB id: 6VY). To compare epitope positions across CoV species, we built three additional structures using Cryo-EM templates from PDB: 5SZS for hCoV-NL63, 6ACD for SARS-CoV and 6NZK for hCoV-OC43. We performed structural modelling using Swiss-Model software (Waterhouse et al., 2018). Structural alignments and image preparation were done with PyMOL (version 2.3.2, Schrodinger, LLC). For positioning of epitopes in the structures with respect to the SARS-CoV-2 spike protein, we performed corresponding amino acid sequence alignments with Clustal Omega. To build models of the post-fusion state for S2 subunit fragments, we used the Cryo-EM structure for murine SARS-CoV, determined by Walls et al. (PDB id: 6B3O) (Walls et al., 2017).

Results

A Highly-Multiplexed Peptide Assay to Evaluate CoV Antibody Responses

To generate a broad and high-resolution view of the antibody response to human coronaviruses, including SARS-CoV-2, we designed and synthesized two separate DNA-barcoded 30mer peptide libraries, using the method described previously (Kozlov et al., 2012) (FIG. 1A). FIG. 1A shows a method and platform for customizable highly-multiplexed peptide-based serology, comprising the following steps: (i) in silico design, (ii-iii) generation of a library of DNA-barcoded peptides from oligonucleotide templates using bulk in vitro reactions (transcription, ligation of a Puromycin (P)-containing adapter, translation, reverse transcription), (iv) serum binding assay and protein G capture, and (v) sequencing and analysis of the distribution of binders by their DNA barcodes.

Figure 1B:
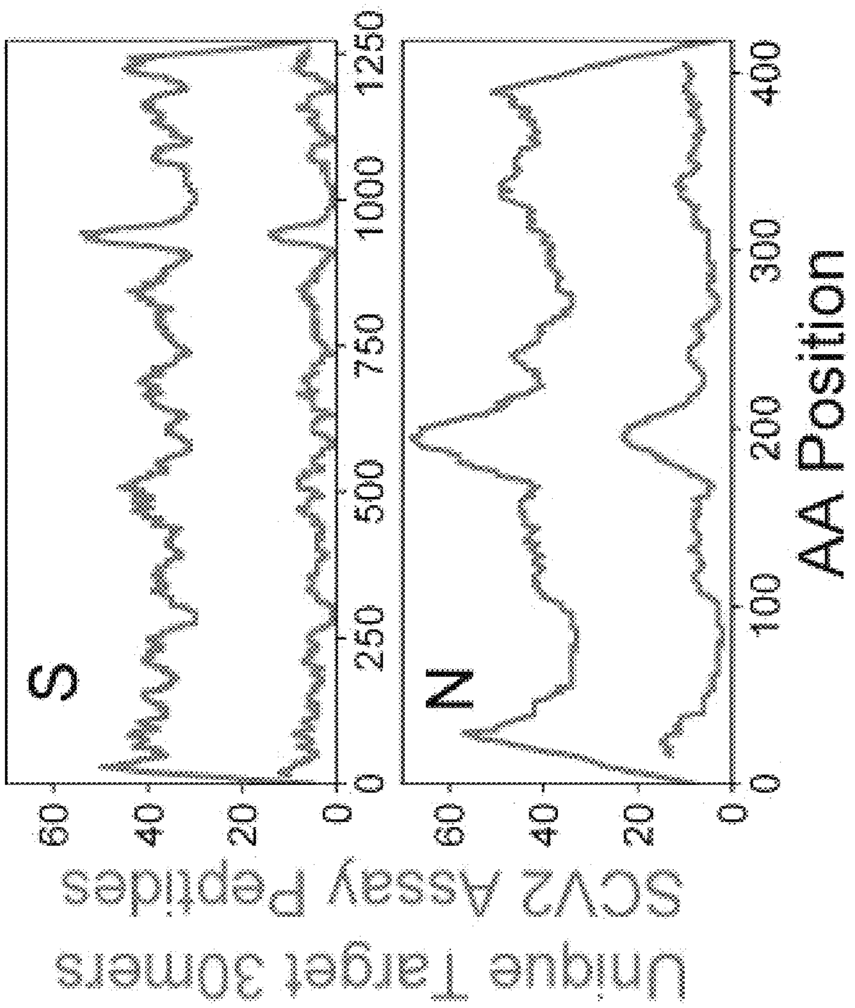

Each library began as a pool of DNA oligonucleotide templates, which was modified using bulk enzymatic steps consisting of transcription, ligation of a puromycin-containing adapter oligo, translation, and reverse transcription. One library was focused on SARS-CoV-2 ('SCV2') and contained 2,107 peptides representing the Spike and Nucleocapsid—the 2 most immunogenic coronavirus proteins—at high redundancy, with an average of 38 peptides covering each amino acid position (FIG. 1B). FIG. 1B shows peptide coverage depth across the SARS-CoV-2 spike (S) and nucleocapsid (N) proteins within the 'SCV2' peptide library. Peptide coverage depth (blue) correlates well with amino acid sequence diversity within the target SARS-CoV-2 sequences (green), calculated as the number of unique 30mers.

Figure 1C:
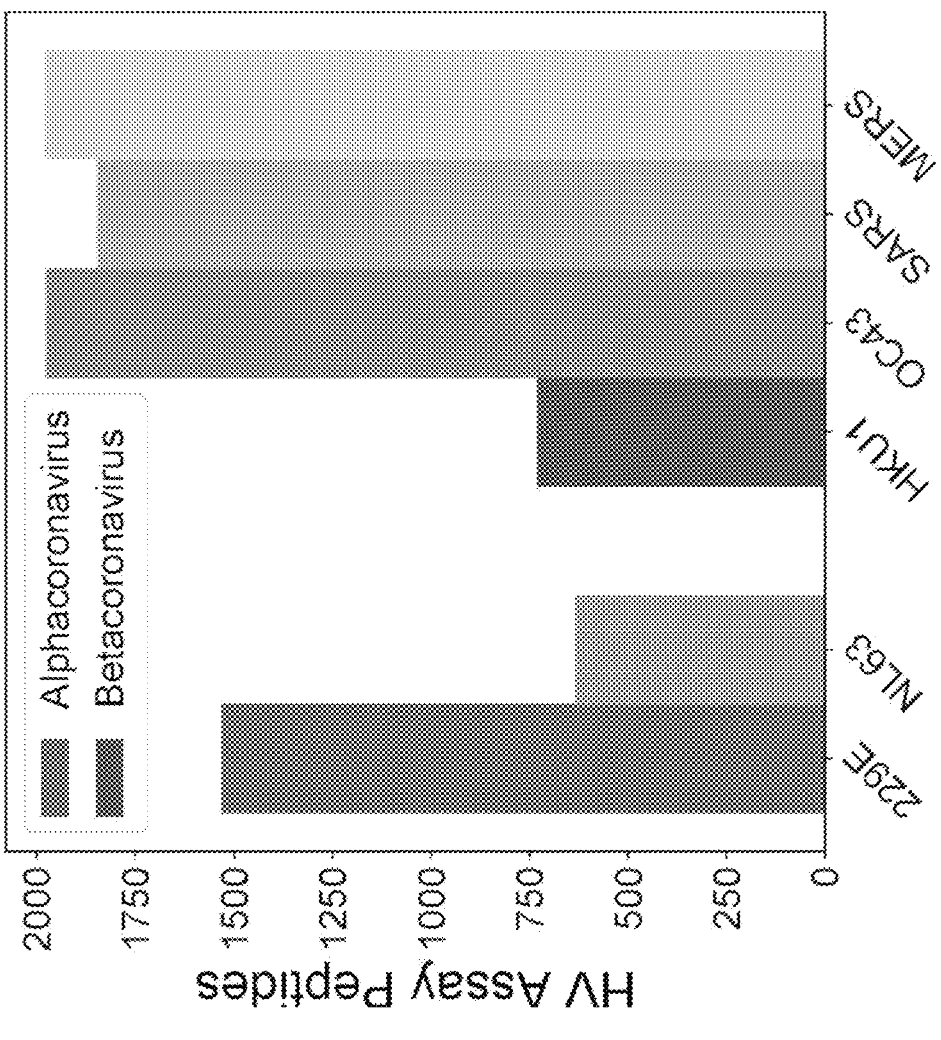

The other library (human virome or 'HV') comprised 244,000 peptides designed to cover the full proteomes of all viruses known to infect humans, as of the end of 2018. Therefore, HV included peptides from the complete proteomes of 6/7 human coronaviruses: HCoV-229E, HCoV-OC43, HCoV-NL63, HCoV-HKU1, SARS-CoV, and MERS-CoV, but not SARS-CoV-2 (FIG. 1C). FIG. 1C shows the number of peptides within the HV pool that were designed from each of the six human coronaviruses known prior to 2019. The SCV2 library also included 393 positive control peptides that we have previously shown are commonly recognized across the human population (unpublished data). The positive controls represent a subset of the HV peptides and were designed from 55 different virus species.

In total, we assayed and analyzed 27 COVID-19 convalescent and 21 SARS-CoV-2 negative (both pre- and post-pandemic) serum samples using our SCV2 PepSeq library (TABLE 1).

TABLE 1

Summary of samples characterized in this study.

| PepSeq Library | Sample Type | Sample Size | Males/Females/ Unreported | Median Age* | Median days from diagnosis* |
|---|---|---|---|---|---|
| SCV2 | COVID-19 Convalescent | 27 | 10/12/5 | 51 | 28.5 |
| | Negative Control | 21 | 11/6/4 | 37 | — |
| HV | Negative Control | 33 | 0/0/33 | NA | |

"NA" = Not available;
"—" = Not applicable.
*Median values were calculated from a subset of total samples for which this information was available.

Figure 6:
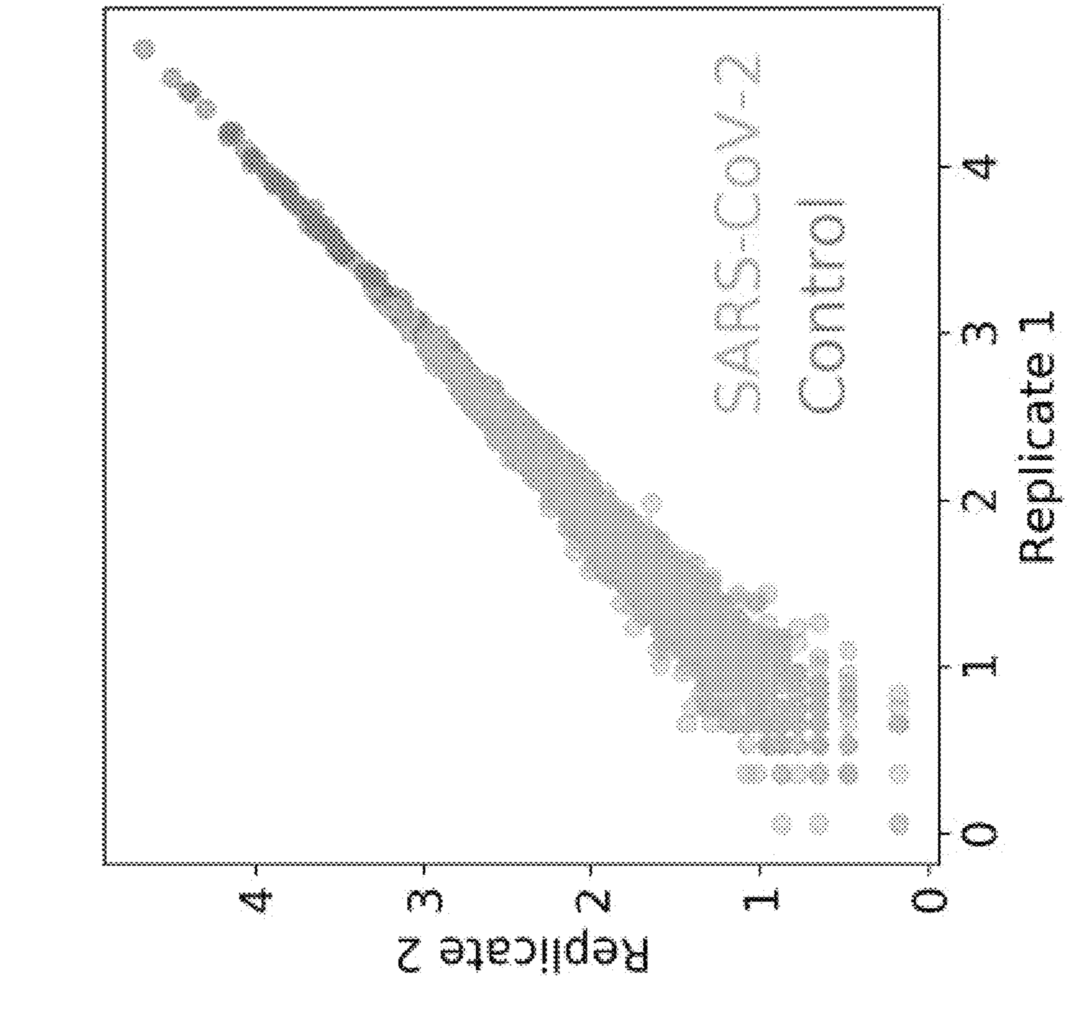
FIG. 6 illustrates the strong correlation between replicate PepSeq assays run separately on the same serum sample.

Separately, we assayed 33 SARS-CoV-2 negative (pre-pandemic) serum samples using the HV PepSeq library. For each assay, we incubated our PepSeq probes overnight with serum (or buffer as a negative control), captured the IgG on protein G beads, washed away the non-binding library members, eluted binders, and then performed PCR and high-throughput sequencing on the DNA tags to identify the distribution of bound peptides. Each sample was run in duplicate, and we observed strong signal concordance between technical replicates of the same sera, including those run on different days (FIG. 6). FIG. 6 shows a strong correlation between replicate PepSeq assays run separately on the same serum sample. Axes show normalized read counts (log 10 scale) for each peptide in the SCV2 library. Grey circles represent unenriched peptides. Colored circles represent SARS-CoV-2 (orange) and non-SARS-CoV-2 control (blue) peptides that have been enriched through interaction with serum antibodies.

Figure 1D:
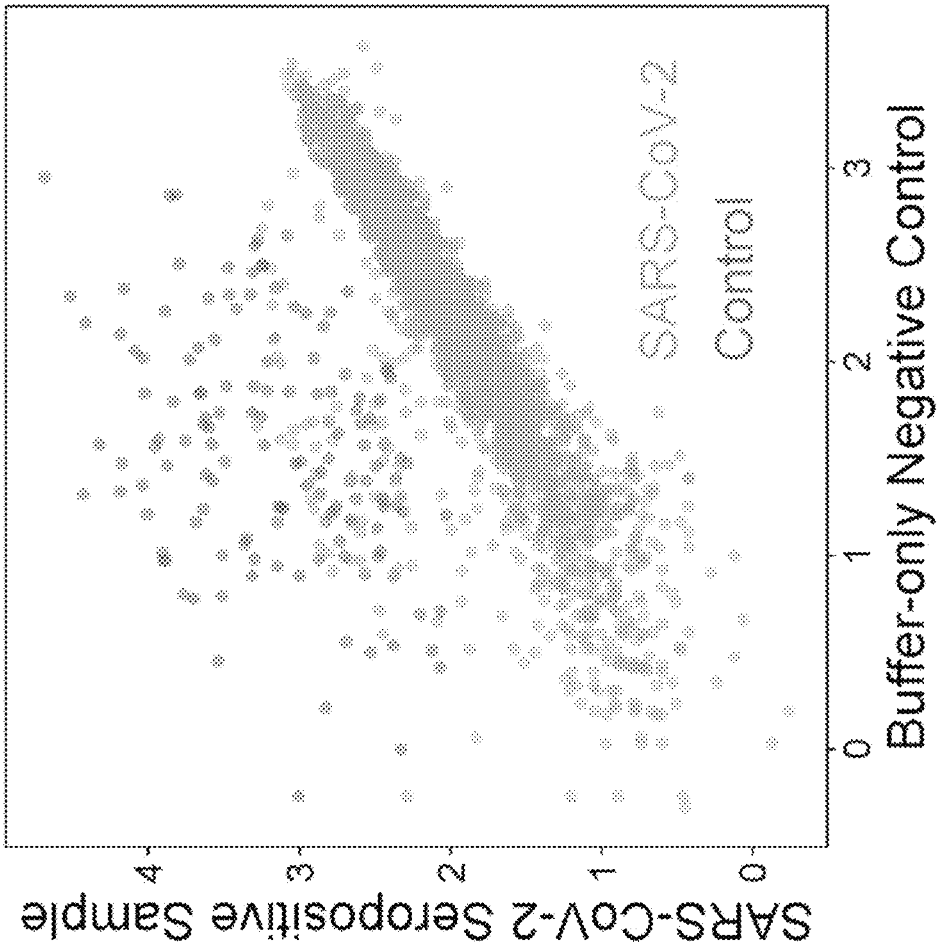

Comparative analysis of peptide abundance between serum and buffer-only negative controls revealed a strong correlation in abundance for the majority of peptides, while a subset of peptides showed distinctly higher relative abundance in each serum sample (FIG. 1D). These latter peptides are those that have been enriched by binding to serum IgG. To quantify peptide enrichment, we calculated Z-scores for each peptide in each sample. For each peptide, relative abundance was normalized to the corresponding value for the buffer-only negative controls, and this normalized value was compared among peptides with similar abundance in the negative controls. Each Z-score corresponds to the number of standard deviations away from the mean.

FIG. 1D shows an example scatter plot illustrating SCV2 PepSeq assay results for a single serum sample. This plot shows normalized sequence read counts (log 10 scale) for each peptide in the SCV2 library. Assay results using an antibody-free negative control are shown on the x-axis, while the results from a SARS-CoV-2 convalescent serum sample are shown on the y-axis. Grey circles represent unenriched peptides, with a strong correlation between the two assays, based on the starting abundance of the different peptides. Colored circles represent SARS-CoV-2 (orange) and non-SARS-CoV-2 control (blue) peptides that have been enriched through interaction with serum antibodies.

Accurate Detection of SARS-CoV-2 Exposure and Identification of Epitopes

Figure 2A:
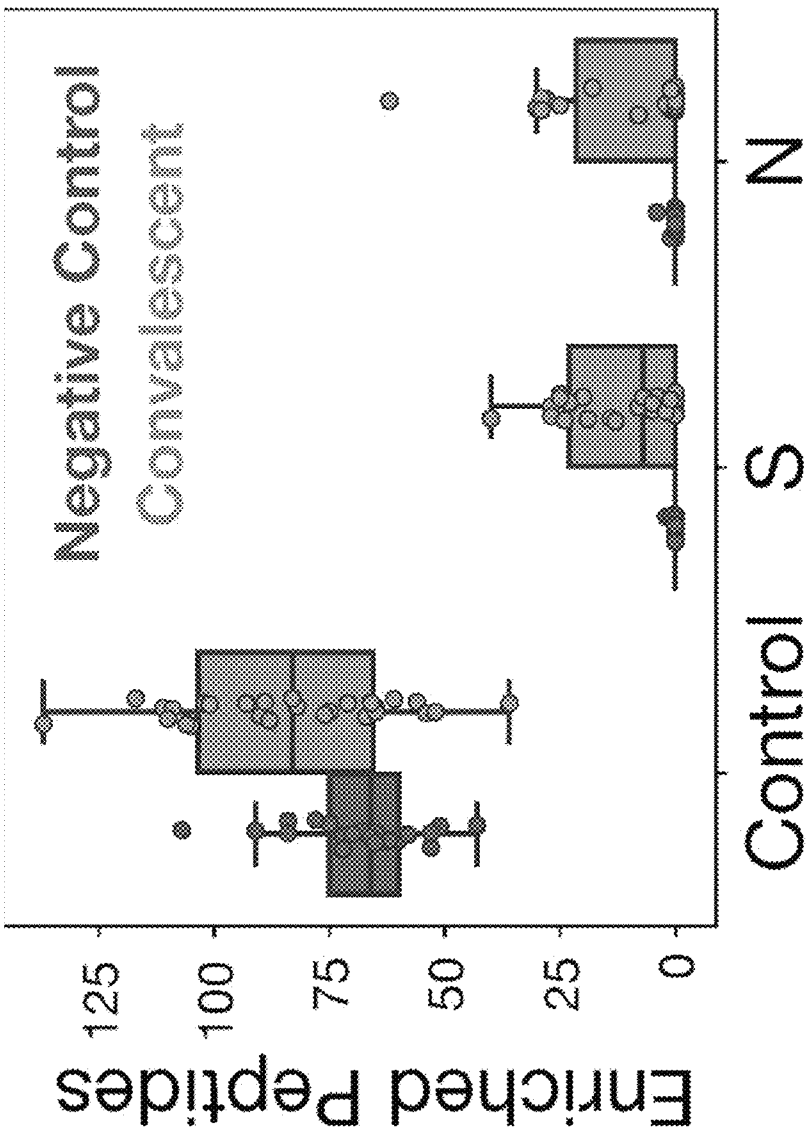
FIGS. 2A-2C illustrate results of the peptide-based assay identifying recurrent reactivities to SARS-CoV-2 peptides and classifying exposure status with high accuracy.
Figure 2B:
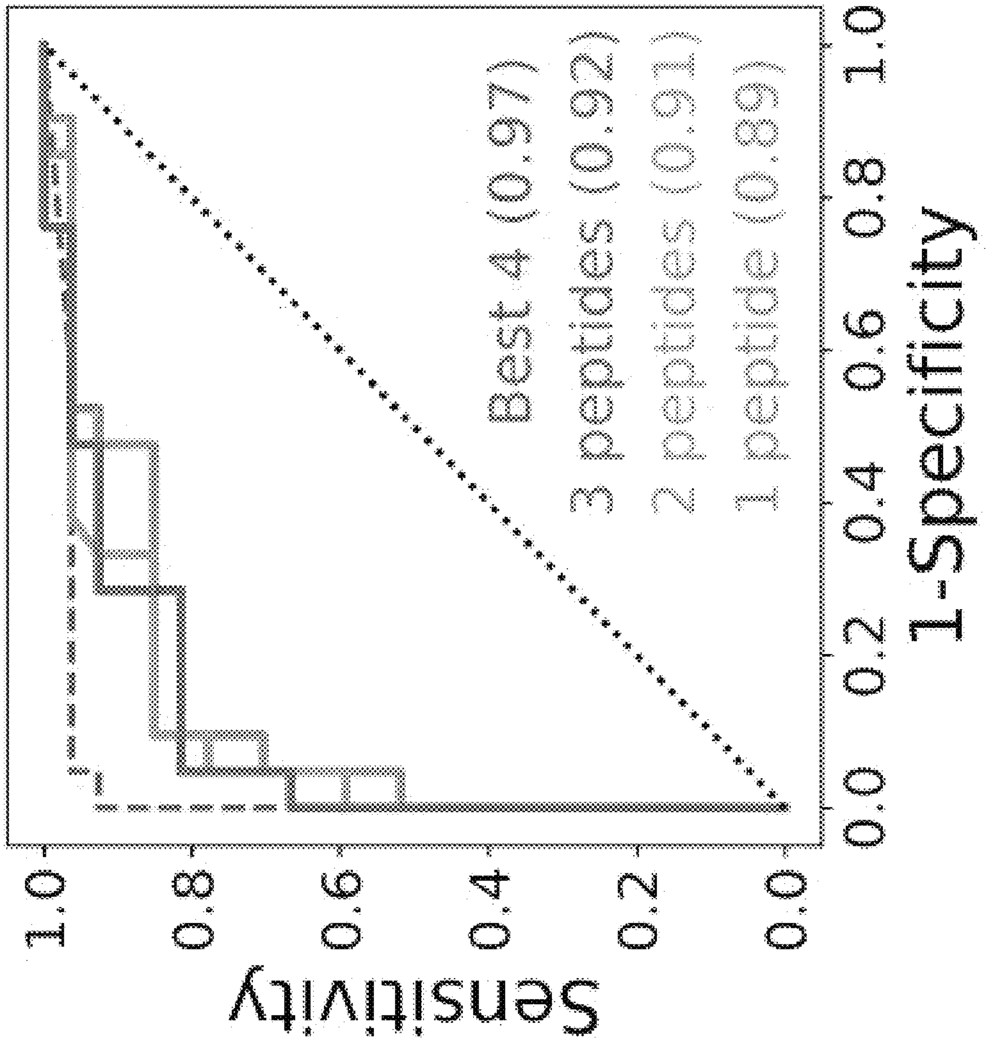
Figure 2C:
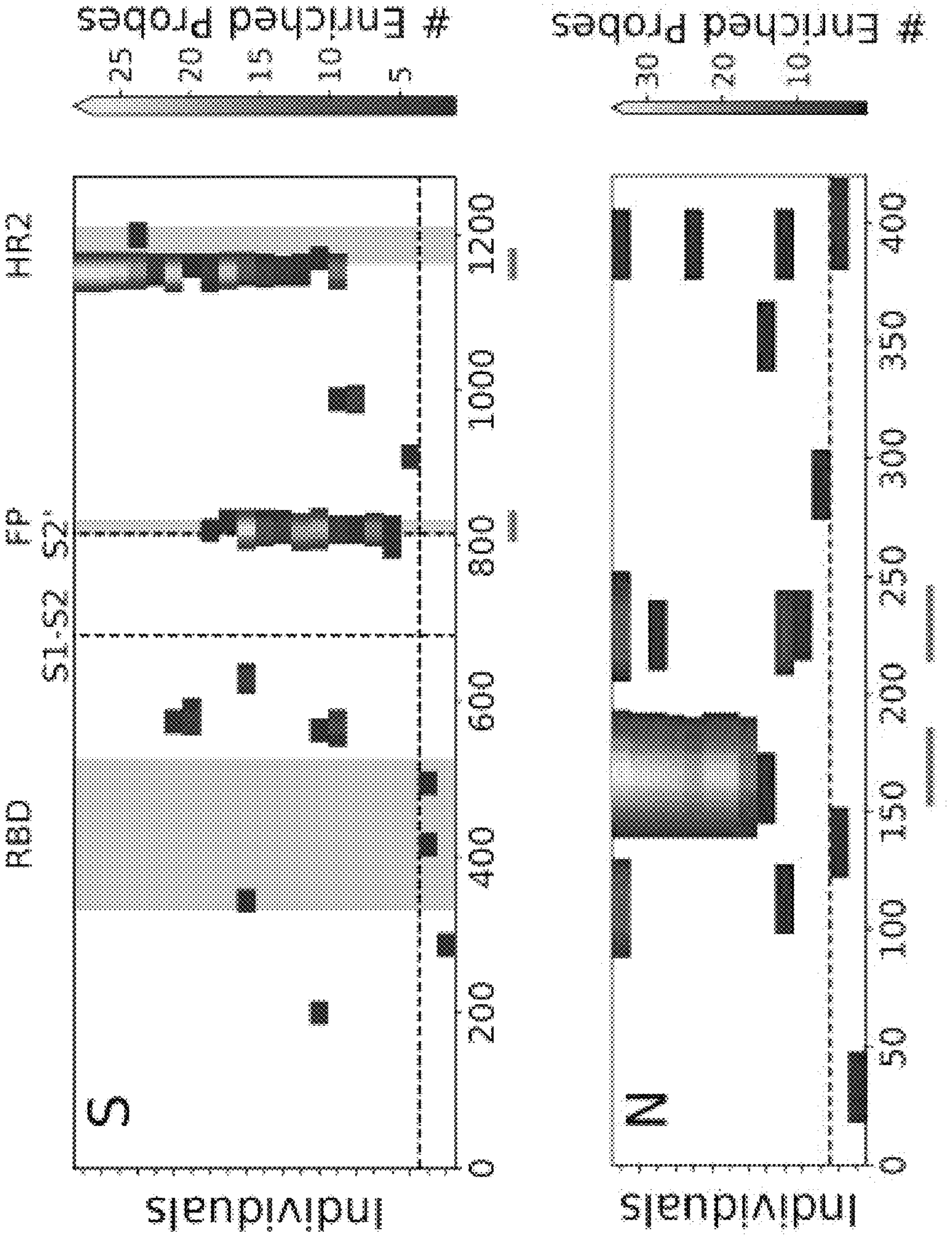

For the SCV2 PepSeq library, we evaluated the sensitivity/specificity for detection of SARS-CoV-2 exposure by generating receiver operating characteristic (ROC) curves with a sliding Z-score threshold and three different criteria for the number of enriched SARS-CoV-2 peptides needed for a positive result (FIG. 2B). The SCV2 assay distinguished COVID-19 convalescent samples from negative controls with high accuracy (AUC=0.89-0.92).

peptides; a peptide was required to meet or exceed this threshold in two technical replicates to be considered enriched. With only one SARS-CoV-2 peptide required for positivity, this threshold corresponded to a sensitivity of 81.5% and a specificity of 91.5%, with five false negative samples and two false positive samples. Notably, while both false positive samples exhibited at least one enriched peptide for both the N and S proteins, none of these peptides corresponded to the widely recognized, immunodominant epitopes observed for the COVID-19 convalescent sera (FIG. 2C). FIG. 2C shows heat maps showing the locations of enriched SARS-CoV-2 peptides within the S and N proteins. Each row represents a single serum sample and each plot includes only samples with at least one enriched peptide. Each position is colored according to the number of enriched peptides that overlap that position. The horizontal dashed line separates SARS-CoV-2 convalescent samples (top) from negative control samples (bottom). The vertical dashed lines in the S protein plot represent the S1-S2 and S2' cleavage sites, respectively. Grey boxes indicate selected functional regions: receptor binding domain (RBD), fusion peptide (FP) and heptad repeat 2 (HR2). The horizontal green lines below each plot in FIG. 2C indicate the positions of the "Best 4" peptides from FIG. 2B.

To explore the potential for increasing sensitivity and specificity using a subset of SARS-CoV-2 peptides, we utilized a decision tree algorithm to identify the most discriminatory subset of peptides from our library. This analysis identified four SARS-CoV-2 peptides (indicated by green lines in FIG. 2C) that were sufficient to detect all 22 convalescent donors that were called positive using the entire peptide set (TABLE 2).

TABLE 2

SARS-CoV-2 peptides chosen by decision tree algorithm for discriminating between COVID-19 convalescent and negative control samples

| Peptide Sequence | Protein | Start position | End position | Reactive conv samples | SEQ ID NO: |
|---|---|---|---|---|---|
| SFKEELDKYFKNHTSPDVDLGDISGINASV | S | 1147 | 1176 | 12 | 1 |
| SKPSKRSFIEDLLFNKVTLADAGFIKQYGD | S | 810 | 839 | 9 | 2 |
| NAAIVLQLPQGTTLPKGFYAEGSRGGSQAS | N | 154 | 183 | 8 | 3 |
| GDAALALLLLDRLNQLESKMSGKGQQQQGQ | N | 215 | 744 | 3 | 4 |

FIG. 2B shows ROC curves for prediction of SARS-CoV-2 exposure based on peptide-level Z-scores calculated for all SCV2 library peptides (solid lines) and for a subset of four peptides identified through a decision tree analysis (dashed line). Positivity of the assay was determined by the enrichment of peptides designed from SARS-CoV-2, and the full library analysis was run with three different thresholds for the number of enriched peptides required for a sample to be considered positive. For the analysis using only the "Best 4" peptides, only a single enriched peptide was required for a positive result. For all analyses, the AUC (shown in parentheses in FIG. 2B) was ≥0.89.

Based on the ROC analysis and a qualitative assessment of the ability to discriminate signal from noise (FIG. 1C), we selected a Z-score threshold of 11 for identifying enriched Using only these four peptides in the ROC analysis of all 48 donors increased the AUC to 0.97. With the same Z-score threshold of 11, the specificity increased to 100%, while sensitivity stayed at 81.5% (FIG. 2B).

As predicted, multiple positive control peptides were found to be enriched in every serum sample that we tested (FIG. 2A). FIG. 2A shows boxplots showing the number of enriched SCV2 library peptides from assays with negative control (blue, n=21) and SARS-CoV-2 convalescent (orange, n=27) serum samples, divided into three different categories: non-SARS-CoV-2 control peptides (Control), and SARS-CoV-2 Spike (S) and Nucleocapsid (N) peptides. All three of these comparisons are statistically significant (t-test, $p<0.05$). Individual data points are shown as circles, the limits of the boxes correspond to the 1st and 3rd quartiles, the black line inside each box corresponds to the median and the whiskers extend to points that lie within 1.5 interquartile ranges of the 1st and 3rd quartiles.

Figure 8A:
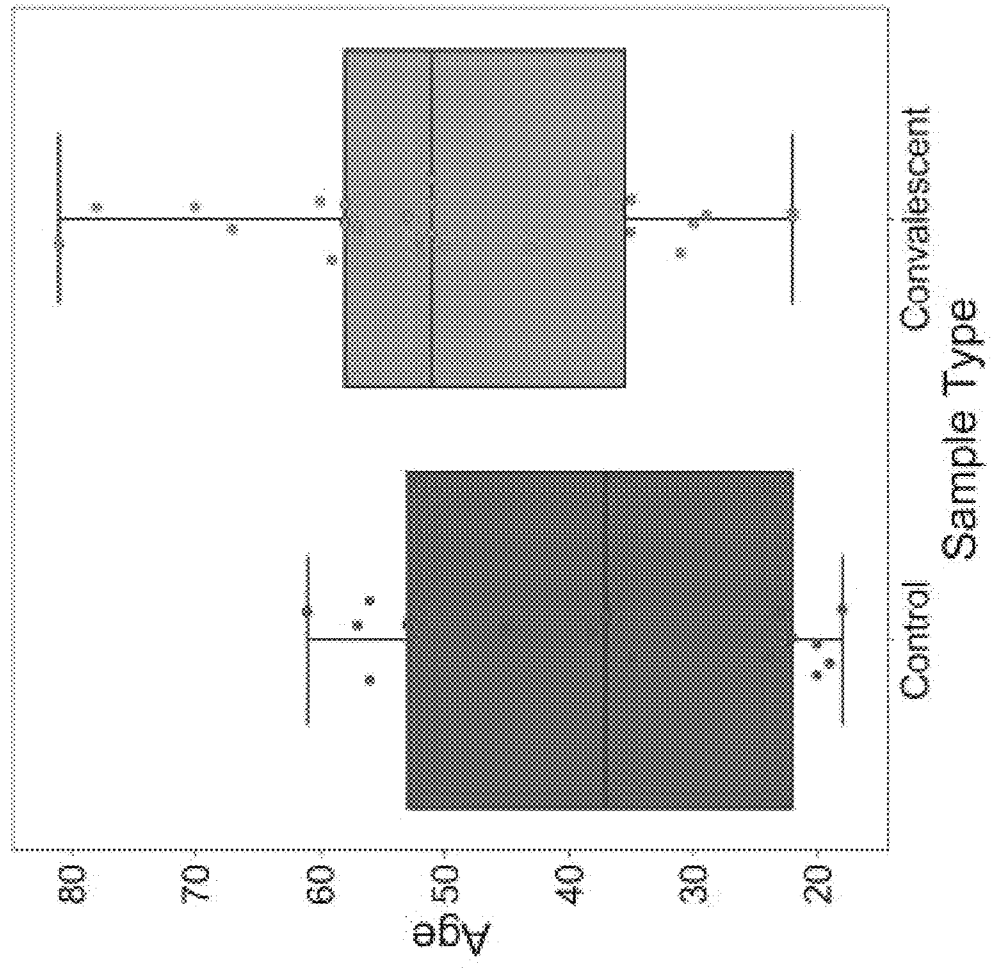
FIGS. 8A-8C illustrate the effect of age and sample source on number of enriched control peptides.

Unexpectedly, we observed a small, but significant increase in the average number of enriched control peptides between convalescent and control donors, which involved peptides designed from a wide variety of virus species (t-test, p=0.01, 1.2 fold difference). However, this difference was small compared to the difference in the number of enriched SARS-CoV-2 peptides (56-fold, p=2e-5). There was a significant difference in age between our convalescent and negative control donors, with our negative control donors being slightly younger on average than our COVID-19 convalescent donors (FIG. 8A, 1.3-fold, p=0.015). FIG. 8A shows boxplots depicting donor age distributions for negative control and convalescent serum/plasma samples. The means of these distributions are significantly different based on a t-test (p=0.022).

Figure 8B:
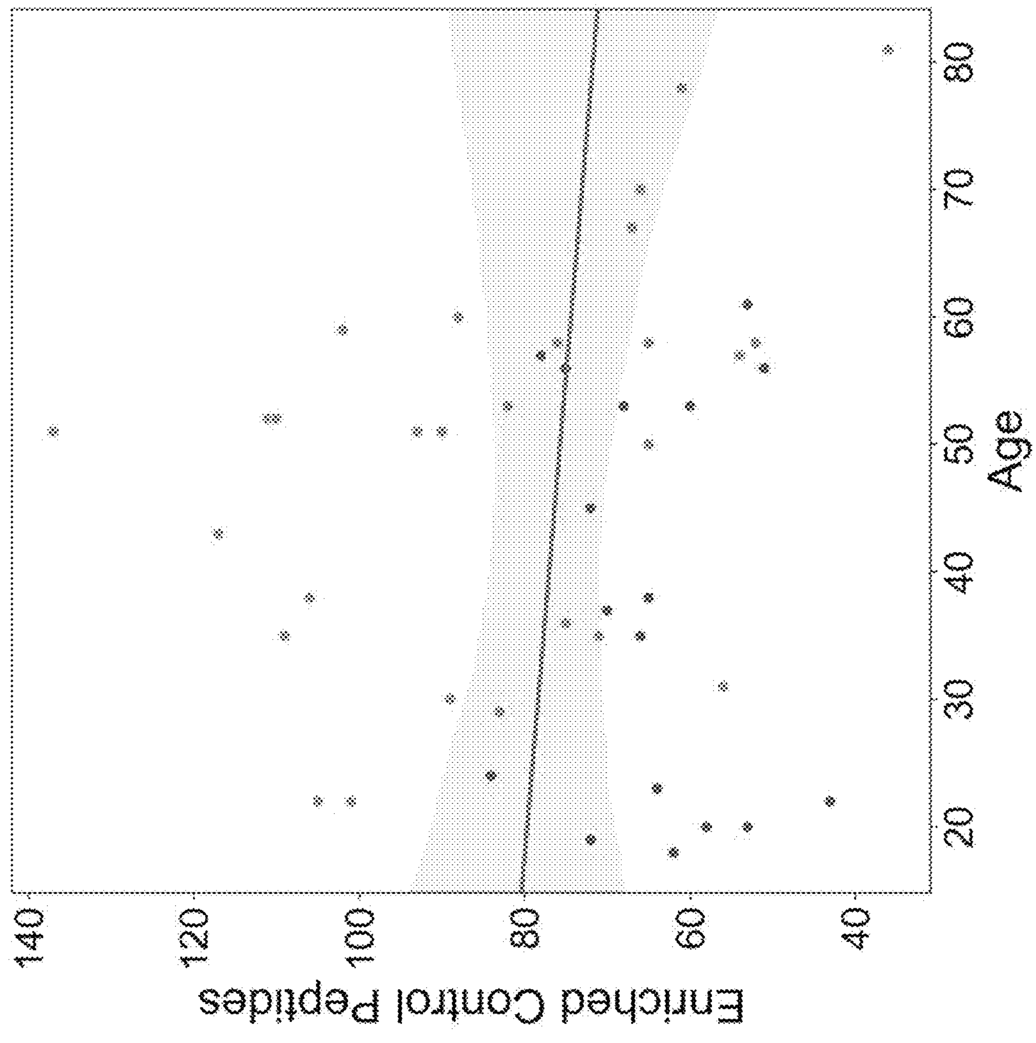

However, within our sample set, we did not observe a correlation between donor age and the number of enriched control peptides (FIG. 8B). FIG. 8B shows a scatterplot comparing donor age (x-axis) and the number of enriched SCV2 library control peptides (y-axis). Each circle represents a single serum/plasma sample. Grey line and band represent the best fit linear regression line and 95% confidence interval, respectively, as estimated by the Seabom regplot( ) function.

Figure 8C:
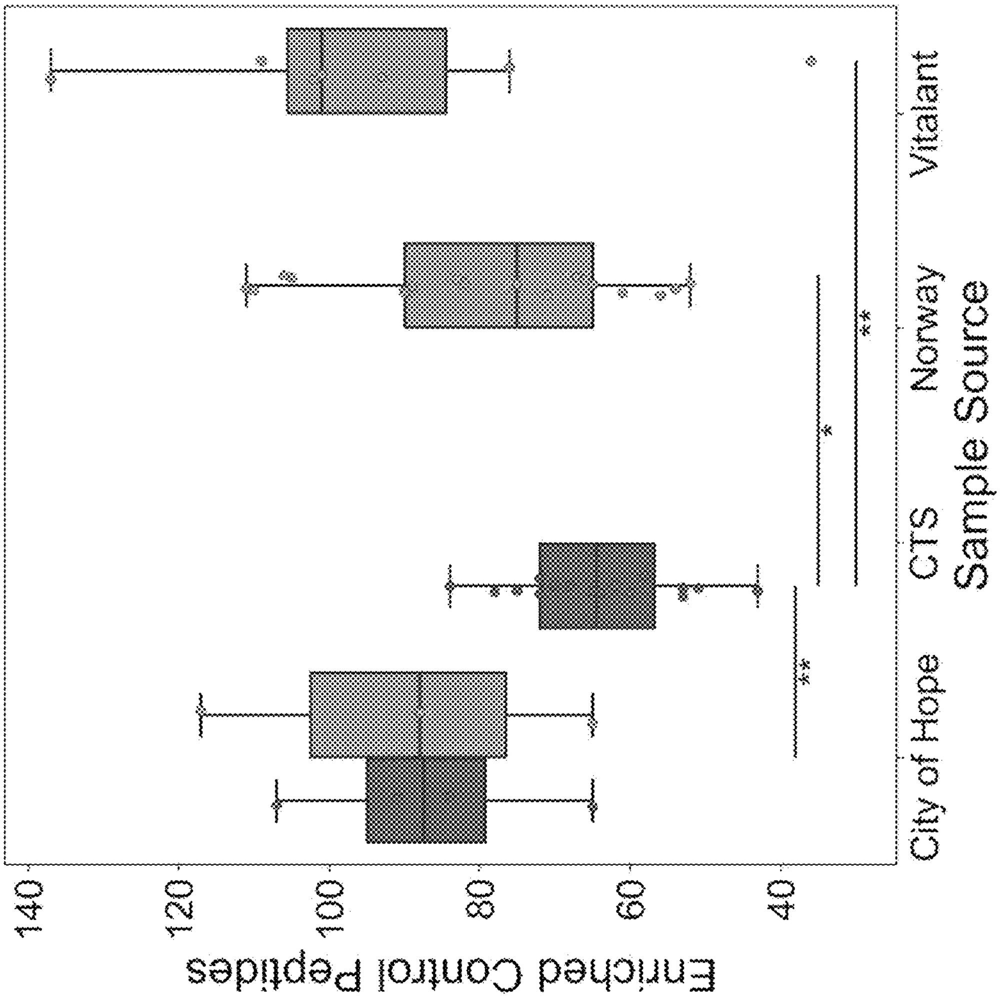

In contrast, we did observe several significant pairwise differences in the number of enriched control peptides when we compared samples obtained from different sources (FIG. 8C). FIG. 8C shows boxplots depicting SCV2 library enriched control peptide distributions for each sample source and type. The mean for the negative control samples from Creative Testing Solutions (CTS) is significantly lower than that for the samples from the three other sources based on t-tests. Significantly different pairs are indicated with horizontal lines: *<0.05, <0.01. For all boxplots, individual data points are shown as circles, the limits of the colored boxes correspond to the 1st and 3rd quartiles, the black line inside each box corresponds to the median and the whiskers extend to points that lie within 1.5 interquartile ranges of the 1st and 3rd quartiles. In FIGS. 8A-8**C, blue is used to indicate negative control samples and orange for convalescent samples.

Specifically, we observed significantly fewer enriched control peptides in our pre-pandemic negative controls (1.2-1.5-fold, p=0.001-0.01). Therefore, this difference can likely be attributed to subtle differences in patient characteristics, sample collection, handling and/or storage among our different donor cohorts. We do not expect this difference to impact the conclusions discussed herein.

In total, we identified IgG reactivity (i.e., peptide enrichment) against 142 and 8 SARS-CoV-2 peptides in convalescent and negative control samples, respectively. All peptides that were enriched in any of the convalescent samples, regardless of the virus from which they were designed, are shown in TABLE 3. TABLE 3 shows the 142 SARS-CoV-2 enriched peptides, including SEQ ID NOS: 1-4 and 275-412, along with the other enriched peptides, including SEQ ID NOS: 5-274 and 413-420.

TABLE 3

Peptides enriched in convalescent samples.

| Peptide sequence | Organism | COVID-19 Conv Samples | Proportion COVID-19 Conv | Negative Control Samples | Proportion Negative Control | SEQ ID NO: |
|---|---|---|---|---|---|---|
| SLIKRQGNRVIDAEPREIPLEYADDLLEAM | Aichivirus A | 17 | 0.63 | 6 | 0.286 | 5 |
| EACWKCSQDKPRRKYNTVPPEEWLYDSDVQ | Aichivirus A | 5 | 0.185 | 0 | 0 | 6 |
| ALPGIRRQGLLTLSADTETNQTLNKITESV | Aichivirus A | 7 | 0.259 | 5 | 0.238 | 7 |
| KFFDKLALLSLPGAYQAKTPEERALAGALT | Aichivirus A | 4 | 0.148 | 1 | 0.048 | 8 |
| TQSGNAAILTGSTAPSFLAYPTATPVPLPN | Aichivirus A | 6 | 0.222 | 2 | 0.09:5 | 9 |
| GSSNKVGSRFSKWWEPAAARALERATDSAI | Aichivirus A | 4 | 0.148 | 0 | 0 | 10 |
| MATQGPRVNWGDEPSKRRGRSNSRGRKSSD | Alphacoronavirus 1 | 1 | 0.037 | 0 | 0 | 11 |
| MSLWRPSEATVYLPPAPVSKVYSTDEYVTR | Alphapapillomavirus 9 | 1 | 0.037 | 0 | 0 | 12 |
| TTGYRFTNFEPFTVNSVNDSLEPVGGLYEI | Betacoronavirus 1 | 13 | 0.481 | 10 | 0.476 | 13 |
| APDVMLNISTPKLPDFKEELDQWFKNQTSV | Betacoronavirus 1 | 21 | 0.778 | 1 | 0.048 | 14 |
| KWADQSDQFRNVQTRGRRAQPKQTVTSQQP | Betacoronavirus 1 | 1 | 0.037 | 2 | 0.095 | 15 |
| AANTAASAHSLGTGRVPALQAAETGASSNS | Enterovirus A | 12 | 0.444 | 11 | 0.524 | 16 |
| VSDYIKGLGDAFGVGFTDAVSREVEALKNH | Enterovirus A | 18 | 0.667 | 15 | 0.714 | 17 |
| DSIADMIDQAVNNQVNRSLTAMQVLPTAAN | Enterovirus A | 10 | 0.37 | 8 | 0.381 | 18 |
| DMANAAKGFEWISNKISKFIDWIKEKIIPA | Enterovirus A | 9 | 0.333 | 9 | 0.429 | 19 |
| PPKFRPVRISLDEKPAPDAISDLLASVDSE | Enterovirus A | 10 | 0.37 | 6 | 0.286 | 20 |
| NLEAIDLHTSAGYPYSALGIKKRDILDPTT | Enterovirus A | 2 | 0.074 | 1 | 0.048 | 21 |
| DKRLEVDFETALFSKYIGNKIYEPDEYMIQ | Enterovirus A | 6 | 0.222 | 6 | 0.286 | 22 |

TABLE 3 -continued

| Peptides enriched in convalescent samples. | | | | | | |
|---|---|---|---|---|---|---|
| Peptide sequence | Organism | COVID-19 Conv Samples | Pro-portion COVID-19 Conv | Negative Control Samples | Pro-portion Negative Control | SEQ ID NO: |
| TAEYQNDPITNAVENAVSALADTTISRVTA | Enterovirus A | 2 | 0.074 | 3 | 0.143 | 23 |
| VSKMKFYMDKYGLDLPYSTYVKDELRSMDK | Enterovirus A | 3 | 0.111 | 7 | 0.333 | 24 |
| FTNINYYKDSYAASAAKHDFTQDPGKFTQP | Enterovirus A | 2 | 0.074 | 4 | 0.19 | 25 |
| SNKETGRLSINGPTRTKLEPSAFYDVFEGS | Enterovirus A | 2 | 0.074 | 3 | 0.143 | 26 |
| QQVPALTAVETGHTSQVAPSDTIQTRHVHN | Enterovirus B | 21 | 0.778 | 15 | 0.714 | 27 |
| VEGAIGRVADTIRSGPSNSEAVPALTAAET | Enterovirus B | 15 | 0.556 | 16 | 0.762 | 28 |
| KDAGYPVINAPSKTKLEPSVFHQVFEGNKE | Enterovirus B | 17 | 0.63 | 13 | 0.619 | 29 |
| NRQDFTQDPSRFTEPVQDVLIKTLPALNSP | Enterovirus B | 6 | 0.222 | 6 | 0.286 | 30 |
| ALYQNDPESALNRAVGRVADTVASGPVNTE | Enterovirus B | 8 | 0.296 | 6 | 0.786 | 31 |
| ASEVTVSDTQPSGPSNSVSVPMLTAAETGH | Enterovirus B | 5 | 0.185 | 7 | 0.333 | 32 |
| DVVEAIESAVARVADTISSGPTNSQAVPAL | Enterovirus B | 8 | 0.296 | 8 | 0.381 | 33 |
| SPFVRQTVFYQNDVQNAIDRAMTRVADTMP | Enterovirus B | 2 | 0.074 | 3 | 0.143 | 34 |
| NEPSNAIERAMVRVADTMASGPANSEQIPA | Enterovirus B | 7 | 0.259 | 5 | 0.238 | 35 |
| SQDNKLQGDVEEAIERAVVHVADTMRSGPS | Enterovirus B | 5 | 0.185 | 3 | 0.143 | 36 |
| ITDYIQSLGNAFGAGFTETISSKAKEVQDM | Enterovirus D | 70 | 0.741 | 13 | 0.619 | 37 |
| IIKTATDTVKSEINAELGVVPSLNAVETGA | Enterovirus D | 13 | 0.481 | 9 | 0.429 | 38 |
| KDKRLKVDFEEAIFSKYVGNKTMLMDEYME | Enterovirus D | 7 | 0.259 | 8 | 0.381 | 39 |
| GVIPSLNAAETGATSNTTPEEAIQTRAVIN | Enterovirus D | 3 | 0.111 | 0 | 0 | 40 |
| RDIFNRQTRDTTEMTKMLDKYGVDLPFVTF | Enterovirus D | 1 | 0.037 | 5 | 0.238 | 41 |
| RGKERAPNALNAIIGNRDSVKAMPHNIVTT | Enterovirus D | 3 | 0.111 | 2 | 0.095 | 42 |
| LFQGPPQFREIKISVSPETPAPDAINDLLR | Enterovirus D | 1 | 0.037 | 0 | 0 | 43 |
| ANYKGKEKTPNALNALIGNRDNVKTMTHNI | Enterovirus D | 1 | 0.037 | 0 | 0 | 44 |
| RRYFTAEQGKIEYIEKSKEAGYPIINAPTQ | Enterovirus E | 7 | 0.259 | 4 | 0.19 | 45 |
| KFTEAVNAFKGLDWIAAKFSKFLDWIKSKI | Enterovirus E | 1 | 0.037 | 0 | 0 | 46 |
| SVDSEDVREYCRQKGWIVQEKITKESLERN | Enterovirus E | 3 | 0.111 | 3 | 0.143 | 47 |
| WMRRRTQKAPKRIRLPHIREDDQPSAHQPL | Human alphaherpesvirus 1 | 14 | 0.519 | 10 | 0.476 | 48 |
| GDFDEAKLAEAREMIRYMALVSAMEHTEHK | Human alphaherpesvirus 1 | 16 | 0.593 | 10 | 0.476 | 49 |
| PLDGCGPLHPSWVSLMPPKQVPETVVDAAC | Human alphaherpesvirus 1 | 13 | 0.481 | 9 | 0.429 | 50 |
| AWGQVHDWTEQTDPWFLDGLGMDRMYWRDT | Human alphaherpesvirus 1 | 11 | 0.407 | 10 | 0.476 | 51 |
| SGTPAPAPPGDGSYLWIPASHYNQLVAGHA | Human alphaherpesvirus 1 | 16 | 0.593 | 10 | 0.476 | 52 |
| PSTQTRAPLPTEPAFPPAATGSQPEASNAE | Human alphaherpesvirus 1 | 13 | 0.481 | 8 | 0.381 | 53 |
| HRPAPGSPPGIPEYAEDPYAISYGGQLDRY | Human alphaherpesvirus 1 | 12 | 0.444 | 9 | 0.429 | 54 |

TABLE 3 -continued

Peptides enriched in convalescent samples.

| Peptide sequence | Organism | COVID-19 Conv Samples | Pro-portion COVID-19 Conv | Negative Control Samples | Pro-portion Negative Control | SEQ ID NO: |
|---|---|---|---|---|---|---|
| AAPASPYIEAENPLYDWGGSALFSPPGRTG | Human alphaherpesvirus 1 | 13 | 0.481 | 10 | 0.476 | 55 |
| WHIPSIQDAATPYHPPATPNNMGLIAGAVG | Human alphaherpesvirus 1 | 12 | 0.444 | 8 | 0.381 | 56 |
| RSMAESDVVMEDVAIAERALGLSAFGVAGG | Human alphaherpesvirus 1 | 12 | 0.444 | 6 | 0.286 | 57 |
| ASGKGPTYIRVADSELYADWSSDSEGERDQ | Human alphaherpesvirus 1 | 11 | 0.407 | 7 | 0.333 | 58 |
| FWVRRRAQMAPKRLRLPHIRDDDAPPSHQP | Human alphaherpesvirus 2 | 7 | 0.259 | 3 | 0.143 | 59 |
| EAYYSESEDEAANDFLVRMGRQQSVLRRRR | Human alphaherpesvirus 2 | 14 | 0.519 | 3 | 0.143 | 60 |
| DQTLQLHREGVSTQDPRFVGAFMAAKAAHL | Human alphaherpesvirus 2 | 8 | 0.296 | 6 | 0.286 | 61 |
| PSEAVRPSRIPRAPRVPREPRVPREPREPR | Human alphaherpesvirus 2 | 9 | 0.333 | 6 | 0.286 | 62 |
| ASGPHETITALVGAVTSLQQELAHMRARTN | Human alphaherpesvirus 2 | 5 | 0.185 | 0 | 0 | 63 |
| RRRHEVEQPEYDCGRDEPDRDFPYYPGEAR | Human alphaherpesvirus 2 | 8 | 0.296 | 5 | 0.238 | 64 |
| KKGTSALLSSKVTNMVLRKRNKARYSPLHN | Human alphaherpesvirus 2 | 5 | 0.185 | 2 | 0.095 | 65 |
| AGVYDAVRTWGPDAEAEPDQMENTYLLPDD | Human alphaherpesvirus 2 | 5 | 0.185 | 1 | 0.048 | 66 |
| APHAWGMLNDMQWLASSDSEEETEVGISDD | Human alphaherpesvirus 2 | 5 | 0.185 | 1 | 0.048 | 67 |
| DRDSSMSLADFHGEEFEKLYEHLEAMGEGE | Human alphaherpesvirus 2 | 4 | 0.148 | 4 | 0.19 | 68 |
| DPIYDEVAPDHEAELYARVQRPGPVPDAEP | Human alphaherpesvirus 2 | 1 | 0.037 | 1 | 0.048 | 69 |
| LENAHEHHGVYNQGRGIDSGERLMQPTQMS | Human alphaherpesvirus 3 | 6 | 0.222 | 5 | 0.238 | 70 |
| AVAPTSAATRKPDPAVAPTSAASRKPDPAV | Human alphaherpesvirus 3 | 8 | 0;296 | 4 | 0.19 | 71 |
| KGLKQLPEGMDPFAEKPNATDTPIEEIGDS | Human alphaherpesvirus 3 | 10 | 0.37 | 2 | 0.095 | 72 |
| DKFREAQEMIKYMTLVSAAERQESKARKKN | Human alphaherpesvirus 3 | 12 | 0.444 | 3 | 0.143 | 73 |
| HAESSWVNRGESSRKAYDHNSPYPNPRNDY | Human alphaherpesvirus 3 | 5 | 0.185 | 4 | 0.19 | 74 |
| VVTTETKSVVKEGIENHVYPTDMSTLPEKS | Human alphaherpesvirus 3 | 4 | 0.148 | 2 | 0.095 | 75 |
| HQPNDSSGSEDDFEDIDEVVAAFREARLRH | Human alphaherpesvirus 3 | 3 | 0.111 | 0 | 0 | 76 |
| EPMYAQVRKPKSRTDTQTTGRITNRSRARS | Human alphaherpesvirus 3 | 1 | 0.037 | 0 | 0 | 77 |
| IPADEEAPTTPEDPRHPLHAHQLVPNSLNV | Human alphaherpesvirus 3 | 6 | 0.222 | 2 | 0.095 | 78 |

TABLE 3 -continued

Peptides enriched in convalescent samples.

| Peptide sequence | Organism | COVID-19 Conv Samples | Pro-portion COVID-19 Conv | Negative Control Samples | Pro-portion Negative Control | SEQ ID NO: |
|---|---|---|---|---|---|---|
| APTPTFAGTQTPVNGNSPWAPTAPLPGDMN | Human betaherpesvirus 5 | 14 | 0.519 | 8 | 0.381 | 79 |
| PANWPRERAWALKNPHLAYNPFRMPTTSTA | Human betaherpesvirus 5 | 14 | 0.519 | 5 | 0.238 | 80 |
| STPRAAVTQTASQNAADEVWALRDQTAESP | Human betaherpesvirus 5 | 4 | 0.148 | 6 | 0.286 | 81 |
| VKYQALATASGEEVAALSHHDSLESRRLRE | Human betaherpesvirus 5 | 5 | 0.185 | 7 | 0.095 | 82 |
| ASEALDPHAFHLLLNTYGRPIRLLRENTTQ | Human betaherpesvirus 5 | 5 | 0.185 | 4 | 0.19 | 83 |
| PSLKPTLGGKAVVGRPPSVPVSGSAPGRLS | Human betaherpesvirus 5 | 10 | 0.37 | 3 | 0.143 | 84 |
| QQNGTDSLDGRTGTQDKGQKPNLLDRLRIR | Human betaherpesvirus 5 | 7 | 0.259 | 7 | 0.095 | 85 |
| EQPTETPPEDLDTLSLAIEAAIQDLRNKSQ | Human betaherpesvirus 5 | 10 | 0.37 | 4 | 0.19 | 86 |
| ASTTPTYPAVTTVYPPSSTAKSSVSNAPPV | Human betaherpesvirus 5 | 6 | 0.222 | 1 | 0.048 | 87 |
| ALYMGSRRIPRKPRYTRLPKHDPDEFWTKT | Human betaherpesvirus 5 | 8 | 0.296 | 2 | 0.095 | 88 |
| GRGSPLTIESHLSDNEEDPIRYVVSVYDEL | Human betaherpesvirus 5 | 6 | 0.222 | 2 | 0.095 | 89 |
| SDPLEAFKTVNRHNWSDEQREHFYDLRNLY | Human betaherpesvirus 6 | 17 | 0.63 | 12 | 0.571 | 90 |
| RKQKKLDLLGSWTKEKNDKAIVHSREVTGD | Human betaherpesvirus 6 | 13 | 0.481 | 12 | 0.571 | 91 |
| NTAANADVFDPVHRLVSEQTGTPFVLNNSD | Human betaherresvirus 6 | 4 | 0.148 | 6 | 0.286 | 92 |
| PESDSVDNAGGKILIKKETLGGRDVRATTP | Human betaherpesvirus 6 | 9 | 0.333 | 6 | 0.786 | 93 |
| KLPGNGEREIDLALQKVKAGERETSDFKVG | Human betaherpesvirus 6 | 8 | 0.296 | 2 | 0.095 | 94 |
| GDEYSQEDALKMLKAIKSLDESYRRKPSSS | Human betaherpesvirus 6 | 9 | 0.333 | 4 | 0.19 | 95 |
| EISDNIYSSPKNSIYLKSKSQQSTTKFTDT | Human betaherpesvirus 6 | 8 | 0.296 | 1 | 0.048 | 96 |
| TTHSTETGVSPHNVSLIKDLRDKDGFRKQK | Human betaherpesvirus 6 | 3 | 0.111 | 3 | 0.143 | 97 |
| VQSPFRLPNADLSRDLDSASFKDALDLKLP | Human betaherpesvirus 6 | 3 | 0.111 | 3 | 0.143 | 98 |
| KEKRKVEDIDKKKEDEKRKQEEKKRNDEDK | Human betaherpesvirus 6 | 4 | 0.148 | 7 | 0.095 | 99 |
| LKNLLNSRKRDPLFQNFSFTEKMQPVRSPF | Human betaherpesvirus 7 | 7 | 0.259 | 1 | 0.048 | 100 |
| QLVKDVKWTPSSSLLDLSRRNDLLQKELFE | Human betaherpesvirus 7 | 5 | 0.185 | 0 | 0 | 101 |
| NKIDYHSTFFLPENEVNRQNGVQSRDQLSK | Human betaherpesvirus 7 | 6 | 0.222 | 4 | 0.19 | 107 |
| DLIDLENSVQKDDDIVNKLVSHLTHSEEDV | Human betaherpesvirus 7 | 5 | 0.185 | 1 | 0.048 | 103 |
| QDFDSGSLLTGKETQNTIFGASKAQENGDK | Human betaherpesvirus 7 | 4 | 0.148 | 0 | 0 | 104 |
| ATPIERSSRSASIISGESVPGFFNDQERLS | Human betaherpesvirus 7 | 3 | 0.111 | 1 | 0.048 | 105 |
| RRKRELETNKDIVYVQLQYLYDTLKDYINT | Human betaherpesvirus 7 | 1 | 0.037 | 0 | 0 | 106 |
| PVLNISRPGSTTPSGNSARYGNNTPRSITP | Human betaherpesvirus 7 | 3 | 0.111 | 0 | 0 | 107 |
| NSVLQATQSVQAQVKEPLDSSPPYLKTNKD | Human betaherpesvirus 7 | 1 | 0.037 | 2 | 0.095 | 108 |
| KRRKEIVHENLQSFDDEHNEMSLPPQDQKS | Human betaherpesvirus 7 | 1 | 0.037 | 0 | 0 | 109 |
| YTVPDLVVEQYNQTILNLTSEISTRENKSA | Human coronavirus 229E | 2 | 0.074 | 0 | 0 | 110 |
| SDRNHNSQDDIMKAVAAALKSLGFDKPQEK | Human coronavirus 229E | 4 | 0.148 | 3 | 0.143 | 111 |
| EFNPSQTSPATVEPVRDEVSIETDIIDEVN | Human coronavirus 229E | 7 | 0.259 | 4 | 0.19 | 112 |
| GAMLSENFTSYGFSNVVEMPKFFYASNGTY | Human coronavirus 229E | 5 | 0.185 | 5 | 0.238 | 113 |
| SNQDDIMAAVAAALEKLGFERPNDASQPQK | Human coronavirus 229E | 1 | 0.037 | 0 | 0 | 114 |
| DYALPSSRRKRRGISSPYRFVTFEPENVSF | Human coronavirus HKU1 | 10 | 0.37 | 2 | 0.095 | 115 |

TABLE 3 -continued

Peptides enriched in convalescent samples.

| Peptide sequence | Organism | COVID-19 Conv Samples | Pro-portion COVID-19 Conv | Negative Control Samples | Pro-portion Negative Control | SEQ ID NO: |
|---|---|---|---|---|---|---|
| KPDMADEIASLVLAKLGKDSKPQQVTKQNA | Human coronavirus HKU1 | 5 | 0.185 | 3 | 0.143 | 116 |
| FGLQDGFYSANFLDDNVLPETYVALPTYYQ | Human coronavirus NL63 | 7 | 0.259 | 6 | 0.286 | 117 |
| NTVLNASIPESKPLADDDSAIIEIVNEVLH | Human coronavirus NL63 | 2 | 0.074 | 3 | 0.143 | 118 |
| ERWRMRRGQRVDLPPKVHFYYLGTGPHKDL | Human coronavirus NL63 | 1 | 0.037 | 0 | 0 | 119 |
| VSNGGNNCTTAVMTYSNFGICADGSLIPVR | Human coronavirus NL63 | 1 | 0.037 | 1 | 0.048 | 120 |
| PGRRPFFHPVGQADYFEYHQEGGPDGEPDM | Human gammaherpesvirus 4 | 71 | 0.778 | 18 | 0.857 | 121 |
| SPSLPSSKKGADEFEAWLEAQDANFEDVQR | Human gammaherpesvirus 4 | 20 | 0.741 | 17 | 0.81 | 122 |
| MMDPNSTSEDVKFTPDPYQVPFVQAFDQAT | Human gammaherpesvirus 4 | 24 | 0.889 | 12 | 0.571 | 123 |
| QHASGEGPGINPISKTELQAIMLALHEQNQ | Human gammaherpesvirus 4 | 16 | 0.593 | Q | 0.429 | 124 |
| EQEYGDKEVKLPHWTPTLHTFQVPKNYTKA | Human gammaherpesvirus 4 | 18 | 0.667 | 5 | 0.238 | 125 |
| GPRHRDGVRRPQKRPSCIGCKGAHGGTGTG | Human gammaherpesvirus 4 | 11 | 0.407 | 13 | 0.619 | 126 |
| QPMEGPLVPEQWMFPGAALSQRVRPGVAQS | Human gammaherpesvirus 4 | 16 | 0.593 | 11 | 0.524 | 127 |
| MHPLTHQSIPNDPDSPEPRSPTVFYNIPPM | Human gammaherpesvirus 4 | 21 | 0.778 | 9 | 0.429 | 128 |
| LPPRVRGGGRVSAAAITWVPKPNVEVWPVD | Human gammaherpesvirus 4 | 15 | 0.556 | 10 | 0.476 | 129 |
| RKPGGPWRPEPNTSSPSMPELSPVLGLHQG | Human gammaherpesvirus 4 | 13 | 0.481 | 6 | 0.286 | 130 |
| SPIHEPESHNSPEAPILFPDDWYPPSIDPA | Human gammaherpesvirus 4 | 20 | 0.741 | 12 | 0.571 | 131 |
| LAAPRRGNVYWVRDAVTGTRVPVRTRPPHP | Human mastadenovirus A | 17 | 0.63 | 12 | 0.571 | 132 |
| IESINDKMSRWKTYAQERHEWEERQPKPVP | Human mastadenovirus A | 18 | 0.667 | 10 | 0.476 | 133 |
| EENDDFNPVYPFDPYDTAHVPFVTPPFTSS | Human mastadenovirus A | 5 | 0.185 | 2 | 0.095 | 134 |
| MSKDIPTPYMWSFQPQMGLAAGAAQDYSSK | Human mastadenovirus A | 11 | 0.407 | 3 | 0.143 | 135 |
| PPGFYTGEFDLPEGNDGFLWDDVTDSLFSP | Human mastadenovirus A | 1 | 0.037 | 0 | 0 | 136 |
| VLEYMKVDPNIQPDVKIRPIKKVAPGLGVQ | Human mastadenovirus A | 7 | 0.259 | 1 | 0.048 | 137 |
| EAPPPSYETVMAAAQTSALEAPYVPPRYLA | Human mastadenovirus A | 1 | 0.037 | 0 | 0 | 138 |
| GHYRAPWGAHTRGRTGRTTVDDVIDSVVAD | Human mastadenovirus A | 1 | 0.037 | 0 | 0 | 139 |
| LKDQNFQQKVVDGLASGINGVVDIANQAVQ | Human mastadenovirus A | 1 | 0.037 | 3 | 0.143 | 140 |
| NNPQVVFYTEDVNLEMPDTHLVFKPTVTDG | Human mastadenovirus A | 1 | 0.037 | 0 | 0 | 141 |
| RASRRRQRHDRQRGLVWEDEDSADDSSVLD | Human mastadenovirus B | 13 | 0.481 | 6 | 0.286 | 142 |
| WPAALVYQESPAPTTVLLPRDAQAEVQMTN | Human mastadenovirus B | 7 | 0.259 | 4 | 0.19 | 143 |
| TLVTRADEPPSYEEAVKLGMPTTRPVAHMA | Human mastadenovirus B | 14 | 0.519 | 9 | 0.429 | 144 |
| SFNPVYPYEDESTSQHPFINPGFISPNGFT | Human mastadenovirus B | 6 | 0.222 | 7 | 0.333 | 145 |
| TVDDTDGTLQENIGTTTPLVKTGESIGLSL | Human mastadenovirus B | 4 | 0.148 | 1 | 0.048 | 146 |

TABLE 3 -continued

| Peptides enriched in convalescent samples. | | | | | | |
|---|---|---|---|---|---|---|
| Peptide sequence | Organism | COVID-19 Conv Samples | Pro-portion COVID-19 Conv | Negative Control Samples | Pro-portion Negative Control | SEQ ID NO: |
| PPLQPFDPPTLHDLYDLEVDGPDDPNEEAV | Human mastadenovirus B | 3 | 0.111 | 1 | 0.048 | 147 |
| EEIEADVEQDPGYVTPAEHEEELKRFLDRE | Human mastadenovirus B | 1 | 0.037 | 0 | 0 | 148 |
| DMNDHAIRGDTFATRAEEKRAEAEAAAEAA | Human mastadenovirus C | 25 | 0.926 | 19 | 0.905 | 149 |
| AATQKQRRPDSKTLTKPKKSTAAAAAGGGA | Human mastadenovirus C | 9 | 0.333 | 6 | 0.286 | 150 |
| TTDYRNTTATGLTSALNLPQVHAFVNDWAS | Human mastadenovirus C | 10 | 0.37 | 7 | 0.333 | 151 |
| PSAPAVSTVDEAIESVVQGARHYANLKNRR | Human mastadenovirus C | 11 | 0.407 | 2 | 0.095 | 152 |
| ARNYTPTPPPVSTVDAAIQTVVRGARRYAK | Human mastadenovirus C | 10 | 0.37 | 4 | 0.19 | 153 |
| EVLDEEEEMMEDWDSLDEEASEAEEVSDET | Human mastadenovirus C | 6 | 0.222 | 5 | 0.238 | 154 |
| ARRTGRRAAMRAARRLAAGIVTVPPRSRRR | Human mastadenovirus C | 5 | 0.185 | 1 | 0.048 | 155 |
| IAPMATGVLGHHTPVTLDLPPPADTQQKPV | Human mastadenovirus C | 5 | 0.185 | 2 | 0.095 | 156 |
| SYESVVSAASVAAALGSPFDAPLDPPFVPP | Human mastadenovirus C | 11 | 0.407 | 8 | 0.381 | 157 |
| TTRPRLLGEEEYLNNSLLQPQREKNLPPAF | Human mastadenovirus C | 6 | 0.222 | 2 | 0.095 | 158 |
| PEDARPVVSDEMLARWLGTRDPQALEQRRK | Human mastadenovirus D | 2 | 0.074 | 1 | 0.048 | 159 |
| MTKRLRVEDDFNPIYPYGYARNQNIPFLTP | Human mastadenovirus D | 1 | 0.037 | 1 | 0.048 | 160 |
| ESYKNEIKKLTYKNNKTTFEDSGNYEHQKL | Human mastadenovirus D | 1 | 0.037 | 1 | 0.048 | 161 |
| EKINQSLTFIRKSDELLHNVNVGKSTTNIM | Human orthopneumovirus | 10 | 0.37 | 6 | 0.286 | 162 |
| FEAFNFVPCSICSGNPTCWAICKRIPNKKP | Human orthopneumovirus | 17 | 0.63 | 10 | 0.476 | 163 |
| NYQRKPLVSFKEDPTPSDNPFSKEYKETIE | Human orthopneumovirus | 2 | 0.074 | 2 | 0.095 | 164 |
| NKLGEKEKEKDKIKSNNEQDENNSVITTII | Human orthopneumovirus | 6 | 0.222 | 3 | 0.143 | 165 |
| STYMLTNSELLSLINDMPITNDQKKLMSSN | Human orthopneumovirus | 14 | 0.519 | 6 | 0.286 | 166 |
| TNKPSTKPHPKIPPKKPKDDYHFEVFNFVP | Human orthopneumovirus | 10 | 0.37 | 2 | 0.095 | 167 |
| CSICGNNQLCKSICKTIPGNKPKKKPTIKP | Human orthopneumovirus | 8 | 0.296 | 1 | 0.048 | 168 |
| QAITCQKPTPEKEKPDVYKNLSFWEVNLKE | Human papillomavirus | 1 | 0.037 | 1 | 0.048 | 169 |
| PPAEKKDPYADLTFWEVDLKERFSLELDQF | Human papillomavirus | 1 | 0.037 | 1 | 0.048 | 170 |
| AGKEGDSIPMEGTDYYIARQDSKLASHIYY | Human papillomavirus | 1 | 0.037 | 1 | 0.048 | 171 |
| AHQPDFGTWNSSEVPTYGTEEWESWWSSFN | Human polvomavirus 1 | 6 | 0.222 | 3 | 0.143 | 172 |
| RVFDGTERLPGDPDMIRYIDKQGQLQTKML | Human polyomavirus 1 | 2 | 0.074 | 1 | 0.048 | 173 |
| LSDEIQRLLRDLEYGFRATLASIGESDPVN | Human polyomavirus 3 | 6 | 0.222 | 5 | 0.238 | 174 |
| NIWQSSQIPTYGTPDWDEWWSQFNTYWEEE | Human polvomavirus 3 | 3 | 0.111 | 0 | 0 | 175 |
| LQSVHKPIHAPYSGMALVPIPEYQLETGIP | Human polyomavirus 3 | 1 | 0.037 | 0 | 0 | 176 |
| DEDITDIENKIARRLADRKQRLSQANNKRD | Human respirovirus 1 | 13 | 0.481 | 4 | 0.19 | 177 |
| NETTDYSSEGIEDLVFDILDLKGKTKSHRY | Human respirovirus 1 | 1 | 0.037 | 0 | 0 | 178 |
| GAIEVAIDHTDITFGAEDTADRDNKNWAND | Human respirovirus 1 | 1 | 0.037 | 0 | 0 | 179 |

TABLE 3 -continued

Peptides enriched in convalescent samples.

| Peptide sequence | Organism | COVID-19 Conv Samples | Pro-portion COVID-19 Conv | Negative Control Samples | Pro-portion Negative Control | SEQ ID NO: |
|---|---|---|---|---|---|---|
| KKQGSQPPTNPTNRTNQDEIDDLFNAFGSN | Human respirovirus 3 | 19 | 0.704 | 12 | 0.571 | 180 |
| EQATESDNIKTEQQNIRDRLNKRLNDKKKQ | Human respirovirus 3 | 7 | 0.259 | 2 | 0.095 | 181 |
| IVLINSIKSERAHESLLQDINNEFMEVTEK | Human respirovirus 3 | 14 | 0.519 | 10 | 0.476 | 187 |
| ENRADQEQGGEPQSSIIQYAWAEGNRNDDR | Human respirovirus 3 | 5 | 0.185 | 1 | 0.048 | 183 |
| SIKSEKAHESLLRDINNEFIGITEKIQMAS | Human respirovirus 3 | 11 | 0.407 | 12 | 0.571 | 184 |
| STHQEDDKRIKKGGKGKDWFKKSKDTDNQT | Human respirovirus 3 | 1 | 0.037 | 0 | 0 | 185 |
| MESDAKNYQVMDSWEEESRDKSTNISSALN | Human respirovirus 3 | 2 | 0.074 | 1 | 0.048 | 186 |
| SLESIGTPDTRSISVVTAATPDDEEEILMK | Human respirovirus 3 | 2 | 0.074 | 0 | 0 | 187 |
| PQRTSGMSSEEFQHSMNQYIRAMHEQYRGS | Human rubulavirus 2 | 14 | 0.519 | s | 0.738 | 188 |
| MAEEPTYTTEQVDELIHAGLGTVDFFLSRP | Human rubulavirus 2 | 5 | 0.185 | 1 | 0.048 | 189 |
| QLPRGRQPISDPFAGANDREIGGQANDTPV | Human rubulavirus 2 | 2 | 0.074 | 1 | 0.048 | 190 |
| PSSSAGLKDDLLENLQAYQKRMGVQMQRFK | Influenza A virus | 8 | 0.296 | 1 | 0.048 | 191 |
| LATGMRNVPEKQTRGIFGAIAGFIENGWEG | Influenza A virus | 2 | 0.074 | 3 | 0.143 | 192 |
| SEQAAEAMEIASQARQMVQAMRTVGTHPSS | Influenza A virus | 3 | 0.111 | 1 | 0.048 | 193 |
| NPLIRHENRMVLASTTAKAMEQMAGSSEQA | Influenza A virus | 3 | 0.111 | 4 | 0.19 | 194 |
| RTLDYHDSNVKNLYEKVRSQLKNNAKEIGN | Influenza A virus | 1 | 0.037 | 0 | 0 | 195 |
| IWDPNGWTGTDNNFSIKQDIVGINEWSGYS | Influenza A virus | 2 | 0.074 | 0 | 0 | 196 |
| ATCEQIADAQHRSHRQMATTTNPLIKHENR | Influenza A virus | 2 | 0.074 | 0 | 0 | 197 |
| VETYVLSIIPSGPLKAEIAQKLEDVFAGKN | Influenza A virus | 3 | 0.111 | 3 | 0.143 | 198 |
| NPHRILDGIDCTLIDALLGDPHCDGFQNET | Influenza A virus | 1 | 0.037 | 0 | 0 | 199 |
| FAVERPIALSKQAVRKMLSMNIEGRDADVK | Influenza B virus | 70 | 0.741 | 11 | 0.524 | 200 |
| TTRPIIRPATLAPPSNKRTRNPSPERATTS | Influenza B virus | 17 | 0.63 | 11 | 0.524 | 201 |
| GTFNAGEFSLPTFDSLNITAASLNNDGLDN | Influenza B virus | 9 | 0.333 | 3 | 0.143 | 202 |
| RTRGKLCPECLNCTDLDVALGRPMCVGTTP | Influenza B virus | 7 | 0.259 | 5 | 0.738 | 203 |
| TNPIEIPIKQTIPNFFFGRDTAEDYDDLDY | Influenza B virus | 6 | 0.222 | 2 | 0.095 | 204 |
| SLSELEVKNLQRLSGAMDELHSEILELDEK | Influenza B virus | 1 | 0.037 | 0 | 0 | 205 |
| SNSPHVVKIATQGEVNVTGVIPLTTTPTKS | Influenza B virus | 5 | 0.185 | 1 | 0.048 | 206 |
| MSNMDIDGINTGTIDKAPEEITSGTSGTTR | Influenza B virus | 3 | 0.111 | 2 | 0.095 | 207 |
| NTAKTMNGMGKGEDVQKLAEELQSNIGVLR | Influenza B virus | 1 | 0.037 | 2 | 0.095 | 208 |
| GEADDHHGDQEMRELLSGLDYEARCISQSG | Influenza C virus | 2 | 0.074 | 2 | 0.095 | 209 |
| YLLPPKFGRCPLAAKEESIPKIPDGLLIPT | Influenza C virus | 2 | 0.074 | 1 | 0.048 | 210 |
| PTYGTDEWEQWWNAFNEENLFCSEEMPSSD | Macaca mulatta polyomavirus 1 | 3 | 0.111 | 1 | 0.048 | 211 |
| VGVLDWLRNSDDDDDEDGGEKNMEDSGHE | Macaca mulatta polyomavirus 1 | 1 | 0.037 | 0 | 0 | 212 |
| RELVINTLVNQGISRDRATYIGMSAYPNVE | Mamastrovirus 1 | 3 | 0.111 | 1 | 0.048 | 213 |
| DIIDTSDEEYENETDRVTLLSTLVNQGMTM | Mamastrovirus 1 | 7 | 0.259 | 5 | 0.238 | 214 |

TABLE 3 -continued

| Peptides enriched in convalescent samples. | | | | | | |
|---|---|---|---|---|---|---|
| Peptide sequence | Organism | COVID-19 Conv Samples | Pro-portion COVID-19 Conv | Negative Control Samples | Pro-portion Negative Control | SEQ ID NO: |
| FDEDPIATLHAVDAERKIRRAIFNALMEEG | Mamasfrovirus 1 | 3 | 0.111 | 1 | 0.048 | 215 |
| DQREKYRHVHEWYVDNLLNRHVLLPSGEVT | Mamastrovirus 1 | 3 | 0.111 | 4 | 0.19 | 216 |
| TSIPRSRASGHGYESDNTEYLDAPDSADQF | Mamastrovirus 1 | 1 | 0.037 | 0 | 0 | 217 |
| EEYGPTPWGPQAFIKSFDKFFYAEPIDFFS | Mamasfrovirus 1 | 1 | 0.037 | 0 | 0 | 218 |
| DRATLLSTLLNQGISVEPATRITNGAFPAR | Mamastrovirus 1 | 4 | 0.148 | 3 | 0.143 | 219 |
| DDEADRFDLHSSYGSEPEDDDENNRVTLLS | Mamastrovirus 1 | 1 | 0.037 | 0 | 0 | 220 |
| VTSDDTDYDTDTEDEDEFFGEDPIAALHAV | Mamasfrovirus 6 | 15 | 0.556 | 7 | 0.333 | 221 |
| SADGANEPVEMLIPVNEWNMKAQYGGNGTL | Mamastrovirus 6 | 2 | 0.074 | 1 | 0.048 | 772 |
| KGLSDEEYEEYKRVREERNGKYSIEEYLQD | Norwalk virus | 16 | 0.593 | 17 | 0.81 | 223 |
| DDFKLKGKLWADDDRSVDYNERLNFEAPPS | Norwalk virus | 4 | 0.148 | 3 | 0.143 | 224 |
| ISGLPDLTTVPQPDATNTAFSVPPLSLREN | Norwalk virus | 10 | 0.37 | 5 | 0.238 | 225 |
| APDIEKAKRDFPGQPDMWKDHFRPDFSHIK | Norwalk virus | 8 | 0.296 | 2 | 0.095 | 226 |
| TTGFFRPYQDWNKKPLPTVDDSKLKKVANI | Norwalk virus | 3 | 0.111 | 0 | 0 | 227 |
| NNYDPTEEIPAPLGTPDFVGKIQGVLTQFT | Norwalk virus | 1 | 0.037 | 1 | 0.048 | 228 |
| AYSVPPLSQREVGEAKEPLPGSILEMWDGE | Norwalk virus | 1 | 0.037 | 0 | 0 | 229 |
| DEEYDEYKKIREERGGKYSIQEYLEDRERF | Norwalk virus | 4 | 0.148 | 3 | 0.143 | 230 |
| MMMASKDAPTNMDGTSGAGQLVPEANTAEP | Norwalk virus | 1 | 0.037 | 3 | 0.143 | 231 |
| VVSYSVKDGVSGLPDLSTVRQPEESNTAFS | Norwalk virus | 1 | 0.037 | 0 | 0 | 232 |
| QDIHLIDDLGQTRKEKDIEMLCNCISSVPF | Parechovirus A | 2 | 0.074 | 0 | 0 | 233 |
| TTNLTQHPSAPTIPFTPDFRNVDNFHSMAY | Parechovirus A | 1 | 0.037 | 0 | 0 | 234 |
| SAPTMPFTPDFSNVDTFHSMAYDVTTGEKN | Parechovirus A | 2 | 0.074 | 2 | 0.095 | 235 |
| QIHKSPVYGAVEVKMGPAVLSKSDPRLEEP | Parechovirus A | 1 | 0.037 | 2 | 0.095 | 236 |
| VPITQNPVENYIDEVLNEVLVVPNIKESHP | Rhinovirus A | 27 | 1 | 21 | 1 | 237 |
| EQYIDGVLNEVLIVPNINESHPSTSNAAPA | Rhinovirus A | 25 | 0.926 | 20 | 0.952 | 238 |
| SAIFQGPISLGAPPPPAIADLLQSVRTPEV | Rhinovirus A | 76 | 0.963 | 20 | 0.952 | 239 |
| IFQGPIDMRNPPPPAITDLLQAVRTPEVIK | Rhinovirus A | 16 | 0.593 | 14 | 0.667 | 240 |
| ADEQGITDYIHTLGEAFGAGFVDNIKDQIQ | Rhinovirus A | 25 | 0.926 | 20 | 0.952 | 241 |
| VMEQNPVEKYTEAVLNEVLAVPNITPSNSQ | Rhinovirus A | 25 | 0.926 | 21 | 1 | 247 |
| NPSGEDMTLFCQMVSSVPFIPPMADLPDKG | Rhinovirus A | 26 | 0.963 | 21 | 1 | 243 |
| KLQPSVFYDVFPGSKEPAVLTSNDPRLEVD | Rhinovirus A | 12 | 0.444 | 17 | 0.81 | 244 |
| DFIADEQGLGDYITSLGRAFGTGFTDQISA | Rhinovirus A | 74 | 0.889 | 18 | 0.857 | 745 |
| PPPPAIMDLLKSVKNPEVIKYCEDNKWIIP | Rhinovirus A | 25 | 0.926 | 19 | 0.905 | 246 |
| TISQTDALTEGLGDELEEVIVEKTKQTLAS | Rhinovirus A | 24 | 0.889 | 19 | 0.905 | 247 |
| ECINDLLRSVDSEEVREYCKRKNWIIPQIP | Rhinovirus B | 70 | 0.741 | 12 | 0.571 | 248 |
| QSLHQETALTEGLEDELMEVIVDKTQQTLA | Rhinovirus B | 18 | 0.667 | 12 | 0.571 | 249 |
| VVPEHQLASHTQGNVSVKYKYTHPGEQGID | Rhinovirus B | 16 | 0.593 | 13 | 0.619 | 250 |
| QLASHDGGTVSVKYKFTHPGDQGIDLSTAE | Rhinovirus B | 18 | 0.667 | 13 | 0.619 | 251 |

TABLE 3 -continued

Peptides enriched in convalescent samples.

| Peptide sequence | Organism | COVID-19 Conv Samples | Pro-portion COVID-19 Conv | Negative Control Samples | Pro-portion Negative Control | SEQ ID NO: |
|---|---|---|---|---|---|---|
| ISDLLKSVDSEEIREYCKQKNWLIPEIPTN | Rhinovirus B | 20 | 0.741 | 12 | 0.571 | 252 |
| HTQSVPALTANETGATLPTRPSDNVETRTT | Rhinovirus B | 19 | 0.704 | 5 | 0.238 | 253 |
| AATKMDFSQDPSKFTEPVKDVMIKTAPALN | Rhinovirus B | 17 | 0.63 | 11 | 0.524 | 254 |
| EDELEEVVIDKMKQVTASSQSGPKHTQKVP | Rhinovirus B | 13 | 0.481 | 5 | 0.238 | 255 |
| ELNMNPINTPTKSKLHPSVFYNVFPGDKEP | Rhinovirus B | 14 | 0.519 | 15 | 0.714 | 256 |
| LMKDTQTISQTEALTEGFEEELEEVVVDKM | Rhinovirus B | 12 | 0.444 | 9 | 0.429 | 257 |
| DVLEEVIVDKAKQTIASINSNSKYTQQVPT | Rhinovirus B | 10 | 0.37 | 2 | 0.095 | 258 |
| VEHNLTAIFQGLGDDTTPGFIIDLLSASKD | Rhinovirus C | 19 | 0.704 | 19 | 0.905 | 259 |
| NPVEDFIDTTLKEVLVVPDTHPSGPVHTTR | Rhinovirus C | 22 | 0.815 | 18 | 0.857 | 260 |
| AHQGLVSDYVNQLGAAFGDGFSSNIKDHLT | Rhinovirus C | 15 | 0.556 | 12 | 0.571 | 261 |
| AYIGGTNANVGYNHTHPGEIGHEIGRNTGR | Rhinovirus C | 12 | 0.444 | 12 | 0.571 | 262 |
| TNDLQNNDPIDTYVHDVLNEVVVVPDTKPS | Rhinovirus C | 18 | 0.667 | 16 | 0.762 | 263 |
| DTPMITQDKNTLQNPVEQFVDDVLEEVLVV | Rhinovirus C | 21 | 0.778 | 14 | 0.667 | 264 |
| IPEHQLAYAGGANASVGYKHTHPGENGHKI | Rhinovirus C | 14 | 0.519 | 9 | 0.429 | 265 |
| SSLSEHQGVTDYITQLGSAFGDGFTSSIKQ | Rhinovirus C | 20 | 0.741 | 13 | 0.619 | 266 |
| LRPYNNLAQTQGPISDYVTQLGNAFGNGFT | Rhinovirus C | 17 | 0.63 | 12 | 0.571 | 267 |
| DPVSDFIDATLQEVLVVPETKPSGPQHTTK | Rhinovirus C | 22 | 0.815 | 13 | 0.619 | 268 |
| PINTPSTTKLYPSVFYEIFPGEKEPAVLSD | Rhinovirus C | 6 | 0.222 | 13 | 0.619 | 269 |
| IDMSKEFNQKNIKTLDEWESGKNPYEPSEV | Rotavirus A | 6 | 0)22 | 2 | 0.095 | 270 |
| NERLQEKEIEKNADAIMENKNGNKKQQLSD | Rotavirus A | 4 | 0.148 | 5 | 0.238 | 271 |
| KEIENNTDVTMENKNKNKNKNNNRKQQLSD | Rotavirus A | 1 | 0.037 | 0 | 0 | 272 |
| KRRNVQQKDVEKEKQIEKMEEKEIKEVKEQ | Rotavirus C | 3 | 0.111 | 0 | 0 | 273 |
| IKTVPLENELKQKEKQRDNKEKNEKENKDE | Rotavirus H | 3 | 0.111 | 1 | 0.048 | 274 |
| FNGLTGTGVLTESNKKFLPFQQFGRDIADT | SARS-CoV-2 | 1 | 0.037 | 0 | 0 | 275 |
| GVLTESNKKFLPFQQFGRDIADTTDAVRDP | SARS-CoV-2 | 1 | 0.037 | 0 | 0 | 276 |
| KKFLPFQQFGRDIADTTDAVRDPQTLEILD | SARS-CoV-2 | 1 | 0.037 | 0 | 0 | 277 |
| KFLPFQQFGRDIADTTDAVRDPQTLEILDI | SARS-CoV-2 | 2 | 0.074 | 0 | 0 | 278 |
| FLPFQQFGRDIADTTDAVRDPQTLEILDIT | SARS-CoV-2 | 2 | 0.074 | 0 | 0 | 279 |
| LPFQQFGRDIADTTDAVRDPQTLEILDITP | SARS-CoV-2 | 3 | 0.111 | 0 | 0 | 280 |
| QILPDPSKPSKRSFIEDLLFNKVTLADAGF | SARS-CoV-2 | 8 | 0.296 | 0 | 0 | 281 |
| DPSKPSKRSFIEDLLFNKVTLADAGFIKQY | SARS-CoV-2 | 5 | 0.185 | 0 | 0 | 282 |
| PSKPSKRSFIEDLLFNKVTLADAGFIKQYG | SARS-CoV-2 | 6 | 0.222 | 0 | 0 | 283 |
| **SKPSKRSFIEDLLFNKVTLADAGFIKQVGD** | SARS-CoV-2 | 9 | 0.333 | 0 | 0 | 2 |
| SSVLNDILSRLDKVEAEVQIDRLITGRLQS | SARS-CoV-2 | 2 | 0.074 | 0 | 0 | 284 |
| NTVYDPLQPELDSTKEELDKYFKNHTSPDV | SARS-CoV-2 | 12 | 0.444 | 0 | 0 | 285 |
| TVYDPLQPELDSFKEELDKATKNHTSPDVD | SARS-CoV-2 | 10 | 0.37 | 0 | 0 | 286 |

TABLE 3 -continued

Peptides enriched in convalescent samples.

| Peptide sequence | Organism | COVID-19 Conv Samples | Pro-portion COVID-19 Conv | Negative Control Samples | Pro-portion Negative Control | SEQ ID NO: |
|---|---|---|---|---|---|---|
| YDPLQPELDSFKEELDKYFKNHTSPDVDLG | SARS-CoV-2 | 6 | 0.222 | 0 | 0 | 287 |
| DPLQPELDSFKEELDKYFKNHTSPDVDLGD | SARS-CoV-2 | 7 | 0.259 | 0 | 0 | 288 |
| LQPELDSFKEELDKYFKNHTSPDVDLGDIS | SARS-CoV-2 | 8 | 0.296 | 0 | 0 | 289 |
| QPELDSFKEELDKYFKNHTSPDVDLGDISG | SARS-CoV-2 | 11 | 0.407 | 0 | 0 | 290 |
| PELDSFKEELDKYFKNHTSPDVDLGDISGI | SARS-CoV-2 | 9 | 0.333 | 0 | 0 | 291 |
| ELDSFKEELDKYFKNHTSPDVDLGDISGIN | SARS-CoV-2 | 8 | 0.296 | 0 | 0 | 292 |
| LDSFKEELDKYFKNHTSPDVDLGDISGINA | SARS-CoV-2 | 8 | 0.296 | 0 | 0 | 293 |
| DSFKEELDKYFKNHTSPDVDLGDISGINAS | SARS-CoV-2 | 11 | 0.407 | 0 | 0 | 294 |
| **SFKEELDKYFKNHTSPDVDLGDISGINASV** | SARS-CoV-2 | 12 | 0.444 | 0 | 0 | 1 |
| NTPKDHIGTRNPANNAAIVLQLPQGTTLPK | SARS-CoV-2 | 8 | 0.296 | 0 | 0 | 295 |
| TPKDHIGTRNPANNAAIVLQLPQGTTLPKG | SARS-CoV-2 | 8 | 0.296 | 0 | 0 | 296 |
| PKDHIGTRNPANNAAIVLQLPQGTTLPKGF | SARS-CoV-2 | 6 | 0.222 | 0 | 0 | 297 |
| KDHIGTRNPANNAAIVLQLPQGTTLPKGFY | SARS-CoV-2 | 7 | 0.259 | 0 | 0 | 298 |
| DHIGTRNPANNAAIVLQLPQGTTLPKGEYA | SARS-CoV-2 | 7 | 0.259 | 0 | 0 | 299 |
| HIGTRNPANNAAIVLQLPQGTTLPKGFYAE | SARS-CoV-2 | 7 | 0.259 | 0 | 0 | 300 |
| IGTRNPANNAAIVLQLPQGTTLPKGFYAEG | SARS-CoV-2 | 8 | 0.296 | 0 | 0 | 301 |
| GTRNPANNAAIVLQLPQGTTLPKGFYAEGS | SARS-CoV-2 | 7 | 0.259 | 0 | 0 | 302 |
| TRNPANNAAIVLQLPQGTTLPKGFYAEGSR | SARS-CoV-2 | 7 | 0.259 | 0 | 0 | 303 |
| RNPANNAAIVLQLPQGTTLPKGFYAEGSRG | SARS-CoV-2 | 8 | 0.296 | 0 | 0 | 304 |
| NPANNAAIVLQLPQGTTLPKGFYAEGSRGG | SARS-CoV-2 | 8 | 0.296 | 0 | 0 | 305 |
| PANNAAIVLQLPQGTTLPKGFYAEGSRGGS | SARS-CoV-2 | 8 | 0.296 | 0 | 0 | 306 |
| ANNAAIVLQLPQGTTLPKGFYAEGSRGGSQ | SARS-CoV-2 | 8 | 0.296 | 0 | 0 | 307 |
| NNAAIVLQLPQGTTLPKGFYAEGSRGGSQA | SARS-CoV-2 | 8 | 0.296 | 0 | 0 | 308 |
| **NAAIVLQLPQGTTLPKGFYAEGSRGGSQAS** | SARS-CoV-2 | 8 | 0.296 | 0 | 0 | 3 |
| AAIVLQLPQGTTLPKGFYAEGSRGGSQASS | SARS-CoV-2 | 7 | 0.259 | 0 | 0 | 309 |
| AIVLQLPQGTTLPKGFYAEGSRGGSQASSR | SARS-CoV-2 | 8 | 0.296 | 0 | 0 | 310 |
| IVLQLPQGTTLPKGFYAEGSRGGSQASSRS | SARS-CoV-2 | 7 | 0.259 | 0 | 0 | 311 |
| VLQLPQGTTLPKGFYAEGSRGGSQASSRSS | SARS-CoV-2 | 8 | 0.296 | 0 | 0 | 312 |
| LQLPQGTTLPKGFYAEGSRGGSQASSRSSS | SARS-CoV-2 | 8 | 0.296 | 0 | 0 | 313 |
| QLPQGTTLPKGFYAEGSRGGSQASSRSSSR | SARS-CoV-2 | 8 | 0.296 | 0 | 0 | 314 |
| LPQGTFLPKGFYAEGSRGGSQASSRSSSRS | SARS-CoV-2 | 8 | 0.296 | 0 | 0 | 315 |
| PQGTTLPKGFYAEGSRGGSQASSRSSSRSR | SARS-CoV-2 | 6 | 0.222 | 0 | 0 | 316 |
| QGTTLPKGFYAEGSRGGSQASSRSSSRSRN | SARS-CoV-2 | 5 | 0.185 | 0 | 0 | 317 |
| AGNGGDAALALLLLDRLNQLESKMSGKGQQ | SARS-CoV-2 | 3 | 0.111 | 0 | 0 | 318 |
| IGTRNPANNASIVLQLPQGTTLPKGFYAEG | SARS-CoV-2 | 7 | 0.259 | 0 | 0 | 319 |
| GTRNPSNNAAIVLQLPQGTTLPKGFYAEGS | SARS-CoV-2 | 7 | 0.259 | 0 | 0 | PO |
| QLPQGTTLPKGFYAEGSRGGSQASSRSSLR | SARS-CoV-2 | 8 | 0.296 | 0 | 0 | 321 |

TABLE 3 -continued

Peptides enriched in convalescent samples.

| Peptide sequence | Organism | COVID-19 Conv Samples | Pro-portion COVID-19 Conv | Negative Control Samples | Pro-portion Negative Control | SEQ ID NO: |
|---|---|---|---|---|---|---|
| AIVLQLPQMPTLPKGFYAEGSRGGSQAYSR | SARS-CoV-2 | 8 | 0.296 | 0 | 0 | 322 |
| IGTRNPANNAAIVLQLPQGTTLPKGFYAKG | SARS-CoV-2 | 8 | 0.296 | 0 | 0 | 323 |
| GIVNNTVYDPLQPELESFKEELDKYFKNHT | SARS-CoV-2 | 7 | 0.259 | 0 | 0 | 324 |
| VNNTVYDPLQPELESFKEELDKYFKNHTSP | SARS-CoV-2 | 7 | 0.259 | 0 | 0 | 325 |
| YDPLQPELDSFKEELDKYFKNHTSLDVDLG | SARS-CoV-2 | 6 | 0.222 | 0 | 0 | 326 |
| **GDAALALLLLDRLNQLESKMSGKGQQQQGQ** | SARS-CoV-2 | 3 | 0.111 | 0 | 0 | 4 |
| TGVLTESNKKFLPFQQFGRDIADITDAVRD | SARS-CoV-2 | 1 | 0.037 | 0 | 0 | 327 |
| DFGGFNFSQILPDPSKPSKRSFIEDLLFNK | SARS-CoV-2 | 3 | 0.111 | 0 | 0 | 328 |
| GGFNFSQILPDPSKPSKRSFIEDLLFNKVT | SARS-CoV-2 | 3 | 0.111 | 0 | 0 | 329 |
| NFSQILPDPSKPSKRSFIEDLLFNKVTLAD | SARS-CoV-2 | 5 | 0.185 | 0 | 0 | 330 |
| SQILPDPSKPSKRSFIEDLLFNKVTLADAG | SARS-CoV-2 | 5 | 0.185 | 0 | 0 | 331 |
| ILPDPSKPSKRSFIEDLLFNKVTLADAGFI | SARS-CoV-2 | 4 | 0.148 | 0 | 0 | 332 |
| LPDPSKPSKRSFIEDLLFNKVTLADAGFIK | SARS-CoV-2 | 6 | 0.222 | 0 | 0 | 333 |
| PDPSKPSKRSFIEDLLFNKVTLADAGFIKQ | SARS-CoV-2 | 4 | 0.148 | 0 | 0 | 334 |
| KPSKRSFIEDLLFNKVTLADAGFIKQYGDC | SARS-CoV-2 | 4 | 0.148 | 0 | 0 | 335 |
| PSKRSFIEDLLFNKVTLADAGFIKQYGDCL | SARS-CoV-2 | 3 | 0.111 | 0 | 0 | 336 |
| SKRSFIEDLLFNKVTLADAGFIKQYGDCLG | SARS-CoV-2 | 4 | 0.148 | 0 | 0 | 337 |
| KRSFIEDLLFNKVTLADAGFIKQYGDCLGD | SARS-COV-2 | 3 | 0.111 | 0 | 0 | 338 |
| FIEDLLFNKVTLADAGFIKQYGDCLGDIAA | SARS-CoV-2 | 3 | 0.111 | 0 | 0 | 339 |
| IEDLLFNKVTLADAGFIKQYGDCLGDIAAR | SARS-CoV-2 | 4 | 0.148 | 0 | 0 | 340 |
| EDLLFNKVTLADAGFIKQYGDCLGDIAARD | SARS-CoV-2 | 1 | 0.037 | 0 | 0 | 341 |
| YFKNHTSPDVDLGDIPGINASVVNIQKEID | SARS-CoV-2 | 1 | 0.037 | 0 | 0 | 342 |
| LPDPSKPSKRSFIEDILFNKVTLADAGFIK | SARS-CoV-2 | 7 | 0.259 | 0 | 0 | 343 |
| FSQILPDSSKPSKRSFIEDLLFNKVTLADA | SARS-CoV-2 | 4 | 0.148 | 0 | 0 | 344 |
| FKNLREFVFKNIDGYFNIYSKHTPINLVRD | SARS-CoV-2 | 1 | 0.037 | 0 | 0 | 345 |
| KDFGGFNFSQILPDPSKPSKRSFIEDLLFN | SARS-CoV-2 | 1 | 0.037 | 0 | 0 | 346 |
| GFNFSQILPDPSKPSKRSFIEDLLFNKVTL | SARS-CoV-2 | 2 | 0.074 | 0 | 0 | 347 |
| DVVIGTVNNTVYDPLQPELDSFKEELDKYF | SARS-CoV-2 | 4 | 0.148 | 0 | 0 | 348 |
| VVIGIVNNTVYDPLQPELDSFKEELDKYFK | SARS-CoV-2 | 2 | 0.074 | 0 | 0 | 349 |
| VIGPINNTVYDPLQPELDSFKEELDKYFKN | SARS-CoV-2 | | 0.111 | 0 | 0 | 350 |
| IGIVNNTVYDPLQPELDSFKEELDKYFKNH | SARS-CoV-2 | 4 | 0.148 | 0 | 0 | 351 |
| GIVNNTVYDPLQPELDSFKEELDKYFKNHT | SARS-CoV-2 | 5 | 0.185 | 0 | 0 | 352 |
| IVNNTVYDPLQPELDSFKEELDKYFKNHTS | SARS-CoV-2 | 5 | 0.185 | 0 | 0 | 353 |
| VNNTVYDPLQPELDSFKEELDKYFKNHTSP | SARS-CoV-2 | 6 | 0.222 | 0 | 0 | 354 |
| NNTVYDPLQPELDSFKEELDKYFKNHTSPD | SARS-CoV-2 | 6 | 0.222 | 0 | 0 | 355 |
| VYDPLQPELDSFKEELDKYFKNHTSPDVDL | SARS-CoV-2 | 5 | 0.185 | 0 | 0 | 356 |

TABLE 3 -continued

Peptides enriched in convalescent samples.

| Peptide sequence | Organism | COVID-19 Conv Samples | Pro-portion COVID-19 Conv | Negative Control Samples | Pro-portion Negative Control | SEQ ID NO: |
|---|---|---|---|---|---|---|
| PLQPELDSFKEELDKYFKNHTSPDVDLGDI | SARS-CoV-2 | 6 | 0.222 | 0 | 0 | 357 |
| FKEELDKYFKNHTSPDVDLGDISGINASVV | SARS-CoV-2 | 6 | 0.222 | 0 | 0 | 358 |
| LQLELDSFKEELDKYFKNHTSPDVDLGDIS | SARS-CoV-2 | 5 | 0.185 | 0 | 0 | 359 |
| FKEELDKYFKNHTSLDVDLGDISGINASVV | SARS-CoV-2 | 5 | 0.185 | 0 | 0 | 360 |
| NNTAAIVLQLPQGTTLSKGFYAEGSRGGSA | SARS-CoV-2 | 2 | 0.074 | 0 | 0 | 361 |
| DRLNEVAKNLNESLIDLQELGKYEQYIKWP | SARS-CoV-2 | 1 | 0.037 | 0 | 0 | 367 |
| LNEVAKNLNESLIDLQELGKYEQYIKWPWY | SARS-CoV-2 | 1 | 0.037 | 0 | 0 | 363 |
| KLDDKDPNFKDQVILLNKHIDAYKTFPPTE | SARS-CoV-2 | 1 | 0.037 | 0 | 0 | 364 |
| GAISSVLNDILSRLDKVEAEVQIDRLITGR | SARS-CoV-2 | 1 | 0.037 | 0 | 0 | 365 |
| ISSVLNDILSRLDKVEAEVQIDRLITGRLQ | SARS-CoV-2 | 1 | 0.037 | 0 | 0 | 366 |
| VLNDILSRLDKVEAEVQIDRLITGRLQSLQ | SARS-CoV-2 | 1 | 0.037 | 0 | 0 | 367 |
| LNDILSRLDKVEAEVQIDRLITGRLQSLQT | SARS-CoV-2 | 1 | 0.037 | 0 | 0 | 368 |
| DETQALPQRQKKQQIVTLLPAADLDDFSKQ | SARS-CoV-2 | 3 | 0.111 | 0 | 0 | 369 |
| AVRDPQTLEILDITPCSFGGVSVITPGTNT | SARS-CoV-2 | 1 | 0.037 | 0 | 0 | 370 |
| RATRRIRGGDGKMKDLSPRWYFYYLGTGPE | SARS-CoV-2 | 1 | 0.037 | 0 | 0 | 371 |
| ATRRIRGGDGKMKDLSPRWYFYYLGTGPEA | SARS-CoV-2 | 1 | 0.037 | 0 | 0 | 372 |
| RIRGGDGKMKDLSPRWYFYYLGTGPEAGLP | SARS-CoV-2 | 1 | 0.037 | 0 | 0 | 373 |
| IRGGDGKMKDLSPRWYFYYLGTGPEAGLPY | SARS-CoV-2 | 1 | 0.037 | 0 | 0 | 374 |
| RGGDGKMKDLSPRWYFYYLGTGPEAGLPYG | SARS-CoV-2 | 1 | 0.037 | 0 | 0 | 375 |
| GGDGKMKDLSPRWYFYYLGTGPEAGLPYGA | SARS-CoV-2 | 1 | 0.037 | 0 | 0 | 376 |
| GDGKMKDLSPRWYFYYLGTGPEAGLPYGAN | SARS-CoV-2 | 1 | 0.037 | 0 | 0 | 377 |
| DGKMKDLSPRWYFYYLGTGPEAGLPYGANK | SARS-CoV-2 | 1 | 0.037 | 0 | 0 | 378 |
| GKMKDLSPRWYFYYLGTGPEAGLPYGANKD | SARS-CoV-2 | 2 | 0.074 | 0 | 0 | 379 |
| KMKDLSPRWYFYYLGTGPEAGLPYGANKDG | SARS-CoV-2 | 1 | 0.037 | 0 | 0 | 380 |
| MKDLSPRWYFYYLGTGPEAGLPYGANKDGI | SARS-CoV-2 | 1 | 0.037 | 0 | 0 | 381 |
| GTTLPKGFYAEGSRGGSQASSRSSSRSRNS | SARS-CoV-2 | 1 | 0.037 | 0 | 0 | 382 |
| SPARMAGNGGDAALALLLLDRLNQLESKMS | SARS-CoV-2 | 1 | 0.037 | 0 | 0 | 383 |
| ARMAGNGGDAALALLLLDRLNQLESKMSGK | SARS-CoV-2 | 1 | 0.037 | 0 | 0 | 384 |
| RMAGNGGDAALALLLLDRLNQLESKMSGKG | SARS-CoV-2 | 2 | 0.074 | 0 | 0 | 385 |
| MAGNGGDAALALLLLDRLNQLESKMSGKGQ | SARS-CoV-2 | 2 | 0.074 | 0 | 0 | 386 |
| GNGGDAALALLLLDRLNQLESKMSGKGQQQ | SARS-CoV-2 | 2 | 0.074 | 0 | 0 | 387 |
| NGGDAALALLLLDRLNQLESKMSGKGQQQQ | SARS-CoV-2 | 1 | 0.037 | 0 | 0 | 388 |
| GGDAALALLLLDRLNQLESKMSGKGQQQQG | SARS-CoV-2 | 2 | 0.074 | 0 | 0 | 389 |
| DAALALLLLDRLNQLESKMSGKGQQQQGQT | SARS-CoV-2 | 1 | 0.037 | 0 | 0 | 390 |
| LALLLLDRLNQLESKMSGKGQQQQGQTVTK | SARS-CoV-2 | 1 | 0.037 | 0 | 0 | 391 |
| LLDRLNQLESKMSGKGQQQQGQTVTKKSAA | SARS-CoV-2 | 1 | 0.037 | 0 | 0 | 392 |
| RATRRIRGGDGKMKYLSPRWYFYYLGTGPE | SARS-CoV-2 | 1 | 0.037 | 0 | 0 | 393 |

TABLE 3 -continued

Peptides enriched in convalescent samples.

| Peptide sequence | Organism | COVID-19 Conv Samples | Pro-portion COVID-19 Conv | Negative Control Samples | Pro-portion Negative Control | SEQ ID NO: |
|---|---|---|---|---|---|---|
| NAAIVLQLPQGTTLSKGFYAEGSRGGSQAS | SARS-CoV-2 | 1 | 0.037 | 0 | 0 | 394 |
| SDAALALLLLDRLNQLESKMSGKGQQQQSQ | SARS-CoV-2 | 1 | 0.037 | 0 | 0 | 395 |
| GKMKDLSPRWYFYYLGTGPEAGLLYGANKD | SARS-CoV-2 | 1 | 0.037 | 0 | 0 | 396 |
| GTTLPKGFYAEGSRGGSQASSRYSSRSRNS | SARS-CoV-2 | 1 | 0.037 | 0 | 0 | 397 |
| DGKMKDLSPRWYFYYLGTGSEAGLPYGANK | SARS-CoV-2 | I | 0.037 | 0 | 0 | 398 |
| NGGDAALALLLLDRLNQLETKMSGKGQQQQ | SARS-CoV-2 | 1 | 0.037 | 0 | 0 | 399 |
| VKQIYKIPPIKDFGGFNFSQILPDPSKPSK | SARS-CoV-2 | 1 | 0.037 | 0 | 0 | 400 |
| QMAYRFNGIGVTQNVLYENQKLIANQFNSA | SARS-CoV-2 | 1 | 0.037 | 0 | 0 | 401 |
| LYQDVNCTEVPVAIHADQLTPTWRVYSTGS | SARS-CoV-2 | 1 | 0.037 | 0 | 0 | 402 |
| YQDVNCTEVPVAIHADQLTPTWRVYSTGSN | SARS-CoV-2 | 1 | 0.037 | 0 | 0 | 403 |
| TEVPVAIHADQLTPTWRVYSTGSNVFQTRA | SARS-CoV-2 | I | 0.037 | 0 | 0 | 404 |
| EVPVAIHADQLTPTWRVYSTGSNVFQTRAG | SARS-CoV-2 | 1 | 0.037 | 0 | 0 | 405 |
| FNFSQILPDPSKPSKRSFIEDLLFNKVTLA | SARS-CoV-2 | 1 | 0.037 | 0 | 0 | 406 |
| RSFIEDLLFNKVTLADAGFIKQYGDCLGDI | SARS-CoV-2 | 1 | 0.037 | 0 | 0 | 407 |
| SFIEDLLFNKVTLADAGFIKQYGDCLGDIA | SARS-CoV-2 | 1 | 0.037 | 0 | 0 | 408 |
| GRRGPEQTQGNFGDQELIRQGTDYKHWPQI | SARS-CoV-2 | 1 | 0.037 | 0 | 0 | 409 |
| SFIEDLLFNKVTLADVGFIKQYGDCLGDIA | SARS-CoV-2 | 1 | 0.037 | 0 | 0 | 410 |
| PNITNLCPFGEVFNATRFTSVYAWNRKRIS | SARS-CoV-2 | 1 | 0.037 | 0 | 0 | 411 |
| SFIEDLLFNKVTLADAGFIKQYGDCLGDIV | SARS-CoV-2 | 1 | 0.037 | 0 | 0 | 412 |
| LQKTVQIKNPKKQAPESFLHTWDFRRGFVT | Torque teno midi virus | 1 | 0.037 | 0 | 0 | 413 |
| QQHTKLQLLQLINNLKKKQKLIQLQTGILD | Torque teno midi virus 11 | 2 | 0.074 | 1 | 0.048 | 414 |
| QIENPERQDPRSILHQWDYRRGFIKERALK | Torque teno midi virus 12 | 1 | 0.037 | 0 | 0 | 415 |
| IQIVNPEKQSPETIIHPWDYRRGLIKEKAL | Torque teno midi virus 7 | 4 | 0.148 | 0 | 0 | 416 |
| KAMLRDWDYRRGIITTTALKRMSEHLQTDS | Torque teno midi virus 8 | 1 | 0.037 | 0 | 0 | 417 |
| ENLQQLILHQQQQQQKLKSNILKLLMDLKH | Torque teno midi virus 8 | 2 | 0.074 | 1 | 0.048 | 418 |
| SQEIPQTQNLQELIQQQQQQQQQLKYNILK | Torque teno midi virus 9 | 2 | 0.074 | 1 | 0.048 | 419 |
| QLQQQLQFLTREMFKTQAGLHINPMLLNQR | Torque teno virus | 2 | 0.074 | 1 | 0.048 | 420 |

There was no overlap between the reactive peptides observed in the convalescent and negative control samples (FIG. 2C). These enriched peptides clustered together into nine reactive regions of the S protein and six reactive regions of the N protein (FIG. 2C), which represents a minimum estimate for the number of epitopes. These epitopes were recognized at a range of prevalences across the sampled population. The most widely-recognized epitopes in S (positions 795-848 and 1127-1177) and N (positions 140-193) were each detected in 41-68% of the convalescent samples that tested positive with our assay (n=22) (FIG. 2C), and >95% (21/22) of these convalescent samples were reactive to at least one of these three immunodominant regions. At the other extreme, six (43%) of the observed epitope regions were each detected in only a single donor. Despite the detection of a variety of SARS-CoV-2 S epitopes in the convalescent donors, very little reactivity was detected to peptides within the RBD, suggesting that these epitopes require protein conformations that are not well represented by linear 30mers.

To evaluate the potential for the identified S protein epitopes to be targeted by neutralizing antibodies, we evaluated these within the context of the protein's structure. Of the S epitopes identified, four were recurrent across multiple convalescent samples, occurring at positions 1127-1177, 795-848, 543-589 and 971-1006 (of SARS-Cov-2 S protein sequence GenBank: YP_009724390.1) and found in 14/27, 11/27, 4/27 and 2/27 convalescent donors, respectively.

Figure 3A:
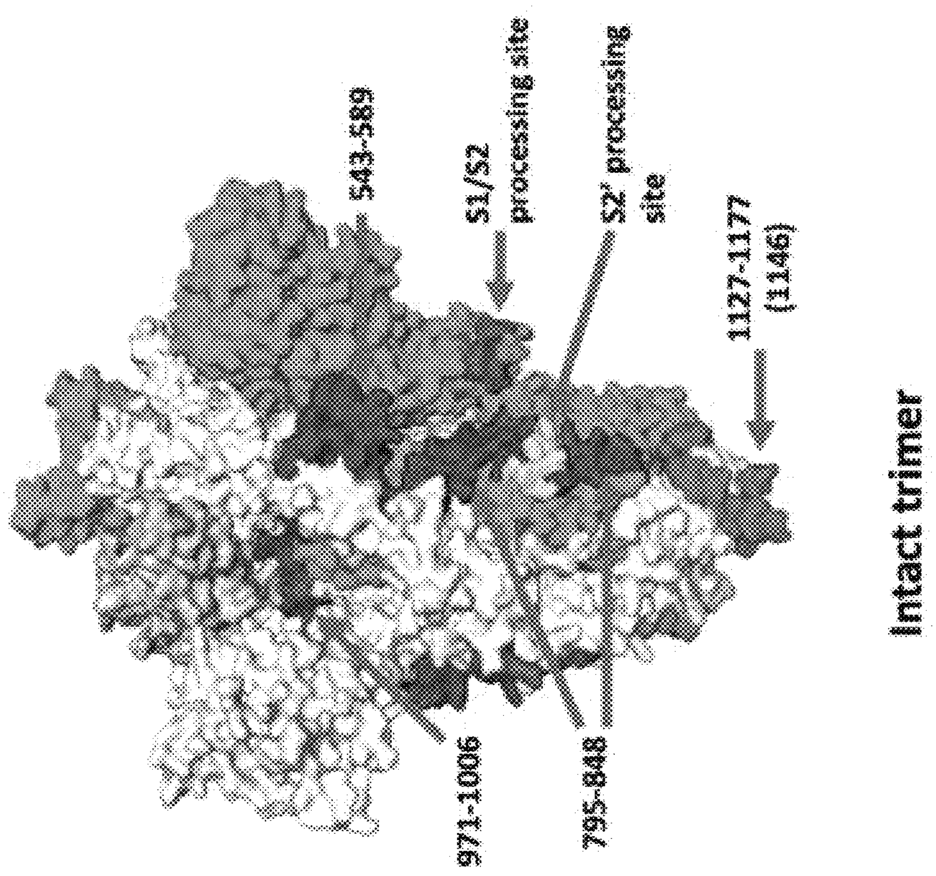
FIGS. 3A-3C illustrate recurrent Spike protein epitopes correspond to accessible and functionally-important sites within the protein structure.

The enriched peptides at each of these four high-confidence regions were mapped onto a rendering of the recently-solved 3-dimensional structure of the native S trimer (FIG. 3A). FIG. 3A shows a space-filling model showing the native SARS-CoV-2 Spike trimer (monomers shown in green, gray and white) with the 4 recurrent epitope regions targeted by COVID-19 convalescent IgG (see also FIG. 2C) highlighted in blue or magenta. Each epitope is identified by its amino acid range within the S protein sequence (GenBank: YP_009724390.1). Protease processing sites are also highlighted, including the S2' site that occurs within the 795-848 epitope.

Figure 3C:
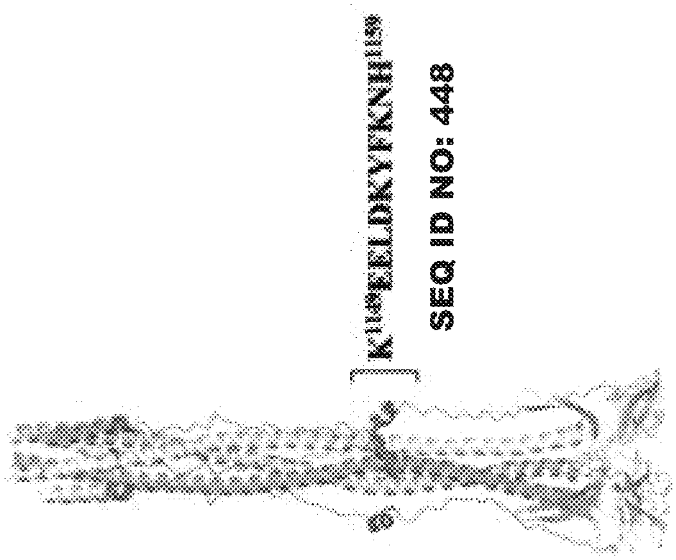
Figure 3B:
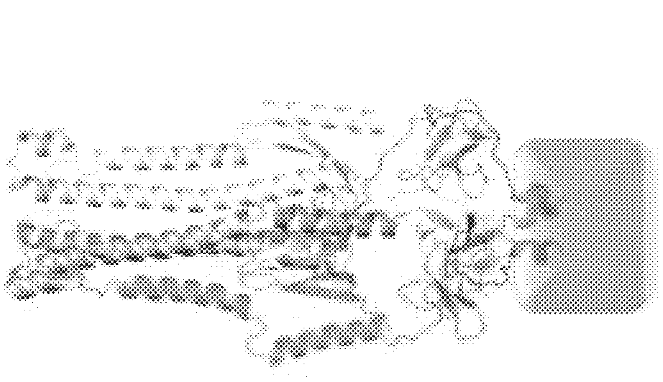

All four epitope regions are accessible for antibody binding on the surface of the trimer. The most widely-recognized reactive region (1127-1177) is located within the 'stem helix' just upstream and partially overlapping with the heptad repeat region 2 (HR2); this region is proximal to the transmembrane domain and partially unresolved in the native structure. The second epitope (795-848) resides at the S2' cleavage site, spanning the fusion peptide whose exposure and incorporation into the host membrane are essential steps in virus entry into cells. Comparison of pre- and post-fusion structures (FIGS. 3B and 3C) indicates that the HR2 epitope lies within a region that undergoes a dramatic conformational rearrangement during fusion. FIG. 3B shows a ribbon model of the S2 subunit after protease processing. The epitope at positions 1127-1177 (magenta) includes a region unresolved in the structure (marked by blue box at the bottom of the structure). FIG. 3C shows a ribbon model of the 6-helical bundle (post-fusion) conformation of the S2 subunit. The 1127-1177 region is again highlighted in magenta, and a comparison with FIG. 3B shows the dramatic conformational rearrangement that occurs at this site.

Antibody Epitopes and Protein Conservation Across the Human CoVs

To compare the SARS-CoV-2 reactivity profile described above with those of the other human coronaviruses, we performed a similar analysis but using the HV library (which covers all of the endemic human CoVs) and focusing on pre-pandemic donors. Applying the same Z-score threshold described above to the HV library, we identified reactivity to at least one endemic human coronavirus in 17 (51.5%) of the negative control samples we tested (n=33). To avoid false positives, we required ≥2 enriched peptides for a sample to be considered seropositive. Across all of the different coronaviruses, the vast majority of the recognized peptides were from the S and N proteins (95% of all enriched coronavirus peptides), with occasional reactivity observed to peptides in Orflab and a single peptide from the Membrane (M) protein recognized in one sample (FIG. 4C). FIG. 4C shows protein-level distribution of enriched HV library peptides across five HCoVs and 33 pre-pandemic control samples. A single peptide could be counted multiple times if enrichment was independently observed in multiple samples. Along with our SCV2 library data, these results indicate that S and N are the predominant antibody targets across all of the human-infecting coronaviruses and that pre-existing anti-CoV reactivity is common in the pre-pandemic population.

Figure 4A:
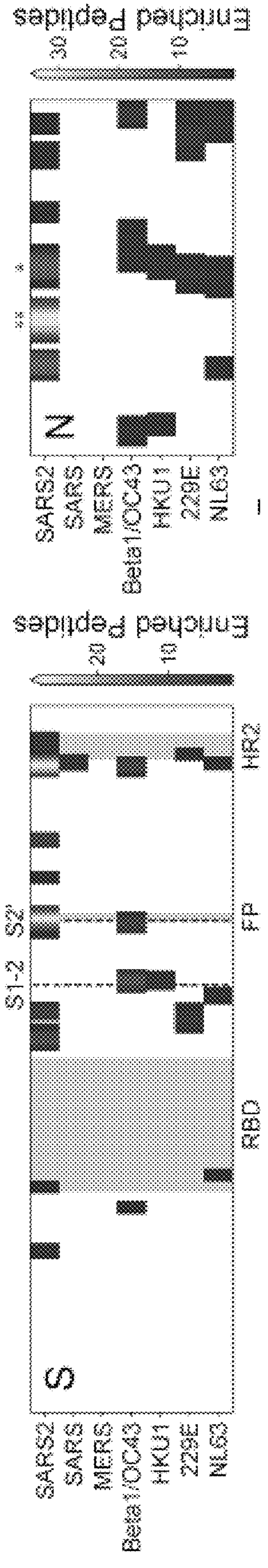
FIGS. 4A-4E illustrate recurrent SARS-CoV-2 epitopes correspond to conserved regions of Spike S2 that are also targeted in the response to other CoVs.

Within the S protein, we observed reactivity to homologous regions across multiple coronavirus species with highly variable percent identity to SARS-CoV-2 depending on the region and virus species (12.1-92.5% identical, average=40%)(FIG. 4A). FIG. 4A shows heat maps illustrating the relative locations of enriched SCV2 (from COVID-19 convalescent samples) and HV (from pre-pandemic controls) library peptides within the S (left) and N (right) proteins and across all human-infecting coronaviruses.

Results have been aggregated across all tested samples and the color at each location indicates the number of unique enriched peptides. The vertical dashed lines in the S protein plot represent the S1-S2 and S2' cleavage sites, respectively. Above the N plot, '**' and '*' indicate the 1st and 2nd most commonly immunogenic regions of this protein in COVID-19 convalescent samples, respectively.

Figure 4B:
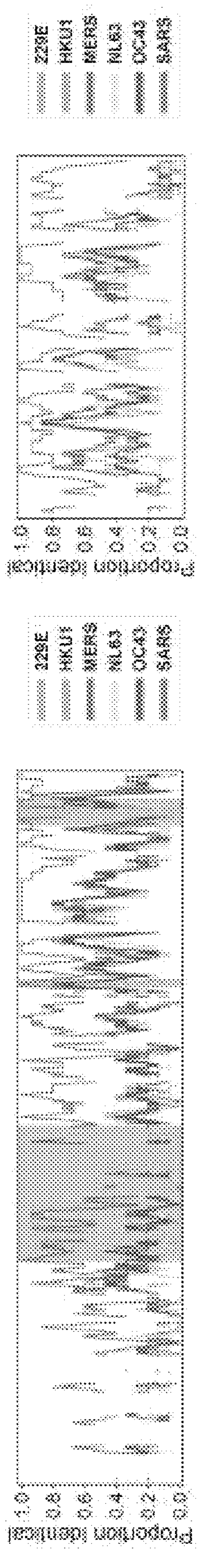
Figure 4C:
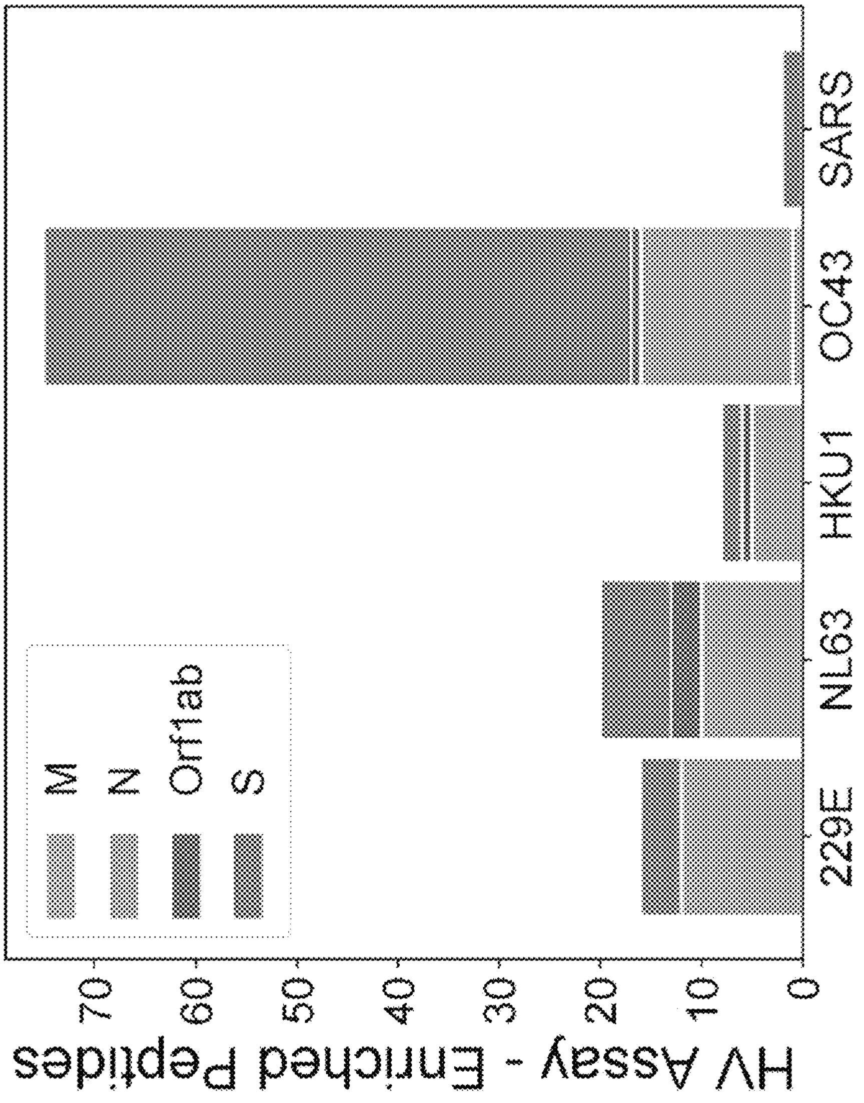

Notably, we observed a correlation between amino acid sequence conservation among members of the Betacoronavirus genus and peptide enrichment in our assay. Across the full S protein, we identified five highly conserved regions (≥70% identical across 15mer sliding windows, blue bars in FIG. 4B) between SARS-CoV-2 and each of the two endemic human betacoronaviruses: hCoV-OC43 and hCoV-HKU1 (four shared, one unique to each virus). All of these regions were located within the S2 subunit (FIG. 4B), and while enriched SARS-CoV-2 peptides covered only 37% of the full S protein, we observed enriched peptides across almost all of the highly conserved regions: 96.4% (107/111) and 75.6% (93/123) of residues within these highly-conserved regions overlapped≥1 enriched peptide for hCoV-OC43 and hCoV-HKU1, respectively. FIG. 4B shows a comparison of amino acid sequence identity between SARS-CoV-2 and the other six human CoVs across the same S and N alignments used in FIG. 4A. A sliding window of 15 amino acids was used and gaps represent windows with ≥30% indels. Blue bars under the S plot indicate regions≥15 amino acids long that exhibit≥70% identity between SARS-CoV-2 and hCoV-OC43 and/or hCoV-HKU1. Grey boxes in FIGS. 4A and 4B indicate selected functional domains: receptor binding domain (RBD), fusion peptide (FP) and heptad repeat 2 (HR2).

Figure 7:
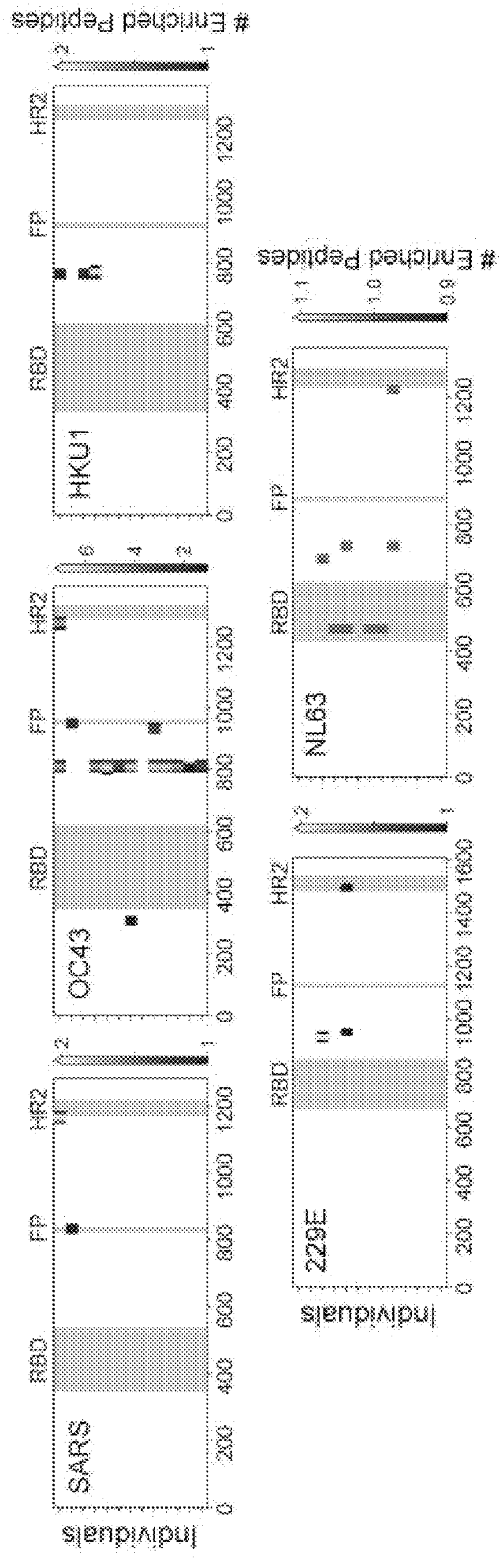
FIG. 7 illustrates the distribution of enriched peptides from CoV Spike proteins in the HV library.

Across the different coronavirus species, the most commonly recognized S protein region, HR2, is also the most commonly reactive SARS-CoV-2 region within our convalescent sera. We detected reactivity in this region to ¾ of the endemic human coronaviruses, though the precise locations of the recognized epitopes likely vary somewhat between species (FIG. 4E). In one pre-pandemic serum sample, we also observed two enriched peptides in this region from the closely-related, epidemic-associated SARS-CoV species; however, these enrichments likely result from cross-reactivity with the endemic hCoV-OC43 (FIG. 7). For the Betacoronavirus 1 species (beta-CoV-1), which includes hCoV-OC43, we also detected reactivity at the same position as the second most immunodominant SARS-CoV-2 epitope, which overlaps the fusion peptide and S2' cleavage site (FIG. 4A). At this epitope region, we observed enrichment of one SARS-CoV peptide within a sample that also exhibited reactivity to homologous hCoV-OC43 peptides, again consistent with cross-reactive antibodies. However, the minimal epitope region contained within all enriched peptides is distinct between beta-CoV-1/hCoV-OC43 and SARS-CoV-2 (yellow residues in FIG. 4D).

Figure 4D:
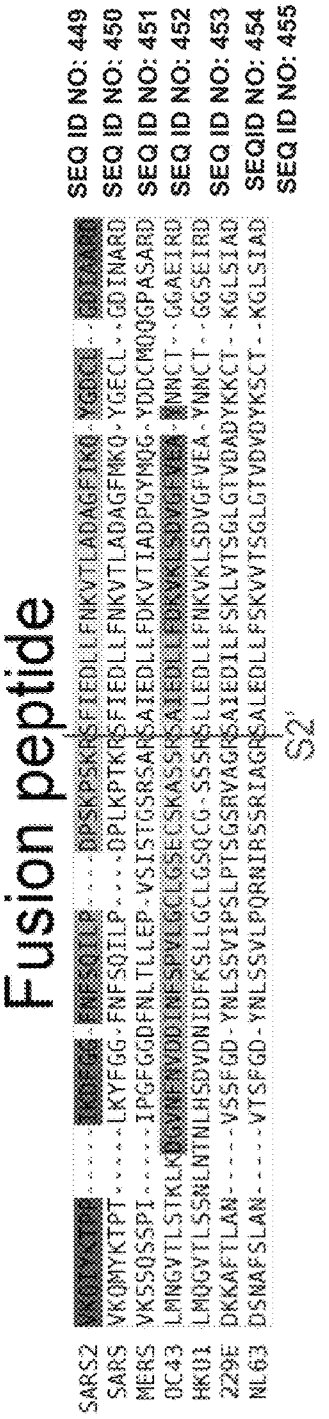
Figure 4D:
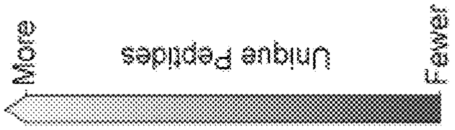
Figure 4E:
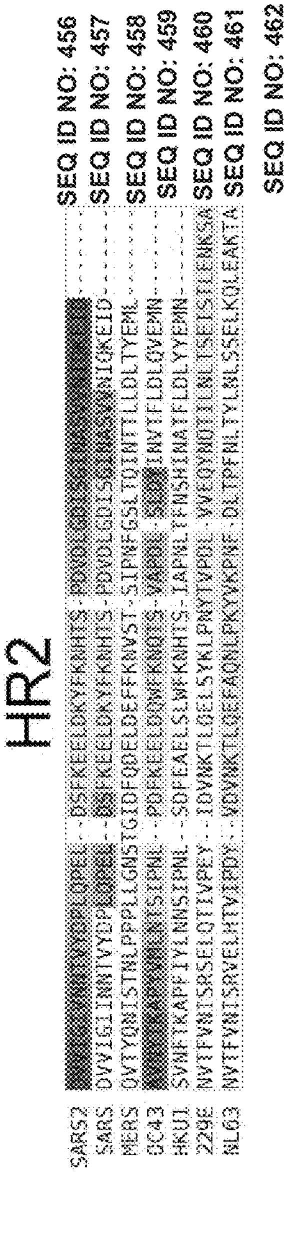

FIGS. 4C and 4D show multiple sequence alignments of the immunodominant and most widely-recognized protein regions of SARS-CoV-2, including representative sequences from each of the seven human coronaviruses. Regions containing enriched peptides are highlighted by colored backgrounds, with bright yellow indicating residues contained within the most unique enriched peptides and dark green indicating those contained within the least unique enriched peptides. SARS-CoV-2 reactivity was determined using the SCV2 peptide library, while reactivity for the other coronaviruses was determined using the HV peptide library.

In contrast, we did not observe any reactivity for the endemic coronaviruses within the most commonly immunogenic SARS-CoV-2 N protein region (shown by double asterisks "**" in FIG. 4A). However, we did observe homologous reactivities in other portions of the N protein. In fact, the second most commonly immunogenic region observed in our COVID-19 convalescent samples (positions 206-252 in FIG. 2C) overlaps with immunogenic regions in all four endemic human coronaviruses (shown by a single asterisk "*" in FIG. 4A). Somewhat surprisingly, however, we observed a somewhat greater similarity in the locations of reactive epitopes between SARS-CoV-2 and the endemic alphacoronaviruses (hCoV-229E and hCoV-NL63) than we did with the endemic betacoronaviruses (hCoV-HKU1 and hCoV-OC43) (FIG. 4A).

Recurrent Interspecies Cross-Reactivity Elicited by SARS-CoV-2 Exposure

Figure 5A:
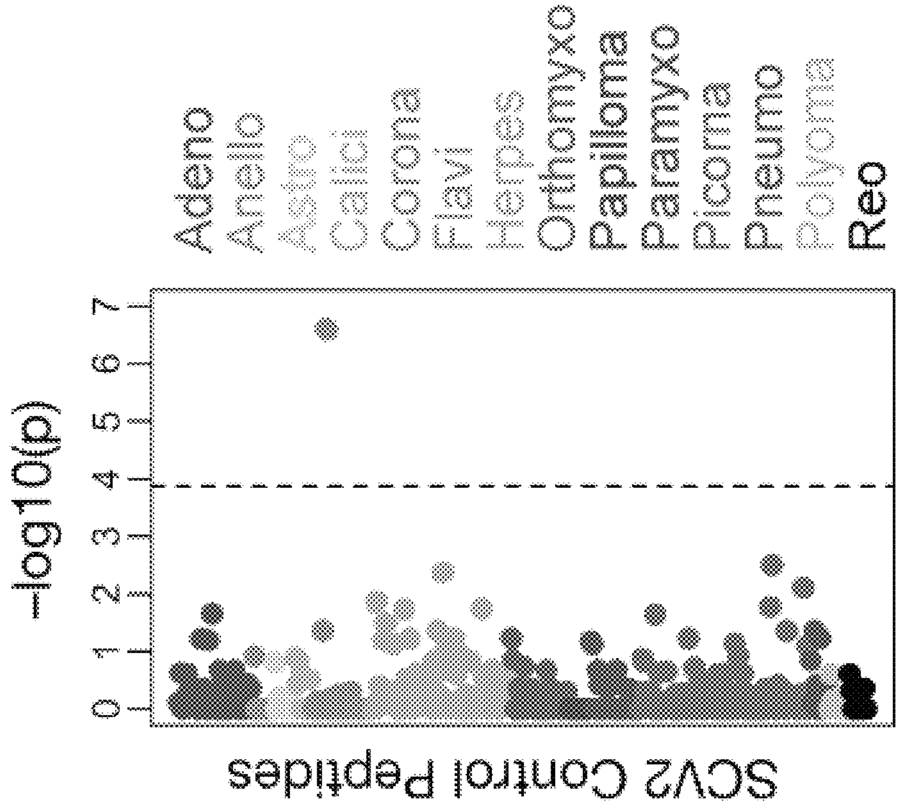

To explore the possibility that the antibody response to SARS-CoV-2 cross-reacts with other viruses, we focused on the panel of control peptides present in both the SCV2 and HV libraries (FIG. 5A). FIG. 5A shows a Fisher's exact test p-values measuring the correlation between donor SARS-CoV-2 status and reactivity for each of 393 control peptides. These peptides were designed from 55 virus species that belong to 14 different families (colors, labels correspond to family names with the omission of "-viridae"), and they recognize epitopes that we previously identified as commonly reactive in the general population. The dashed vertical line shows the Bonferroni-corrected threshold for significance.

This panel comprises 393 peptides from 55 virus species (range: 1-11 per species; 22 from the Coronaviridae family) for which we have previously observed recurrent reactivity in the general population. Consistent with previous results (not shown) and expected viral prevalences, we observed a range of positivity rates, including 25-100% for Rhinovirus-derived peptides and 0-48% for endemic human CoV-derived peptides. Comparing convalescent and negative control groups, Fisher's exact tests identified a single peptide as significantly different between the groups at a Bonferroni-corrected threshold of $p<1.3e-4$ (FIG. 5A). This peptide was enriched in 21/27 convalescents and 1/21 controls ($p=2.5e-7$), and was designed from a beta-CoV-1 strain. Although it was designed from a bovine coronavirus sequence, the peptide is 86.7% identical to the corresponding 30mer region in hCoV-OC43 (26/30 identical residues) and 100% identical to hCoV-OC43 across the 18 C-terminal residues. This peptide (SEQ ID NO: 14) corresponds to positions 1218-1247 of the beta-CoV-1 Spike protein and it precisely overlaps the immunodominant HR2 region we identified based on SARS-CoV-2 peptides. Therefore, we hereafter refer to this peptide (SEQ ID NO: 14) as 'Beta1-HR2'. Beta1-HR2 also exhibits a high degree of conservation with SARS-CoV-2, particularly in the C-terminal portion of the peptide (66.7% identical across 18 C-terminal residues) (FIG. 5B). FIG. 5B shows sequence alignments between SARS-CoV-2 (SARS2) and the Betacoronavirus 1 strain, human coronavirus OC43 (OC43), at two Spike protein regions covered by SCV2 library control peptides designed from Betacoronavirus 1 (Beta1) sequences. Residues are colored according to amino acid properties: small non-polar (orange), hydrophobic (green), polar (pink), negatively charged (red) and positively charged (blue).

Figure 5C:
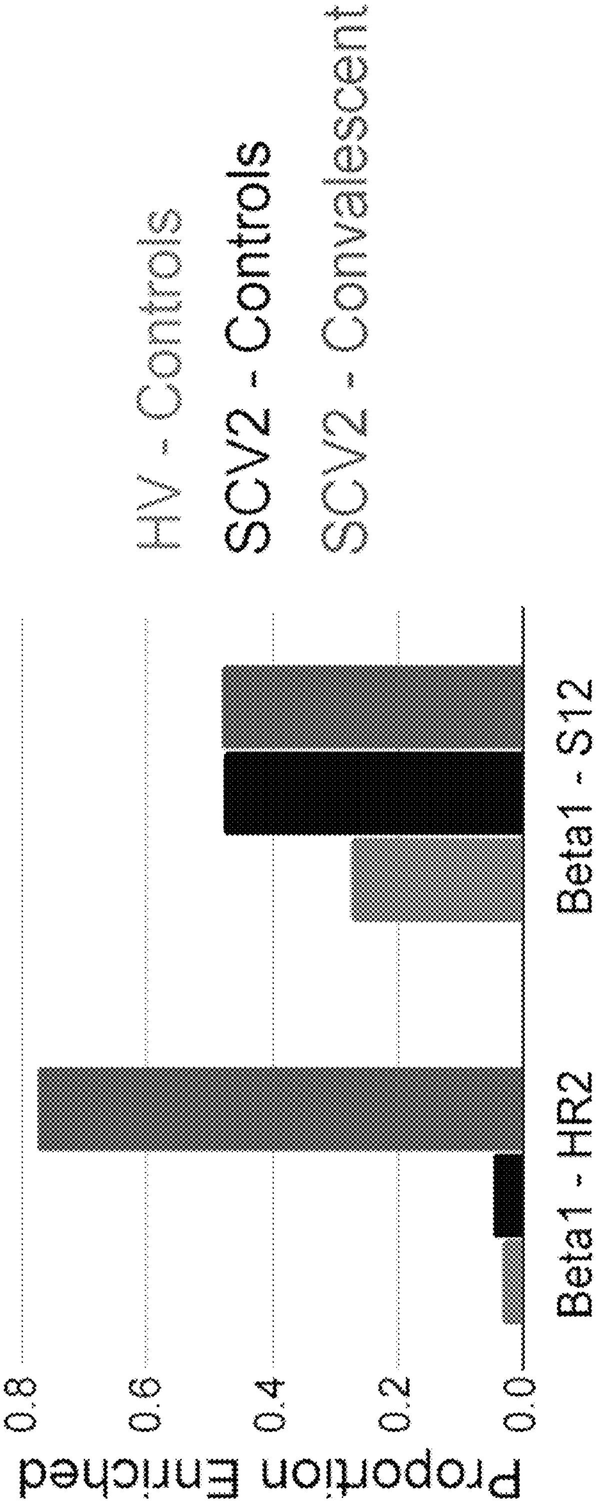

By comparison, a second Spike-derived beta-CoV-1 peptide ('Beta1-S12') was reactive in about half of all samples tested (13/27 convalescents and 10/21 controls), indicating a high level of exposure to beta-CoV-1/hCoV-OC43 that did not differ between the groups (FIG. 5C). FIG. 5C shows the proportion of samples reactive to the two Betacoronavirus 1 peptides shown in FIG. 5B. Two separate sets of negative controls are shown, those assayed with the HV peptide library (grey, n=33) and those assayed with the SCV2 peptide library (black, n=21). In FIG. 5C, results from COVID-19 convalescent samples are shown in red (n=27). Notably, the sequences of SARS-CoV-2 and beta-CoV-1 are highly divergent at the region covered by Beta1-S12 (13.3% identical) (FIG. 5B).

Figure 5D:
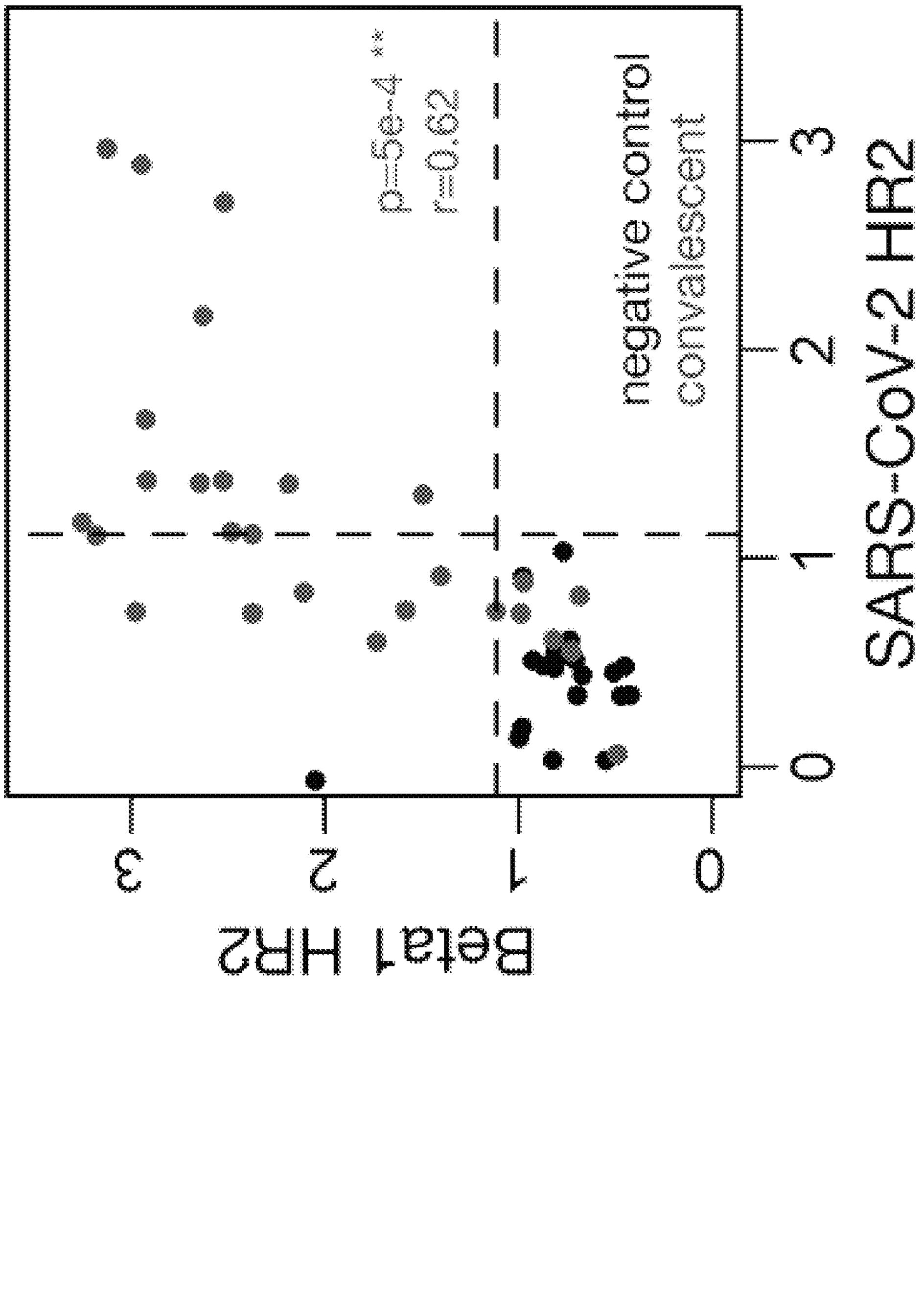

To further test the hypothesis that reactivity to Beta1-HR2 represents cross-reactivity with SARS-CoV-2, we compared donor-level reactivity to this peptide and the homologous SARS-CoV-2 peptide, referred to herein as SARS-CoV-2-HR2 (FIG. 5D). FIG. 5D shows a quantitative comparison of reactivities to homologous HR2 peptides from SARS-CoV-2 and Beta1-CoV across the donor cohort. Axes represent log 10 (2+Z-scores) and dashed lines indicate threshold for significance (Z-score≥11). We observed a significant positive correlation between measured reactivity against these two peptides in convalescent donors ($r=0.62$, $p=5e-4$), and all of the donors reactive to SARS-CoV-2-HR2 were also reactive to Beta1-HR2. However, an additional six convalescent donors were reactive to Beta1-CoV, despite a lack of reactivity to any SARS-CoV-2 peptides overlapping the HR2 epitope. Moreover, for donors reactive to either HR region, the signal strength for Beta1-HR2 was up to ~170-fold (mean~10-fold) higher than for SARS-CoV-2-HR2, indicating that the anti-HR2 antibodies elicited by SARS-CoV-2 infection actually bind better to Beta1-HR2.

Discussion

Like most viruses, SARS-CoV-2 elicits a robust antibody response whose targets are likely to be important determinants of disease outcome and the extent of protection conferred following natural infection or vaccination. In this study, we describe a customizable platform that enables epitope-resolved profiling of the antibody response ('PepSeq'), and its application to the study of human CoVs including SARS-CoV-2. Using this system, we identify immunodominant epitopes in both the S and N proteins, several of which overlap conserved, functional sites in the Spike S2 subunit, and therefore have the potential to be sites of broadly neutralizing reactivity. By examining reactivity in pre-pandemic donors to homologous peptides from multiple human CoVs, we also show that the response to SARS-CoV-2 strongly cross-reacts with an endemic human CoV at one of these epitopes.

By independently testing reactivity across thousands of potential epitopes, we identified several with promise for use in both diagnostics and functional characterization assays. For two of the epitopes, we detected in the S2 subunit of Spike structural considerations, as well as previous characterization of related epitopes (Keng et al., 2005; Lai et al., 2005; Poh et al., 2020), strongly indicate neutralization potential. In these cases, a peptide-based assay may provide a facile means of profiling functional reactivities independently of cell/viral culture, and in a way that complements ACE2:RBD binding inhibition assays that cannot measure S2 reactivity (Tan et al.). We also identified a set of 4 peptides across the S and N proteins that together exhibit great potential for generating an accurate profile of SARS-CoV-2 exposure. Although the precise diagnostic performance of this particular set needs to be quantified on a larger, independent sample set, our results provide a blueprint for a new generation of peptide-based diagnostics that would be easier to manufacture, and in some cases more informative, than existing full-protein/domain assays.

Our PepSeq analysis identified a novel epitope contained within positions 1127-1177 in Spike, where the minimal reactive sequence is FKEELDKYF (SEQ ID NO: 421), as the most widely-recognized SARS-CoV-2 linear epitope target in convalescent donors (FIG. 2C). This region is located within the 'stem helix', directly N-terminal of the heptad-repeat 2 (HR2) region. While largely unresolved in the prefusion structure, analysis of post-fusion structures of CoV Spike proteins indicate that HR2 undergoes a ~180° reorientation during the formation of the 6-helix bundle in which it comes into close contact with the heptad-repeat 1 (HR1) region (Walls et al., 2017). HR-derived peptides that disrupt the HR1:HR2 interaction have previously been shown to inhibit infection by other CoVs (Xia et al., 2019) (Liu et al., 2004), highlighting the strong potential for functional targeting of this region. Moreover, neutralizing monoclonal antibodies raised against related CoVs, including SARS-CoV (which has >95% amino acid-level identity at the stem helix of HR2), have been shown to bind a region directly adjacent to the one that we identified in this study (Routledge et al., 1991)(Lai et al., 2005)(Keng et al., 2005). Strikingly, our analysis of reactivity across the human-infecting CoVs indicated that sites in the proximity of HR2 are also recognized in the responses to at least three of the four endemic species (FIG. 4A). Since portions of this region are highly conserved across species (FIG. 4B), cross-reactivity with pre-existing anti-CoV antibodies likely accounts for some of its immunodominance in the response to SARS-CoV-2.

A second immunodominant reactivity that we identified in Spike S2 also occurs in a region whose sequence is highly-conserved across CoV species: positions 795-848, where the minimal reactive sequence is EDLLFN (SEQ ID NO: 422), which overlaps the S2' cleavage site and the Fusion Peptide (FP). Since the minimal region needed to explain the reactive peptides included residues on both sides of S2' in many donors, this reactivity has the potential to block proteolytic processing and thereby prevent maturation of the S protein. Alternatively, and perhaps additionally, binding of antibody to the FP is expected to prevent its insertion into the host membrane and therefore prevent fusion and cell entry. A recent study, using a lower-throughput peptide-based approach also identified this FP epitope as reactive in two SARS-CoV-2 convalescent donors, and while they did not characterize the mechanism of action, they demonstrated the neutralization potential of antibodies against this epitope using antibody depletion assays (Poh et al., 2020). This study also reported an epitope downstream of the Spike RBD to which antibodies also exhibited neutralization potential. We observed reactivity to this same epitope in four of our SARS-CoV-2 convalescent donors, the epitope have positions 543-589, where the minimal reactive sequence is LPFQQFGRDIADT (SEQ ID NO: 423)). In addition to Spike S2 epitopes, we detected an immunodominant reactivity at positions 140-193 (see also SEQ ID NO: 3) of the SARS-CoV-2 nucleocapsid (N) protein, which lies at the C-terminal end of the domain that is primarily responsible for binding viral RNA (Chang et al., 2009). Unlike the reactivities described in Spike S2, this region does not appear to be targeted in the response to other CoVs (FIG. 4A).

Despite well-documented serological reactivity in studies using the full-length RBD antigen (Amanat et al., 2020), we observed very little reactivity to peptides designed from the RBDs of human CoVs, including SARS-CoV-2 (FIGS. 2C and 3A). This lack of reactivity in our assay, as well as a similar absence of reactivity in a recent study using a lower-throughput peptide-based approach (Poh et al., 2020), suggests that antibodies to the RBD recognize conformational epitopes and/or depend on post-translational modifications. Like other peptide-based antibody assays, PepSeq is limited to the detection of epitopes that are well-represented by short linear peptides and do not require post-translational modifications. The dependence of RBD epitopes on secondary/tertiary structure is supported by structural analyses of the footprints of neutralizing antibodies bound to Spike RBD, which indicate the involvement of residues that are distal in the linear sequence (Pinto et al., 2020; Yuan et al.). The identification of epitopes like these will require lower throughput approaches including mutagenesis and/or structural studies.

The observation that ~80% of SARS-CoV-2 convalescent donors react strongly to a Beta1-HR2 peptide targeted in ~5% of our negative control samples (FIG. 5C) is, to our knowledge, the first identification of a B cell epitope for which there is cross-reactivity between the pandemic virus and an endemic pathogen. The fact that antibodies against Beta1-HR2 occur in individuals who also have antibodies targeting SARS-CoV-2-HR2, but with, on average, approximately 5× greater signal strength, is most consistent with a model in which pre-existing B cell clones raised against hCoV-OC43 are recruited into the response to SARS-CoV-2. In further support of this hypothesis, the one pre-pandemic donor in which we observed a strong Beta1-HR2 response with our HV assay also exhibited reactivity to two HR2 peptides designed from SARS-CoV (no SARS-CoV-2 peptides are present in our HV library)(FIG. 7). Pre-existing cross-reactive clones would be expected to have a range of intrinsic affinities for the homologous SARS-CoV-2 epitope, and these could be further improved by somatic mutation. However, by analogy with other viruses, the fact that presumed exposure to OC43 precedes exposure to SARS-CoV-2 may limit the efficiency with which the response can be redirected, due to 'imprinting' (Gostic et al., 2016; Monto et al., 2017), which could account for the systematic difference in affinities to the corresponding epitopes from the two species. Under this model, the ~20% of convalescent donors who exhibit detectable reactivity to Beta1-HR2 but not to SARS-CoV-2-HR2 (upper left quadrant of FIG. 5D) represent cases where pre-existing antibodies to OC43 bind only weakly to SARS-CoV-2 (below the threshold of the PepSeq assay) and have been unable to acquire a high affinity against the new virus. This model also suggests that anti-Beta1-HR2 B cell memory that is capable of cross-reacting with SARS-CoV-2 is prevalent in the general population—consistent with the near universal seropositivity reported for HCoV-OC43 (Gorse et al., 2010)—although often below our limit of detection. Our findings raise the possibility that the nature of an individual's antibody response to prior hCoV-OC43 infection may impact the course of COVID-19 disease.

The HR2 cross-reactivity characterized here represents a possible source of background reactivity for SARS-CoV-2 serological assays that include the S2 subunit of Spike, which would be absent in those targeting only the RBD, for which sequence conservation is lower across species (Khan et al., 2020). Furthermore, based on the level of sequence conservation at the S2' cleavage/fusion peptide site, we expect that similar cross-reactivity may also occur at this site, and, in fact, we observed preliminary evidence for such cross-reactivity in one of the pre-pandemic controls analyzed with our HV library (FIG. 7). In FIG. 7, each row represents a pre-pandemic negative control sample that was determined to be seropositive for at least one of the non-SARS-CoV-2 human infecting coronaviruses (i.e., enrichment of ≥2 peptides from a non-SARS-CoV-2 coronavirus). The same 13 samples are shown in the same order in each plot. The focal coronavirus species is indicated in the top left corner of each plot: SARS-CoV ('SARS'), Beta1-CoV/hCoV-OC43 ('OC43'), hCoV-HKU1 ('HKU1'), hCoV-229E ('229E'), and hCoV-NL63 ('NL63'). Each position is colored according to the number of enriched peptides that overlap that position. Grey boxes indicate selected functional regions: receptor binding domain (RBD), fusion peptide (FP) and heptad repeat 2 (HR2). Both samples exhibiting reactivity to SARS-CoV peptides (top two rows) also exhibit hCoV-OC43 reactivity in homologous regions, consistent with cross-reactivity between peptides derived from endemic and epidemic coronavirus species. Both serum samples exhibiting reactivity to SARS-CoV peptides were collected in 2019 (16 years after the SARS-CoV epidemic) in Bethesda, MD, USA. Given the timing of these samples and the very small number of documented SARS-CoV cases in the US (Centers for Disease Control and Prevention (CDC), 2003), it is highly unlikely that these individuals have actually been exposed to SARS-CoV.

Due to the absence of an hCoV-OC43 S2' control peptide in our SCV2 library, we were not able to directly evaluate the potential for this cross-reactivity in COVID-19 convalescent donors. Nonetheless, our findings indicate that analysis of S2 reactivity is crucial for a complete assessment of the humoral response to SARS-CoV-2 and is consistent with the observation that S2-only assays provide an equally strong correlate of neutralization compared to RBD-only assays. Our findings also indicate that the incorporation of related beta-CoV antigens may improve the sensitivity of SARS-CoV-2 serological analyses, and in particular, that a differential analysis of SARS-CoV-2 and hCoV-OC43 Spike reactivity may provide an important measure of the efficiency with which pre-existing cross-reactive responses can be redirected.

The identification of broadly-immunogenic epitopes in conserved functional domains of SARS-CoV-2 Spike S2, including cross-reactivity with an endemic human CoV, also has implications for the design of therapeutic antibodies and vaccines. SARS-CoV-2 vaccines currently under development predominantly use 2 forms of the S antigen—whole protein or the RBD—and in each case are designed primarily to elicit neutralizing antibodies. Relative to RBD-focused vaccines, we hypothesize that vaccines that include the Spike HR2 and FP sites. (i) will be able to induce a broader array of neutralizing reactivities, (ii) may be more capable of rapidly recruiting pre-existing memory B cells that are prevalent in the population and (iii) may be less prone to viral escape due to a lower tolerance for amino acid substitutions. In particular, the identification of HR2 as a conserved, functionally-important and broadly-immunogenic site capable of eliciting cross-reacting antibodies, makes this region a candidate for the development of broadly-neutralizing responses against betacoronaviruses.

The epitope regions identified herein may be used in peptide-based diagnostics, development of subunit vaccines, and development of therapeutic binders, including monoclonal antibodies. The correlation between reactivity to SARS-CoV-2 and the endemic Coronavirus may be used to develop enhanced (more sensitive, more informative) diagnostic assays.

Characterization of Additional SARS-CoV-2 Antibody Epitopes

Figure 9A:
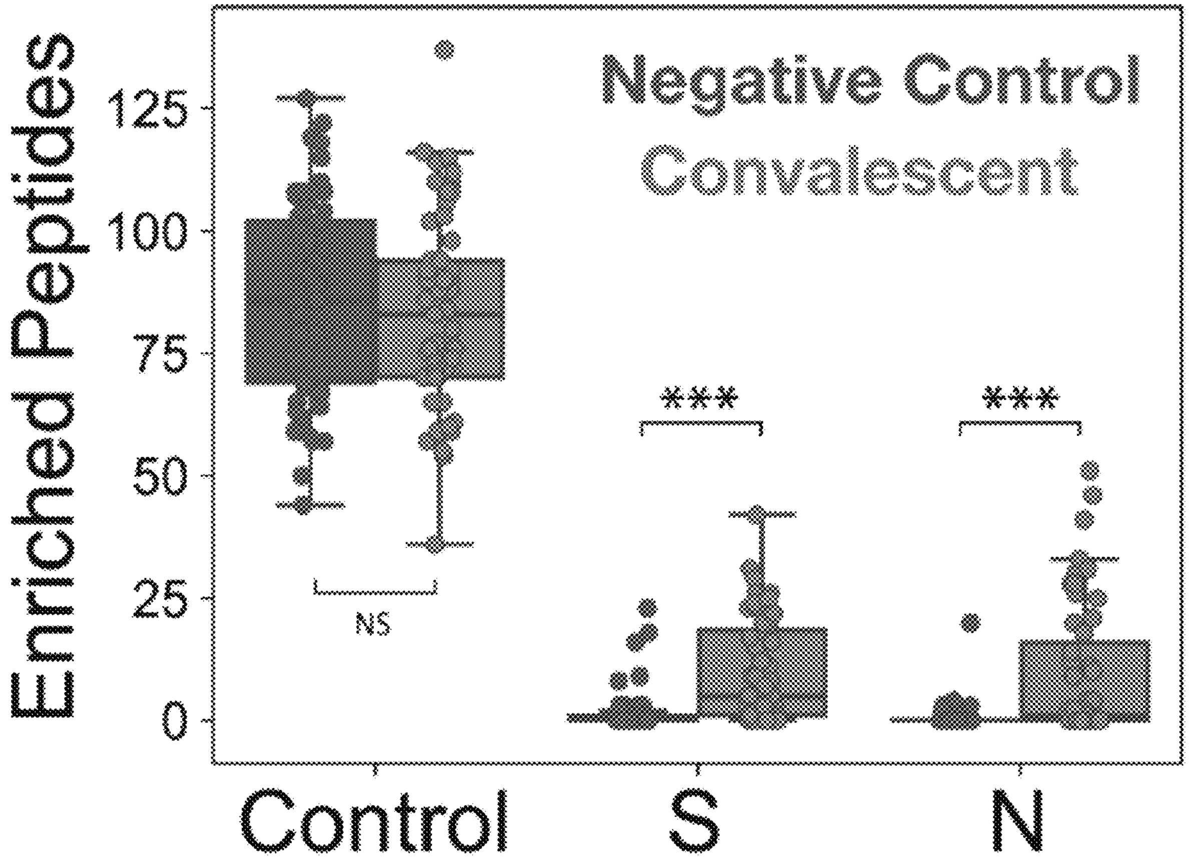
FIGS. 9A-9E illustrate the identification of recurrent reactivities to SARS-CoV-2 peptides and classification of exposure status with PepSeq.

As expected, multiple positive control peptides were found to be enriched in every serum sample that we tested (FIG. 9A), and there was no significant difference between convalescent and negative samples in the number of enriched control peptides (t test, p=0.47). In contrast, we detected significantly more SARS-CoV-2 peptides enriched in convalescent samples compared to controls in both target proteins (t test; S: p=2.2e-7, 6.2-fold difference; N: p=1.9e-6, 15.7-fold difference) (FIG. 9A). We observed at least 1 enriched SARS-CoV-2 peptide from 50/55 convalescent samples (91%), with an average of 18 enriched peptides per sample; while enriched SARS-CoV-2 peptides were only observed in 25/68 (37%) negative samples, with an average of 2 enriched peptides per sample. For the convalescent donors, there was no correlation between the number of enriched control and SARS-CoV-2 peptides (p=0.94). Therefore, the absence of SARS-CoV-2 reactivity in some convalescent samples does not appear to be related to sample quality or a generally low concentration of IgG. We also did not observe a significant effect of gender in overall SARS-CoV-2 reactivity in convalescent donors (t test, p=0.56), nor a significant correlation between SARS-CoV-2 reactivity and the number of days between PCR diagnosis and sample collection (Pearson correlation=−0.13, p=0.35). Notably, however, the five convalescent donors without detectable SARS-CoV-2 peptide enrichment were well below the median age of the full convalescent donor population (22-43 versus 50). In fact, overall, we observed a significant positive correlation between age and the number of enriched SARS-CoV-2 peptides in convalescent donors (Pearson correlation=0.33, p=0.014), while a weak trend in the opposite direction was observed for the number of enriched control peptides (Pearson correlation=−0.21, p=0.13), indicating that this pattern was not due to an overall higher level of reactivity in samples from older patients.

Figure 9B:
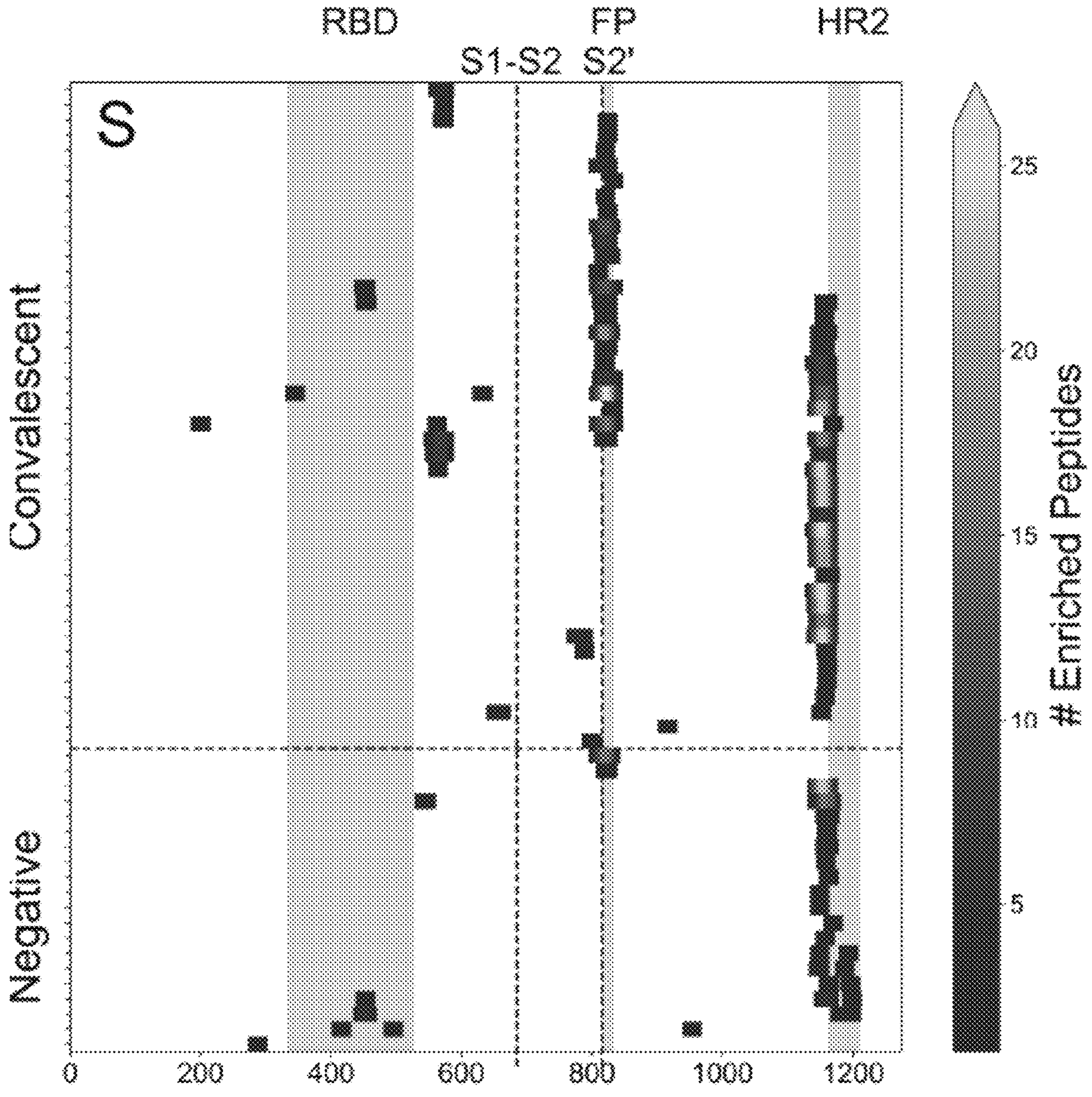
Figure 9C:
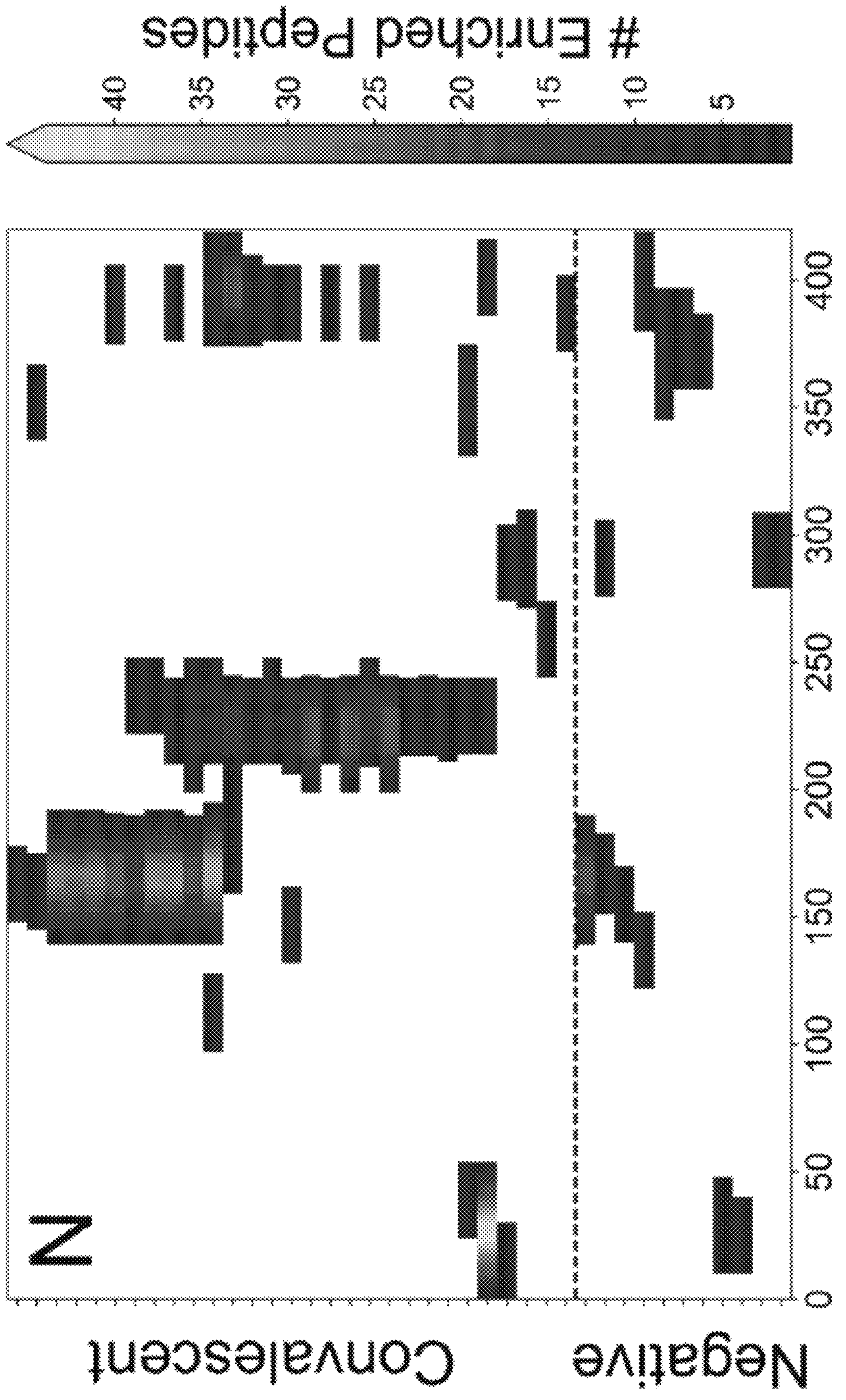

In total, we identified IgG reactivity (i.e., peptide enrichment) against 229 and 95 SARS-CoV-2 peptides in convalescent and negative control samples, respectively; 70 of these peptides were enriched in both sample types. The peptides enriched in convalescent samples clustered together into 10 putative epitopes within the S protein and 9 putative epitopes within the N protein (FIGS. 9B and 9C; TABLE 4). These epitopes were recognized at a range of prevalences across the sampled population. The 6 most widely recognized epitopes-S positions 560-572, 819-824, and 1,150-1,156 and N positions 166-169, 223-229, and 390-402-were each detected in 13%-49% of the convalescent samples tested (median=28.2%, n=55), and all of the convalescent samples with at least 1 enriched SARS-CoV-2 peptide were reactive to at least 1 of these 6 immunodominant regions (FIGS. 9B and 9C). Notably, we also observed the enrichment of peptides from 4/6 of these immunodominant regions in negative control samples, although at much lower rates (1.5%-20% reactive, median=2.2%, n=68). At the other extreme, 9 (47%) of the observed epitope regions were each detected in only a single convalescent donor. Overall, relatively little reactivity was detected to peptides within the RBD, suggesting that these epitopes require protein conformations that are not well represented by linear 30-mer peptides.

To evaluate the potential for the highly recurrent S protein epitopes to be targeted by neutralizing antibodies, we evaluated these within the context of the structure of the protein. The inferred core regions (i.e., sequences present in all enriched peptides from assays of convalescent donors) of each of these epitopes were mapped onto a rendering of the three-dimensional structure of the native S trimer. All three epitope regions are accessible for antibody binding on the surface of the trimer. The most widely recognized region (1,150-1,156) is located within the "stem helix" just upstream and partially overlapping with the heptad repeat region 2 (HR2). This region is proximal to the transmembrane domain and unresolved in the native structure; however, comparison of pre- and post-fusion structures indicated that the HR2 epitope lies within a region that undergoes a dramatic conformational rearrangement during fusion. The second epitope (819-824) resides near the S2' cleavage site, spanning the fusion peptide (FP), whose exposure and incorporation into the host membrane are essential steps in virus entry into cells. Based on their proximity to these important functional sites, these epitopes are hereafter referred to as HR2 and FP, respectively. Finally, the 560-572 epitope occurs in the subdomain SD1 region (in the S1 subunit but C-terminal of the RBD).

Figure 9D:
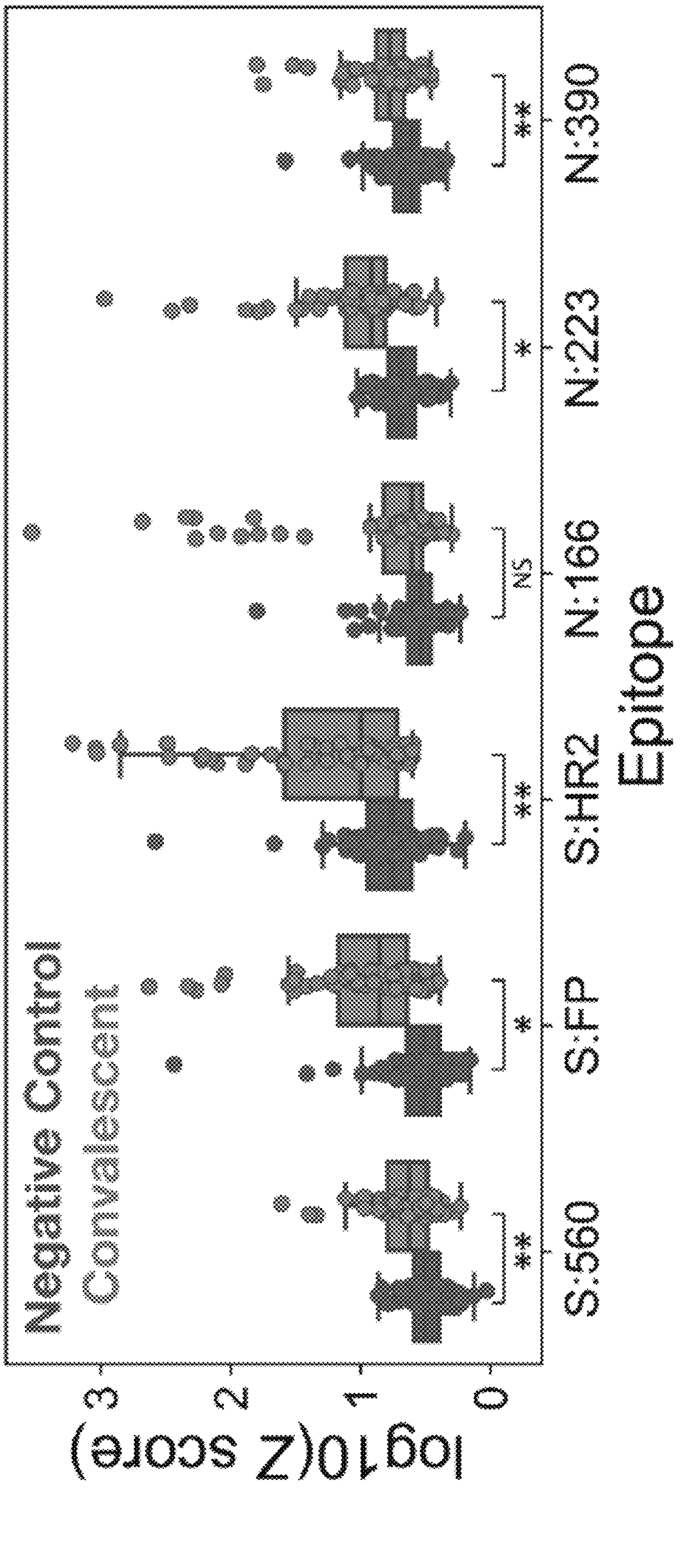
Figure 9E:
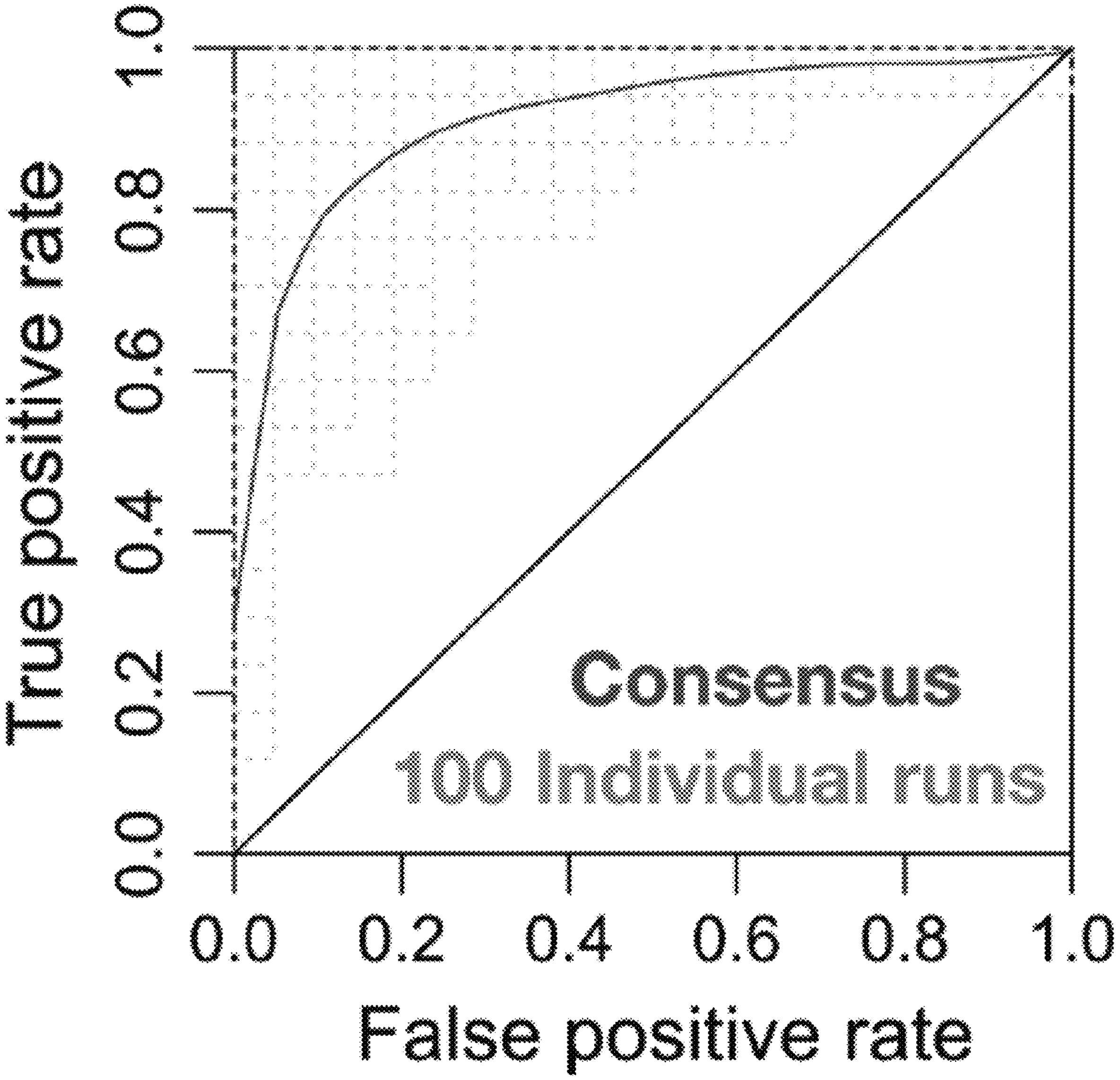

To explore the diagnostic potential of the six highly recurrent S and N epitopes, we compared the maximum Z scores per epitope across the full set of convalescent and negative samples (FIG. 9D). Across all six epitopes, we observed an overall shift toward higher Z scores in convalescent samples, which suggests the presence of additional antibody reactivity at these epitopes that is below our current enrichment thresholds. In fact, at 5/6 of these epitopes, we observed a significant difference in the mean of the Z score distributions between convalescent and negative samples (t test, S560: p=0.001, FP: p=0.036, HR2: p=0.008, N223: p=0.043, N390: p=0.008). To estimate the combined diagnostic performance of these six epitopes, we built logistic regression models using the maximum peptide Z score for each of the epitopes as features and the donor status (convalescent versus negative) as the predicted outcome. Cross-validated models each trained on a randomly selected subset of 70% of donors and tested on the remaining 30/6 gave a mean area under the curve of 0.92 (FIG. 9E).

FIGS. 9A-9E illustrate how PepSeq identified recurrent reactivities to SARS-CoV-2 peptides and classifies exposure status. FIG. 9A depicts boxplots showing the number of enriched SCV2 library peptides from assays with negative control (blue, n=68) and COVID-19 convalescent (orange, n=55) samples, divided into 3 different categories non-SARS-CoV-2 control peptides (Control), and SARS-CoV-2 Spike (S) and Nucleocapsid (N) peptides. ***t test with p<1e−5, NS, not significant). Individual data points are shown as circles, the limits of the boxes correspond to the 1st and 3rd quartiles, the black line inside each box corresponds to the median, and the whiskers extend to points that lie within 1.5 interquartile ranges of the 1st and 3rd quartiles.

FIGS. 9B and 9C depict heatmaps showing the locations of enriched SARS-CoV-2 peptides within the S and N proteins, respectively Each row represents a single serum/plasma sample and each plot includes only samples with at least 1 enriched peptide from the focal protein. Each position is colored according to the number of enriched peptides that overlap that position. The horizontal dashed line separates COVID-19 convalescent samples (top) from negative control samples (bottom). The vertical dashed lines in FIG. 9B represent the S1-S2 and S2' cleavage sites, respectively. The gray boxes indicate selected functional regions receptor binding domain (RBD), fusion peptide (FP), and heptad repeat 2 (HR2).

FIG. 9D depicts boxplots showing the distribution of Z scores across all assayed samples for the 6 most common epitope reactivities observed in FIGS. 9B and 9C. For each sample/epitope combination, the Z score of the most enriched, overlapping peptide is presented. Boxplots were drawn as described for FIG. 9A, with convalescent samples in orange and negative controls in blue. t test. *p<0.05, **p<0.01, NS, not significant.

FIG. 9E depicts receiver-operating curves showing sensitivity/specificity across a range of thresholds with which logistic regression models trained on randomly selected subsets of 70% of the donors were able to classify the remaining 30% of donors as either negative control or convalescent, using log-transformed Z scores for the 6 epitopes described in FIG. 9D as features. The red curve shows the average of 100 individual runs Each patient sample was assayed in duplicate. Enriched peptides were determined based on consistent signal across replicates and Z scores shown as averages across replicates.

Additional experimental work by the inventors supporting the present invention is presented in Ladner J T, et al. Epitope-resolved profiling of the SARS-CoV-2 antibody response identifies cross-reactivity with endemic human coronaviruses. Cell Rep Med. 2021 Jan. 19; 2(1):100189. doi: 10.1016/j.xcrm.2020.100189. PMID: 33495758; PMCID: PMC7816965, which is hereby incorporated by reference.

TABLE 4

Putative epitope regions inferred using SCV2 PepSeq library.

| Protein | First Residue | Last Residue | Sequence* | Enriched COV-19 Convalescent Samples | Enriched Negative Control Samples | SEQ ID NO: |
|---|---|---|---|---|---|---|
| Spike | 186 | 215 | FKNLREFVFKNIDGYFKIYSKHTPINLVRD | 1 | 0 | 424 |
| | 273 | 302 | RTFLLKYNENGTITDAVDCALDPLSETKCT | 0 | 1 | 425 |
| | 330 | 359 | PNITNLCPFGEVFNATRFASVYAWNRKRIS | 1 | 0 | 426 |
| | 402 | 431 | IRGDEVRQIAPGQTGKIADYNYKLPDDFTG | 0 | 1 | 417 |
| | 441 | 464 | LDSKVGGNYNYLYRLFRKSNLKPF | 2 | 2 | 428 |
| | 481 | 510 | NGVEGFNCYFPQSYGFQPTNGVGYQPYRV | 0 | 1 | 429 |
| | 532 | 559 | NLVKNKCVNFNFNGLTGTGVLTESNKKF | 0 | 1 | 430 |
| | **560** | **572** | **LPFQQFGRRDIADT** | **7** | **0** | **423** |
| | 619 | 647 | EVPVAIHADQLTPTWRVYSTGSNVFQTRA | 1 | 0 | 431 |
| | 647 | 668 | AGCLIGAEHVNNSYECDIPIGA | 1 | 0 | 432 |
| | 785 | 791 | VKQIYKT | 3 | 0 | 433 |
| | **819** | **824** | **EDLLFN** | **22** | **2** | **422** |
| | 901 | 930 | QMAYRFNGIGVTQNVLYENQKLIANQFNSA | 1 | 0 | 401 |
| | 939 | 968 | SSTASALGKLQDVVNQNAQALNTLVKQLSS | 0 | 1 | 434 |
| | **1150** | **1156** | **EELDKYF** | **27** | **14** | **435** |
| | 1155 | 1184 | YFKNHTSPDVDLGDISGINASVVNIQKEID | 1 | 1 | 436 |
| | 1184 | 1195 | DRLNEVAKNLNE | 0 | 4 | 437 |

TABLE 4 -continued

Putative epitope regions inferred using SCV2 PepSeq library.

| Protein | First Residue | Last Residue | Sequence* | Enriched COV-19 Convalescent Samples | Enriched Negative Control Samples | SEQ ID NO: |
|---|---|---|---|---|---|---|
| Nucleocapsid | 25 | 30 | GSNQNG | 3 | 2 | 438 |
| | 99 | 127 | GKMKDLSPRWYFYYLGTGPEAGLPYGANK | 1 | 0 | 439 |
| | 133 | 152 | VATEGALNTPKDHIGTRNPA | 1 | 1 | 440 |
| | 166 | 169 | **TLPK** | **12** | **3** | **441** |
| | 223 | 229 | **LLDRLNQ** | **19** | **0** | **442** |
| | 245 | 274 | TVTKKSAAEASKKPRQKRTATKAYNVTQAF | 1 | 0 | 443 |
| | 281 | 301 | QTQGNFGDQFLIRQGTDYKHW | 2 | 3 | 444 |
| | 346 | 361 | FKDQVILLNKHIDAYK | 2 | 0 | 445 |
| | 3643 | 375 | PKKDKKKK | 0 | 3 | 446 |
| | 390 | 402 | **QTVTLLPAADLDD** | **11** | **1** | **447** |

*Reported epitopes represent inferred minimally reactive regions based on enriched peptides across all samples. These regions may not represent the full epitope, due to slight differences in epitopes recognized across different individuals. All positions and sequences relative to GenBank: YP_009724390.1 (Spike) and YP_009724397.2 (Nucleocapsid).

Some embodiments of the invention may comprise the administration of a pharmaceutical composition to the subject that has been previously diagnosed with a viral infection, such as coronavirus infection. For example, in some embodiments, the subject may have been previously diagnosed with COVID-19 by one skilled in the art (e.g., a physician or a veterinarian) such that a therapeutic treatment is warranted by the diagnosis. Moreover, in other embodiments, the invention may comprise the administration of a pharmaceutical composition to a subject that may have not yet been exposed to a coronavirus-infected environment or individual. As such, the administration of the pharmaceutical composition may function as a vaccine or prophylactic agent to limit any potential viral infection that could occur, or to improve the subject's immune response to the virus.

All headings are for the convenience of the reader and should not be used to limit the meaning of the text that follows the heading, unless so specified.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

REFERENCES

Amanat, F., Stadlbauer, D., Strohmeier, S., Nguyen, T. H. O., Chromikova, V., McMahon, M., Jiang, K., Arunkumar, G. A., Jurczyszak, D., Polanco, J., et al. (2020). A serological assay to detect SARS-CoV-2 seroconversion in humans. Nat. Med.

Callow, K. A., Parry, H. F., Sergeant, M., and Tyrrell, D. A. (1990). The time course of the immune response to experimental coronavirus infection of man. Epidemiol. Infect. 105, 435-446.

Casadevall, A., and Pirofski, L.-A. (2020). The convalescent sera option for containing COVID-19. J. Clin. Invest. 130, 1545-1548.

Chang, C.-K., Hsu, Y.-L., Chang, Y.-H., Chao, F.-A., Wu, M.-C., Huang, Y.-S., Hu, C.-K., and Huang, T.-H. (2009). Multiple nucleic acid binding sites and intrinsic disorder of severe acute respiratory syndrome coronavirus nucleocapsid protein: implications for ribonucleocapsid protein packaging. J. Virol. 83, 2255-2264.

Chi, X., Yan, R., Zhang, J., Zhang, G., Zhang, Y., Hao, M., Zhang, Z., Fan, P., Dong, Y., Yang, Y., et al. (2020). A neutralizing human antibody binds to the N-terminal domain of the Spike protein of SARS-CoV-2. Science.

Deeks, J. J., Dinnes, J., Takwoingi, Y., Davenport, C., Spijker, R., Taylor-Phillips, S., Adriano, A., Beese, S., Dretzke, J., Ferrante di Ruffano, L., et al. (2020). Antibody tests for identification of current and past infection with SARS-CoV-2. Cochrane Database Syst. Rev. 6, CD013652.

Dijkman, R., Jebbink, M. F., El Idrissi, N. B., Pyrc, K., Müller, M. A., Kuijpers, T. W., Zaaijer, H. L., and van der Hoek, L. (2008). Human coronavirus NL63 and 229E seroconversion in children. J. Clin. Microbiol. 46, 2368-2373.

Du, L., He, Y., Zhou, Y., Liu, S., Zheng, B.-J., and Jiang, S. (2009). The spike protein of SARS-CoV—a target for vaccine and therapeutic development. Nat. Rev. Microbiol. 7, 226-236.

Eroshenko, N., Gill, T., Keaveney, M. K., Church, G. M., Trevejo, J. M., and Raj aniemi, H. (2020). Implications of antibody-dependent enhancement of infection for SARS-CoV-2 countermeasures. Nat. Biotechnol.

Fink, Z. W., Martinez, V., Altin, J., and Ladner, J. T. (2020). PepSIRF: a flexible and comprehensive tool for the analysis of data from highly-multiplexed DNA-barcoded peptide assays. arXiv.

Fleri, W., Paul, S., Dhanda, S. K., Mahajan, S., Xu, X., Peters, B., and Sette, A. (2017). The Immune Epitope Database and Analysis Resource in Epitope Discovery and Synthetic Vaccine Design. Front. Immunol. 8, 278.

Friesen, R. H. E., Lee, P. S., Stoop, E. J. M., Hoffman, R. M. B., Ekiert, D. C., Bhabha, G., Yu, W., Juraszek, J., Koudstaal, W., Jongeneelen, M., et al. (2014). A common solution to group 2 influenza virus neutralization. Proc. Natl. Acad. Sci. U.S.A 111, 445-450.

Gorse, G. J., Patel, G. B., Vitale, J. N., and O'Connor, T. Z. (2010). Prevalence of antibodies to four human coronaviruses is lower in nasal secretions than in serum. Clin. Vaccine Immunol. 17, 1875-1880.

Gostic, K. M., Ambrose, M., Worobey, M., and Lloyd-Smith, J. O. (2016). Potent protection against H5N1 and H7N9 influenza via childhood hemagglutinin imprinting. Science 354, 722-726.

Grifoni, A., Weiskopf, D., Ramirez, S. I., Mateus, J., Dan, J. M., Moderbacher, C. R., Rawlings, S. A., Sutherland, A., Premkumar, L., Jadi, R. S., et al. (2020). Targets of T Cell Responses to SARS-CoV-2 Coronavirus in Humans with COVID-19 Disease and Unexposed Individuals. Cell 181, 1489-1501.e15.

Halstead, S. B., and O'rourke, E. J. (1977). Antibody-enhanced dengue virus infection in primate leukocytes. Nature 265, 739-741.

Hansen, J., Baum, A., Pascal, K. E., Russo, V., Giordano, S., Wloga, E., Fulton, B. O., Yan, Y., Koon, K., Patel, K., et al. (2020). Studies in humanized mice and convalescent humans yield a SARS-CoV-2 antibody cocktail. Science.

Hoofnagle, J. H., Gerety, R. J., Ni, L. Y., and Barker, L. F. (1974). Antibody to hepatitis B core antigen. A sensitive indicator of hepatitis B virus replication. N. Engl. J. Med. 290, 1336-1340.

Katzelnick, L. C., Gresh, L., Halloran, M. E., Mercado, J. C., Kuan, G., Gordon, A., Balmaseda, A., and Harris, E. (2017). Antibody-dependent enhancement of severe dengue disease in humans. Science 358, 929-932.

Keng, C.-T., Zhang, A., Shen, S., Lip, K.-M., Fielding, B. C., Tan, T. H. P., Chou, C.-F., Loh, C. B., Wang, S., Fu, J., et al. (2005). Amino acids 1055 to 1192 in the S2 region of severe acute respiratory syndrome coronavirus S protein induce neutralizing antibodies: implications for the development of vaccines and antiviral agents. J. Virol. 79, 3289-3296.

Khan, S., Nakajima, R., Jain, A., de Assis, R. R., Jasinskas, A., Obiero, J. M., Adenaiye, O., Tai, S., Hong, F., Milton, D. K., et al. (2020). Analysis of Serologic Cross-Reactivity Between Common Human Coronaviruses and SARS-CoV-2 Using Coronavirus Antigen Microarray. bioRxiv.

Khurana, S., Loving, C. L., Manischewitz, J., King, L. R., Gauger, P. C., Henningson, J., Vincent, A. L., and Golding, H. (2013). Vaccine-induced anti-HA2 antibodies promote virus fusion and enhance influenza virus respiratory disease. Sci. Transl. Med. 5, 200ra114.

Kozlov, I. A., Thomsen, E. R., Munchel, S. E., Villegas, P., Capek, P., Gower, A. J., Pond, S. J. K., Chudin, E., and Chee, M. S. (2012). A highly scalable peptide-based assay system for proteomics. PLoS One 7, e37441.

Krammer, F., and Simon, V. (2020). Serology assays to manage COVID-19. Science 368, 1060-1061.

Lai, S.-C., Chong, P. C.-S., Yeh, C.-T., Liu, L. S.-J., Jan, J.-T., Chi, H.-Y., Liu, H.-W., Chen, A., and Wang, Y.-C. (2005). Characterization of neutralizing monoclonal antibodies recognizing a 15-residues epitope on the spike protein HR2 region of severe acute respiratory syndrome coronavirus (SARS-CoV). J. Biomed. Sci. 12, 711-727.

Larman, H. B., Zhao, Z., Laserson, U., Li, M. Z., Ciccia, A., Gakidis, M. A. M., Church, G. M., Kesari, S., Leproust, E. M., Solimini, N. L., et al. (2011). Autoantigen discovery with a synthetic human peptidome. Nat. Biotechnol. 29, 535-541.

Liu, A., Li, Y., Peng, J., Huang, Y., and Xu, D. (2020). Antibody responses against SARS-CoV-2 in COVID-19 patients. J. Med. Virol.

Liu, S., Xiao, G., Chen, Y., He, Y., Niu, J., Escalante, C. R., Xiong, H., Farmar, J., Debnath, A. K., Tien, P., et al. (2004). Interaction between heptad repeat 1 and 2 regions in spike protein of SARS-associated coronavirus: implications for virus fusogenic mechanism and identification of fusion inhibitors. Lancet 363, 938-947.

Lu, R., Zhao, X., Li, J., Niu, P., Yang, B., Wu, H., Wang, W., Song, H., Huang, B., Zhu, N., et al. (2020). Genomic characterisation and epidemiology of 2019 novel coronavirus: implications for virus origins and receptor binding. Lancet 395, 565-574.

Lubroth, J., Grubman, M. J., Burrage, T. G., Newman, J. F., and Brown, F. (1996). Absence of protein 2C from clarified foot-and-mouth disease virus vaccines provides the basis for distinguishing convalescent from vaccinated animals. Vaccine 14, 419-427.

Lucchese, G., Stufano, A., Trost, B., Kusalik, A., and Kanduc, D. (2007). Peptidology: short amino acid modules in cell biology and immunology. Amino Acids 33, 703-707.

Lv, H., Wu, N. C., Tsang, O. T.-Y., Yuan, M., Perera, R. A. P. M., Leung, W. S., So, R. T. Y., Chan, J. M. C., Yip, G. K., Chik, T. S. H., et al. (2020). Cross-reactive Antibody Response between SARS-CoV-2 and SARS-CoV Infections. Cell Rep. 31, 107725.

Mina, M. J., Kula, T., Leng, Y., Li, M., de Vries, R. D., Knip, M., Silj ander, H., Rewers, M., Choy, D. F., Wilson, M. S., et al. (2019). Measles virus infection diminishes preexisting antibodies that offer protection from other pathogens. Science 366, 599-606.

Monto, A. S., Malosh, R. E., Petrie, J. G., and Martin, E. T. (2017). The Doctrine of Original Antigenic Sin: Separating Good From Evil. J. Infect. Dis. 215, 1782-1788.

Ni, L., Ye, F., Cheng, M.-L., Feng, Y., Deng, Y.-Q., Zhao, H., Wei, P., Ge, J., Gou, M., Li, X., et al. (2020). Detection of SARS-CoV-2-Specific Humoral and Cellular Immunity in COVID-19 Convalescent Individuals. Immunity 52, 971-977.e3.

Nie, J., Li, Q., Wu, J., Zhao, C., Hao, H., Liu, H., Zhang, L., Nie, L., Qin, H., Wang, M., et al. (2020). Establishment and validation of a pseudovirus neutralization assay for SARS-CoV-2. Emerg. Microbes Infect. 9, 680-686.

Pillay, T. S. (2020). Gene of the month: the 2019-nCoV/SARS-CoV-2 novel coronavirus spike protein. J. Clin. Pathol. 73, 366-369.

Pinto, D., Park, Y.-J., Beltramello, M., Walls, A. C., Tortorici, M. A., Bianchi, S., Jaconi, S., Culap, K., Zatta, F., De Marco, A., et al. (2020). Cross-neutralization of SARS-CoV-2 by a human monoclonal SARS-CoV antibody. Nature.

Poh, C. M., Carissimo, G., Wang, B., Amrun, S. N., Lee, C. Y.-P., Chee, R. S.-L., Fong, S.-W., Yeo, N. K.-W., Lee, W.-H., Torres-Ruesta, A., et al. (2020). Two linear epitopes on the SARS-CoV-2 spike protein that elicit neutralising antibodies in COVID-19 patients. Nat. Commun. 11, 2806.

Price, J. V., Tangsombatvisit, S., Xu, G., Yu, J., Levy, D., Baechler, E. C., Gozani, O., Varma, M., Utz, P. J., and Liu, C. L. (2012). On silico peptide microarrays for high-resolution mapping of antibody epitopes and diverse protein-protein interactions. Nat. Med. 18, 1434-1440.

Robbiani, D. F., Gaebler, C., Muecksch, F., Lorenzi, J. C. C., Wang, Z., Cho, A., Agudelo, M., Barnes, C. O., Gazumyan, A., Finkin, S., et al. (2020). Convergent Antibody Responses to SARS-CoV-2 Infection in Convalescent Individuals. bioRxiv.

Routledge, E., Stauber, R., Pfleiderer, M., and Siddell, S. G. (1991). Analysis of murine coronavirus surface glycoprotein functions by using monoclonal antibodies. J. Virol. 65, 254-262.

Shiryaev, S. A., Thomsen, E. R., Cieplak, P., Chudin, E., Cheltsov, A. V., Chee, M. S., Kozlov, I. A., and Strongin, A. Y. (2012). New details of HCV NS3/4A proteinase functionality revealed by a high-throughput cleavage assay. PLoS One 7, e35759.

Tan, C. W., Chia, W. N., Chen, M. I.-C., Hu, Z., Young, B. E., Tan, Y.-J., Yi, Y., Lye, D. C., Anderson, D. E., and Wang, L.-F. A SARS-CoV-2 surrogate virus neutralization test (sVNT) based on antibody-mediated blockage of ACE2-spike (RBD) protein-protein interaction.

Thanh Le, T., Andreadakis, Z., Kumar, A., Gomez Roman, R., Tollefsen, S., Saville, M., and Mayhew, S. (2020). The COVID-19 vaccine development landscape. Nat. Rev. Drug Discov. 19, 305-306.

Walls, A. C., Tortorici, M. A., Snijder, J., Xiong, X., Bosch, B.-J., Rey, F. A., and Veesler, D. (2017). Tectonic conformational changes of a coronavirus spike glycoprotein promote membrane fusion. Proc. Natl. Acad. Sci. U.S.A 114, 11157-11162.

Waterhouse, A., Bertoni, M., Bienert, S., Studer, G., Tauriello, G., Gumienny, R., Heer, F. T., de Beer, T. A. P., Rempfer, C., Bordoli, L., et al. (2018). SWISS-MODEL: homology modelling of protein structures and complexes. Nucleic Acids Res. 46, W296W303.

Whitman, J. D., Hiatt, J., Mowery, C. T., Shy, B. R., Yu, R., Yamamoto, T. N., Rathore, U., Goldgof, G. M., Whitty, C., Woo, J. M., et al. (2020). Test performance evaluation of SARS-CoV-2 serological assays. medRxiv.

Xia, S., Yan, L., Xu, W., Agrawal, A. S., Algaissi, A., Tseng, C.-T. K., Wang, Q., Du, L., Tan, W., Wilson, I. A., et al. (2019). A pan-coronavirus fusion inhibitor targeting the HR1 domain of human coronavirus spike. Sci Adv 5, eaav4580.

Xu, G. J., Kula, T., Xu, Q., Li, M. Z., Vernon, S. D., Ndung'u, T., Ruxrungtham, K., Sanchez, J., Brander, C., Chung, R. T., et al. (2015). Viral immunology. Comprehensive serological profiling of human populations using a synthetic human virome. Science 348, aaa0698.

Yuan, M., Wu, N. C., Zhu, X., Lee, C.-C. D., So, R. T. Y., Lv, H., Mok, C. K. P., and Wilson, I. A. A highly conserved cryptic epitope in the receptor-binding domains of SARS-CoV-2 and SARS-CoV.

Zhu, N., Zhang, D., Wang, W., Li, X., Yang, B., Song, J., Zhao, X., Huang, B., Shi, W., Lu, R., et al. (2020). A Novel Coronavirus from Patients with Pneumonia in China, 2019. N. Engl. J. Med. 382, 727-733.

Zost, S. J., Gilchuk, P., Case, J. B., Binshtein, E., Chen, R. E., Reidy, J. X., Trivette, A., Nargi, R. S., Sutton, R. E., Suryadevara, N., et al. (2020). Potently neutralizing human antibodies that block SARS-CoV-2 receptor binding and protect animals. bioRxiv.

Centers for Disease Control and Prevention (CDC) (2003). Revised U.S. surveillance case definition for severe acute respiratory syndrome (SARS) and update on SARS cases—United States and worldwide, December 2003. MMWR Morb. Mortal. Wkly. Rep. 52, 1202-1206.

Jia, N., Liu, H.-B., Ni, X.-B., Bell-Sakyi, L., Zheng, Y.-C., Song, J.-L., Li, J., Jiang, B.-G., Wang, Q., Sun, Y., et al. (2019). Emergence of human infection with Jingmen tick virus in China: A retrospective study. EBioMedicine.

Woolhouse, M. E. J., and Brierley, L. (2018). Epidemiological characteristics of human-infective RNA viruses. Sci Data 5, 180017.

What is claimed is:

1. A method of detecting in a sample a presence of an antibody that binds to a spike protein or a nucleocapsid protein of a severe acute respiratory syndrome-associated coronavirus (SARS-COV), the method comprising:

providing a biological sample from a subject suspected to be infected with a SARS-COV;

contacting the biological sample with a peptide consisting of the amino acid sequence: EDLLFN (SEQ ID NO: 422); and detecting antigen-antibody complexes formed.

2. The method of claim 1, wherein the SARS-COV is severe acute respiratory syndrome coronavirus 2 (SARS-COV-2).

3. The method of claim 1, wherein the biological sample is whole blood, serum, or plasma.

4. The method of claim 1, wherein the subject is a human.

5. The method of claim 1, wherein the method of detecting antigen-antibody complexes comprises a technique selected from the group consisting of flow cytometry, immunohistochemistry, enzyme-linked immunosorbent assay (ELISA), Western Blot, and immunoaffinity chromatography.

* * * * *